(12) United States Patent
Bindschaedler et al.

(10) Patent No.: US 10,407,383 B2
(45) Date of Patent: Sep. 10, 2019

(54) CYCLOPENTENE AND CYCLOPENTADIENE COMPOUNDS FOR CONTROLLING INVERTEBRATE PESTS

(71) Applicant: BASF SE, Ludwigshafen (DE)

(72) Inventors: Pascal Bindschaedler, Roemerberg (DE); Wolfgang Von Deyn, Neustadt (DE); Arun Narine, Mannheim (DE); Karsten Koerber, Eppelheim (DE); Franz-Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 69 days.

(21) Appl. No.: 15/114,646

(22) PCT Filed: Feb. 3, 2015

(86) PCT No.: PCT/EP2015/052142
§ 371 (c)(1),
(2) Date: Jul. 27, 2016

(87) PCT Pub. No.: WO2015/114157
PCT Pub. Date: Aug. 6, 2015

(65) Prior Publication Data
US 2016/0355466 A1    Dec. 8, 2016

Related U.S. Application Data

(60) Provisional application No. 61/934,873, filed on Feb. 3, 2014, provisional application No. 61/983,475, filed on Apr. 24, 2014.

(51) Int. Cl.
| | |
|---|---|
| *C07C 237/52* | (2006.01) |
| *A01N 37/10* | (2006.01) |
| *A01N 37/18* | (2006.01) |
| *A01N 37/46* | (2006.01) |
| *A01N 43/20* | (2006.01) |
| *A01N 43/40* | (2006.01) |
| *A01N 43/54* | (2006.01) |
| *C07C 63/70* | (2006.01) |
| *C07C 69/78* | (2006.01) |
| *C07C 233/65* | (2006.01) |
| *C07C 233/66* | (2006.01) |
| *C07C 233/76* | (2006.01) |
| *C07D 213/40* | (2006.01) |
| *C07D 213/75* | (2006.01) |
| *C07D 239/26* | (2006.01) |
| *C07D 239/42* | (2006.01) |
| *C07D 239/48* | (2006.01) |
| *C07D 331/04* | (2006.01) |

(52) U.S. Cl.
CPC ............ *C07C 237/52* (2013.01); *A01N 37/10* (2013.01); *A01N 37/18* (2013.01); *A01N 37/46* (2013.01); *A01N 43/20* (2013.01); *A01N 43/40* (2013.01); *A01N 43/54* (2013.01); *C07C 63/70* (2013.01); *C07C 69/78* (2013.01); *C07C 233/65* (2013.01); *C07C 233/66* (2013.01); *C07C 233/76* (2013.01); *C07D 213/40* (2013.01); *C07D 213/75* (2013.01); *C07D 239/26* (2013.01); *C07D 239/42* (2013.01); *C07D 239/48* (2013.01); *C07D 331/04* (2013.01); *C07C 2601/02* (2017.05); *C07C 2601/10* (2017.05)

(58) Field of Classification Search
None
See application file for complete search history.

(56) References Cited

FOREIGN PATENT DOCUMENTS

| | | |
|---|---|---|
| JP | 2008 266230 | 11/2008 |
| JP | 2010 116389 | 5/2010 |
| JP | 2013 540115 | 10/2013 |
| RU | 2 117 658 | 8/1998 |
| WO | WO 92/15555 | 9/1992 |
| WO | WO 2008/128711 | 10/2008 |
| WO | WO 2010/043315 | 4/2011 |
| WO | WO 2011/043315 | 4/2011 |
| WO | WO 2012/042006 | 4/2012 |
| WO | WO 2013/026724 | 2/2013 |
| WO | WO 2013/026726 | 2/2013 |
| WO | WO 2013/037626 | 3/2013 |

(Continued)

OTHER PUBLICATIONS

International Preliminary Report on Patentability dated Aug. 9, 2016, prepared in International Application No. PCT/EP2015/052142.

(Continued)

*Primary Examiner* — Jeffrey S Lundgren
*Assistant Examiner* — Tori Strong
(74) *Attorney, Agent, or Firm* — Brinks Gilson & Lione

(57) ABSTRACT

The present invention relates to cyclopent(adi)ene compounds of formula I

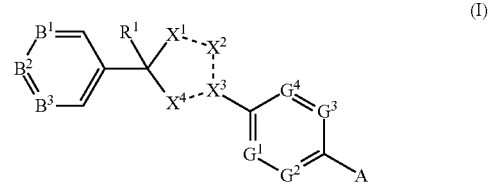

wherein the variables are as defined in the claims and description. The compounds are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

23 Claims, No Drawings

(56) References Cited

FOREIGN PATENT DOCUMENTS

| WO | WO 2013/092943 | 6/2013 |
| WO | WO 2013/190050 | 12/2013 |
| WO | WO 2014/202751 | 12/2014 |
| WO | WO 2014/203911 | 12/2014 |
| WO | WO 2014/206907 | 12/2014 |
| WO | WO 2014/206908 | 12/2014 |
| WO | WO 2014/206909 | 12/2014 |
| WO | WO 2014/206910 | 12/2014 |
| WO | WO 2015/128358 | 9/2015 |

OTHER PUBLICATIONS

International Search Report dated Mar. 18, 2015, prepared in International Application No. PCT/EP2015/052142.

CYCLOPENTENE AND CYCLOPENTADIENE COMPOUNDS FOR CONTROLLING INVERTEBRATE PESTS

This application is a National Stage application of International Application No. PCT/EP2015/052142, filed Feb. 3, 2015, which claims the benefit of U.S. Provisional Application No. 61/934,873, filed Feb. 3, 2014 and U.S. Provisional Application No. 61/983,475, filed Apr. 24, 2014.

The present invention relates to cyclopent(adi)ene (i.e. cyclopentene and cyclopentadiene) compounds which are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

Invertebrate pests and in particular arthropods and nematodes destroy growing and harvested crops and attack wooden dwelling and commercial structures, causing large economic loss to the food supply and to property. While a large number of pesticidal agents are known, due to the ability of target pests to develop resistance to said agents, there is an on-going need for new agents for combating invertebrate pests, in particular insects, arachnids and nematodes.

Related compounds are described in WO 2013/026724, WO 2013/026726, WO 2013/037626, WO 2013/092943 and WO 2012/042006. However, these documents do not describe compounds having the characteristic substituents and substituents' arrangement as claimed in the present invention; WO 2013/026724 and WO 2013/026726 relating to compounds containing dihydrofuran moieties and WO 2013/037626 and WO 2013/092943 relating to compounds containing isothiazoline moieties. WO 2012/042006 describes inter alia compounds containing cyclopentene moieties, but the (het)aryl groups bound thereto carry an imine(-derived) substituent, which is not provided for in the present compounds.

It is an object of the present invention to provide compounds that have a good pesticidal activity, in particular insecticidal activity, and show a broad activity spectrum against a large number of different invertebrate pests, especially against difficult to control arthropod pests and/or nematodes.

The object of the present invention is moreover to provide compounds which are less persistent, bioaccumulative and/or toxic than the compounds of the prior art. Especially isoxazoline insecticides of the prior art show a high persistency in the soil and thus accumulate there.

It has been found that these objectives can be achieved by cyclopent(adi)ene compounds of the formula I below, by their stereoisomers and by their salts, in particular their agriculturally or veterinarily acceptable salts.

Therefore, in a first aspect, the invention relates to cyclopentene or cyclopentadiene compounds of the formula I

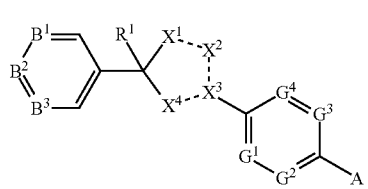
(I)

wherein
the ring

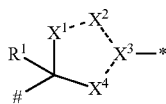

is selected from following rings II-1 to II-3:

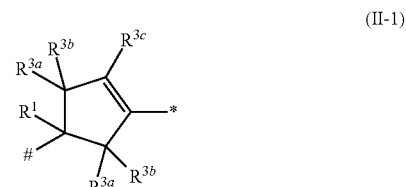
(II-1)

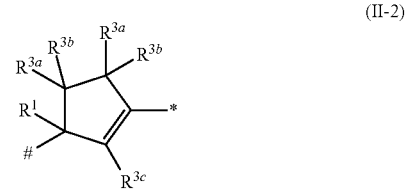
(II-2)

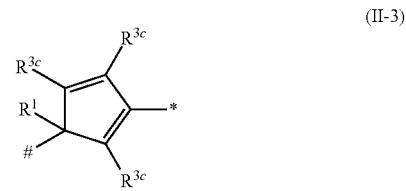
(II-3)

wherein
\# is the attachment point to the ring with the ring members $B^1$, $B^2$ and $B^3$; and
\* is the attachment point to the ring with the ring members $G^1$, $G^2$, $G^3$ and $G^4$;
A is a group $A^1$, $A^2$ or $A^3$;
wherein
$A^1$ is a group of following formula:

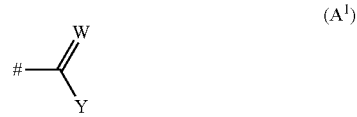
(A¹)

wherein
\# denotes the attachment point to the remainder of the molecule;
W is selected from O and S;
Y is selected from hydrogen, —N($R^5$)$R^6$ and —O$R^9$;
$A^2$ is a group of following formula:

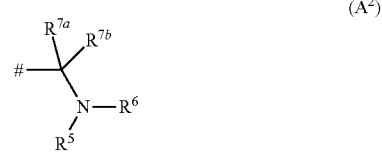
(A²)

wherein
# denotes the attachment point to the remainder of the molecule;

$A^3$ is a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and $SO_2$, as ring members, or is a 8-, 9- or 10-membered saturated, partially unsaturated or maximally unsaturated heterobicyclic ring containing 1, 2, 3 or 4 heteroatoms or heteroatom groups selected from N, O, S, NO, SO and $SO_2$, as ring members, where the heteromonocyclic or heterobicyclic ring is optionally substituted with one or more substituents $R^{11}$;

$B^1$, $B^2$ and $B^3$ are each independently selected from the group consisting of N and $CR^2$, with the proviso that at most two of $B^1$, $B^2$ and $B^3$ are N;

$G^1$, $G^2$, $G^3$ and $G^4$ are each independently selected from the group consisting of N and $CR^4$, with the proviso that at most two of $G^1$, $G^2$, $G^3$ and $G^4$ are N;

$R^1$ is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl-, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and —C(=O)$OR^{15}$;

each $R^2$ is independently selected from the group consisting of hydrogen, halogen, cyano, azido, nitro, —SCN, —$SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$,
—Si$(R^{12})_3$, —$OR^9$, —S(O)$_n R^9$, —$NR^{10a}R^{10b}$,
phenyl which may be substituted by 1, 2, 3, 4 or 5 radicals $R^{11}$, and a 3-, 4-, 5-, 6-7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromono- or heterobicyclic ring may be substituted by one or more radicals $R^{11}$;

$R^{3a}$, $R^{3b}$, $R^{3c}$ are each independently selected from the group consisting of hydrogen, halogen, hydroxyl, —$CO_2R^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group =O, =C$(R^{3e})_2$, =NOH or =$NOCH_3$;

$R^{3d}$ is selected from the group consisting of hydrogen, $C_1$-$C_6$-alkyl and $C_1$-$C_3$-alkyloxy-$C_1$-$C_3$-alkyl-;

each $R^{3e}$ is independently selected from the group consisting of hydrogen, halogen, $CH_3$ and $CF_3$;

each $R^4$ is independently selected from the group consisting of hydrogen, halogen, cyano, azido, nitro, —SCN, —$SF_5$, $C_1$-$C_6$-alkyl which may be partially or fully halogenated and/or may be substituted by one or more radicals $R^8$, $C_3$-$C_8$-cycloalkyl which may be partially or fully halogenated and/or may be substituted by one or more radicals $R^8$, $C_2$-$C_6$-alkenyl which may be partially or fully halogenated and/or may be substituted by one or more radicals $R^8$, $C_2$-$C_6$-alkynyl which may be partially or fully halogenated and/or may be substituted by one or more radicals $R^8$,
—Si$(R^{12})_3$, —$OR^9$, —S(O)$_n R^9$, —$NR^{10a}R^{10b}$,
phenyl which may be substituted by 1, 2, 3, 4 or 5 radicals $R^{11}$, and a 3-, 4-, 5-, 6-7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and $SO_2$, as ring members, where the heteromonocyclic or heterobicyclic ring may be substituted by one or more radicals $R^{11}$;

each $R^5$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$; and —S(O)$_n R^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$, —$OR^9$, —$NR^{10a}R^{10b}$, —S(O)$_n R^9$, —C(=O)$NR^{10a}N(R^{10a})R^{10b}$, —Si$(R^{12})_3$, —C(=O)$R^8$, —CH=$NOR^9$,
phenyl which may be substituted with 1, 2, 3, 4, or 5 substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;

or $R^5$ and $R^6$ together form a group =C$(R^8)_2$, =S(O)$_m(R^9)_2$, =$NR^{10a}$ or =$NOR^9$;

$R^{7a}$, $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more radicals $R^8$;

each $R^8$ is independently selected from the group consisting of cyano, azido, nitro, —SCN, —$SF_5$, $C_3$-$C_8$-cycloalkyl, $C_3$-$C_8$-halocycloalkyl, where the cycloaliphatic moieties in the two last-mentioned radicals may be substituted by one or more radicals $R^{13}$;
—Si$(R^{12})_3$, —$OR^9$, —$OSO_2R^9$, —S(O)$_n R^9$, —$N(R^{10a})R^{10b}$, —C(=O)$N(R^{10a})R^{10b}$, —C(=S)$N(R^{10a})R^{10b}$, —C(=O)$OR^9$, —CH=$NOR^9$,
phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =$C(R^{13})_2$; =S; =$S(O)_m(R^{15})_2$, =$S(O)_m R^{15}N(R^{14a})R^{14b}$, =$NR^{10a}$, =$NOR^9$; or =$NN(R^{10a})R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and $SO_2$, as ring members, and where the carbocyclic or heterocyclic ring is optionally substituted with one or more substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in these six radicals may be substituted by one or more radicals $R^{13}$; and $R^8$ in the groups —C(=O)$R^8$ and =$C(R^8)_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$, —$C_1$-$C_6$-alkyl-C(=O)$OR^{15}$, —$C_1$-$C_6$-alkyl-C(=O)N($R^{14a}$)$R^{14b}$, —$C_1$-$C_6$-alkyl-C(=S)N($R^{14a}$)$R^{14b}$, —$C_1$-$C_6$-alkyl-C(=$NR^{14}$)N($R^{14a}$)$R^{14b}$, —Si($R^{12}$)$_3$, —$S(O)_n R^{15}$, —$S(O)_n N(R^{14a})R^{14b}$, —$N(R^{10a})R^{10b}$, —N=$C(R^{13})_2$, —C(=O)$R^{13}$, —C(=O)N($R^{14a}$)$R^{14b}$, —C(=S)N($R^{14a}$)$R^{14b}$, —C(=O)$OR^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$; and $R^9$ in the groups —$S(O)_n R^9$ and —$OSO_2 R^9$ is additionally selected from the group consisting of $C_1$-$C_6$-alkoxy and $C_1$-$C_6$-haloalkoxy;

$R^{10a}$, $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$; —$C_1$-$C_6$-alkyl-C(=O)$OR^{15}$, —$C_1$-$C_6$-alkyl-C(=O)N($R^{14a}$) $R^{14b}$, —$C_1$-$C_6$-alkyl-C(=S)N($R^{14a}$)$R^{14b}$, —$C_1$-$C_6$-alkyl-C(=$NR^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio, —$S(O)_n R^{15}$, —$S(O)_n N(R^{14a})R^{14b}$, —C(=O)$R^{13}$, —C(=O)$OR^{15}$, —C(=O)N($R^{14a}$)$R^{14b}$, —C(=S)$R^{13}$, —C(=S)$SR^{15}$, —C(=S)N($R^{14a}$)$R^{14b}$, —C(=$NR^{14}$)$R^{13}$;

phenyl, optionally substituted with 1, 2, 3, 4 or 5 substituents $R^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more substituents $R^{16}$;

or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and $SO_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring optionally carries one or more substituents $R^{16}$;

or $R^{10a}$ and $R^{10b}$ together form a group =$C(R^{13})_2$, =$S(O)_m(R^{15})_2$, =$S(O)_m R^{15}N(R^{14a})R^{14b}$, =$NR^{14}$ or =$NOR^{15}$;

$R^{11}$ is independently selected from the group consisting of halogen, cyano, azido, nitro, —SCN, —$SF_5$, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more radicals $R^8$, —$OR^9$, —$NR^{10a}R^{10b}$, —$S(O)_n R^9$, —Si($R^{12}$)$_3$;

phenyl, optionally substituted with 1, 2, 3, 4, or 5 substituents selected independently from $R^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and $SO_2$, as ring members, where the heterocyclic ring is optionally substituted with one or more substituents selected independently from $R^{16}$;

or two $R^{11}$ present on the same ring carbon atom of an unsaturated or partially unsaturated heterocyclic ring may together form a group =O, =$C(R^{13})_2$; =S; =$S(O)_m(R^{15})_2$; =$S(O)_m R^{15}N(R^{14a})R^{14b}$, =$NR^{14}$, =$NOR^{15}$, or =$NN(R^{14a})R^{14b}$;

or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from C=O, C=S and C=$NR^{14}$ as ring members, and wherein the ring may be substituted by one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5 substituents $R^{16}$;

each $R^{13}$ is independently selected from the group consisting of cyano, nitro, —OH, —SH, —SCN, —SF$_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, —C(=O)N($R^{14a}$)$R^{14b}$, $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted or carry 1, 2, 3, 4 or 5 substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by 1, 2 or 3 substituents $R^{16}$;

or two $R^{13}$ present on the same carbon atom of an alkyl, alkenyl, alkynyl or cycloalkyl group may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

and $R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo;

and $R^{13}$ in the groups =C($R^{13}$)$_2$, —N=C($R^{13}$)$_2$, —C(=O)$R^{13}$, —C(=S)$R^{13}$ and —C(=N$R^{14}$)$R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_6$-cycloalkyl which may be substituted by 1 or 2 substituents selected from halogen and cyano; and oxo; $C_3$-$C_8$-cycloalkyl which may be unsubstituted, partially or fully halogenated and/or may carry 1 or 2 radicals selected from cyano, $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano; and oxo;

phenyl, benzyl, pyridyl, phenoxy, wherein the cyclic moieties in the four last-mentioned radicals may be unsubstituted and/or carry 1, 2, 3 or 4 substituents selected from halogen, cyano, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, and ($C_1$-$C_6$-alkoxy)carbonyl; and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$;

$R^{14a}$ and $R^{14b}$, independently of each other, have one of the meanings given for $R^{14}$;

or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

or $R^{14a}$ and $R^{14}$ or $R^{14b}$ and $R^{14}$, together with the nitrogen atoms to which they are bound in the group —C(=N$R^{14}$)N($R^{14a}$)$R^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$- alkylsulfinyl, $C_1$-$C_4$-alkylsulfonyl and oxo; $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, aminocarbonyl, $C_1$-$C_4$-alkylaminocarbonyl, di-($C_1$-$C_4$-alkyl)-aminocarbonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from cyano, $C_3$-$C_4$-cycloalkyl, $C_1$-$C_4$-alkoxy, $C_1$-$C_4$-haloalkoxy and oxo;

$C_3$-$C_8$-cycloalkyl which may be unsubstituted, partially or fully halogenated and/or may carry 1 or 2 radicals selected from cyano, $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

each n is independently 0, 1 or 2; and
each m is independently 0 or 1;
and the N-oxides, stereoisomers and agriculturally or veterinarily acceptable salts thereof.

The present invention also provides an agricultural composition comprising at least one compound of the formula I as defined herein, a stereoisomer thereof and/or at least one agriculturally acceptable salt thereof and at least one inert liquid and/or solid agriculturally acceptable carrier.

The present invention also provides a veterinary composition comprising at least one compound of the formula I as defined herein, a stereoisomer thereof and/or at least one veterinarily acceptable salt thereof and at least one inert liquid and/or solid verterinarily acceptable carrier.

The present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula I, a stereoisomer thereof and/or a salt thereof as defined herein. In a specific embodiment the method does not comprise the treatment of the human or animal body.

Especially, the method serves for protecting plants from attack or infestation by invertebrate pests, and comprises treating the plants with a pesticidally effective amount of at least one compound of the formula I as defined herein, a stereoisomer thereof and/or at least one agriculturally acceptable salt thereof.

The method especially further serves for protecting plant propagation material and/or the plants which grow therefrom from attack or infestation by invertebrate pests, and comprises treating the plant propagation material with a pesticidally effective amount of at least one compound of the formula I as defined herein, a stereoisomer thereof and/or at least one agriculturally acceptable salt thereof.

The present invention also relates to plant propagation material, in particular seed, comprising at least one compound of formula I and/or an agriculturally acceptable salt thereof as defined herein.

The present invention further relates to a method for treating or protecting an animal from infestation or infection by parasites which comprises bringing the animal in contact with a parasiticidally effective amount of at least one compound of the formula I, a stereoisomer thereof and/or at least one veterinarily acceptable salt thereof as defined herein. Bringing the animal in contact with the compound I, its salt or the veterinary composition of the invention means applying or administering it to the animal.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the 5-membered cyclopent(adi)ene ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of any nitrogen-containing heterocyclic group present in any heteroaromatic ring containing $B^1$, $B^2$ and $B^3$ as ring members and in which one or two of $B^1$, $B^2$ and $B^3$ are N, in any heteroaromatic ring containing $G^1$, $G^2$, $G^3$ and $G^4$ as ring members and in which one or two of $G^1$, $G^2$, $G^3$ and $G^4$ are N, in substituents $R^2$, $R^4$, $R^6$, $R^8$, $R^9$, $R^{10a}$, $R^{10b}$, $R^{11}$, $R^{13}$, $R^{14}$, $R^{14a}$, $R^{14b}$, $R^{15}$, or $R^{16}$, or by oxidizing any amino group, e.g. a —N($R^5$)$R^6$ group, with a suitable oxidizing agent, such as peroxo carboxylic acids or other peroxides. The person skilled in the art knows if and in which positions compounds of the present invention may form N-oxides.

The compounds of the present invention may be amorphous or may exist in one ore more different crystalline states (polymorphs) which may have a different macroscopic properties such as stability or show different biological properties such as activities. The present invention includes both amorphous and crystalline compounds of the formula I, mixtures of different crystalline states of the respective compound I, as well as amorphous or crystalline salts thereof.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally acceptable salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethylammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

By the term "veterinarily acceptable salts" is meant salts of those cations or anions which are known and accepted in the art for the formation of salts for veterinary use. Suitable acid addition salts, e.g. formed by compounds of formula I containing a basic nitrogen atom, e.g. an amino group, include salts with inorganic acids, for example hydrochlorids, sulphates, phosphates, and nitrates and salts of organic acids for example acetic acid, maleic acid, dimaleic acid, fumaric acid, difumaric acid, methane sulfenic acid, methane sulfonic acid, and succinic acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "non-cultivated plants" and in particular "cultivated plants".

The term "non-cultivated plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/ agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxyl-phenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora infestans* derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl"), 2 to 6 ("$C_2$-$C_6$-alkenyl"), 2 to 8 ("$C_2$-$C_8$-alkenyl") or 2 to 10 ("$C_2$-$C_{10}$-alkenyl") carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "haloalkenyl" as used herein, which is also expressed as "alkenyl which is partially or fully halogenated", refers to unsaturated straight-chain or branched hydrocarbon radicals having 2 to 3 ("$C_2$-$C_3$-haloalkenyl"), 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl"), 2 to 6 ("$C_2$-$C_6$-alkynyl"), 2 to 8 ("$C_2$-$C_8$-alkynyl"), or 2 to 10 ("$C_2$-$C_{10}$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "haloalkynyl" as used herein, which is also expressed as "alkynyl which is partially or fully halogenated", refers to unsaturated straight-chain or branched hydrocarbon radicals having 2 to 3 ("$C_2$-$C_3$-haloalkynyl"), 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 2 to 8 ("$C_2$-$C_8$-haloalkynyl") or 2 to 10 ("$C_2$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "cycloalkyl" as used herein refers to mono- or bi- or polycyclic saturated hydrocarbon radicals having 3 to 8 ("$C_3$-$C_8$-cycloalkyl"), in particular 3 to 6 ("$C_3$-$C_6$-cycloalkyl") or 3 to 5 ("$C_3$-$C_8$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "halocycloalkyl" as used herein, which is also expressed as "cycloalkyl which is partially or fully halogenated", refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") or 3 to 5 ("$C_3$-$C_8$-halocycloalkyl") or 3 to 4 ("$C_3$-$C_4$-halocycloalkyl") carbon ring members (as mentioned above) in which some or all of the hydrogen atoms are replaced by halogen atoms as mentioned above, in particular fluorine, chlorine and bromine.

The term "cycloalkyl-$C_1$-$C_4$-alkyl" refers to a $C_3$-$C_8$-cycloalkyl group ("$C_3$-$C_8$-cycloalkyl-$C_1$-$C_4$-alkyl"), preferably a $C_3$-$C_6$-cycloalkyl group ("$C_3$-$C_6$-cycloalkyl-$C_1$-$C_4$-alkyl"), more preferably a $C_3$-$C_4$-cycloalkyl group ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl. Examples for $C_3$-$C_8$-cycloalkyl-$C_1$-$C_4$-alkyl, apart those mentioned for $C_3$-$C_6$-cycloalkyl-$C_1$-$C_4$-alkyl, are cycloheptylmethyl, cycloheptylethyl, cyclooctylmethyl and the like.

$C_3$-$C_6$-cycloalkylmethyl is for example cyclopropylmethyl, cyclobutylmethyl, cyclopentylmethyl and cyclohexylmethyl.

The term "$C_3$-$C_8$-halocycloalkyl-$C_1$-$C_4$-alkyl" refers to a $C_3$-$C_8$-halocycloalkyl group as defined above which is bound to the remainder of the molecule via a $C_1$-$C_4$-alkyl group, as defined above.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethylethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, OCH$_2$F, OCHF$_2$, OCF$_3$, OCH$_2$Cl, OCHCl$_2$, OCCl$_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or OC$_2$F$_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, OCH$_2$—C$_2$F$_5$, OCF$_2$—C$_2$F$_5$, 1-(CH$_2$F)-2-fluoroethoxy, 1-(CH$_2$Cl)-2-chloroethoxy or 1-(CH$_2$Br)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_3$-alkoxy-$C_1$-$C_3$-alkyl" as used herein, refers to a straight-chain or branched alkyl group having 1 to 3 carbon atoms, as defined above, where one hydrogen atom is replaced by a $C_1$-$C_3$-alkoxy group, as defined above. The term "$C_1$-$C_4$-alkoxy-$C_1$-$C_4$-alkyl" as used herein, refers to a straight-chain or branched alkyl group having 1 to 4 carbon atoms, as defined above, where one hydrogen atom is replaced by a $C_1$-$C_4$-alkoxy group, as defined above. The term "$C_1$-$C_6$-alkoxy-$C_1$-$C_6$-alkyl" as used herein, refers to a straight-chain or branched alkyl group having 1 to 6 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tert-butoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "$C_1$-$C_4$-alkoxy-methyl" as used herein, refers to methyl in which one hydrogen atom is replaced by a $C_1$-$C_4$-alkoxy group, as defined above. The term "$C_1$-$C_6$-alkoxy-methyl" as used herein, refers to methyl in which one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tert-butoxymethyl, pentyloxymethyl, hexyloxymethyl and the like.

$C_1$-$C_6$-Haloalkoxy-$C_1$-$C_6$-alkyl is a straight-chain or branched alkyl group having from 1 to 6, especially 1 to 4 carbon atoms (=$C_1$-$C_6$-haloalkoxy-$C_1$-$C_4$-alkyl), wherein one of the hydrogen atoms is replaced by a $C_1$-$C_6$-alkoxy group and wherein at least one, e.g. 1, 2, 3, 4 or all of the remaining hydrogen atoms (either in the alkoxy moiety or in the alkyl moiety or in both) are replaced by halogen atoms. $C_1$-$C_4$-Haloalkoxy-$C_1$-$C_4$-alkyl is a straight-chain or branched alkyl group having from 1 to 4 carbon atoms, wherein one of the hydrogen atoms is replaced by a $C_1$-$C_4$-alkoxy group and wherein at least one, e.g. 1, 2, 3, 4 or all of the remaining hydrogen atoms (either in the alkoxy moiety or in the alkyl moiety or in both) are replaced by halogen atoms. Examples are difluoromethoxymethyl ($CHF_2OCH_2$), trifluoromethoxymethyl, 1-difluoromethoxyethyl, 1-trifluoromethoxyethyl, 2-difluoromethoxyethyl, 2-trifluoromethoxyethyl, difluoro-methoxy-methyl ($CH_3OCF_2$), 1,1-difluoro-2-methoxyethyl, 2,2-difluoro-2-methoxyethyl and the like.

The term "$C_1$-$C_2$-alkylthio" is a $C_1$-$C_2$-alkyl group, as defined above, attached via a sulfur atom. The term "$C_1$-$C_3$-alkylthio" is a $C_1$-$C_3$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_3$-Alkylthio is additionally, for example, n-propylthio or 1-methylethylthio (isopropylthio). $C_1$-$C_4$-Alkylthio is additionally, for example, butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_3$-haloalkylthio" is a $C_1$-$C_3$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHCl_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_3$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio or 1-($CH_2Br$)-2-bromoethylthio. $C_1$-$C_4$-Haloalkylthio is additionally, for example, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [$S(O)_2$] group. The term "$C_1$-$C_3$-alkylsulfonyl" is a $C_1$-$C_3$-alkyl group, as defined above, attached via a sulfonyl [$S(O)_2$] group. The term "$C_1$-$C_4$-alkylsulfonyl" is a $C_1$-$C_4$-alkyl group, as defined above, attached via a sulfonyl [$S(O)_2$] group. The term "$C_1$-$C_6$-alkylsulfonyl" is a $C_1$-$C_6$-alkyl group, as defined above, attached via a sulfonyl [$S(O)_2$] group. The term "$C_1$-$C_{10}$-alkylsulfonyl" is a $C_1$-$C_{10}$-alkyl group, as defined above, attached via a sulfonyl [$S(O)_2$] group. $C_1$-$C_2$-Alkylsulfonyl is methylsulfonyl or ethylsulfonyl. $C_1$-$C_3$-Alkylsulfonyl is additionally, for example, n-propylsulfonyl or 1-methylethylsulfonyl (isopropylsulfonyl). $C_1$-$C_4$-Alkylsulfonyl is additionally, for example, butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$—C-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [$S(O)_2$] group. The term "$C_1$-$C_3$-haloalkylsulfonyl" is a $C_1$-$C_3$-haloalkyl group, as defined above, attached via a sulfonyl [$S(O)_2$] group. The term "$C_1$-$C_4$-haloalkylsulfonyl" is a $C_1$-$C_4$-haloalkyl group, as defined above, attached via a sulfonyl [$S(O)_2$] group. The term "$C_1$-$C_6$-haloalkylsulfonyl" is a $C_1$-$C_6$-haloalkyl group, as defined above, attached via a sulfonyl [$S(O)_2$] group. The term "$C_1$-$C_{10}$-haloalkylsulfonyl" is a $C_1$-$C_{10}$-haloalkyl group, as defined above, attached via a sulfonyl [$S(O)_2$] group. $C_1$-$C_2$-Haloalkylsulfonyl is, for example, $S(O)_2CH_2F$, $S(O)_2CHF_2$, $S(O)_2CF_3$, $S(O)_2CH_2Cl$, $S(O)_2CHCl_2$, $S(O)_2CCl_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or $S(O)_2C_2F_5$. $C_1$-$C_3$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, $S(O)_2CH_2$—$C_2F_5$, $S(O)_2CF_2$—$C_2F_5$, 1-($CH_2F$)-2-fluoroethylsulfonyl, 1-($CH_2Cl$)-2-chloroethylsulfonyl or 1-($CH_2Br$)-2-bromoethylsulfonyl. $C_1$-$C_4$-Haloalkylsulfonyl is additionally, for example, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The substituent "oxo" replaces a $CH_2$ group by a $C(=O)$ group.

The term "alkylcarbonyl" is a $C_1$-$C_6$-alkyl ("$C_1$-$C_6$-alkylcarbonyl"), preferably a $C_1$-$C_4$-alkyl ("$C_1$-$C_4$-alkylcarbonyl") group, as defined above, attached via a carbonyl [$C(=O)$] group. Examples are acetyl (methylcarbonyl), propionyl (ethylcarbonyl), propylcarbonyl, isopropylcarbonyl, n-butylcarbonyl and the like.

The term "haloalkylcarbonyl" is a $C_1$-$C_6$-haloalkyl ("$C_1$-$C_6$-haloalkylcarbonyl"), preferably a $C_1$-$C_4$-haloalkyl ("$C_1$-$C_4$-haloalkylcarbonyl") group, as defined above, attached via a carbonyl [$C(=O)$] group. Examples are trifluoromethylcarbonyl, 2,2,2-trifluoroethylcarbonyl and the like.

The term "alkoxycarbonyl" is a $C_1$-$C_6$-alkoxy ("$C_1$-$C_6$-alkoxycarbonyl"), preferably a $C_1$-$C_4$-alkoxy ("$C_1$-$C_4$-alkoxycarbonyl") group, as defined above, attached via a carbonyl [$C(=O)$] group. Examples are methoxycarbonyl), ethoxycarbonyl, propoxycarbonyl, isopropoxycarbonyl, n-butoxycarbonyl and the like.

The term "haloalkoxycarbonyl" is a $C_1$-$C_6$-haloalkoxy ("$C_1$-$C_6$-haloalkoxycarbonyl"), preferably a $C_1$-$C_4$-haloalkoxy ("$C_1$-$C_4$-haloalkoxycarbonyl") group, as defined above, attached via a carbonyl [$C(=O)$] group. Examples are trifluoromethoxycarbonyl, 2,2,2-trifluoroethoxycarbonyl and the like.

The term "$C_1$-$C_4$-alkylamino" is a group —$N(H)C_1$-$C_4$-alkyl. Examples are methylamino, ethylamino, propylamino, isopropylamino, butylamino and the like.

The term "di-($C_1$-$C_4$-alkyl)amino" is a group —$N(C_1$-$C_4$-alkyl)$_2$. Examples are dimethylamino, diethylamino, ethylmethylamino, dipropylamino, diisopropylamino, methylpropylamino, methylisopropylamino, ethylpropylamino, ethylisopropylamino, dibutylamino and the like.

The term "$C_1$-$C_4$-alkylaminocarbonyl" is a group —$C(O)N(H)C_1$-$C_4$-alkyl. Examples are methylaminocarbonyl, ethylaminocarbonyl, propylaminocarbonyl, isopropylaminocarbonyl, butylaminocarbonyl and the like.

The term "di-($C_1$-$C_4$-alkyl)amino" is a group —$C(O)N(C_1$-$C_4$-alkyl)$_2$. Examples are dimethylaminocarbonyl, diethylaminocarbonyl, ethylmethylaminocarbonyl, dipropylaminocarbonyl, diisopropylaminocarbonyl, methylpropylaminocarbonyl, methylisopropylaminocarbonyl, ethylpropylaminocarbonyl, ethylisopropylaminocarbonyl, dibutylaminocarbonyl and the like.

The term "3-, 4-, 5-, 6-, 7-, 8-, 9- or 10-membered saturated, partially unsaturated or maximally unsaturated heterocyclic ring containing 1, 2 or 3 (or 4) heteroatoms or heteroatom groups selected from N, O, S, NO, SO and $SO_2$, as ring members" denotes a 3-, 4-, 5-, 6-, 7- or 8-membered saturated, partially unsaturated or maximum unsaturated heteromonocyclic ring or a 8-, 9- or 10-membered saturated, partially unsaturated or maximally unsaturated heterobicyclic ring containing 1, 2 or 3 (or 4) heteroatoms or heteroatom groups selected from N, O, S, NO, SO and $SO_2$, as ring members.

Unsaturated rings contain at least one C—C and/or C—N and/or N—N double bond(s). Maximally unsaturated rings contain as many conjugated C—C and/or C—N and/or N—N double bonds as allowed by the ring size. Maximally unsaturated 5- or 6-membered heterocyclic rings are aromatic. The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

The term "3-, 4-, 5- or 6-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic"] as used herein denotes monocyclic radicals, the monocyclic radicals being saturated, partially unsaturated or maximum unsaturated (including aromatic). The term "3-, 4-, 5-, 6- or 7-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic"] as used herein denotes monocyclic radicals, the monocyclic radicals being saturated, partially unsaturated or maximum unsaturated (including aromatic). The term "3-, 4-, 5-, 6-, 7- or 8-membered saturated, partially unsaturated or maximum unsaturated heterocyclic ring containing 1, 2 or 3 (or 4) heteroatoms or heteroatom groups selected from N, O, S, NO, SO and $SO_2$, as ring members" [wherein "maximum unsaturated" includes also "aromatic"] as used herein further also encompasses 8-membered heteromonocyclic radicals containing 1, 2 or 3 (or 4) heteroatoms or heteroatom groups selected from N, O, S, NO, SO and $SO_2$, as ring members, the monocyclic radicals being saturated, partially unsaturated or maximum unsaturated (including aromatic). Unsaturated rings contain at least one C—C and/or C—N and/or N—N double bond(s). Maximum unsaturated rings contain as many conjugated C—C and/or C—N and/or N—N double bonds as allowed by the ring size. Maximum unsaturated 5- or 6-membered heterocyclic rings are aromatic. 7- and 8-membered rings cannot be aromatic. They are homoaromatic (7-membered ring, 3 double bonds) or have 4 double bonds (8-membered ring). The heterocyclic ring may be attached to the remainder of the molecule via a carbon ring member or via a nitrogen ring member. As a matter of course, the heterocyclic ring contains at least one carbon ring atom. If the ring contains more than one O ring atom, these are not adjacent.

Examples of a 3-, 4-, 5-, 6- or 7-membered saturated heterocyclic ring include: Oxiranyl, thiiranyl, aziridinyl, oxetanyl, thietanyl, azetidinyl, tetrahydrofuran-2-yl, tetrahydrofuran-3-yl, tetrahydrothien-2-yl, tetrahydrothien-3-yl, pyrrolidin-1-yl, pyrrolidin-2-yl, pyrrolidin-3-yl, pyrazolidin-1-yl, pyrazolidin-3-yl, pyrazolidin-4-yl, pyrazolidin-5-yl, imidazolidin-1-yl, imidazolidin-2-yl, imidazolidin-4-yl, oxazolidin-2-yl, oxazolidin-3-yl, oxazolidin-4-yl, oxazolidin-5-yl, isoxazolidin-2-yl, isoxazolidin-3-yl, isoxazolidin-4-yl, isoxazolidin-5-yl, thiazolidin-2-yl, thiazolidin-3-yl, thiazolidin-4-yl, thiazolidin-5-yl, isothiazolidin-2-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-1-yl, 1,3,4-triazolidin-2-yl, 2-tetrahydropyranyl, 4-tetrahydropyranyl, 1,3-dioxan-5-yl, 1,4-dioxan-2-yl, piperidin-1-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-1-yl, piperazin-2-yl, 1,3,5-hexahydrotriazin-1-yl, 1,3,5-hexahydrotriazin-2-yl and 1,2,4-hexahydrotriazin-3-yl, morpholin-2-yl, morpholin-3-yl, morpholin-4-yl, thiomorpholin-2-yl, thiomorpholin-3-yl, thiomorpholin-4-yl, 1-oxothiomorpholin-2-yl, 1-oxothiomorpholin-3-yl, 1-oxothiomorpholin-4-yl, 1,1-dioxothiomorpholin-2-yl, 1,1-dioxothiomorpholin-3-yl, 1,1-dioxothiomorpholin-4-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of an 8-membered saturated heterocyclic ring include: oxocanyl, azocanyl, 1,2-, 1,3-, 1,4- and 1,5-diazocanyl and the like.

Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl. Examples of an 8-membered partially unsaturated heterocyclic ring include: dihydroazocinyl, tetrahydrazocinyl, hexahydroazocinyl and the like.

Examples for a 3-, 4-, 5-, 6- or 7-membered maximally unsaturated (including aromatic) heterocyclic ring are 5- or 6-membered heteroaromatic rings, such as 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 2-pyridinyl, 3-pyridinyl, 4-pyridinyl, 1-oxopyridin-2-yl, 1-oxopyridin-3-yl, 1-oxopyridin-4-yl, 3-pyridazinyl, 4-pyridazinyl, 2-pyrimidinyl, 4-pyrimidinyl, 5-pyrimidinyl and 2-pyrazinyl, and also homoaromatic radicals, such as 1H-azepine, 1H-[1,3]-diazepine and 1H-[1,4]-diazepine. Examples of an 8-membered maximally unsaturated saturated heterocyclic ring include: azocinyl, 1,2-, 1,3-, 1,4- and 1,5-diazocinyl and the like.

Examples for a 8-, 9- or 10-membered saturated heterobicyclic ring containing 1, 2 or 3 (or 4) heteroatoms or heteroatom groups selected from N, O, S, NO, SO and SO$_2$, as ring members are:
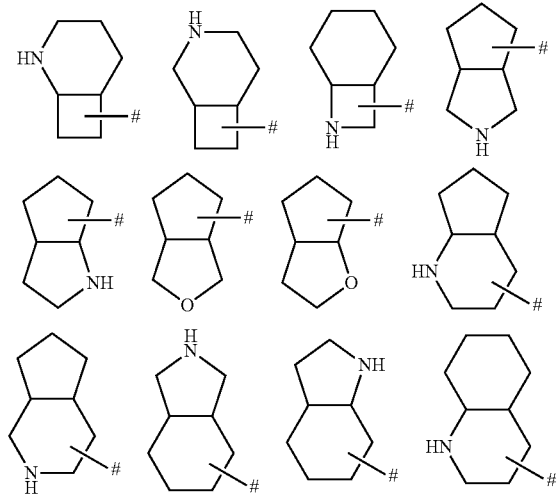
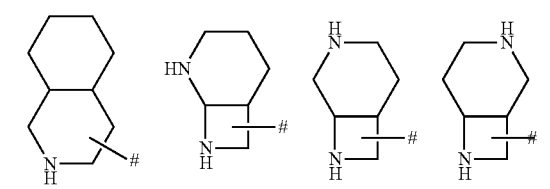
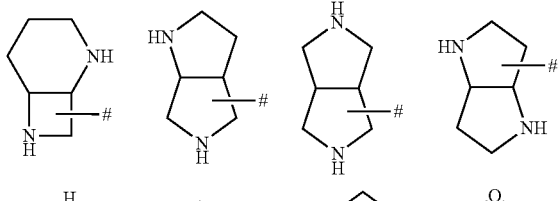
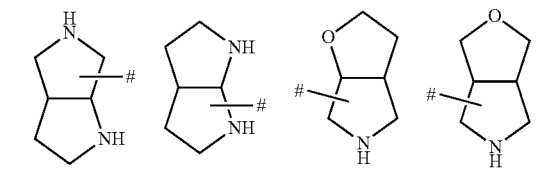
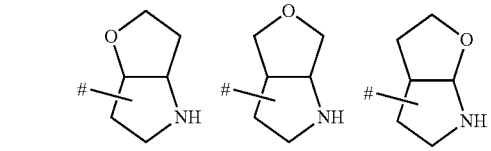
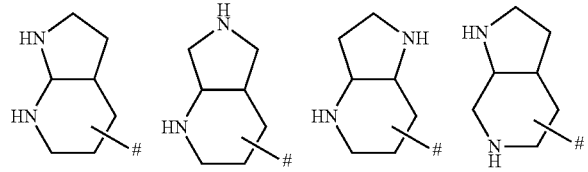
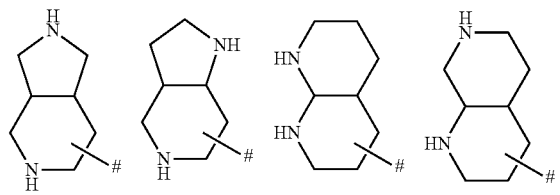
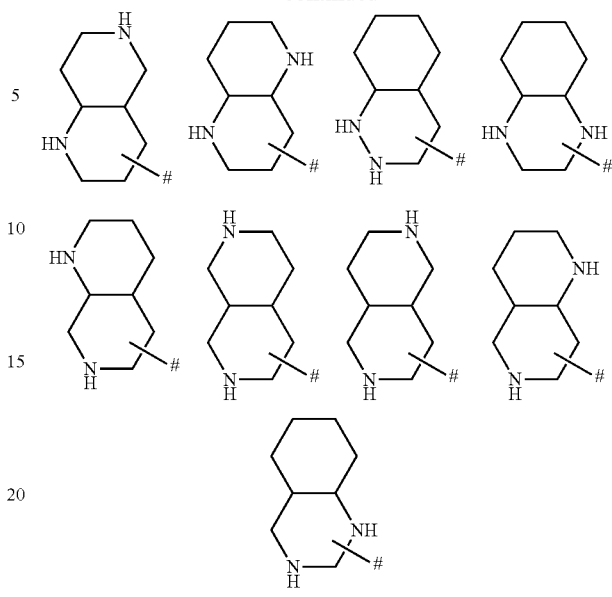
Examples for a 8-, 9- or 10-membered partially unsaturated heterobicyclic ring containing 1, 2 or 3 (or 4) heteroatoms or heteroatom groups selected from N, O, S, NO, SO and SO$_2$, as ring members are:
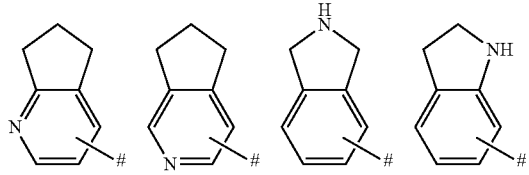
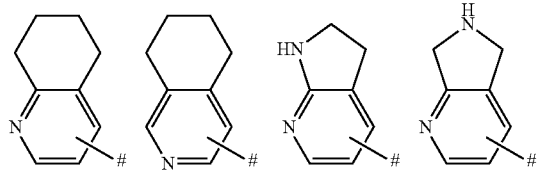
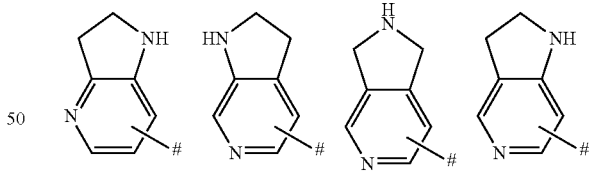
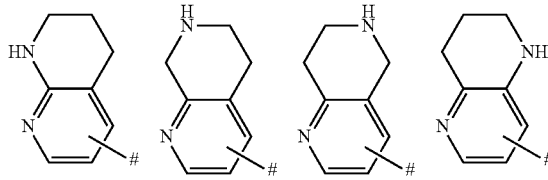
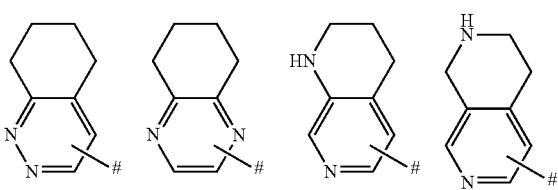

-continued

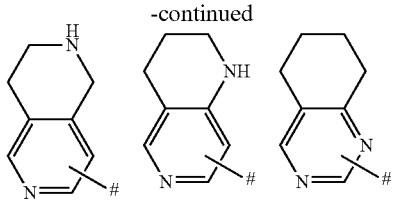

Examples for a 8-, 9- or 10-membered maximally unsaturated heterobicyclic ring containing 1, 2 or 3 (or 4) heteroatoms or heteroatom groups selected from N, O, S, NO, SO and SO$_2$, as ring members are:

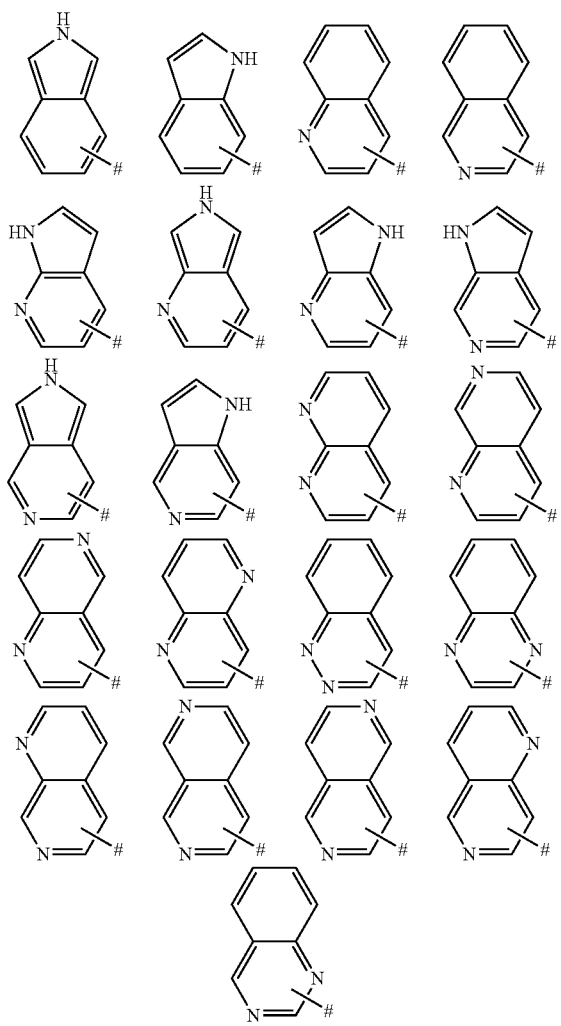

In the above structures # denotes the attachment point to the remainder of the molecule. The attachment point is not restricted to the ring on which is shown, but can be on either of the fused rings, and may be on a carbon or on a nitrogen ring atom. If the rings carry one or more substituents, these may be bound to carbon and/or to nitrogen ring atoms (if the latter are not part of a double bond).

The remarks made below concerning preferred embodiments of the variables of the compounds of formula I, especially with respect to their substituents A, A$^1$, A$^2$, A$^3$, B$^1$, B$^2$, B$^3$, G$^1$, G$^2$, G$^3$, G$^4$, R$^1$, R$^2$, R$^{3a}$, R$^{3b}$, R$^{3c}$, R$^{3d}$, R$^{3e}$, R$^4$, R$^5$, R$^6$, R$^{7a}$, R$^{7b}$, R$^8$, R$^9$, R$^{10a}$, R$^{10b}$, R$^{11}$, R$^{12}$, R$^{13}$, R$^{14}$, R$^{14a}$, R$^{14b}$, R$^{15}$, R$^{16}$, m and n, the features of the use and method according to the invention and of the composition of the invention are valid both on their own and, in particular, in every possible combination with each other.

In one embodiment of the invention, the compound of formula I is a compound of formula I.1

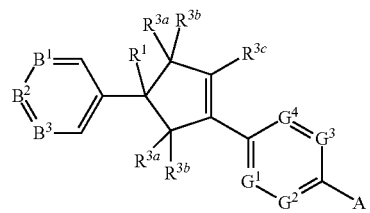

(I.1)

i.e. the ring

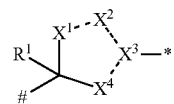

is a ring II-1.

B$^1$, B$^2$, B$^3$, G$^1$, G$^2$, G$^3$, G$^4$, A, R$^1$, R$^{3a}$, R$^{3b}$ and R$^{3c}$ have one of the above general or, in particular, one of the below preferred meanings.

In another embodiment of the invention, the compound of formula I is a compound of formula I.2

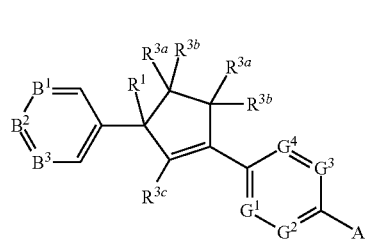

(I.2)

i.e. the ring

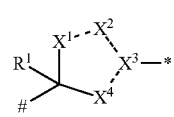

is a ring II-2.

B$^1$, B$^2$, B$^3$, G$^1$, G$^2$, G$^3$, G$^4$, A, R$^1$, R$^{3a}$, R$^{3b}$ and R$^{3c}$ have one of the above general or, in particular, one of the below preferred meanings.

In another embodiment of the invention, the compound of formula I is a compound of formula I.3

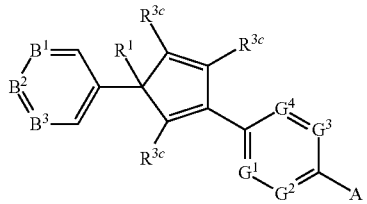
(I.3)

i.e. the ring

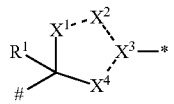

is a ring II-3.
$B^1$, $B^2$, $B^3$, $G^1$, $G^2$, $G^3$, $G^4$, A, $R^1$, $R^{3a}$, $R^{3b}$ and $R^{3c}$ have one of the above general or, in particular, one of the below preferred meanings.

In a preferred embodiment of the invention, A is $A^1$.

In $A^1$, W is preferably O.

In $A^1$, Y is preferably $N(R^5)R^6$; wherein $R^5$ and $R^6$ have one of the above general meanings, or, in particular, one of the below preferred meanings.

In an alternatively preferred embodiment, in $A^1$ Y is hydrogen.

In an alternatively preferred embodiment, in $A^1$ Y is $-OR^9$. $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, one of the following preferred meanings: CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-54

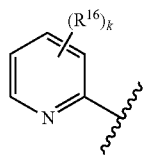
E-1

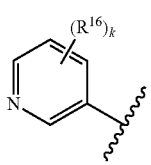
E-2

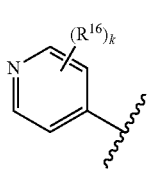
E-3

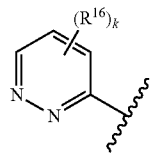
E-4

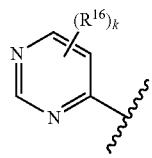
E-5

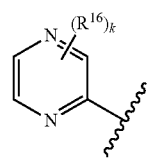
E-6

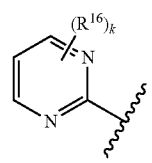
E-7

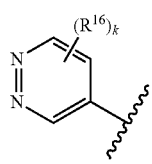
E-8

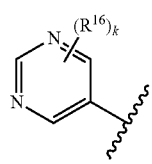
E-9

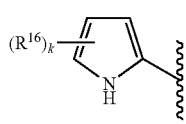
E-10

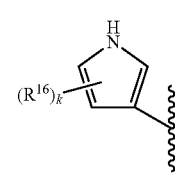
E-11

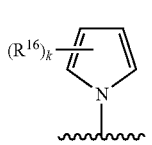
E-12

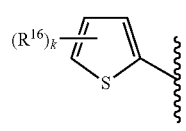
E-13

-continued

| | |
|---|---|
| E-14 | (thiophene with $(R^{16})_k$) |
| E-15 | (furan with $(R^{16})_k$) |
| E-16 | (isoxazole-type with $(R^{16})_k$) |
| E-17 | (isoxazole with $(R^{16})_k$) |
| E-18 | (isoxazole with $(R^{16})_k$) |
| E-19 | (isoxazole with $(R^{16})_k$) |
| E-20 | (isothiazole with $(R^{16})_k$) |
| E-21 | (isothiazole with $(R^{16})_k$) |
| E-22 | (isothiazole with $(R^{16})_k$) |
| E-23 | (pyrazole with $(R^{16})_k$) |
| E-24 | (pyrazole with $(R^{16})_k$) |

-continued

| | |
|---|---|
| E-25 | (pyrazole with $(R^{16})_k$) |
| E-26 | (oxazole with $(R^{16})_k$) |
| E-27 | (oxazole with $(R^{16})_k$) |
| E-28 | (oxazole with $(R^{16})_k$) |
| E-29 | (thiazole with $(R^{16})_k$) |
| E-30 | (thiazole with $(R^{16})_k$) |
| E-31 | (thiazole with $(R^{16})_k$) |
| E-32 | (imidazole with $(R^{16})_k$) |
| E-33 | (imidazole with $(R^{16})_k$) |
| E-34 | (imidazole with $(R^{16})_k$) |
| E-35 | (thiadiazole with $R^{16}$) |

-continued
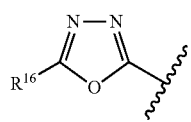 E-36
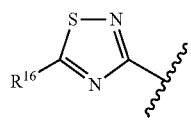 E-37
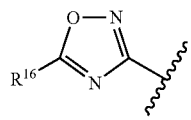 E-38
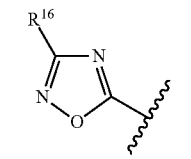 E-39
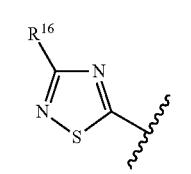 E-40
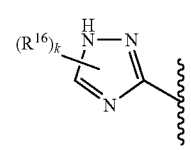 E-41
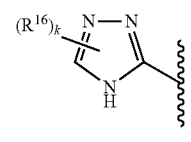 E-42
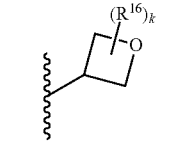 E-43
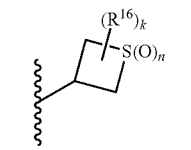 E-44
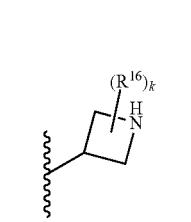 E-45
-continued
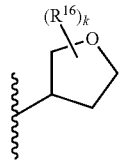 E-46
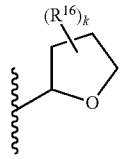 E-47
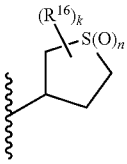 E-48
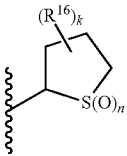 E-49
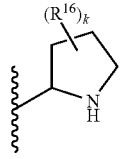 E-50
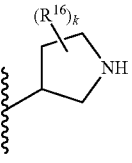 E-51
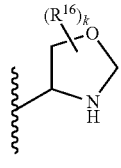 E-52
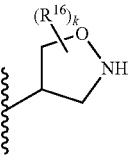 E-53
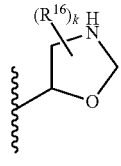 E-54
wherein
⌇ denotes the bonding point to the remainder of the molecule;

k is 0, 1, 2 or 3,
n is 0, 1 or 2; and
each $R^{16}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)aminocarbonyl;
or
two $R^{16}$ present on the same carbon atom of a saturated ring may form together =O or =S.

In particular $R^9$ is selected from hydrogen, $C_1$-$C_6$-alkyl and $C_1$-$C_6$-haloalkyl, and specifically from hydrogen and $C_1$-$C_6$-alkyl.

More preferably, in $A^1$, W is O and Y is —N($R^5$)$R^6$; wherein $R^5$ and $R^6$ have one of the above general meanings, or, in particular, one of the below preferred meanings.

In alternatively more preferred embodiment, in $A^1$, W is O and Y is H.

In alternatively more preferred embodiment, in $A^1$, W is O and Y is —O$R^9$, where $R^9$ has one of the above general meanings, or, in particular, is selected from hydrogen, $C_1$-$C_6$-alkyl, $C_1$-$C_6$-haloalkyl and $C_1$-$C_6$-alkyl substituted by one radical $R^{13}$, where $R^{13}$ has one of the above general meanings, or, in particular, is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl and a heterocyclic ring selected from rings of formulae E-1 to E-54 as defined above. In particular, W is O and $R^9$ is selected from hydrogen, $C_1$-$C_6$-alkyl and $C_1$-$C_6$-haloalkyl and specifically from hydrogen and $C_1$-$C_6$-alkyl.

Compounds I wherein Y is —O$R^9$ have biological activity, but are also useful as intermediate compounds in the preparation of compounds I wherein Y is —N($R^5$)$R^6$. Thus, the invention also relates to intermediate compounds I wherein A is $A^1$ wherein Y is —O$R^9$, wherein $R^9$ has one of the above-defined general meanings or, preferably, one of the above-defined preferred meanings; and to the use of such compounds in the preparation of compounds I wherein Y is —N($R^5$)$R^6$.

Compounds I wherein Y is H have biological activity, too, but are especially useful as intermediate compounds in the preparation of compounds I wherein Y is —N($R^5$)$R^6$. Thus, the invention also relates to intermediate compounds I wherein A is $A^1$ wherein Y is hydrogen; and to the use of such compounds in the preparation of compounds I wherein Y is —N($R^5$)$R^6$.

In —N($R^5$)$R^6$ as a radical Y,
$R^5$ is preferably selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl and $C_3$-$C_8$-halocycloalkyl, where the aforementioned aliphatic and cycloaliphatic radicals may be substituted by 1, 2 or 3, preferably 1, radicals $R^8$; and
$R^6$ is preferably selected from hydrogen, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more, preferably 1, 2 or 3, in particular 1, substituents $R^8$, —O$R^9$, —N$R^{10a}R^{10b}$, —S(O)$_n$$R^9$, —C(=O)N$R^{10a}$N($R^{10a}$)$R^{10b}$, —C(=O)$R^8$, —CH=NO$R^9$, phenyl which may be substituted with 1, 2, 3, 4, or 5, preferably 1, 2 or 3, in particular 1, substituents $R^{11}$, and
a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;
or
$R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, SO, $SO_2$, N, NH, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;
or
$R^5$ and $R^6$ together form a group =C($R^8$)$_2$, =S(O)$_m$($R^9$)$_2$, =N$R^{10a}$ or =NO$R^9$;
wherein $R^8$, $R^9$, $R^{10a}$, $R^{10b}$ and $R^{11}$ have one of the above general meanings, or, in particular, one of the below preferred meanings.

More preferably, in —N($R^5$)$R^6$ as a radical Y,
$R^5$ is selected from hydrogen, $C_1$-$C_6$-alkyl, $C_2$-$C_3$-alkynyl and —$CH_2$—CN; and
$R^6$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, where the eight last-mentioned aliphatic and cycloaliphatic radicals may carry 1, 2 or 3 radicals $R^8$; $C_1$-$C_6$-alkoxy, $C_1$-$C_6$-haloalkoxy, —N($R^{10a}$)$R^{10b}$, —CH=NO$R^9$, phenyl which may be substituted with 1, 2, 3, 4, or 5 substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more substituents $R^{11}$;
wherein $R^8$, $R^9$, $R^{10a}$, $R^{10b}$ and $R^{11}$ have one of the above general meanings, or, in particular, one of the below preferred meanings;
or
$R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or $R^5$ and $R^6$, together with the nitrogen atom to which they are bound, form a group $=S(R^9)_2$, where $R^9$ is selected from $C_1$-$C_6$-alkyl and $C_1$-$C_6$-haloalkyl.

Even more preferably, in $-N(R^5)R^6$ as a radical Y, $R^5$ is selected from hydrogen, $C_1$-$C_6$-alkyl, $C_2$-$C_3$-alkynyl and $CH_2$—CN; and $R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_{10}$-haloalkenyl, $C_2$-$C_6$-alkynyl, $C_3$-$C_6$-cycloalkyl which may be substituted by 1 or 2 substituents selected from F, CN and pyridyl; $-N(R^{10a})R^{10b}$, $-CH=NOR^9$, phenyl which may be substituted with 1, 2, 3, 4, or 5, preferably 1, 2 or 3, in particular 1, substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;

wherein $R^8$, $R^9$, $R^{10a}$, $R^{10b}$ and $R^{11}$ have one of the above general meanings, or, in particular, one of the below preferred meanings;
or $R^5$ and $R^6$, together with the nitrogen atom to which they are bound, form a 3-, 4-, 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;
or $R^5$ and $R^6$, together with the nitrogen atom to which they are bound, form a group $=S(R^9)_2$, where $R^9$ is selected from $C_1$-$C_6$-alkyl and $C_1$-$C_6$-haloalkyl.

Particularly preferably, in $-N(R^5)R^6$ as a radical Y, $R^5$ selected from hydrogen, $C_1$-$C_6$-alkyl, $C_2$-$C_3$-alkynyl and $CH_2$—CN; and $R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl; $-N(R^{10a})R^{10b}$; $-CH=NOR^9$; phenyl which may be substituted with 1, 2, 3, 4, or 5, preferably 1, 2 or 3, in particular 1, substituents $R^{11}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{11}$;

wherein $R^8$ is independently selected from OH, CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl, $C_1$-$C_6$-haloalkylsulfonyl, $-C(=O)N(R^{10a})R^{10b}$, phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heteromonocyclic ring containing 1, 2 or 3 heteroatoms or heteroatom groups independently selected from N, O, S, NO, SO and $SO_2$, as ring members, where the heteromonocyclic ring may be substituted with one or more, preferably 1, 2 or 3, in particular 1, substituents $R^{16}$;

wherein $R^{10a}$ in $-C(=O)N(R^{10a})R^{10b}$ as a meaning for $R^8$ is selected from the group consisting of hydrogen, $C_1$-$C_6$-alkyl, $C_2$-$C_3$-alkynyl and $CH_2$—CN;

$R^{10b}$ in $-C(=O)N(R^{10a})R^{10b}$ as a meaning for $R^8$ is selected from the group consisting of hydrogen, $C_1$-$C_6$-alkyl, $C_2$-$C_4$-alkenyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_3$-$C_6$-cycloalkylmethyl, $C_1$-$C_6$-alkoxy, $C_1$-$C_6$-haloalkoxy, phenyl which is optionally substituted with 1, 2, 3, 4 or 5, preferably 1, 2 or 3, in particular 1, substituents selected from the group consisting of halogen, cyano, nitro, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio; and a heterocyclic ring selected from rings of formulae E-1 to E-54 as defined above; and each $R^{16}$ as a substituent on phenyl or the heterocyclic rings is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{16}$ present on the same carbon atom of a saturated heterocyclic ring may form together =O or =S;

$R^9$ is selected from hydrogen, $C_1$-$C_6$-alkyl and $C_1$-$C_6$-haloalkyl;

$R^{10a}$ in $-N(R^{10a})R^{10b}$ as a meaning for $R^6$ is selected from hydrogen and $C_1$-$C_6$-alkyl;

$R^{10b}$ in $-N(R^{10a})R^{10b}$ as a meaning for $R^6$ is selected from hydrogen, $-C(=O)N(R^{14a})R^{14b}$, phenyl, optionally substituted with 1, 2, 3, 4 or 5 substituents $R^{16}$, and a heterocyclic ring selected from rings of formulae E-1 to E-54 as defined above; and each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; or two $R^{11}$ present on the same carbon atom of a saturated heterocyclic ring may form together =O or =S;
or $R^5$ and $R^6$, together with the nitrogen atom to which they are bound, form a 5- or 6-membered saturated heterocyclic ring, where the ring may further contain 1 or 2 heteroatoms or heteroatom-containing groups selected from O, S, SO, $SO_2$, NH and C=O as ring members, wherein the heterocyclic ring may be substituted with 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy and $C_1$-$C_6$-haloalkoxy;

or

R⁵ and R⁶ together form a group =S(R⁹)₂, where R⁹ is selected from $C_1$-$C_6$-alkyl and $C_1$-$C_6$-haloalkyl.

In particular, in N(R⁵)R⁶ as a radical Y,

R⁵ is hydrogen or $C_1$-$C_3$-alkyl;

R⁶ is selected from hydrogen, $C_1$-$C_6$-alkyl, $C_1$-$C_6$-haloalkyl, $C_1$-$C_4$-alkyl which carries one radical R⁸, wherein R⁸ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F, CN and pyridyl;
—N(R¹⁰ᵃ)R¹⁰ᵇ, wherein R¹⁰ᵃ is selected from hydrogen and $C_1$-$C_6$-alkyl and R¹⁰ᵇ is selected from hydrogen, —C(=O)N(R¹⁴ᵃ)R¹⁴ᵇ, wherein R¹⁴ᵃ is selected from the group consisting of hydrogen and $C_1$-$C_6$-alkyl and R¹⁴ᵇ is selected from the group consisting of hydrogen, $C_1$-$C_6$-alkyl, $C_2$-$C_4$-alkynyl, CH₂—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy; phenyl, optionally substituted with 1, 2, 3, 4 or 5, preferably 1, 2 or 3, in particular 1, substituents R¹⁶, wherein each R¹⁶ independently has one of the meanings given below for R¹¹; and a heteroaromatic ring selected from rings of formulae E-1 to E-42 as defined above, where however each R¹⁶ has independently one of the meanings given below for R¹¹;
—CH=NOR⁹, wherein R⁹ is selected from hydrogen, $C_1$-$C_6$-alkyl and $C_1$-$C_6$-haloalkyl;
phenyl which may be substituted with 1, 2, 3, 4, or 5, preferably 1, 2 or 3, in particular 1, substituents R¹¹, wherein R¹¹ is as defined below; and a heteromonocyclic ring selected from rings of formulae F-1 to F-54

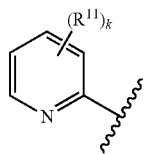
F-1

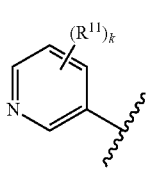
F-2

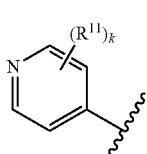
F-3

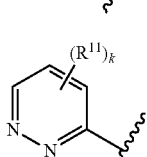
F-4

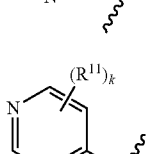
F-5

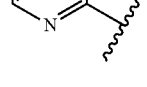

-continued

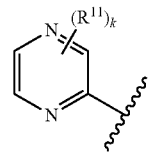
F-6

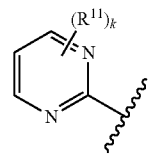
F-7

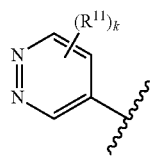
F-8

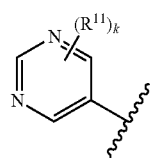
F-9

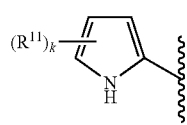
F-10

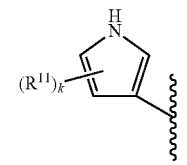
F-11

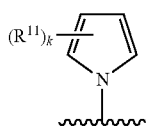
F-12

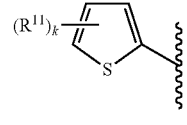
F-13

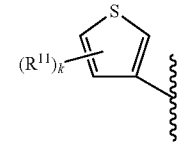
F-14

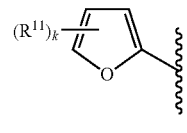
F-15

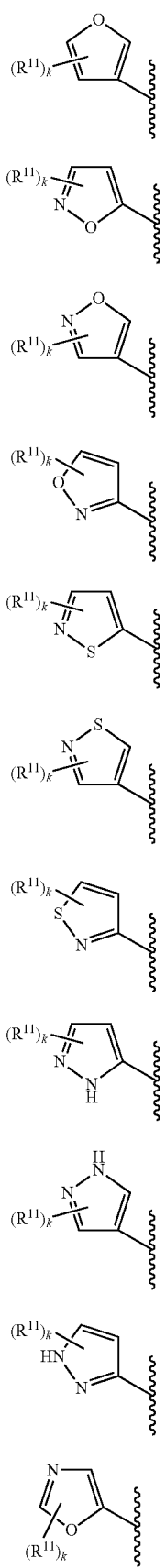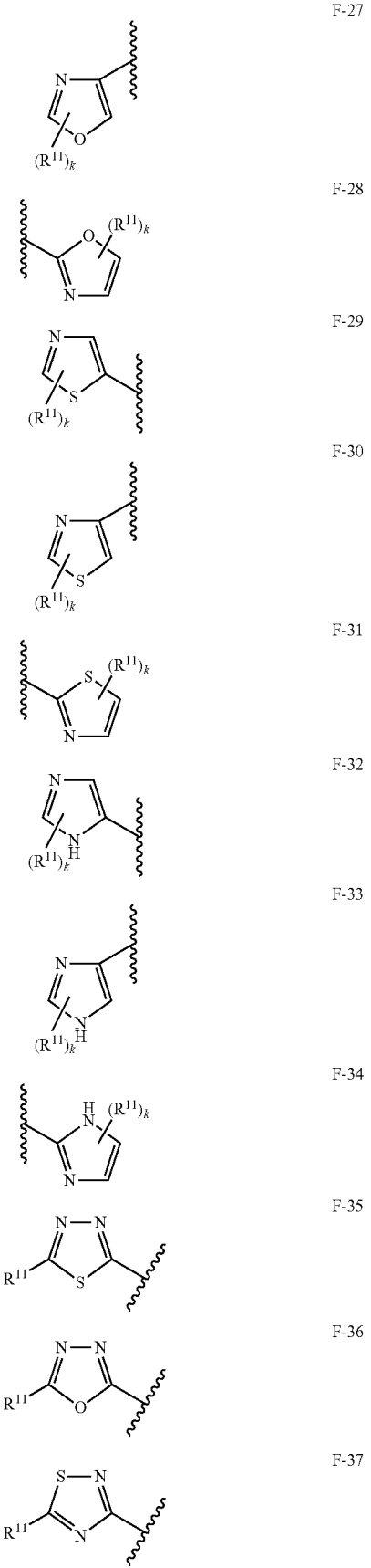

-continued

F-38 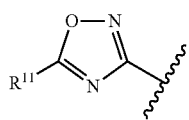

F-39 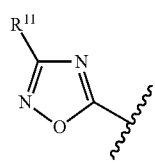

F-40 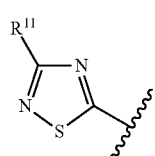

F-41 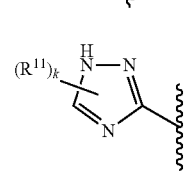

F-42 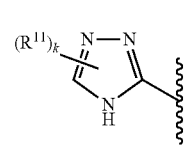

F-43 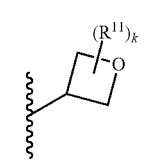

F-44 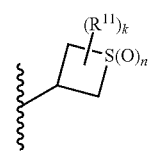

F-45 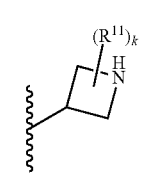

F-46 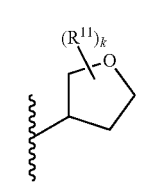

F-47 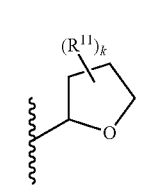

-continued

F-48 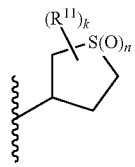

F-49 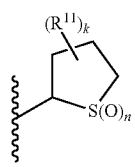

F-50 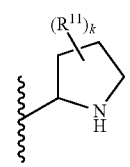

F-51 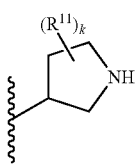

F-52 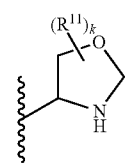

F-53 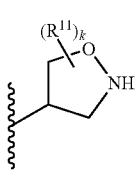

F-54 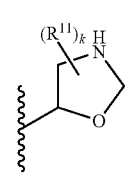

wherein

⌇ denotes the bonding point to the remainder of the molecule;

k is 0, 1, 2 or 3, n is 0, 1 or 2, and each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated heterocyclic ring may form together =O or =S;

$R^8$ is selected from OH, CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5, preferably 1, 2 or 3, in particular 1, substituents $R^{16}$, and a heterocyclic ring selected from rings of formulae E-1 to E-54 as defined above;

wherein $R^{10a}$ is selected from the group consisting of hydrogen and $C_1$-$C_6$-alkyl;

$R^{10b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_6$-alkoxy and $C_1$-$C_6$-haloalkoxy; and each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

Even more particularly, in —N($R^5$)$R^6$ as a radical Y, $R^5$ is hydrogen or $C_1$-$C_3$-alkyl;

$R^6$ is selected from hydrogen, $C_1$-$C_6$-alkyl, $C_1$-$C_6$-haloalkyl, $C_1$-$C_4$-alkyl which carries one radical $R^8$; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F and CN; —N($R^{10a}$)$R^{10b}$, —CH=NO$R^9$;

phenyl which may be substituted with 1, 2, 3, 4, or 5 substituents $R^{11}$, and a heteromonocyclic ring selected from rings of formulae F-1 to F-54;

wherein $R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5 substituents $R^{16}$, and a heterocyclic ring selected from rings of formulae E-1 to E-54 as defined above; wherein $R^{10a}$ in —C(=O)N($R^{10a}$)$R^{10b}$ as a meaning for $R^8$ is selected from the group consisting of hydrogen and $C_1$-$C_6$-alkyl;

$R^{10b}$ in —C(=O)N($R^{10a}$)$R^{10b}$ as a meaning for $R^8$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, $R^9$ is selected from hydrogen, $C_1$-$C_6$-alkyl and $C_1$-$C_6$-haloalkyl;

$R^{10a}$ in —N($R^{10a}$)$R^{10b}$ as a meaning for $R^6$ is hydrogen;

$R^{10b}$ in —N($R^{10a}$)$R^{10b}$ as a meaning for $R^6$ is —C(=O)N($R^{14a}$)$R^{14b}$ or a heteroaromatic ring selected from rings of formulae E-1 to E-42 as defined above; wherein $R^{14a}$ is selected from the group consisting of hydrogen and $C_1$-$C_6$-alkyl; and $R^{14b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_4$-alkoxy and $C_1$-$C_4$-haloalkoxy; and $R^{11}$ and $R^{16}$; independently of each occurrence and independently of each other (also in rings E-1 to E-54, E-1 to E-42 and F-1 to F-54), are selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated heterocyclic ring may form together =O or =S; or two $R^{16}$ present on the same carbon atom of a saturated heterocyclic ring may form together =O or =S.

Even more particularly, in —N($R^5$)$R^6$ as a radical Y, $R^5$ is hydrogen;

$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 substituents selected from F and CN; —N($R^{10a}$)$R^{10b}$; —CH=NO$R^9$;

phenyl which may be substituted with 1, 2, 3, 4, or 5 substituents $R^{11}$, and a heteromonocyclic ring selected from rings of formulae F-1 to F-54;

wherein $R^8$ is selected from CN, $C_3$-$C_8$-cycloalkyl which optionally carries a CN substituent, $C_3$-$C_8$-halocycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, phenyl, optionally substituted with 1, 2, 3, 4 or 5 substituents $R^{16}$, and a heterocyclic ring selected from rings of formulae E-1 to E-54 as defined above; wherein $R^{10a}$ in —C(=O)N($R^{10a}$)$R^{10b}$ as a meaning for $R^8$ is selected from the group consisting of hydrogen and $C_1$-$C_6$-alkyl;

$R^{10b}$ in —C(=O)N($R^{10a}$)$R^{10b}$ as a meaning for $R^8$ is selected from the group consisting of hydrogen, $C_1$-$C_6$-alkyl, $C_2$-$C_4$-alkynyl, $CH_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, $R^9$ is selected from hydrogen, $C_1$-$C_6$-alkyl and $C_1$-$C_6$-haloalkyl;

$R^{10a}$ in —N($R^{10a}$)$R^{10b}$ as a meaning for $R^6$ is hydrogen;

$R^{10b}$ in —N($R^{10a}$)$R^{10b}$ as a meaning for $R^6$ is —C(=O)N($R^{14a}$)$R^{14b}$ or a heteroaromatic ring selected from rings of formulae E-1 to E-42 as defined above, wherein $R^{14a}$ is selected from the group consisting of hydrogen and $C_1$-$C_6$-alkyl; and $R^{14b}$ is selected from the group consisting of hydrogen, $C_1$-$C_6$-alkyl, $C_1$-$C_6$-haloalkyl, $C_2$-$C_4$-alkynyl, $C_3$-$C_6$-cycloalkyl, $C_3$-$C_6$-halocycloalkyl, $CH_2$—CN, $C_1$-$C_4$-alkoxy and $C_1$-$C_4$-haloalkoxy; and $R^{11}$ and $R^{16}$; independently of each occurrence and independently of each other (also in rings E-1 to E-54, E-1 to E-42 and F-1 to F-54), are selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated heterocyclic ring may form together =O or =S;

or two $R^{16}$ present on the same carbon atom of a saturated heterocyclic ring may form together =O or =S.

In an alternative embodiment of the invention, A is $A^2$.

Preferably, $R^{7a}$ and $R^{7b}$ in the group $A^2$ are independently of each other selected from hydrogen, cyano, $C_1$-$C_4$-alkyl and $C_1$-$C_4$-haloalkyl, and more preferably from hydrogen, $C_1$-$C_4$-alkyl and $C_1$-$C_4$-haloalkyl. Even more preferably, one of $R^{7a}$ and $R^{7b}$ is hydrogen and the other is hydrogen or methyl. Specifically, both are hydrogen.

In the group $A^2$, $R^5$ is preferably selected from hydrogen, cyano, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted with one or more, preferably 1, 2 or 3, in particular 1, substituents $R^8$; and $R^6$ is preferably selected from hydrogen, $C_1$-$C_6$-alkyl, $C_3$-$C_6$-cycloalkyl, $C_2$-$C_6$-alkenyl, $C_2$-$C_6$-alkynyl, wherein the four last-mentioned aliphatic and cycloaliphatic radicals may be partially or fully halogenated and/or may be substituted by one or more, preferably 1, 2 or 3, in particular 1, substituents $R^8$, —$OR^9$, —$NR^{10a}R^{10b}$, —$S(O)_nR^9$, —$C(=O)NR^{10a}N(R^{10a})R^{10b}$, —$C(=O)R^8$, and a 3-, 4-, 5-, 6- or 7-membered saturated, partially unsaturated or maximally unsaturated heteromonocyclic or heterobicyclic ring containing 1, 2, 3 or 4 heteroatoms or heteroatom groups independently selected from N, O, S, NO, SO and $SO_2$, as ring members, where the heteromonocyclic or heterobicyclic ring may be substituted with one or more, preferably 1, 2 or 3, in particular 1, substituents $R^{11}$;

or $R^5$ and $R^6$, together with the nitrogen atom to which they are bound, form a 3-, 4-, 5- or 6-membered saturated, partially unsaturated or maximally unsaturated heterocyclic ring, where the ring may further contain 1, 2, 3 or 4 heteroatoms or heteroatom-containing groups selected from O, S, N, SO, $SO_2$, C=O and C=S as ring members, wherein the heterocyclic ring may be substituted with 1, 2, 3, 4 or 5, preferably 1, 2 or 3, in particular 1, substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more, preferably 1, 2 or 3, in particular 1, radicals $R^8$, and phenyl which may be substituted with 1, 2, 3, 4 or 5, preferably 1, 2 or 3, in particular 1, substituents $R^{11}$;

or $R^5$ and $R^6$ together form a group =$C(R^8)_2$, =$S(O)_m(R^9)_2$, =$NR^{10a}$ or =$NOR^9$;

wherein m, n, $R^8$, $R^9$, $R^{10a}$, $R^{10b}$ and $R^{11}$ have one of the above general meanings, or, in particular, one of the below preferred meanings.

More preferably, in the group $A^2$, $R^5$ is selected from hydrogen, $C_1$-$C_4$-alkyl, $C_2$-$C_3$-alkynyl, —$CH_2$—CN and $C_1$-$C_6$-alkoxy-methyl- and preferably from hydrogen and $C_1$-$C_4$-alkyl; and $R^6$ is —$C(=O)R^8$;

wherein $R^8$ has one of the above general meanings, or, in particular, one of the below preferred meanings.

$R^8$ in —$C(=O)R^8$ as a meaning of the radicals $R^5$ and $R^6$ of the group $A^2$ is preferably selected from the group consisting of hydrogen, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl, $C_3$-$C_8$-halocycloalkyl, where the aliphatic and cycloaliphatic moieties in the eight last-mentioned radicals may be substituted by one or more, preferably 1, 2 or 3, in particular 1, radicals $R^{13}$; —$OR^9$, —$S(O)_nR^9$, —$N(R^{10a})R^{10b}$, —$C(=O)N(R^{10a})R^{10b}$, —$CH=NOR^9$, phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$, wherein n, $R^9$, $R^{10a}$, $R^{10b}$, $R^{13}$ and $R^{16}$ have one of the above general meanings, or, in particular, one of the below preferred meanings.

More preferably, $R^8$ in —$C(=O)R^8$ as a meaning of the radicals $R^5$ and $R^6$ of the group $A^2$ is selected from the group consisting of hydrogen, $C_1$-$C_6$-alkyl, $C_1$-$C_6$-haloalkyl, $C_1$-$C_6$-alkyl substituted with one radical $R^{13}$, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl which optionally carries a CN substituent, $C_3$-$C_8$-halocycloalkyl, —$N(R^{10a})R^{10b}$, —$C(=O)N(R^{10a})R^{10b}$, —$CH=NOR^9$, phenyl, optionally substituted with 1, 2, 3, 4 or 5, preferably 1, 2 or 3, in particular 1, substituents $R^{16}$, and a 3-, 4-, 5- or 6-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents $R^{16}$, wherein $R^9$, $R^{10a}$, $R^{10b}$, $R^{13}$ and $R^{16}$ have one of the above general meanings, or, in particular, one of the below preferred meanings.

$R^9$ in —$CH=NOR^9$ as a meaning of $R^8$ in the group —$C(=O)R^8$ as a meaning of the radicals $R^5$ and $R^6$ of the group $A^2$ is preferably selected from hydrogen, $C_1$-$C_6$-alkyl and $C_1$-$C_6$-haloalkyl.

$R^{10a}$ and $R^{10b}$ in —$C(=O)N(R^{10a})R^{10b}$ and —$N(R^{10a})R^{10b}$ as a meaning of $R^8$ in the group —$C(=O)R^8$ as a meaning of the radicals $R^5$ and $R^6$ of the group $A^2$ are, independently of each other, preferably selected from hydrogen, $C_1$-$C_6$-alkyl, $C_1$-$C_6$-haloalkyl, $C_2$-$C_3$-alkenyl, $C_2$-$C_3$-haloalkenyl, $C_2$-$C_3$-alkynyl, $C_2$-$C_3$-haloalkynyl, $C_3$-$C_6$-cycloalkyl which optionally carries a CN substituent, $C_3$-$C_8$- halocycloalkyl, where the aliphatic and cycloaliphatic moieties in the 9 last-mentioned radicals may be substituted by one or more radicals $R^{13}$; $-C(=O)NR^{14a})R^{14b}$, phenyl, optionally substituted with 1, 2, 3, 4 or 5 substituents $R^{16}$; and a heteromonocyclic ring selected from rings of formulae E-1 to E-54 as defined above.

$R^{13}$ in $R^8$ in the radicals $R^5$ and $R^6$ of the group $A^2$ is preferably selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $-C(=O)N(R^{14a})R^{14b}$, phenyl, optionally substituted with 1, 2, 3, 4 or 5 substituents $R^{16}$; and a heterocyclic ring selected from rings of formulae E-1 to E-54 as defined above.

$R^{14a}$ and $R^{14b}$ in $-C(=O)NR(^{14a})R^{14b}$ as a meaning for $R^{10a}$ and $R^{10b}$ as well as a meaning for $R^{13}$, independently of each other and independently of each occurrence, are preferably selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, wherein the six last-mentioned aliphatic radicals may carry 1 substituent selected from cyano, $C_1$-$C_4$-alkoxy, $C_1$-$C_4$-haloalkoxy, $C_3$-$C_4$-cycloalkyl which may be substituted by 1 cyano group; and $C_3$-$C_4$-halocycloalkyl; $C_3$-$C_8$-cycloalkyl which may carry 1 cyano group; and $C_3$-$C_8$-halocycloalkyl; and more preferably from hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl-, $C_1$-$C_4$-alkoxy and $C_1$-$C_4$-haloalkoxy.

Preferably, each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

In particular, $R^8$ in $-C(=O)R^8$ as a meaning of the radicals $R^5$ and $R^6$ of the group $A^2$ is selected from the group consisting of hydrogen, $C_1$-$C_6$-alkyl, $C_1$-$C_6$-haloalkyl, $C_1$-$C_4$-alkyl substituted by one radical $R^{13}$, $C_2$-$C_4$-alkenyl, $C_2$-$C_4$-haloalkenyl, $C_2$-$C_4$-alkynyl, $C_2$-$C_4$-haloalkynyl, $C_3$-$C_8$-cycloalkyl which optionally carries a CN substituent, $C_3$-$C_8$-halocycloalkyl, $-N(R^{10a})R^{10b}$, $-C(=O)N(R^{10a})R^{10b}$, $-CH=NOR^9$, phenyl which is optionally substituted with 1, 2, 3, 4 or 5 substituents $R^{16}$; and a heterocyclic ring selected from rings of formulae E-1 to E-54 as defined above, wherein $R^9$ is selected from hydrogen, $C_1$-$C_6$-alkyl and $C_1$-$C_6$-haloalkyl;

$R^{10a}$ is selected from hydrogen, $C_1$-$C_4$-alkyl, $C_1$-$C_4$-haloalkyl and $C_3$-$C_6$-cycloalkyl, and preferably from hydrogen and $C_1$-$C_4$-alkyl;

$R^{10b}$ is selected from hydrogen, $C_1$-$C_6$-alkyl, $C_1$-$C_6$-haloalkyl, $C_3$-$C_6$-cycloalkyl which optionally carries a CN substituent; $-C(=O)N(R^{14a})R^{14b}$; phenyl, optionally substituted with 1, 2, 3, 4 or 5 substituents $R^{16}$; and a heteromonocyclic ring selected from rings of formulae E-1 to E-54 as defined above;

$R^{13}$ is selected from CN, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $-C(=O)N(R^{14a})R^{14b}$, phenyl, optionally substituted with 1, 2, 3, 4 or 5 substituents $R^{16}$; and a heterocyclic ring selected from rings of formulae E-1 to E-54 as defined above;

$R^{14a}$ is selected from hydrogen and $C_1$-$C_6$-alkyl;

$R^{14b}$ is selected from hydrogen, $C_1$-$C_6$-alkyl, $C_1$-$C_6$-haloalkyl, $CH_2$—CN, $C_2$-$C_4$-alkenyl, $C_2$-$C_4$-alkynyl, $C_3$-$C_6$-cycloalkyl, $C_3$-$C_6$-halocycloalkyl, $C_3$-$C_6$-cycloalkylmethyl-, $C_1$-$C_4$-alkoxy and $C_1$-$C_4$-haloalkoxy; and each $R^{16}$ as a substituent on phenyl or heterocyclic rings of formulae E-1 to E-54 is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{16}$ present on the same carbon atom of a saturated heterocyclic ring may form together =O or =S.

In an alternative embodiment of the invention, A is $A^3$.

$A^3$ is preferably selected from a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and $SO_2$, as ring members, where the heteromonocyclic ring is optionally substituted with one or more, preferably 1, 2 or 3, in particular 1, substituents $R^{11}$, where $R^{11}$ has one of the above general meanings, or, in particular, one of the below preferred meanings.

More preferably, $A^3$ is selected from a 3-, 4-, 5-, 6- or 7-membered saturated heteromonocyclic ring containing 1 or 2 heteroatoms or heteroatom groups selected from N, O, S, NO, SO and $SO_2$, as ring members, a 5-, 6- or 7-membered partially unsaturated heteromonocyclic ring containing 1, 2 or 3 heteroatoms or heteroatom groups selected from N, O, S, NO, SO and $SO_2$, as ring members, and a 5- or 6-membered aromatic heteromonocyclic ring containing 1, 2, 3 or 4 heteroatoms selected from N, O and S as ring members, where the heteromonocyclic ring is optionally substituted with one or more, preferably 1, 2 or 3, in particular 1, substituents $R^{11}$ where $R^{11}$ has one of the above general meanings, or, in particular, one of the below preferred meanings.

$A^3$ is even more preferably selected from rings of formulae D-1 to D-173

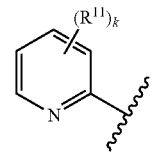

D-1

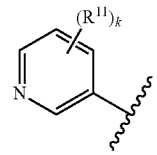

D-2

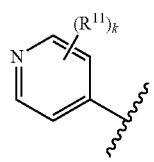
D-3
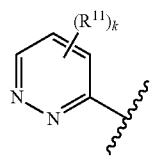
D-4
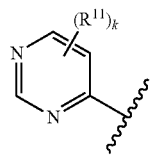
D-5
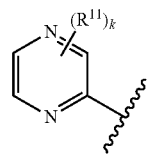
D-6
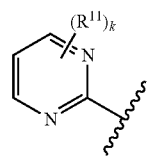
D-7
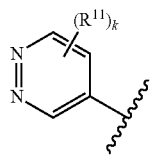
D-8
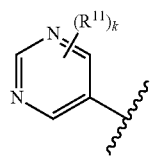
D-9
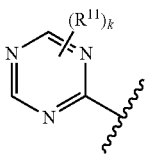
D-10
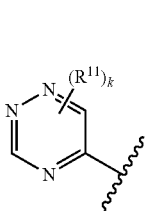
D-11
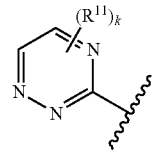
D-12
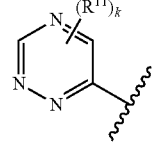
D-13
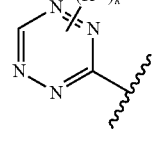
D-14
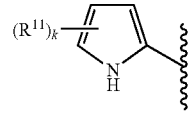
D-15
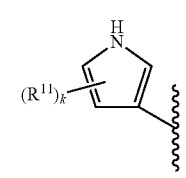
D-16
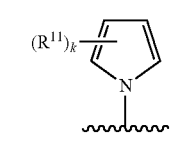
D-17
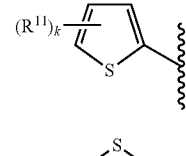
D-18
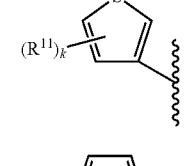
D-19
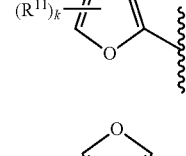
D-20
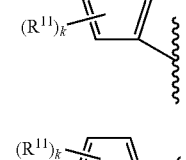
D-21
D-22

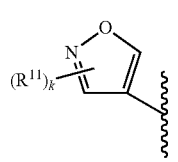 D-23
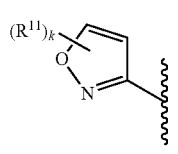 D-24
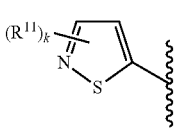 D-25
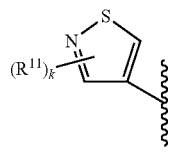 D-26
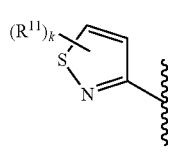 D-27
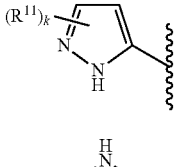 D-28
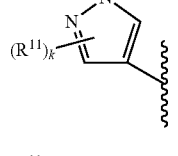 D-29
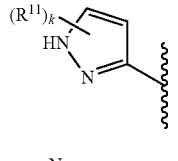 D-30
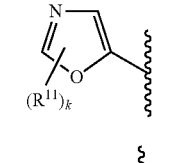 D-31
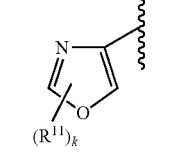 D-32
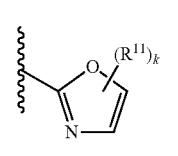 D-33
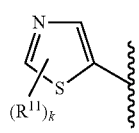 D-34
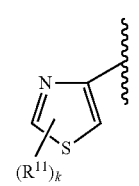 D-35
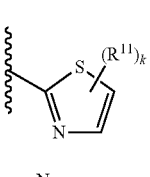 D-36
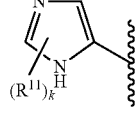 D-37
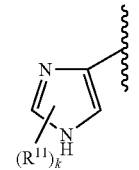 D-38
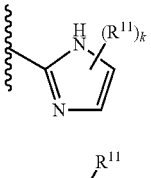 D-39
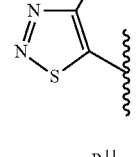 D-40
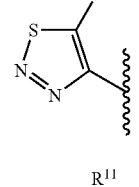 D-41
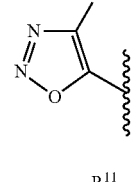 D-42
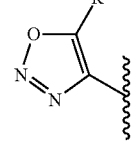 D-43

-continued
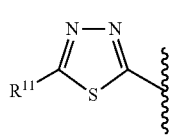
D-44
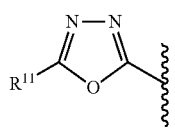
D-45
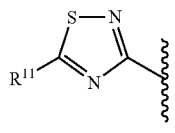
D-46
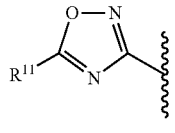
D-47
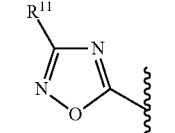
D-48
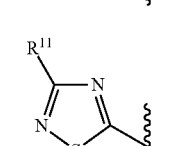
D-49
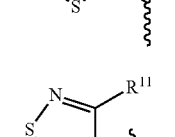
D-50
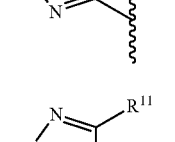
D-51
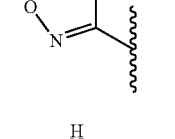
D-52
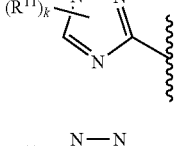
D-53
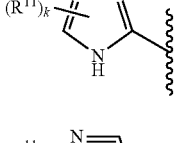
D-54
-continued
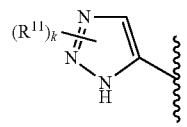
D-55
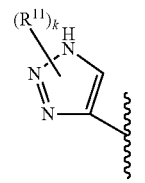
D-56
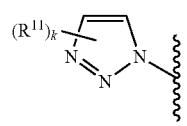
D-57
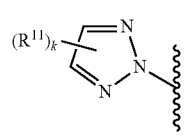
D-58
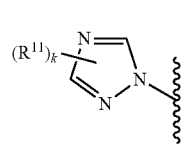
D-59
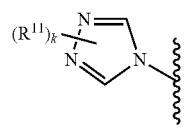
D-60
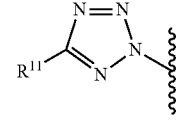
D-61
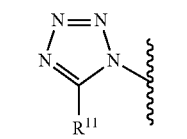
D-62
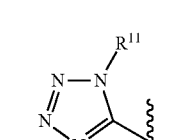
D-63
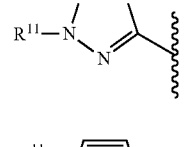
D-64
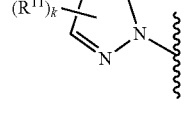
D-65

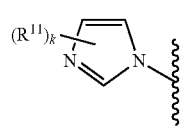 D-66
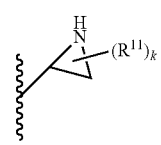 D-67
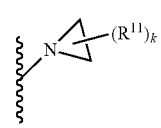 D-68
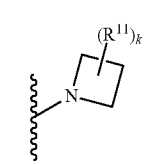 D-69
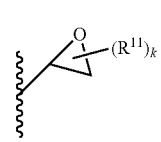 D-70
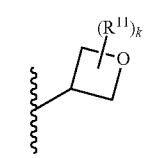 D-71
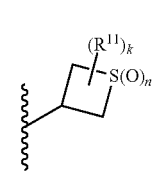 D-72
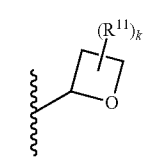 D-73
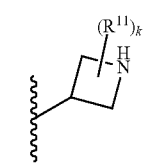 D-74
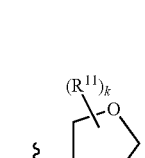 D-75
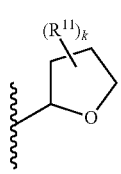 D-76
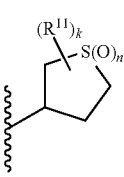 D-77
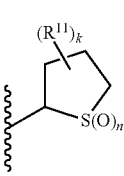 D-78
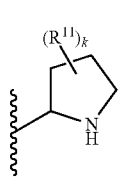 D-79
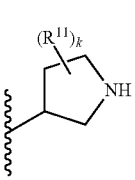 D-80
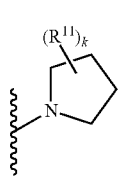 D-81
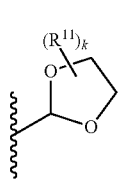 D-82
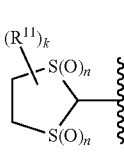 D-83
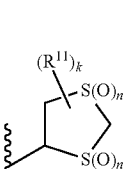 D-84

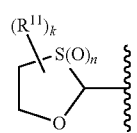 D-85
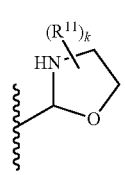 D-86
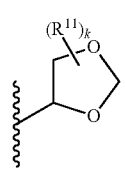 D-87
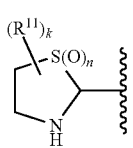 D-88
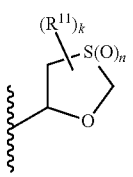 D-89
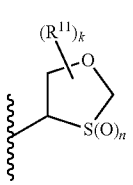 D-90
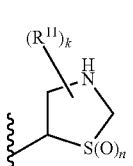 D-91
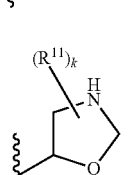 D-92
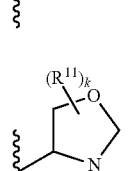 D-93
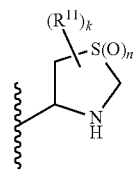 D-94
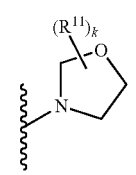 D-95
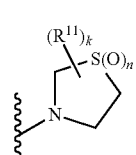 D-96
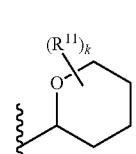 D-97
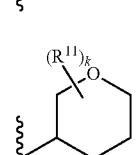 D-98
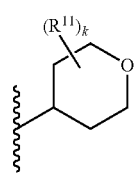 D-99
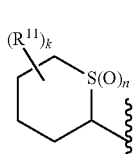 D-100
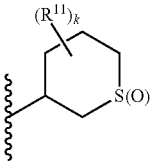 D-101
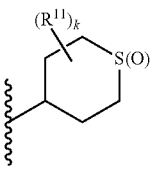 D-102

| | |
|---|---|
| D-103 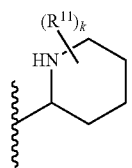 | D-112 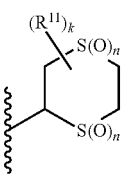 |
| D-104 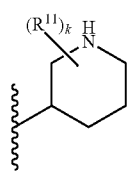 | D-113 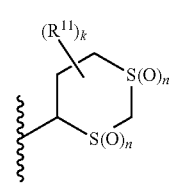 |
| D-105 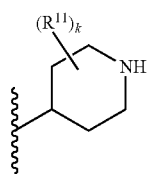 | D-114 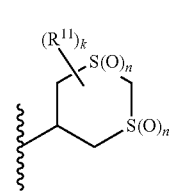 |
| D-106 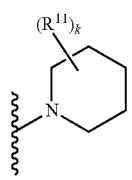 | D-115 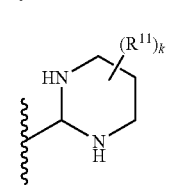 |
| D-107 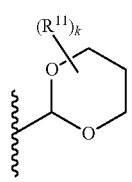 | D-116 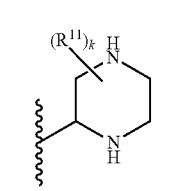 |
| D-108 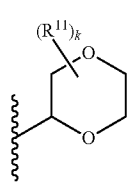 | D-117 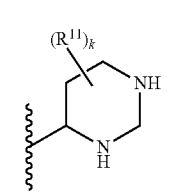 |
| D-109 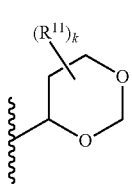 | D-118 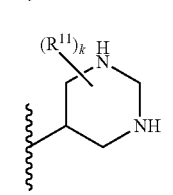 |
| D-110 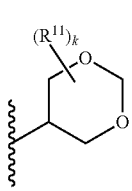 | D-119 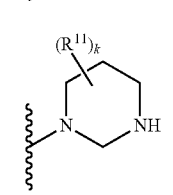 |
| D-111 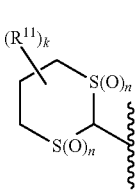 | D-120 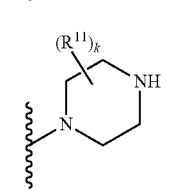 |

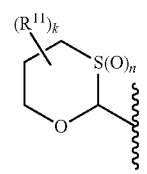 D-121
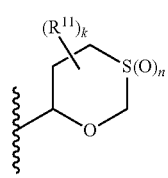 D-122
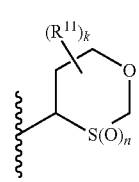 D-123
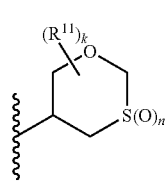 D-124
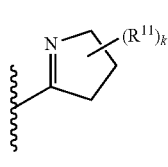 D-125
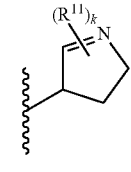 D-126
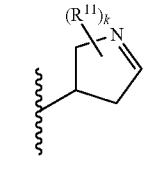 D-127
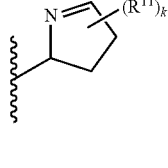 D-128
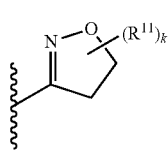 D-129
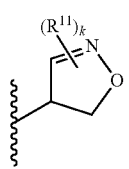 D-130
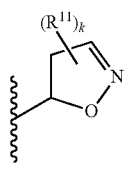 D-131
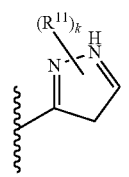 D-132
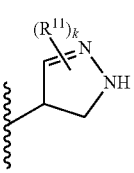 D-133
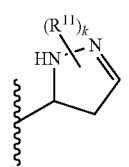 D-134
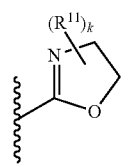 D-135
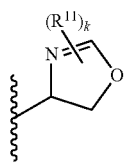 D-136
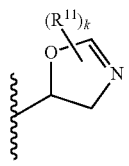 D-137
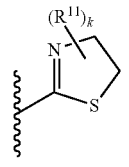 D-138

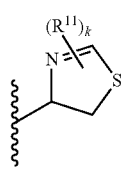 D-139
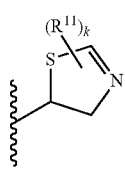 D-140
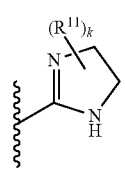 D-141
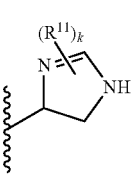 D-142
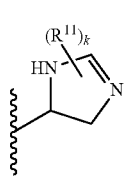 D-143
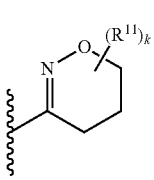 D-144
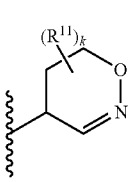 D-145
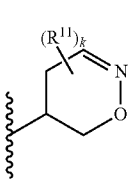 D-146
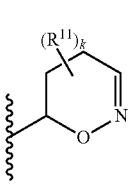 D-147
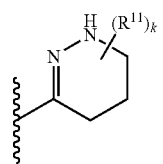 D-148
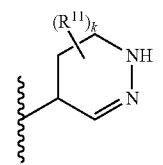 D-149
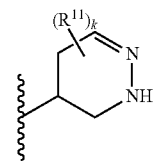 D-150
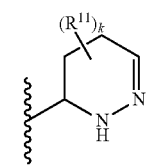 D-151
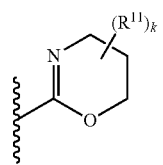 D-152
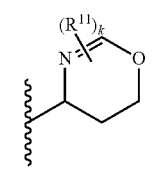 D-153
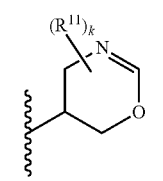 D-154
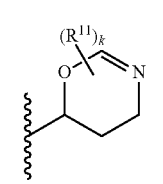 D-155
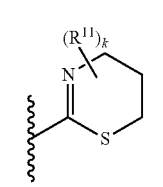 D-156

-continued

D-157 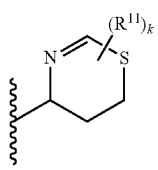

D-158 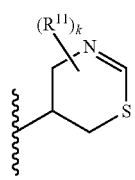

D-159 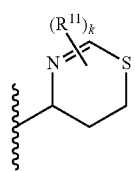

D-160 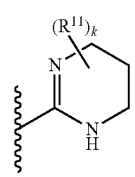

D-161 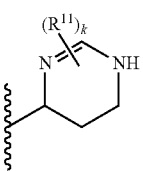

D-162 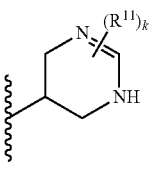

D-163 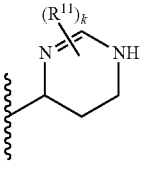

D-164 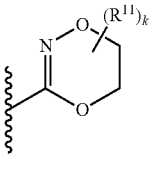

D-165 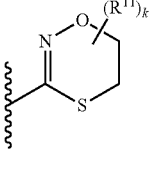

-continued

D-166 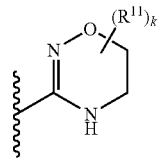

D-167 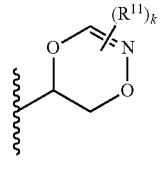

D-168 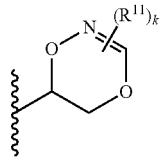

D-169 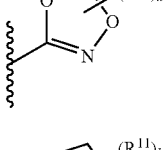

D-170 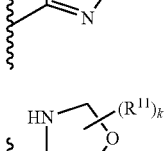

D-171 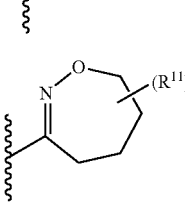

D-172 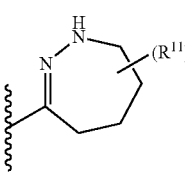

D-173 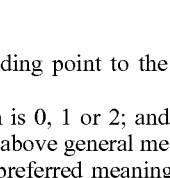

wherein

⸹ denotes the bonding point to the remainder of the molecule;

k is 0, 1, 2 or 3, n is 0, 1 or 2; and $R^{11}$ has one of the above general meanings, or, in particular, one of the below preferred meanings;

and is in particular selected from D-59, D-65 and D-66 and is specifically D-59.

Preferably, in the above rings D-1 to D-173, each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or two $R^{11}$ present on the same carbon atom of a saturated or partially unsaturated ring may form together =O or =S.

Among the radicals $A^1$, $A^2$ and $A^3$, preference is given to $A^1$.

Preferably, $B^1$, $B^2$ and $B^3$ are $CR^2$.

More preferably, $B^1$ is $CR^2$, where $R^2$ is not hydrogen, and $B^2$ and $B^3$ are $CR^2$, where $R^2$ has one of the above general meanings or, in particular, one of the below preferred meanings.

Preferably, $R^2$ is selected from hydrogen, halogen, cyano, azido, nitro, —SCN, —$SF_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$; —$OR^9$, —$S(O)_nR^9$ and —$NR^{10a}R^{10b}$, wherein $R^8$, $R^9$, $R^{10a}$ and $R^{10b}$ have one of the above general meanings, or, in particular, one of the below preferred meanings.

More preferably, $R^2$ is selected from hydrogen, halogen, $C_1$-$C_2$-haloalkyl and $C_1$-$C_2$-haloalkoxy, even more preferably from hydrogen, F, Cl, Br, $CF_3$ and $OCF_3$.

Preferably, $G^1$, $G^2$, $G^3$ and $G^4$ are $CR^4$, where $R^4$ has one of the above general meanings, or, in particular, one of the below preferred meanings.

More preferably, $G^1$, $G^3$ and $G^4$ are CH and $G^2$ is $CR^4$, where $R^4$ has one of the above general meanings, or, in particular, one of the below preferred meanings.

Preferably, $R^4$ is selected from hydrogen, hydrogen, halogen, cyano, $C_1$-$C_4$-alkyl, $C_1$-$C_4$-haloalkyl, $C_3$-$C_5$-cycloalkyl, $C_3$-$C_5$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, $C_1$-$C_4$-alkylthio and $C_1$-$C_4$-haloalkylthio, and in particular from hydrogen, F, Cl, Br, $CH_3$ and $CF_3$.

Preferably, $R^1$ is selected from $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl $C_3$-$C_6$-halocycloalkyl or C(=O)$OR^{13}$; more preferably, from $C_1$-$C_4$-alkyl, $C_1$-$C_4$-haloalkyl, $C_3$-$C_6$-cycloalkyl, $C_3$-$C_6$-halocycloalkyl and C(=O)$OR^{15}$, even more preferably from $C_1$-$C_4$-alkyl, $C_1$-$C_4$-haloalkyl and —C(=O)$OR^{15}$, and particularly preferably from $C_1$-$C_4$-haloalkyl and —C(=O)$OR^{15}$, wherein $R^{15}$ is preferably $C_1$-$C_4$-alkyl. In particular, $R^1$ is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Preferably, $R^{3a}$, $R^{3b}$ and $R^{3c}$ are selected, independently of each other, from hydrogen and halogen, preferably hydrogen and fluorine, and are in particular hydrogen.

If not specified otherwise above, $R^8$, $R^9$, $R^{10a}$, $R^{10b}$, $R^{11}$, $R^{12}$, $R^{13}$, $R^{15}$ and $R^{16}$ have following preferred meanings:

In case $R^8$ is a substituent on an alkyl, alkenyl or alkynyl group, it is preferably selected from the group consisting of cyano, $C_3$-$C_8$-cycloalkyl, $C_3$-$C_8$-halocycloalkyl, —$OR^9$, —$SR^9$, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on an alkyl, alkenyl or alkynyl group, it is even more preferably selected from the group consisting of cyano, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-haloalkylthio, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below. In particular it is selected from the group consisting of cyano, $C_3$-$C_6$-cycloalkyl, $C_3$-$C_6$-halocycloalkyl, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is preferably selected from the group consisting of cyano, $C_1$-$C_6$-alkyl, $C_1$-$C_6$-haloalkyl, $C_1$-$C_6$-alkoxy-$C_1$-$C_6$-alkyl, —$OR^9$, —$OSO_2R^9$, —$SR^9$, —N($R^{10a}$)$R^{10b}$, —C(=O)N($R^{10a}$)$R^{10b}$, —C(=S)N($R^{10a}$)$R^{10b}$, —C(=O)$OR^9$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case $R^8$ is a substituent on a cycloalkyl group, it is even more preferably selected from the group consisting of cyano, $C_1$-$C_4$-alkyl, $C_1$-$C_3$-haloalkyl, $C_1$-$C_4$-alkoxy and $C_1$-$C_3$-haloalkoxy. In particular, $R^8$ as a substituent on a cycloalkyl group is selected from cyano, $C_1$-$C_4$-alkyl and $C_1$-$C_3$-haloalkyl.

In case of $R^8$ in a group —C(=O)$R^8$, =C($R^8$)$_2$ or —C(=NR^6)$R^8$, $R^8$ is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —$OR^9$, —$SR^9$, —N($R^{10a}$)$R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^9$, $R^{10a}$, $R^{10b}$ and $R^{16}$ have one of the meanings given above or in particular one of the preferred meanings given below.

In case of $R^8$ in a group —C(=O)$R^8$, =C($R^8$)$_2$ or —C(=N$R^6$)$R^8$, $R^8$ is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, —N($R^{10a}$)$R^{10b}$, phenyl which may be substituted by 1, 2, 3, 4 or 5 radicals $R^{16}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$; where $R^{10a}$, $R^{10b}$ and $R^{16}$ have has one of the meanings given above or in particular one of the preferred meanings given below.

Preferably, each $R^9$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{16}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{16}$, where $R^{16}$ has one of the meanings given above or in particular one of the preferred meanings given below.

More preferably, each $R^9$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{16}$; and a 5- or 6-membered heteroaromatic ring containing 1, 2 or 3 heteroatoms selected from N, O and S, as ring members, where the heteroaromatic ring may be substituted by one or more radicals $R^{16}$; where $R^{16}$ has one of the meanings given above or in particular one of the preferred meanings given below.

$R^{10a}$ and $R^{10b}$ are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkylcarbonyl, $C_1$-$C_4$-haloalkylcarbonyl, $C_1$-$C_4$-alkylaminocarbonyl, $C_1$-$C_4$-haloalkylaminocarbonyl, $C_3$-$C_6$-cycloalkylaminocarbonyl, $C_3$-$C_6$-halocycloalkylaminocarbonyl, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio;

or, $R^{10a}$ and $R^{10b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, CN, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_1$-$C_4$-alkoxy, $C_1$-$C_4$-haloalkoxy, $C_1$-$C_4$-alkylthio and $C_1$-$C_4$-haloalkylthio.

More preferably, $R^{10a}$ and $R^{10b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl, and a 3- or 4-membered saturated heterocyclic ring comprising 1 heteroatom or heteroatom group selected from N, O, S, NO, SO and $SO_2$, as ring member, where the heterocyclic ring is optionally substituted with one or more, preferably 1, 2 or 3, in particular 1, substituents selected from halogen, CN, $C_1$-$C_4$-alkyl, $C_1$-$C_4$-haloalkyl, $C_1$-$C_4$-alkoxy and $C_1$-$C_4$-haloalkoxy; and are specifically, independently of each other, selected from hydrogen, $C_1$-$C_4$-alkyl and $C_1$-$C_4$-haloalkyl.

Each $R^{11}$ and each $R^{16}$ are independently of each occurrence and independently of each other preferably selected from halogen, CN, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl and $C_1$-$C_4$-haloalkylsulfonyl, and more preferably from halogen, CN, $C_1$-$C_4$-alkyl, $C_1$-$C_4$-haloalkyl, $C_1$-$C_4$-alkoxy and $C_1$-$C_4$-haloalkoxy.

Each $R^{12}$ is preferably selected from $C_1$-$C_4$-alkyl and is in particular methyl.

In case $R^{13}$ is a substituent on an alkyl, alkenyl or alkynyl group, it is preferably selected from the group consisting of cyano, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is preferably selected from the group consisting of cyano, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

In case $R^{13}$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^{13}$ as a substituent on a cycloalkyl group is selected from halogen, $C_1$-$C_4$-alkyl and $C_1$-$C_3$-haloalkyl.

In case of $R^{13}$ in a group —C(=O)$R^{13}$, —C(=S)$R^{13}$, =C($R^{13}$)$_2$ or —C(=N$R^{14}$)$R^{13}$, $R^8$ is preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, —OH, —SH, $C_1$-$C_6$-alkoxy, $C_1$-$C_6$-haloalkoxy and phenyl which may be substituted by 1, 2 or 3 radicals selected from halogen, $C_1$-$C_4$-alkyl, $C_1$-$C_4$-haloalkyl, $C_1$-$C_4$-alkoxy and $C_1$-$C_4$-haloalkoxy.

$R^{14}$, $R^{14a}$ and $R^{14b}$ are, independently of each other, preferably selected from hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy;

or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

More preferably, $R^{14}$, $R^{14a}$ and $R^{14b}$ are, independently of each other, selected from hydrogen, $C_1$-$C_4$-alkyl, $C_1$-$C_4$-haloalkyl, $C_3$-$C_6$-cycloalkyl, $C_3$-$C_6$-halocycloalkyl and benzyl, where the phenyl ring in benzyl is optionally substituted 1, 2 or 3, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy;

or, $R^{14a}$ and $R^{14b}$, together with the nitrogen atom to which they are bound, form a 5- or 6-membered saturated, partially unsaturated or aromatic heterocyclic ring, which additionally may contain 1 or 2 further heteroatoms or heteroatom groups selected from N, O, S, NO, SO and $SO_2$, as ring members, where the heterocyclic ring may carry 1 or 2, in particular 1, substituents selected from halogen, $C_1$-$C_4$-alkyl, $C_1$-$C_4$-haloalkyl, $C_1$-$C_4$-alkoxy and $C_1$-$C_4$-haloalkoxy.

Each $R^{15}$ is preferably selected from hydrogen, $C_1$-$C_6$-alkyl, $C_1$-$C_6$-haloalkyl, phenyl, benzyl, pyridyl and phenoxy, wherein the four last-mentioned radicals may be unsubstituted and/or carry 1, 2 or 3 substituents selected from $C_1$-$C_6$-alkyl, $C_1$-$C_6$-haloalkyl, $C_1$-$C_6$-alkoxy and $C_1$-$C_6$-haloalkoxy.

In a particular embodiment, the invention relates to compounds I.A

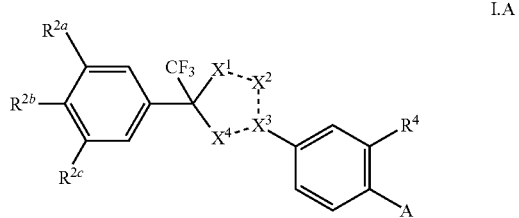

(I.A)

wherein $R^{2a}$, $R^{2b}$ and $R^{2c}$ have one of the general or, in particular, one of the preferred meanings given above for $R^2$, the middle "X-ring" with $X^1$, $X^2$, $X^3$ and $X^4$ as ring members is as defined above (i.e. is of formula II-1, II-2 or II-3, with $R^1$ being $CF_3$), and A and $R^4$ have one of the above-given general or, in particular, one of the above-given preferred meanings.

In particular, in compounds I.A
$R^{2a}$, $R^{2b}$ and $R^{2c}$ are selected from hydrogen and halogen, in particular from hydrogen, F and Cl;
$R^4$ is selected from methyl and halogen, in particular from methyl and Cl, and is specifically Cl; and
A is $A^1$,
  where
  W is O; and
  Y is $NR^5R^6$ or $OR^9$, where
    $R^5$ is hydrogen;
    $R^6$ is selected from hydrogen, $C_1$-$C_4$-alkyl, $C_1$-$C_4$-haloalkyl, $C_1$-$C_4$-alkyl which carries one radical $R^8$, $C_2$-$C_4$-alkenyl, $C_2$-$C_6$-alkynyl, $C_3$-$C_6$-cycloalkyl which may be substituted by 1 or 2 substituents selected from F and CN; $-N(R^{10a})R^{10b}$, wherein $R^{10a}$ is hydrogen and $R^{10b}$ is a heteroaromatic ring selected from rings of formulae E-1 to E-42 as defined above (especially E-1 to E-9; specifically E-1 and E-7); and a heteromonocyclic ring selected from rings of formulae F-1 to F-54 as defined above (especially F-48);
      wherein
      $R^8$ is selected from $C_3$-$C_6$-cycloalkyl, $C_3$-$C_8$-halocycloalkyl, $-C(=O)N(R^{10a})R^{10b}$, and a heterocyclic ring selected from rings of formulae E-1 to E-54 (especially E-1 to E-9; specifically E-1 and E-7) as defined above; wherein
      $R^{10a}$ is hydrogen;
      $R^{10b}$ is selected from the group consisting of hydrogen, $C_1$-$C_6$-alkyl and $C_1$-$C_6$-haloalkyl; and
    $R^{11}$ and $R^{16}$ in the above E- and F-rings, independently of each occurrence and independently of each other, are selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkylcarbonyl, $C_1$-$C_4$-haloalkylcarbonyl, aminocarbonyl, $C_1$-$C_4$-alkylaminocarbonyl and di-($C_1$-$C_4$-alkyl)-aminocarbonyl; or
      two $R^{11}$ present on the same carbon atom of a saturated heterocyclic ring may form together =O or =S; or
      two $R^{16}$ present on the same carbon atom of a saturated heterocyclic ring may form together =O or =S; and
    $R^9$ is selected from the group consisting of hydrogen, $C_1$-$C_6$-alkyl and $C_1$-$C_6$-haloalkyl.

In the above E- and F-rings k is specifically 0.

Examples of preferred compounds are compounds of the following formulae Ia.1 to Ia.81, where $R^{2a}$, $R^{2b}$ and $R^{2c}$ have one of the general or preferred meanings given above for $R^2$ and the other variables have one of the general or preferred meanings given above. Examples of preferred compounds are the individual compounds compiled in the tables 1 to 15942 below. Moreover, the meanings mentioned below for the individual variables in the tables are per se, independently of the combination in which they are mentioned, a particularly preferred embodiment of the substituents in question.

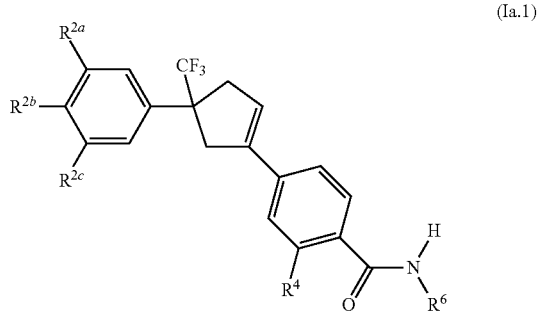

(Ia.1)

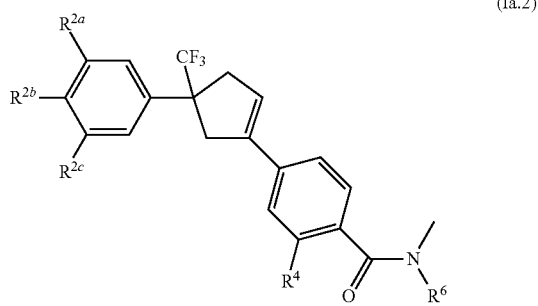

(Ia.2)

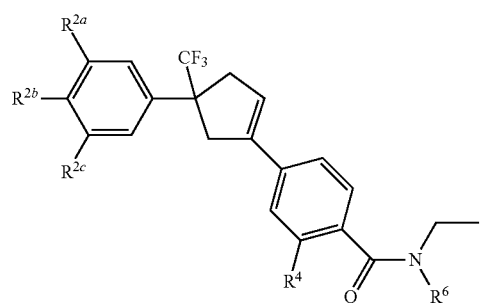
(Ia.3)
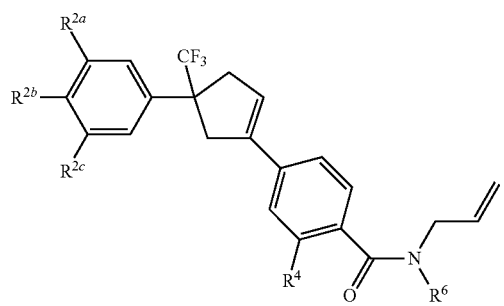
(Ia.4)
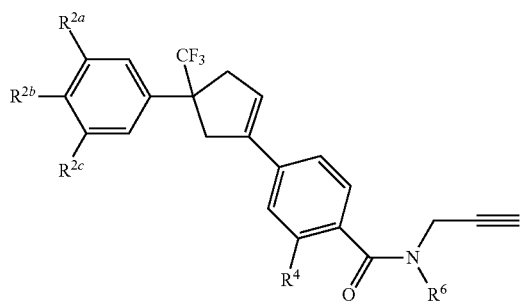
(Ia.5)
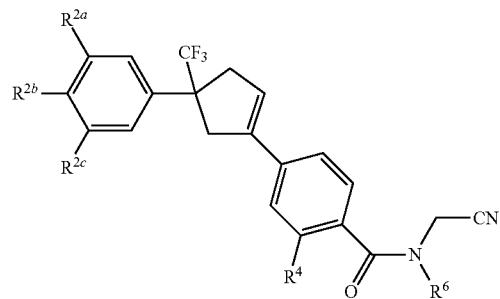
(Ia.6)
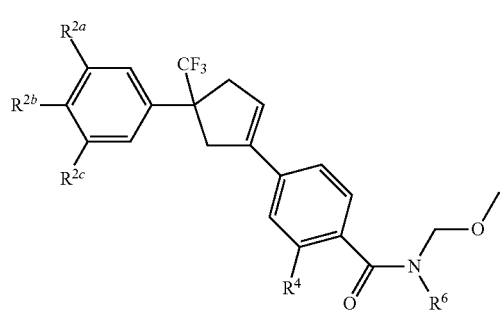
(Ia.7)
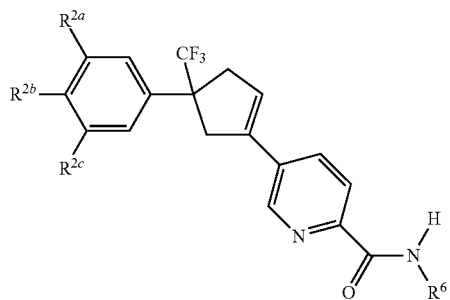
(Ia.8)
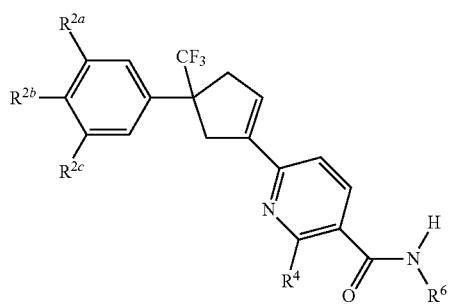
(Ia.9)
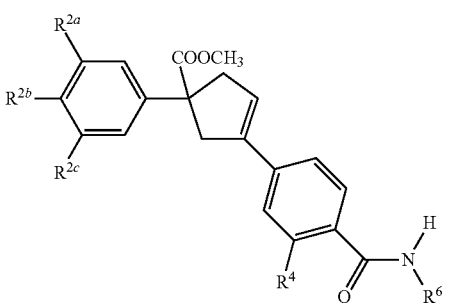
(Ia.10)
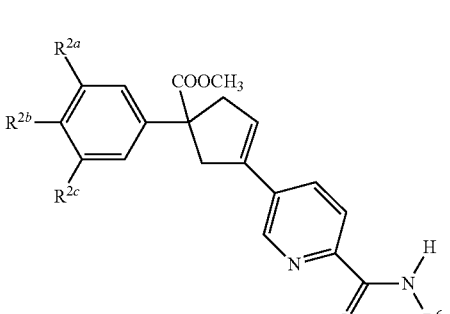
(Ia.11)
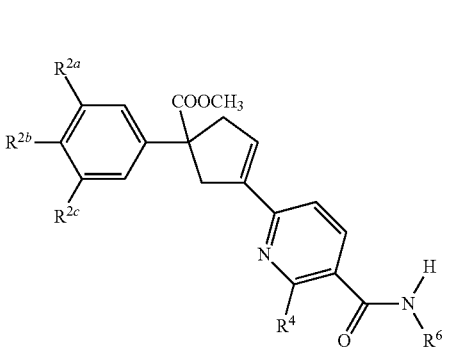
(Ia.12)

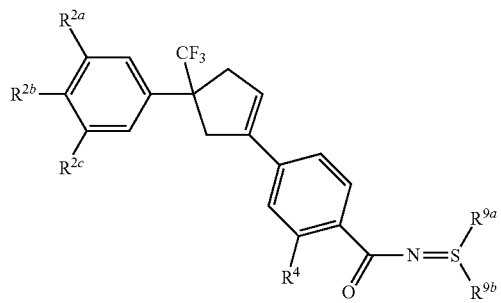
(Ia.13)
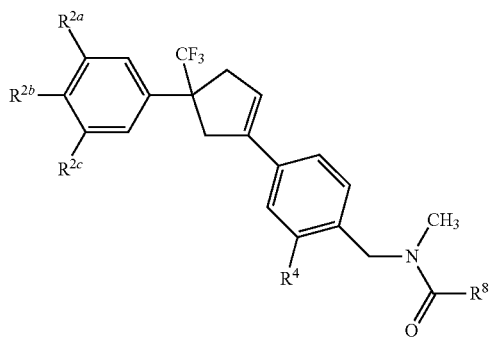
(Ia.17)
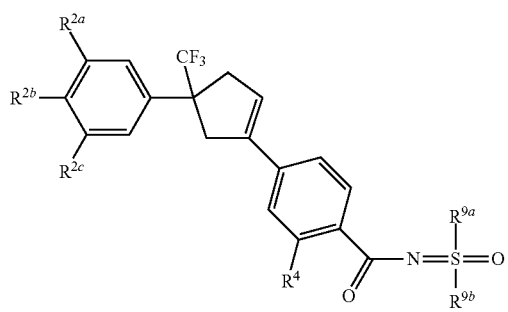
(Ia.14)
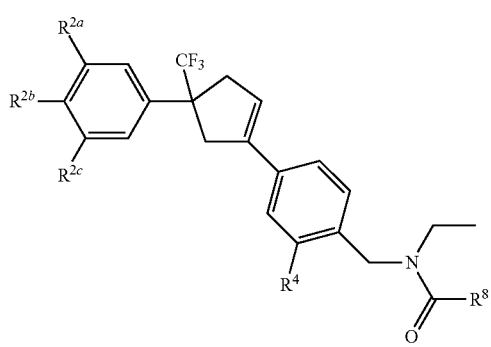
(Ia.18)
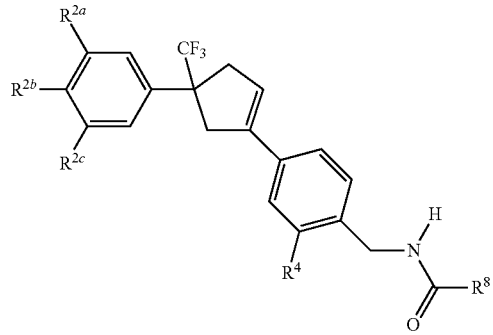
(Ia.15)
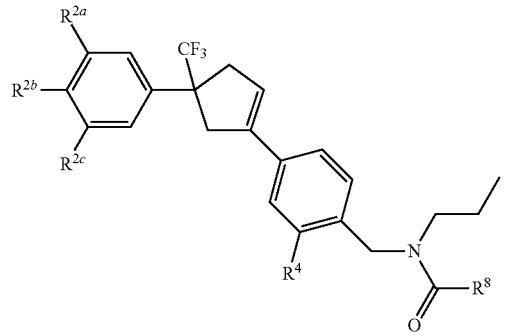
(Ia.19)
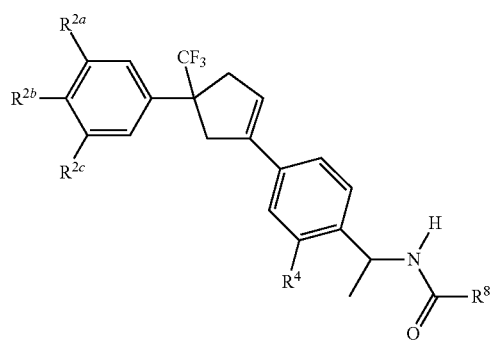
(Ia.16)
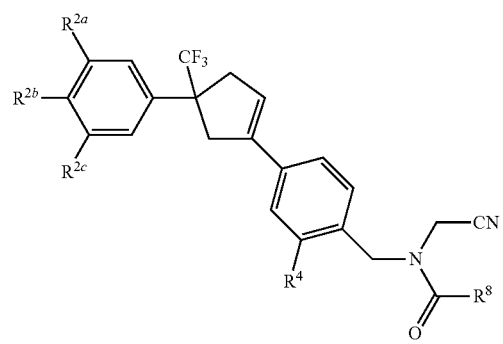
(Ia.20)

-continued
(Ia.21)
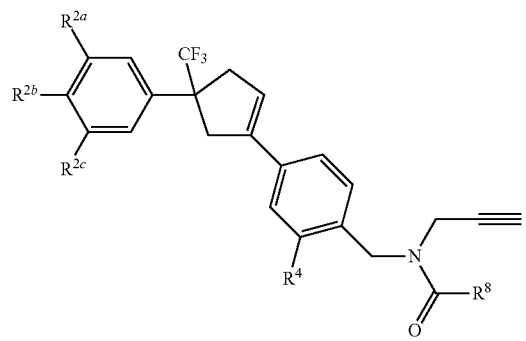
(Ia.22)
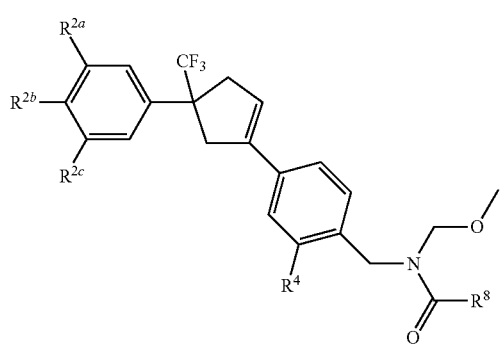
(Ia.23)
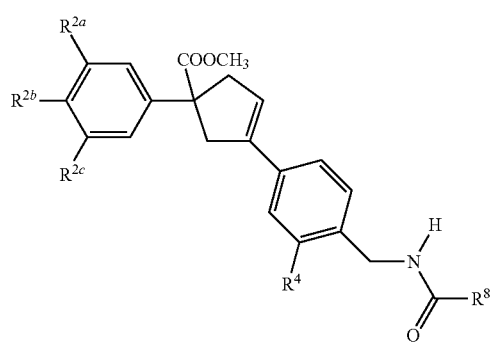
(Ia.24)
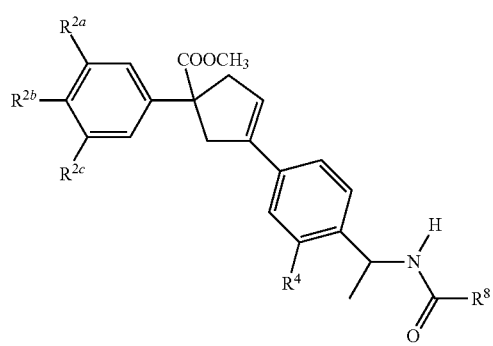
-continued
(Ia.25)
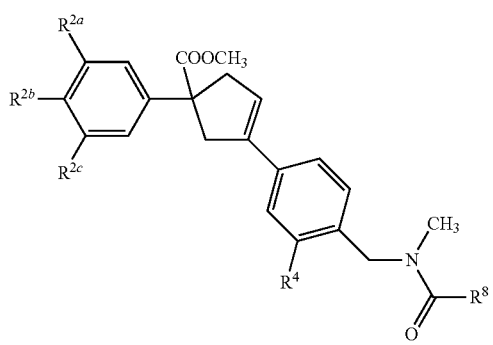
(Ia.26)
(Ia.27)
(Ia.28)
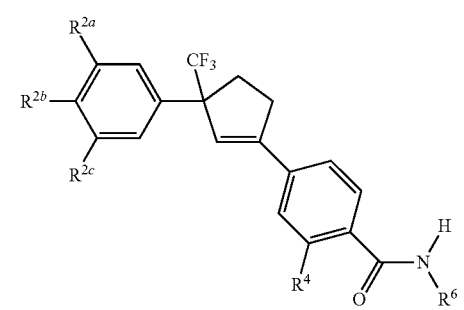
(Ia.29)

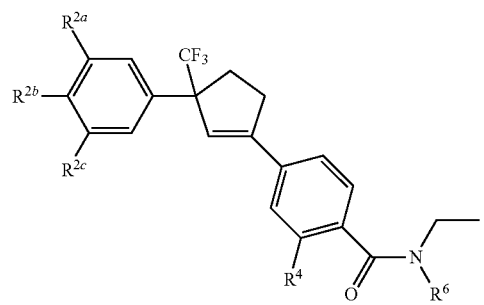
(Ia.30)
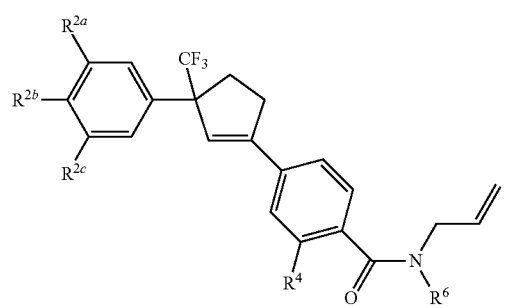
(Ia.31)
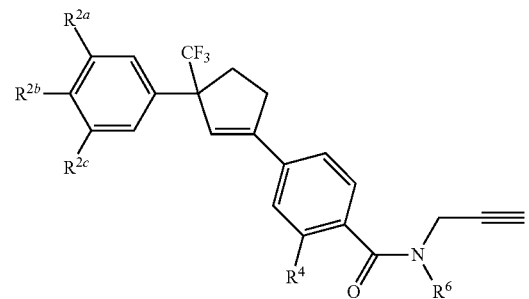
(Ia.32)
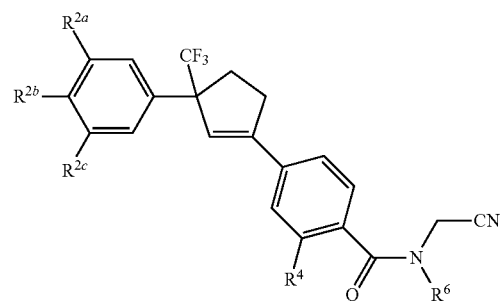
(Ia.33)
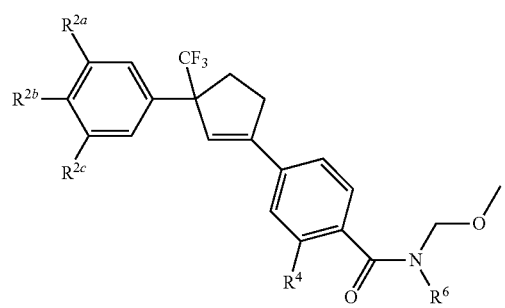
(Ia.34)
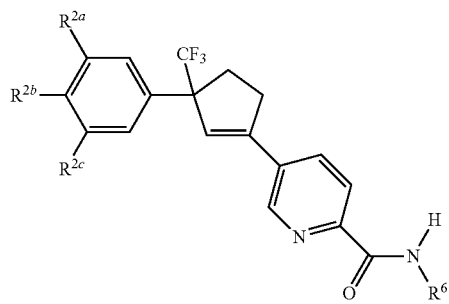
(Ia.35)
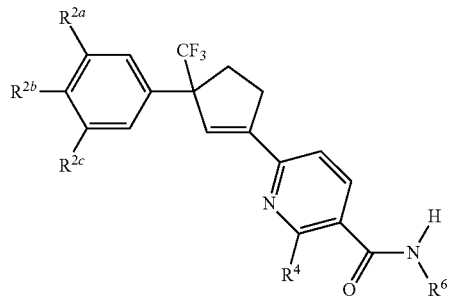
(Ia.36)
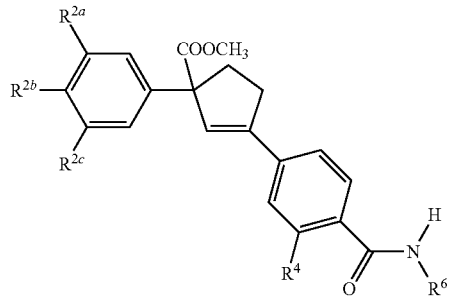
(Ia.37)
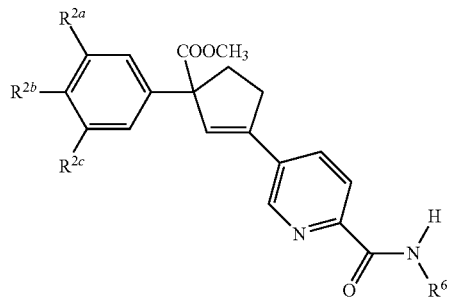
(Ia.38)
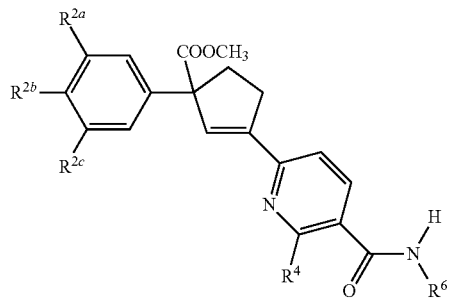
(Ia.39)

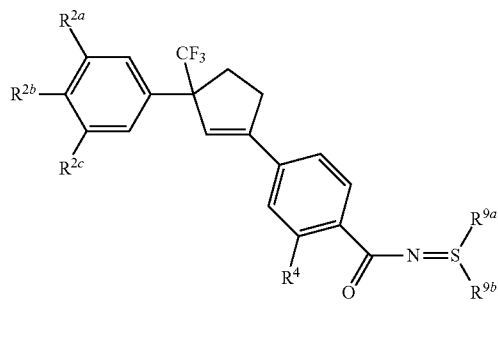
(Ia.40)
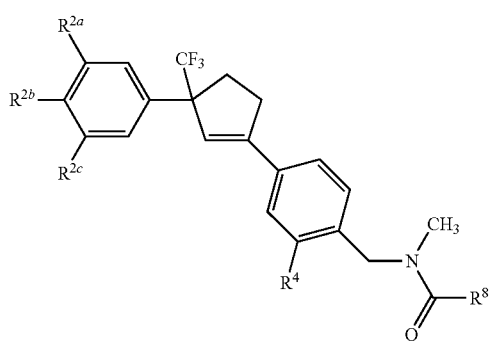
(Ia.44)
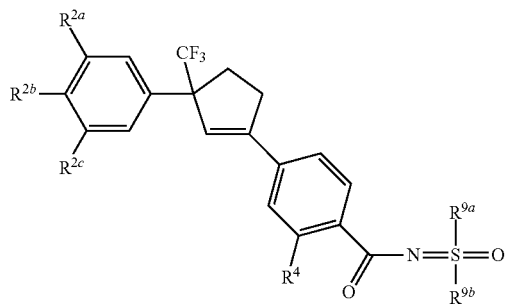
(Ia.41)
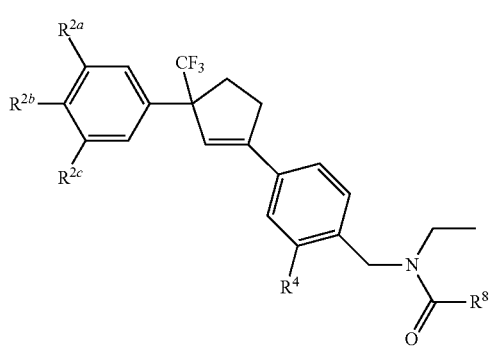
(Ia.45)
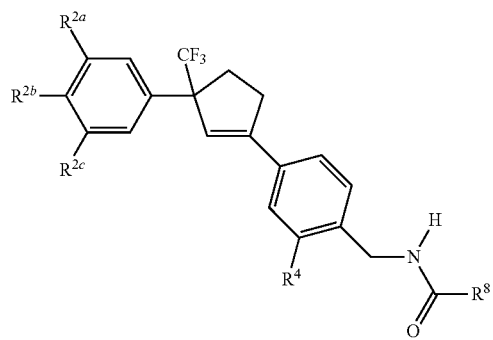
(Ia.42)
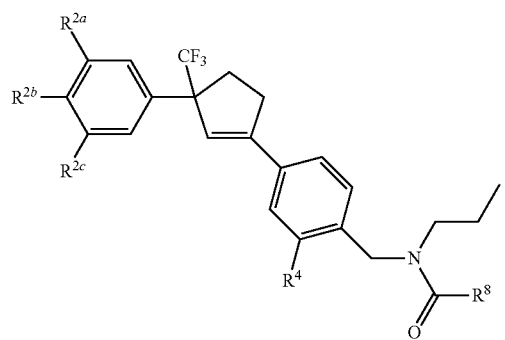
(Ia.46)
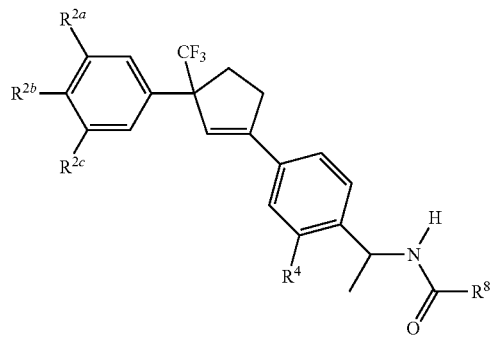
(Ia.43)
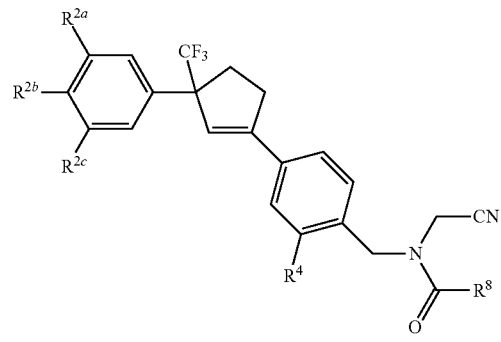
(Ia.47)

-continued
(Ia.48)
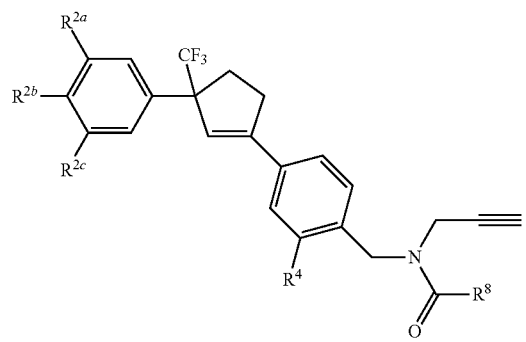
(Ia.49)
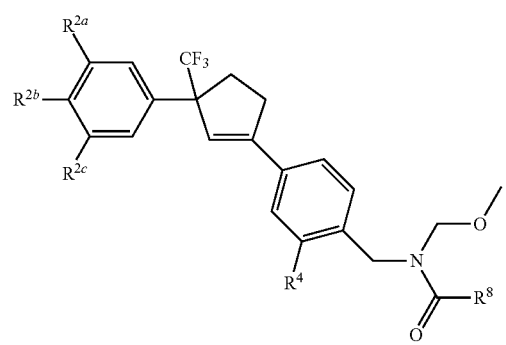
(Ia.50)
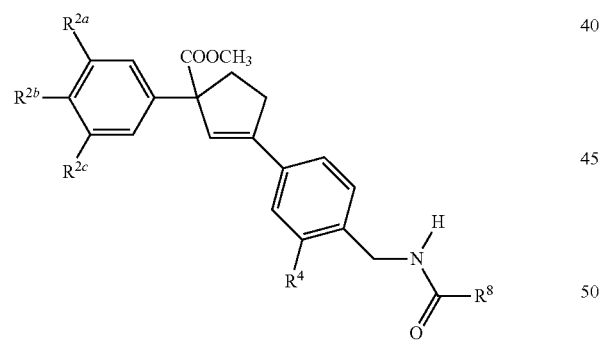
(Ia.51)
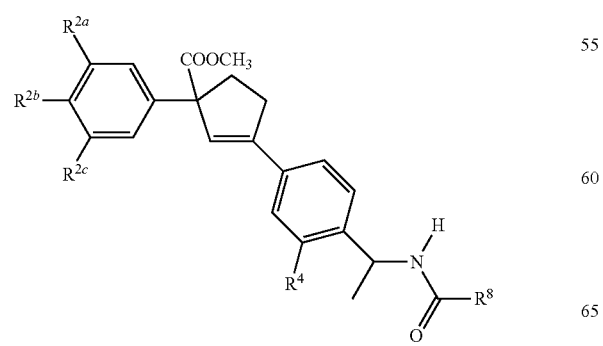
-continued
(Ia.52)
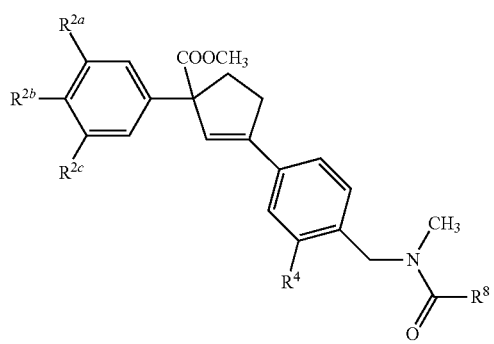
(Ia.53)
(Ia.54)
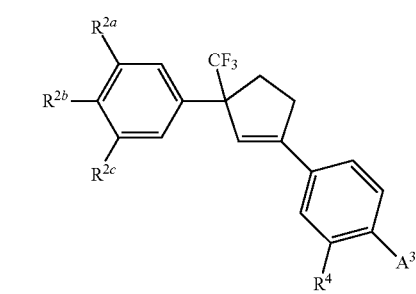
(Ia.55)

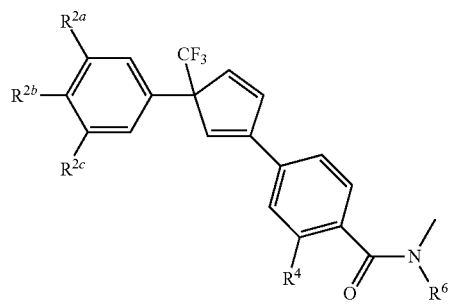
(Ia.56)
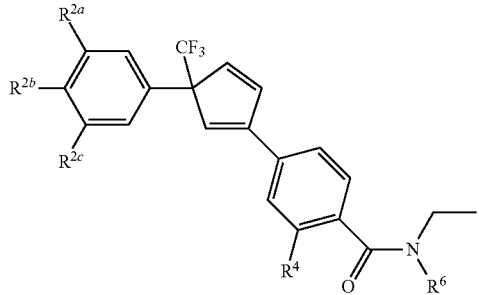
(Ia.57)
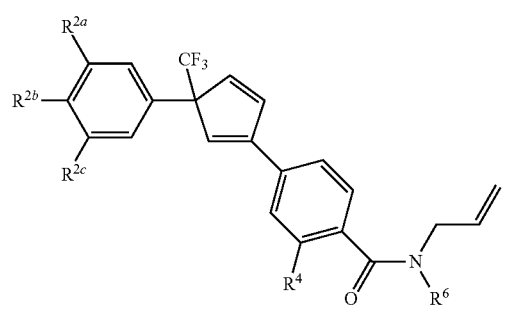
(Ia.58)
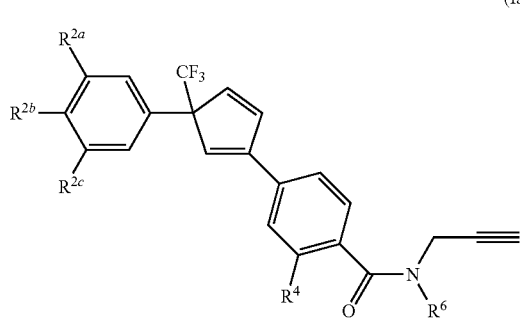
(Ia.59)
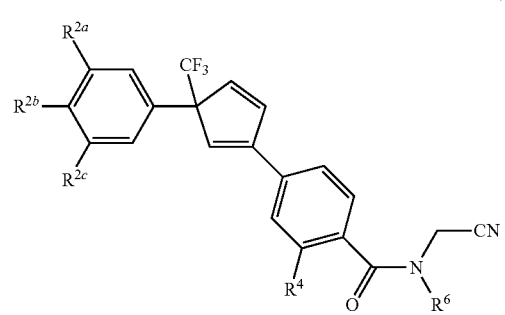
(Ia.60)
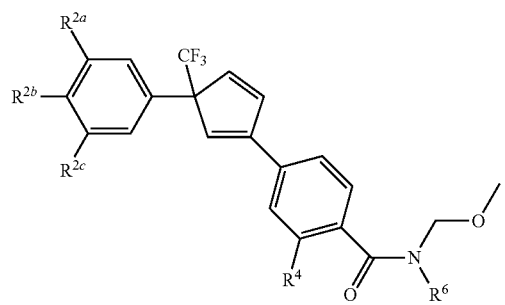
(Ia.61)
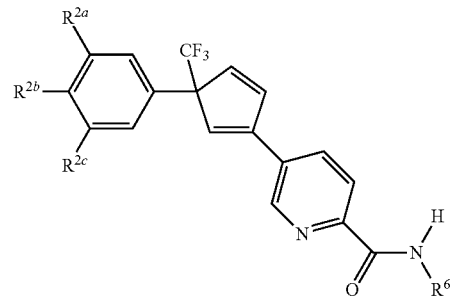
(Ia.62)
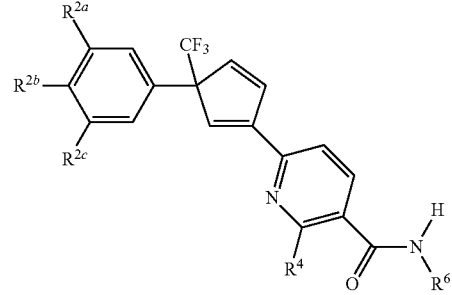
(Ia.63)
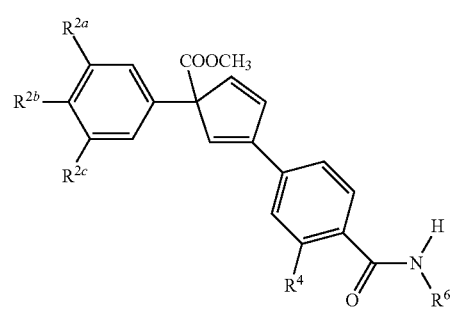
(Ia.64)
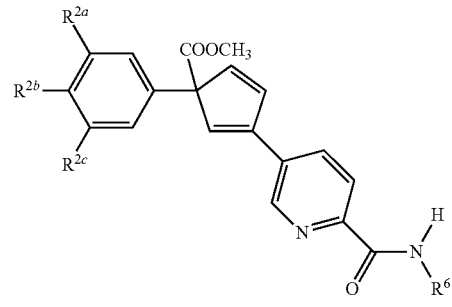
(Ia.65)

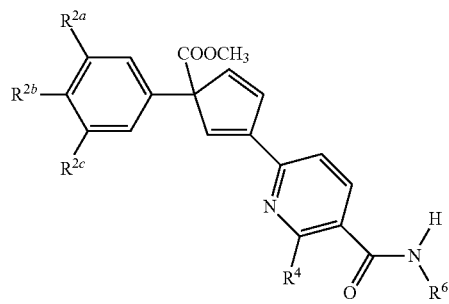
(Ia.66)
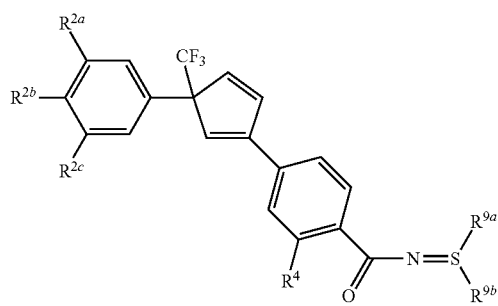
(Ia.67)
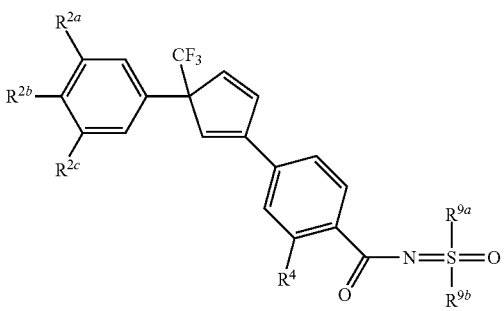
(Ia.68)
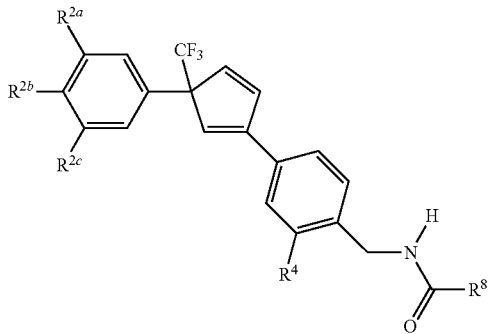
(Ia.69)
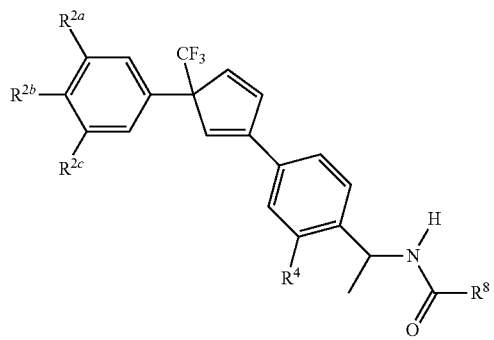
(Ia.70)
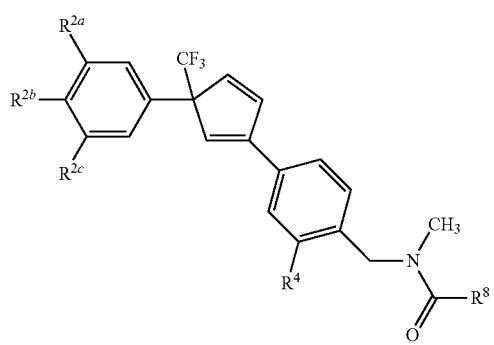
(Ia.71)
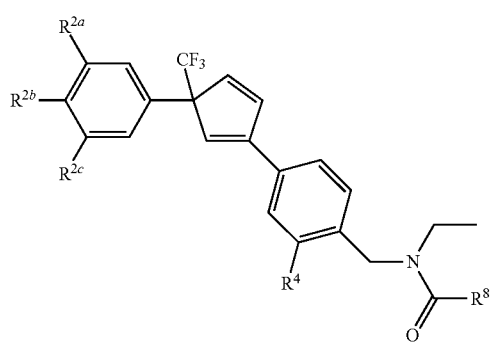
(Ia.72)
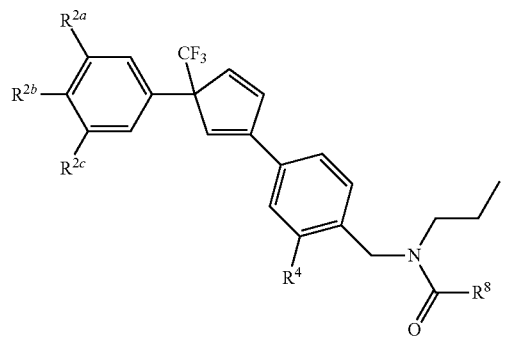
(Ia.73)

(Ia.74)
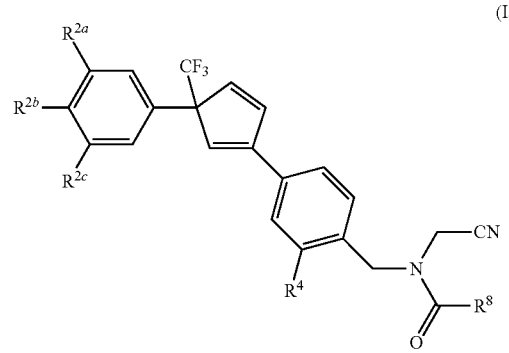
(Ia.75)
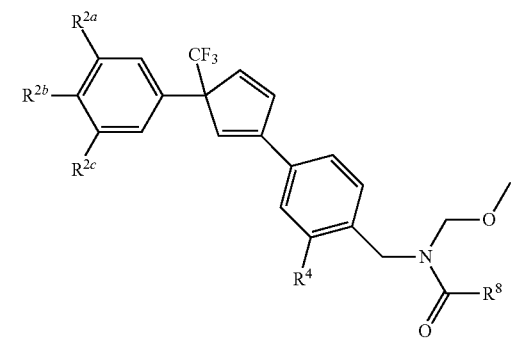
(Ia.76)
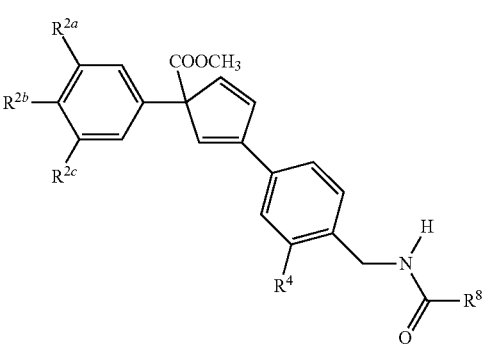
(Ia.77)
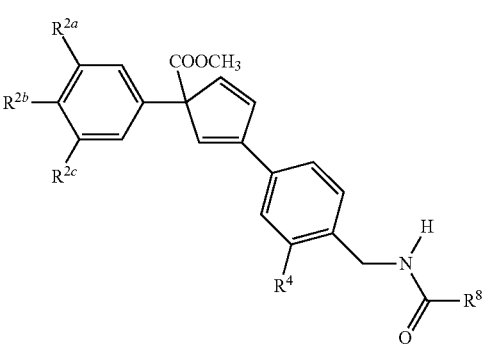
(Ia.78)
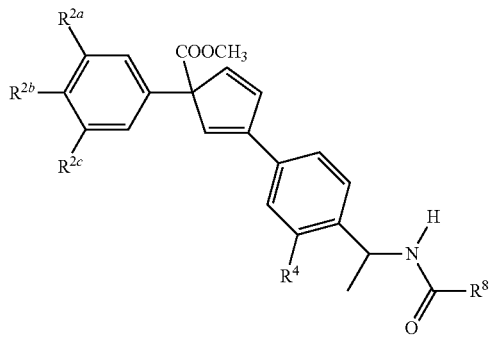
(Ia.79)
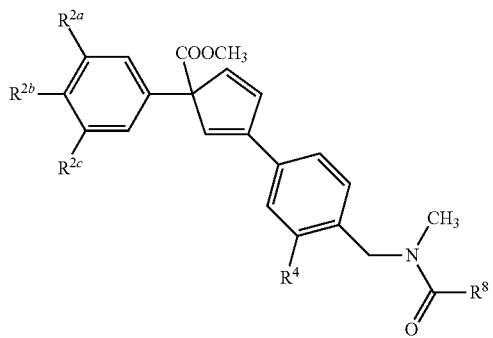
(Ia.80)
(Ia.81)
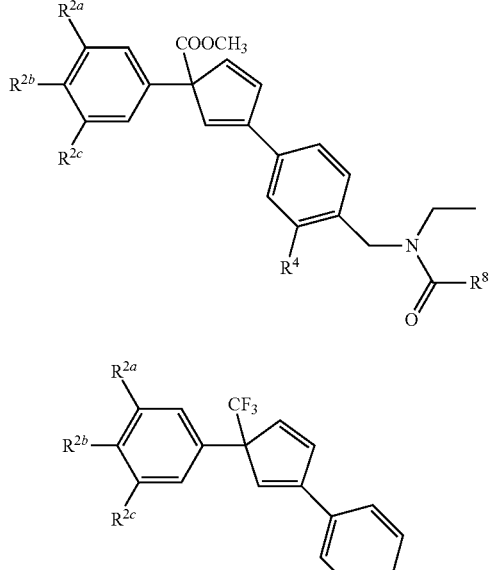
Table 1
Compounds of the formula Ia.1 in which $R^6$ is hydrogen, and the combination of $R^{2a}$, $R^{2b}$, $R^{2c}$ and $R^4$ for a compound corresponds in each case to one row of Table A
Table 2
Compounds of the formula Ia.1 in which $R^6$ is methyl, and the combination of $R^{2a}$, $R^{2b}$, $R^{2c}$ and $R^4$ for a compound corresponds in each case to one row of Table A Table 3
Compounds of the formula Ia.1 in which $R^6$ is ethyl, and the combination of $R^{2a}$, $R^{2b}$, $R^{2c}$ and $R^4$ for a compound corresponds in each case to one row of Table A Table 4
Compounds of the formula Ia.1 in which $R^6$ is n-propyl, and the combination of $R^{2a}$, $R^{2b}$, $R^{2c}$ and $R^4$ for a compound corresponds in each case to one row of Table A Table 5
Compounds of the formula Ia.1 in which $R^6$ is isopropyl, and the combination of $R^{2a}$, $R^{2b}$, $R^{2c}$ and $R^4$ for a compound corresponds in each case to one row of Table A Table 6
Compounds of the formula Ia.1 in which $R^6$ is n-butyl, and the combination of $R^{2a}$, $R^{2b}$, $R^{2c}$ and $R^4$ for a compound corresponds in each case to one row of Table A Table 7
Compounds of the formula Ia.1 in which $R^6$ is sec-butyl, and the combination of $R^{2a}$, $R^{2b}$, $R^{2c}$ and $R^4$ for a compound corresponds in each case to one row of Table A Table 8
Compounds of the formula Ia.1 in which $R^6$ is isobutyl, and the combination of $R^{2a}$, $R^{2b}$, $R^{2c}$ and $R^4$ for a compound corresponds in each case to one row of Table A Table 9
Compounds of the formula Ia.1 in which $R^6$ is tert-butyl, and the combination of $R^{2a}$, $R^{2b}$, $R^{2c}$ and $R^4$ for a compound corresponds in each case to one row of Table A Table 10
Compounds of the formula Ia.1 in which $R^6$ is $CH_2$—C$(CH_3)_3$, and the combination of $R^{2a}$, $R^{2b}$, $R^{2c}$ and $R^4$ for a compound corresponds in each case to one row of Table A Table 11
Compounds of the formula Ia.1 in which $R^6$ is —$CH_2CN$, and the combination of $R^{2a}$, $R^{2b}$, $R^{2c}$ and $R^4$ for a compound corresponds in each case to one row of Table A Table 12
Compounds of the formula Ia.1 in which $R^6$ is —$CH_2$—CH=$CH_2$, and the combination of $R^{2a}$, $R^{2b}$, $R^{2c}$ and $R^4$ for a compound corresponds in each case to one row of Table A Table 13
Compounds of the formula Ia.1 in which $R^6$ is —$CH_2$—$CH_2$—CH=$CH_2$, and the combination of $R^{2a}$, $R^{2b}$, $R^{2c}$ and $R^4$ for a compound corresponds in each case to one row of Table A Table 14
Compounds of the formula Ia.1 in which $R^6$ is —$CH_2$C—CH, and the combination of $R^{2a}$, $R^{2b}$, $R^{2c}$ and $R^4$ for a compound corresponds in each case to one row of Table A Table 15
Compounds of the formula Ia.1 in which $R^6$ is —$CH_2CH_2$C=CH, and the combination of $R^{2a}$, $R^{2b}$, $R^{2c}$ and $R^4$ for a compound corresponds in each case to one row of Table A Table 16
Compounds of the formula Ia.1 in which $R^6$ is —$CH_2CH_2OH$, and the combination of $R^{2a}$, $R^{2b}$, $R^{2c}$ and $R^4$ for a compound corresponds in each case to one row of Table A Table 17
Compounds of the formula Ia.1 in which $R^6$ is —$CH_2CH_2OCH_3$, and the combination of $R^{2a}$, $R^{2b}$, $R^{2c}$ and $R^4$ for a compound corresponds in each case to one row of Table A Table 18
Compounds of the formula Ia.1 in which $R^6$ is —$CH_2CH_2OCH_2CH_3$, and the combination of $R^{2a}$, $R^{2b}$, $R^{2c}$ and $R^4$ for a compound corresponds in each case to one row of Table A Table 19
Compounds of the formula Ia.1 in which $R^6$ is —$CH_2CH_2OCH_2CH$=$CH_2$, and the combination of $R^{2a}$, $R^{2b}$, $R^{2c}$ and $R^4$ for a compound corresponds in each case to one row of Table A Table 20
Compounds of the formula Ia.1 in which $R^6$ is —$CH_2CH_2OCH_2$C—CH, and the combination of $R^{2a}$, $R^{2b}$, $R^{2c}$ and $R^4$ for a compound corresponds in each case to one row of Table A Table 21
Compounds of the formula Ia.1 in which $R^6$ is —$CH_2CH_2OCH_2$-cyclopropyl, and the combination of $R^{2a}$, $R^{2b}$, $R^{2c}$ and $R^4$ for a compound corresponds in each case to one row of Table A Table 22
Compounds of the formula Ia.1 in which $R^6$ is —$CH_2CH_2OCF_3$, and the combination of $R^{2a}$, $R^{2b}$, $R^{2c}$ and $R^4$ for a compound corresponds in each case to one row of Table A Table 23
Compounds of the formula Ia.1 in which $R^6$ is —$CH_2CH_2OCH_2CF_3$, and the combination of $R^{2a}$, $R^{2b}$, $R^{2c}$ and $R^4$ for a compound corresponds in each case to one row of Table A Table 24
Compounds of the formula Ia.1 in which $R^6$ is —CH$(CH_3)CH_2OCH_3$, and the combination of $R^{2a}$, $R^{2b}$, $R^{2c}$ and $R^4$ for a compound corresponds in each case to one row of Table A Table 25
Compounds of the formula Ia.1 in which $R^6$ is —CH$(CH_3)CH_2OCH_2CH_3$, and the combination of $R^{2a}$, $R^{2b}$, $R^{2c}$ and $R^4$ for a compound corresponds in each case to one row of Table A Table 26
Compounds of the formula Ia.1 in which $R^6$ is —$CH_2CH_2SCH_3$, and the combination of $R^{2a}$, $R^{2b}$, $R^{2c}$ and $R^4$ for a compound corresponds in each case to one row of Table A Table 27
Compounds of the formula Ia.1 in which $R^6$ is —$CH_2CH_2S(O)CH_3$, and the combination of $R^{2a}$, $R^{2b}$, $R^{2c}$ and $R^4$ for a compound corresponds in each case to one row of Table A Table 28
Compounds of the formula Ia.1 in which $R^6$ is —$CH_2CH_2S(O)_2CH_3$, and the combination of $R^{2a}$, $R^{2b}$, $R^{2c}$ and $R^4$ for a compound corresponds in each case to one row of Table A Table 29
Compounds of the formula Ia.1 in which $R^6$ is —$CH_2CH_2SCH_2CH_3$, and the combination of $R^{2a}$, $R^{2b}$, $R^{2c}$ and $R^4$ for a compound corresponds in each case to one row of Table A Table 30
Compounds of the formula Ia.1 in which $R^6$ is —$CH_2CH_2S(O)CH_2CH_3$, and the combination of $R^{2a}$, $R^{2b}$, $R^{2c}$ and $R^4$ for a compound corresponds in each case to one row of Table A Table 31
Compounds of the formula Ia.1 in which $R^6$ is $-CH_2CH_2S(O)_2CH_2CH_3$, and the combination of $R^{2a}$, $R^{2b}$, $R^{2c}$ and $R^4$ for a compound corresponds in each case to one row of Table A Table 32
Compounds of the formula Ia.1 in which $R^6$ is $-CH_2CH_2S(O)_2CH_2CH=CH_2$, and the combination of $R^{2a}$, $R^{2b}$, $R^{2c}$ and $R^4$ for a compound corresponds in each case to one row of Table A Table 33
Compounds of the formula Ia.1 in which $R^6$ is $-CH_2CH_2S(O)_2CH_2C\equiv CH$, and the combination of $R^{2a}$, $R^{2b}$, $R^{2c}$ and $R^4$ for a compound corresponds in each case to one row of Table A Table 34
Compounds of the formula Ia.1 in which $R^6$ is $-CH_2CH_2S(O)_2CH_2$-cyclopropyl, and the combination of $R^{2a}$, $R^{2b}$, $R^{2c}$ and $R^4$ for a compound corresponds in each case to one row of Table A Table 35
Compounds of the formula Ia.1 in which $R^6$ is $-CH(CH_3)CH_2SCH_3$, and the combination of $R^{2a}$, $R^{2b}$, $R^{2c}$ and $R^4$ for a compound corresponds in each case to one row of Table A Table 36
Compounds of the formula Ia.1 in which $R^6$ is $-CH(CH_3)CH_2S(O)CH_3$, and the combination of $R^{2a}$, $R^{2b}$, $R^{2c}$ and $R^4$ for a compound corresponds in each case to one row of Table A Table 37
Compounds of the formula Ia.1 in which $R^6$ is $-CH(CH_3)CH_2S(O)_2CH_3$, and the combination of $R^{2a}$, $R^{2b}$, $R^{2c}$ and $R^4$ for a compound corresponds in each case to one row of Table A Table 38
Compounds of the formula Ia.1 in which $R^6$ is $-C(CH_3)_2CH_2SCH_3$, and the combination of $R^{2a}$, $R^{2b}$, $R^{2c}$ and $R^4$ for a compound corresponds in each case to one row of Table A Table 39
Compounds of the formula Ia.1 in which $R^6$ is $-C(CH_3)_2CH_2S(O)CH_3$, and the combination of $R^{2a}$, $R^{2b}$, $R^{2c}$ and $R^4$ for a compound corresponds in each case to one row of Table A Table 40
Compounds of the formula Ia.1 in which $R^6$ is $-C(CH_3)_2CH_2S(O)_2CH_3$, and the combination of $R^{2a}$, $R^{2b}$, $R^{2c}$ and $R^4$ for a compound corresponds in each case to one row of Table A Table 41
Compounds of the formula Ia.1 in which $R^6$ is $-CH_2CH_2SCF_3$, and the combination of $R^{2a}$, $R^{2b}$, $R^{2c}$ and $R^4$ for a compound corresponds in each case to one row of Table A Table 42
Compounds of the formula Ia.1 in which $R^6$ is $NH_2$, and the combination of $R^{2a}$, $R^{2b}$, $R^{2c}$ and $R^4$ for a compound corresponds in each case to one row of Table A Table 43
Compounds of the formula Ia.1 in which $R^6$ is $CH_2CHF_2$, and the combination of $R^{2a}$, $R^{2b}$, $R^{2c}$ and $R^4$ for a compound corresponds in each case to one row of Table A Table 44
Compounds of the formula Ia.1 in which $R^6$ is $CH_2CF_3$, and the combination of $R^{2a}$, $R^{2b}$, $R^{2c}$ and $R^4$ for a compound corresponds in each case to one row of Table A Table 45
Compounds of the formula Ia.1 in which $R^6$ is $CH_2CH_2CF_3$, and the combination of $R^{2a}$, $R^{2b}$, $R^{2c}$ and $R^4$ for a compound corresponds in each case to one row of Table A Table 46
Compounds of the formula Ia.1 in which $R^6$ is $CH(CH_3)CF_3$, and the combination of $R^{2a}$, $R^{2b}$, $R^{2c}$ and $R^4$ for a compound corresponds in each case to one row of Table A Table 47
Compounds of the formula Ia.1 in which $R^6$ is $CH(CF_3)_2$, and the combination of $R^{2a}$, $R^{2b}$, $R^{2c}$ and $R^4$ for a compound corresponds in each case to one row of Table A Table 48
Compounds of the formula Ia.1 in which $R^6$ is $CH_2CH_2CH_2CF_3$, and the combination of $R^{2a}$, $R^{2b}$, $R^{2c}$ and $R^4$ for a compound corresponds in each case to one row of Table A Table 49
Compounds of the formula Ia.1 in which $R^6$ is $CH_2CH=CF_2$, and the combination of $R^{2a}$, $R^{2b}$, $R^{2c}$ and $R^4$ for a compound corresponds in each case to one row of Table A Table 50
Compounds of the formula Ia.1 in which $R^6$ is $CH_2CF=CF_2$, and the combination of $R^{2a}$, $R^{2b}$, $R^{2c}$ and $R^4$ for a compound corresponds in each case to one row of Table A Table 51
Compounds of the formula Ia.1 in which $R^6$ is $CH_2CH_2CH=CF_2$, and the combination of $R^{2a}$, $R^{2b}$, $R^{2c}$ and $R^4$ for a compound corresponds in each case to one row of Table A Table 52
Compounds of the formula Ia.1 in which $R^6$ is $CH_2CH_2CF=CF_2$, and the combination of $R^{2a}$, $R^{2b}$, $R^{2c}$ and $R^4$ for a compound corresponds in each case to one row of Table A Table 53
Compounds of the formula Ia.1 in which $R^6$ is cyclopropyl, and the combination of $R^{2a}$, $R^{2b}$, $R^{2c}$ and $R^4$ for a compound corresponds in each case to one row of Table A Table 54
Compounds of the formula Ia.1 in which $R^6$ is 1-cyanocyclopropyl, and the combination of $R^{2a}$, $R^{2b}$, $R^{2c}$ and $R^4$ for a compound corresponds in each case to one row of Table A Table 55
Compounds of the formula Ia.1 in which $R^6$ is 1-(pyridin-2-yl)-cyclopropyl, and the combination of $R^{2a}$, $R^{2b}$, $R^{2c}$ and $R^4$ for a compound corresponds in each case to one row of Table A Table 56
Compounds of the formula Ia.1 in which $R^6$ is cyclobutyl, and the combination of $R^{2a}$, $R^{2b}$, $R^{2c}$ and $R^4$ for a compound corresponds in each case to one row of Table A Table 57
Compounds of the formula Ia.1 in which $R^6$ is 1-cyanocyclobutyl, and the combination of $R^{2a}$, $R^{2b}$, $R^{2c}$ and $R^4$ for a compound corresponds in each case to one row of Table A Table 58
Compounds of the formula Ia.1 in which $R^6$ is 3,3-difluorocyclobutyl, and the combination of $R^{2a}$, $R^{2b}$, $R^{2c}$ and $R^4$ for a compound corresponds in each case to one row of Table A Table 59
Compounds of the formula Ia.1 in which $R^6$ is cyclopentyl, and the combination of $R^{2a}$, $R^{2b}$, $R^{2c}$ and $R^4$ for a compound corresponds in each case to one row of Table A Table 60
Compounds of the formula Ia.1 in which $R^6$ is 1-cyano-cyclopentyl, and the combination of $R^{2a}$, $R^{2b}$, $R^{2c}$ and $R^4$ for a compound corresponds in each case to one row of Table A Table 61
Compounds of the formula Ia.1 in which $R^6$ is cyclohexyl, and the combination of $R^{2a}$, $R^{2b}$, $R^{2c}$ and $R^4$ for a compound corresponds in each case to one row of Table A Table 62
Compounds of the formula Ia.1 in which $R^6$ is 1-cyano-cyclohexyl, and the combination of $R^{2a}$, $R^{2b}$, $R^{2c}$ and $R^4$ for a compound corresponds in each case to one row of Table A Table 63
Compounds of the formula Ia.1 in which $R^6$ is —$CH_2$-cyclopropyl, and the combination of $R^{2a}$, $R^{2b}$, $R^{2c}$ and $R^4$ for a compound corresponds in each case to one row of Table A Table 64
Compounds of the formula Ia.1 in which $R^6$ is —$CH_2$-(1-cyano-cyclopropyl), and the combination of $R^{2a}$, $R^{2b}$, $R^{2c}$ and $R^4$ for a compound corresponds in each case to one row of Table A Table 65
Compounds of the formula Ia.1 in which $R^6$ is —$CH_2$-(1-fluoro-cyclopropyl), and the combination of $R^{2a}$, $R^{2b}$, $R^{2c}$ and $R^4$ for a compound corresponds in each case to one row of Table A Table 66
Compounds of the formula Ia.1 in which $R^6$ is —$CH_2$-(1-chloro-cyclopropyl), and the combination of $R^{2a}$, $R^{2b}$, $R^{2c}$ and $R^4$ for a compound corresponds in each case to one row of Table A Table 67
Compounds of the formula Ia.1 in which $R^6$ is —$CH_2$-(1-bromo-cyclopropyl), and the combination of $R^{2a}$, $R^{2b}$, $R^{2c}$ and $R^4$ for a compound corresponds in each case to one row of Table A Table 68
Compounds of the formula Ia.1 in which $R^6$ is —$CH_2$-(2,2-difluorocyclopropyl), and the combination of $R^{2a}$, $R^{2b}$, $R^{2c}$ and $R^4$ for a compound corresponds in each case to one row of Table A Table 69
Compounds of the formula Ia.1 in which $R^6$ is —$CH_2$-(2,2-dichlorocyclopropyl), and the combination of $R^{2a}$, $R^{2b}$, $R^{2c}$ and $R^4$ for a compound corresponds in each case to one row of Table A Table 70
Compounds of the formula Ia.1 in which $R^6$ is —$CH_2$-(2,2-dibromocyclopropyl), and the combination of $R^{2a}$, $R^{2b}$, $R^{2c}$ and $R^4$ for a compound corresponds in each case to one row of Table A Table 71
Compounds of the formula Ia.1 in which $R^6$ is —$CH_2$-cyclobutyl, and the combination of $R^{2a}$, $R^{2b}$, $R^{2c}$ and $R^4$ for a compound corresponds in each case to one row of Table A Table 72
Compounds of the formula Ia.1 in which $R^6$ is —$CH_2$-(1-cyano-cyclobutyl), and the combination of $R^{2a}$, $R^{2b}$, $R^{2c}$ and $R^4$ for a compound corresponds in each case to one row of Table A Table 73
Compounds of the formula Ia.1 in which $R^6$ is —$CH_2$-(1-fluoro-cyclobutyl), and the combination of $R^{2a}$, $R^{2b}$, $R^{2c}$ and $R^4$ for a compound corresponds in each case to one row of Table A Table 74
Compounds of the formula Ia.1 in which $R^6$ is —$CH_2$-(1-chloro-cyclobutyl), and the combination of $R^{2a}$, $R^{2b}$, $R^{2c}$ and $R^4$ for a compound corresponds in each case to one row of Table A Table 75
Compounds of the formula Ia.1 in which $R^6$ is —$CH_2$-(2,2-difluorocyclobutyl), and the combination of $R^{2a}$, $R^{2b}$, $R^{2c}$ and $R^4$ for a compound corresponds in each case to one row of Table A Table 76
Compounds of the formula Ia.1 in which $R^6$ is —$CH_2$-(3,3-difluorocyclobutyl), and the combination of $R^{2a}$, $R^{2b}$, $R^{2c}$ and $R^4$ for a compound corresponds in each case to one row of Table A Table 77
Compounds of the formula Ia.1 in which $R^6$ is —$CH_2$-(2,2,3,3-tetrafluorocyclobutyl), and the combination of $R^{2a}$, $R^{2b}$, $R^{2c}$ and $R^4$ for a compound corresponds in each case to one row of Table A Table 78
Compounds of the formula Ia.1 in which $R^6$ is —$CH_2$-(2,2,3,3,4,4-hexafluorocyclobutyl), and the combination of $R^{2a}$, $R^{2b}$, $R^{2c}$ and $R^4$ for a compound corresponds in each case to one row of Table A Table 79
Compounds of the formula Ia.1 in which $R^6$ is —$CH_2$-cyclopentyl, and the combination of $R^{2a}$, $R^{2b}$, $R^{2c}$ and $R^4$ for a compound corresponds in each case to one row of Table A Table 80
Compounds of the formula Ia.1 in which $R^6$ is —$CH_2$-(-1-fluoro-cyclopentyl), and the combination of $R^{2a}$, $R^{2b}$, $R^{2c}$ and $R^4$ for a compound corresponds in each case to one row of Table A Table 81
Compounds of the formula Ia.1 in which $R^6$ is —$CH_2$-(1-chloro-cyclopentyl), and the combination of $R^{2a}$, $R^{2b}$, $R^{2c}$ and $R^4$ for a compound corresponds in each case to one row of Table A Table 82
Compounds of the formula Ia.1 in which $R^6$ is —$CH_2$-(1-cyano-cyclopentyl), and the combination of $R^{2a}$, $R^{2b}$, $R^{2c}$ and $R^4$ for a compound corresponds in each case to one row of Table A Table 83
Compounds of the formula Ia.1 in which $R^6$ is —$CH_2$-(2,2-difluorocyclopentyl), and the combination of $R^{2a}$, $R^{2b}$, $R^{2c}$ and $R^4$ for a compound corresponds in each case to one row of Table A Table 84
Compounds of the formula Ia.1 in which $R^6$ is —$CH_2$-(3,3-difluorocyclopentyl), and the combination of $R^{2a}$, $R^{2b}$, $R^{2c}$ and $R^4$ for a compound corresponds in each case to one row of Table A Table 85
Compounds of the formula Ia.1 in which $R^6$ is —$CH_2$-cyclohexyl, and the combination of $R^{2a}$, $R^{2b}$, $R^{2c}$ and $R^4$ for a compound corresponds in each case to one row of Table A Table 86
Compounds of the formula Ia.1 in which $R^6$ is —$CH_2$-(1-fluorocyclohexyl), and the combination of $R^{2a}$, $R^{2b}$, $R^{2c}$ and $R^4$ for a compound corresponds in each case to one row of Table A Table 87
Compounds of the formula Ia.1 in which $R^6$ is —$CH_2$-(1-chlorocyclohexyl), and the combination of $R^{2a}$, $R^{2b}$, $R^{2c}$ and $R^4$ for a compound corresponds in each case to one row of Table A Table 88
Compounds of the formula Ia.1 in which $R^6$ is —$CH_2$-(1-cyanocyclohexyl), and the combination of $R^{2a}$, $R^{2b}$, $R^{2c}$ and $R^4$ for a compound corresponds in each case to one row of Table A Table 89
Compounds of the formula Ia.1 in which $R^6$ is thietan-3-yl, and the combination of $R^{2a}$, $R^{2b}$, $R^{2c}$ and $R^4$ for a compound corresponds in each case to one row of Table A Table 90
Compounds of the formula Ia.1 in which $R^6$ is 1-oxo-thietan-3-yl, and the combination of $R^{2a}$, $R^{2b}$, $R^{2c}$ and $R^4$ for a compound corresponds in each case to one row of Table A Table 91
Compounds of the formula Ia.1 in which $R^6$ is 1,1-dioxo-thietan-3-yl, and the combination of $R^{2a}$, $R^{2b}$, $R^{2c}$ and $R^4$ for a compound corresponds in each case to one row of Table A Table 92
Compounds of the formula Ia.1 in which $R^6$ is 3-methyl-thietan-3-yl, and the combination of $R^{2a}$, $R^{2b}$, $R^{2c}$ and $R^4$ for a compound corresponds in each case to one row of Table A Table 93
Compounds of the formula Ia.1 in which $R^6$ is 3-methyl-1-oxo-thietan-3-yl, and the combination of $R^{2a}$, $R^{2b}$, $R^{2c}$ and $R^4$ for a compound corresponds in each case to one row of Table A Table 94
Compounds of the formula Ia.1 in which $R^6$ is 3-methyl-1,1-di-oxo-thietan-3-yl, and the combination of $R^{2a}$, $R^{2b}$, $R^{2c}$ and $R^4$ for a compound corresponds in each case to one row of Table A Table 95
Compounds of the formula Ia.1 in which $R^6$ is —$CH_2$-thietan-3-yl, and the combination of $R^{2a}$, $R^{2b}$, $R^{2c}$ and $R^4$ for a compound corresponds in each case to one row of Table A Table 96
Compounds of the formula Ia.1 in which $R^6$ is —$CH_2$-(1-oxo-thietan-3-yl), and the combination of $R^{2a}$, $R^{2b}$, $R^{2c}$ and $R^4$ for a compound corresponds in each case to one row of Table A Table 97
Compounds of the formula Ia.1 in which $R^6$ is —$CH_2$-(1,1-di-oxo-thietan-3-yl), and the combination of $R^{2a}$, $R^{2b}$, $R^{2c}$ and $R^4$ for a compound corresponds in each case to one row of Table A Table 98
Compounds of the formula Ia.1 in which $R^6$ is tetrahydrothiophen-3-yl, and the combination of $R^{2a}$, $R^{2b}$, $R^{2c}$ and $R^4$ for a compound corresponds in each case to one row of Table A Table 99
Compounds of the formula Ia.1 in which $R^6$ is 1-oxo-tetrahydrothiophen-3-yl, and the combination of $R^{2a}$, $R^{2b}$, $R^{2c}$ and $R^4$ for a compound corresponds in each case to one row of Table A Table 100
Compounds of the formula Ia.1 in which $R^6$ is 1,1-dioxo-tetrahydrothiophen-3-yl, and the combination of $R^{2a}$, $R^{2b}$, $R^{2c}$ and $R^4$ for a compound corresponds in each case to one row of Table A Table 101
Compounds of the formula Ia.1 in which $R^6$ is $CH_2$—$CONH_2$, and the combination of $R^{2a}$, $R^{2b}$, $R^{2c}$ and $R^4$ for a compound corresponds in each case to one row of Table A Table 102
Compounds of the formula Ia.1 in which $R^6$ is phenyl, and the combination of $R^{2a}$, $R^{2b}$, $R^{2c}$ and $R^4$ for a compound corresponds in each case to one row of Table A Table 103
Compounds of the formula Ia.1 in which $R^6$ is pyridin-2-yl, and the combination of $R^{2a}$, $R^{2b}$, $R^{2c}$ and $R^4$ for a compound corresponds in each case to one row of Table A Table 104
Compounds of the formula Ia.1 in which $R^6$ is pyridin-3-yl, and the combination of $R^{2a}$, $R^{2b}$, $R^{2c}$ and $R^4$ for a compound corresponds in each case to one row of Table A Table 105
Compounds of the formula Ia.1 in which $R^6$ is pyridin-4-yl, and the combination of $R^{2a}$, $R^{2b}$, $R^{2c}$ and $R^4$ for a compound corresponds in each case to one row of Table A Table 106
Compounds of the formula Ia.1 in which $R^6$ is pyrimidin-2-yl, and the combination of $R^{2a}$, $R^{2b}$, $R^{2c}$ and $R^4$ for a compound corresponds in each case to one row of Table A Table 107
Compounds of the formula Ia.1 in which $R^6$ is pyrimidin-4-yl, and the combination of $R^{2a}$, $R^{2b}$, $R^{2c}$ and $R^4$ for a compound corresponds in each case to one row of Table A Table 108
Compounds of the formula Ia.1 in which $R^6$ is pyrimidin-5-yl, and the combination of $R^{2a}$, $R^{2b}$, $R^{2c}$ and $R^4$ for a compound corresponds in each case to one row of Table A Table 109
Compounds of the formula Ia.1 in which $R^6$ is thiazol-2-yl, and the combination of $R^{2a}$, $R^{2b}$, $R^{2c}$ and $R^4$ for a compound corresponds in each case to one row of Table A Table 110
Compounds of the formula Ia.1 in which $R^6$ is 4-trifluoromethylthiazol-2-yl, and the combination of $R^{2a}$, $R^{2b}$, $R^{2c}$ and $R^4$ for a compound corresponds in each case to one row of Table A Table 111
Compounds of the formula Ia.1 in which $R^6$ is oxetan-3-yl, and the combination of $R^{2a}$, $R^{2b}$, $R^{2c}$ and $R^4$ for a compound corresponds in each case to one row of Table A Table 112
Compounds of the formula Ia.1 in which $R^6$ is tetrahydrofuran-2-yl, and the combination of $R^{2a}$, $R^{2b}$, $R^{2c}$ and $R^4$ for a compound corresponds in each case to one row of Table A Table 113
Compounds of the formula Ia.1 in which $R^6$ is tetrahydrofuran-3-yl, and the combination of $R^{2a}$, $R^{2b}$, $R^{2c}$ and $R^4$ for a compound corresponds in each case to one row of Table A Table 114
Compounds of the formula Ia.1 in which $R^6$ is 2-oxotetrahydrofuran-3-yl, and the combination of $R^{2a}$, $R^{2b}$, $R^{2c}$ and $R^4$ for a compound corresponds in each case to one row of Table A Table 115
Compounds of the formula Ia.1 in which $R^6$ is 2-oxopyrrolidin-3-yl, and the combination of $R^{2a}$, $R^{2b}$, $R^{2c}$ and $R^4$ for a compound corresponds in each case to one row of Table A Table 116
Compounds of the formula Ia.1 in which $R^6$ is 1-methyl-2-oxopyrrolidin-3-yl, and the combination of $R^{2a}$, $R^{2b}$, $R^{2c}$ and $R^4$ for a compound corresponds in each case to one row of Table A Table 117
Compounds of the formula Ia.1 in which $R^6$ is 2-oxo-1-(2,2,2-trifluoroethyl)-pyrrolidin-3-yl, and the combination of $R^{2a}$, $R^{2b}$, $R^{2c}$ and $R^4$ for a compound corresponds in each case to one row of Table A Table 118
Compounds of the formula Ia.1 in which $R^6$ is azetidin-3-yl, and the combination of $R^{2a}$, $R^{2b}$, $R^{2c}$ and $R^4$ for a compound corresponds in each case to one row of Table A Table 119
Compounds of the formula Ia.1 in which $R^6$ is 1-acetyl-azetidin-3-yl, and the combination of $R^{2a}$, $R^{2b}$, $R^{2c}$ and $R^4$ for a compound corresponds in each case to one row of Table A Table 120
Compounds of the formula Ia.1 in which $R^6$ is —NH-phenyl, and the combination of $R^{2a}$, $R^{2b}$, $R^{2c}$ and $R^4$ for a compound corresponds in each case to one row of Table A Table 121
Compounds of the formula Ia.1 in which $R^6$ is —NH-pyridin-2-yl, and the combination of $R^{2a}$, $R^{2b}$, $R^{2c}$ and $R^4$ for a compound corresponds in each case to one row of Table A Table 122
Compounds of the formula Ia.1 in which $R^6$ is —NH-pyridin-3-yl, and the combination of $R^{2a}$, $R^{2b}$, $R^{2c}$ and $R^4$ for a compound corresponds in each case to one row of Table A Table 123
Compounds of the formula Ia.1 in which $R^6$ is —NH-pyridin-4-yl, and the combination of $R^{2a}$, $R^{2b}$, $R^{2c}$ and $R^4$ for a compound corresponds in each case to one row of Table A Table 124
Compounds of the formula Ia.1 in which $R^6$ is —N(CH$_3$)-pyridin-2-yl, and the combination of $R^{2a}$, $R^{2b}$, $R^{2c}$ and $R^4$ for a compound corresponds in each case to one row of Table A Table 125
Compounds of the formula Ia.1 in which $R^6$ is —NH-pyrimidin-2-yl, and the combination of $R^{2a}$, $R^{2b}$, $R^{2c}$ and $R^4$ for a compound corresponds in each case to one row of Table A Table 126
Compounds of the formula Ia.1 in which $R^6$ is —NH-pyrimidin-4-yl, and the combination of $R^{2a}$, $R^{2b}$, $R^{2c}$ and $R^4$ for a compound corresponds in each case to one row of Table A Table 127
Compounds of the formula Ia.1 in which $R^6$ is —NH-pyrimidin-5-yl, and the combination of $R^{2a}$, $R^{2b}$, $R^{2c}$ and $R^4$ for a compound corresponds in each case to one row of Table A Table 128
Compounds of the formula Ia.1 in which $R^6$ is —CH$_2$—COOCH$_3$, and the combination of $R^{2a}$, $R^{2b}$, $R^{2c}$ and $R^4$ for a compound corresponds in each case to one row of Table A Table 129
Compounds of the formula Ia.1 in which $R^6$ is —CH$_2$—COO—CH$_2$CH$_3$, and the combination of $R^{2a}$, $R^{2b}$, $R^{2c}$ and $R^4$ for a compound corresponds in each case to one row of Table A Table 130
Compounds of the formula Ia.1 in which $R^6$ is —CH$_2$—CONH—CH$_3$, and the combination of $R^{2a}$, $R^{2b}$, $R^{2c}$ and $R^4$ for a compound corresponds in each case to one row of Table A Table 131
Compounds of the formula Ia.1 in which $R^6$ is —CH$_2$—CONH—CH$_2$CH$_3$, and the combination of $R^{2a}$, $R^{2b}$, $R^{2c}$ and $R^4$ for a compound corresponds in each case to one row of Table A Table 132
Compounds of the formula Ia.1 in which $R^6$ is —CH$_2$—CONH—CH$_2$CHF$_2$, and the combination of $R^{2a}$, $R^{2b}$, $R^{2c}$ and $R^4$ for a compound corresponds in each case to one row of Table A Table 133
Compounds of the formula Ia.1 in which $R^6$ is —CH$_2$—CONH—CH$_2$CF$_3$, and the combination of $R^{2a}$, $R^{2b}$, $R^{2c}$ and $R^4$ for a compound corresponds in each case to one row of Table A Table 134
Compounds of the formula Ia.1 in which $R^6$ is —CH$_2$—CONH-cyclopropyl, and the combination of $R^{2a}$, $R^{2b}$, $R^{2c}$ and $R^4$ for a compound corresponds in each case to one row of Table A Table 135
Compounds of the formula Ia.1 in which $R^6$ is —CH$_2$—CONH-isopropyl, and the combination of $R^{2a}$, $R^{2b}$, $R^{2c}$ and $R^4$ for a compound corresponds in each case to one row of Table A Table 136
Compounds of the formula Ia.1 in which $R^6$ is —CH$_2$—CONH—CH(CF$_3$)CH$_3$, and the combination of $R^{2a}$, $R^{2b}$, $R^{2c}$ and $R^4$ for a compound corresponds in each case to one row of Table A Table 137
Compounds of the formula Ia.1 in which $R^6$ is —CH$_2$—CONH—CH(CF$_3$)$_2$, and the combination of $R^{2a}$, $R^{2b}$, $R^{2c}$ and $R^4$ for a compound corresponds in each case to one row of Table A Table 138
Compounds of the formula Ia.1 in which $R^6$ is —CH$_2$—CONH—CH$_2$CH$_2$CF$_3$, and the combination of $R^{2a}$, $R^{2b}$, $R^{2c}$ and $R^4$ for a compound corresponds in each case to one row of Table A Table 139
Compounds of the formula Ia.1 in which $R^6$ is —CH$_2$—CONH—CH$_2$CN, and the combination of $R^{2a}$, $R^{2b}$, $R^{2c}$ and $R^4$ for a compound corresponds in each case to one row of Table A Table 140
Compounds of the formula Ia.1 in which $R^6$ is —CH$_2$—CONH—CH$_2$CH=CH$_2$, and the combination of $R^{2a}$, $R^{2b}$, $R^{2c}$ and $R^4$ for a compound corresponds in each case to one row of Table A Table 141
Compounds of the formula Ia.1 in which $R^6$ is —CH$_2$—CONH—CH$_2$C≡CH, and the combination of $R^{2a}$, $R^{2b}$, $R^{2c}$ and $R^4$ for a compound corresponds in each case to one row of Table A Table 142
Compounds of the formula Ia.1 in which $R^6$ is —CH$_2$—CON(CH$_3$)—CH$_2$CF$_3$, and the combination of $R^{2a}$, $R^{2b}$, $R^{2c}$ and $R^4$ for a compound corresponds in each case to one row of Table A Table 143

Compounds of the formula Ia.1 in which $R^6$ is —CH($CH_3$)—CONH—$CH_2CF_3$, and the combination of $R^{2a}$, $R^{2b}$, $R^{2c}$ and $R^4$ for a compound corresponds in each case to one row of Table A Table 144

Compounds of the formula Ia.1 in which $R^6$ is —$CH_2$—CONH—$CH_2$-cyclopropyl, and the combination of $R^{2a}$, $R^{2b}$, $R^{2c}$ and $R^4$ for a compound corresponds in each case to one row of Table A Table 145

Compounds of the formula Ia.1 in which $R^6$ is —$CH_2$—CONH—$CH_2$-(1-cyano-cyclopropyl), and the combination of $R^{2a}$, $R^{2b}$, $R^{2c}$ and $R^4$ for a compound corresponds in each case to one row of Table A Table 146

Compounds of the formula Ia.1 in which $R^6$ is —$CH_2$—CONH-thietan-3-yl, and the combination of $R^{2a}$, $R^{2b}$, $R^{2c}$ and $R^4$ for a compound corresponds in each case to one row of Table A Table 147

Compounds of the formula Ia.1 in which $R^6$ is —$CH_2$—CONH-1-oxo-thietan-3-yl, and the combination of $R^{2a}$, $R^{2b}$, $R^{2c}$ and $R^4$ for a compound corresponds in each case to one row of Table A Table 148

Compounds of the formula Ia.1 in which $R^6$ is —$CH_2$—CONH-1,1-dioxo-thietan-3-yl, and the combination of $R^{2a}$, $R^{2b}$, $R^{2c}$ and $R^4$ for a compound corresponds in each case to one row of Table A Table 149

Compounds of the formula Ia.1 in which $R^6$ is benzyl, and the combination of $R^{2a}$, $R^{2b}$, $R^{2c}$ and $R^4$ for a compound corresponds in each case to one row of Table A Table 150

Compounds of the formula Ia.1 in which $R^6$ is 2-fluorobenzyl, and the combination of $R^{2a}$, $R^{2b}$, $R^{2c}$ and $R^4$ for a compound corresponds in each case to one row of Table A Table 151

Compounds of the formula Ia.1 in which $R^6$ is 3-fluorobenzyl, and the combination of $R^{2a}$, $R^{2b}$, $R^{2c}$ and $R^4$ for a compound corresponds in each case to one row of Table A Table 152

Compounds of the formula Ia.1 in which $R^6$ is 4-fluorobenzyl, and the combination of $R^{2a}$, $R^{2b}$, $R^{2c}$ and $R^4$ for a compound corresponds in each case to one row of Table A Table 153

Compounds of the formula Ia.1 in which $R^6$ is 2-chlorobenzyl, and the combination of $R^{2a}$, $R^{2b}$, $R^{2c}$ and $R^4$ for a compound corresponds in each case to one row of Table A Table 154

Compounds of the formula Ia.1 in which $R^6$ is 3-chlorobenzyl, and the combination of $R^{2a}$, $R^{2b}$, $R^{2c}$ and $R^4$ for a compound corresponds in each case to one row of Table A Table 155

Compounds of the formula Ia.1 in which $R^6$ is 4-chlorobenzyl, and the combination of $R^{2a}$, $R^{2b}$, $R^{2c}$ and $R^4$ for a compound corresponds in each case to one row of Table A Table 156

Compounds of the formula Ia.1 in which $R^6$ is pyridazin-4-yl-methyl, and the combination of $R^{2a}$, $R^{2b}$, $R^{2c}$ and $R^4$ for a compound corresponds in each case to one row of Table A Table 157

Compounds of the formula Ia.1 in which $R^6$ is tetrahydrofuran-2-yl-methyl, and the combination of $R^{2a}$, $R^{2b}$, $R^{2c}$ and $R^4$ for a compound corresponds in each case to one row of Table A Table 158

Compounds of the formula Ia.1 in which $R^6$ is [1,2,3]-thiadiazol-5-yl-methyl, and the combination of $R^{2a}$, $R^{2b}$, $R^{2c}$ and $R^4$ for a compound corresponds in each case to one row of Table A Table 159

Compounds of the formula Ia.1 in which $R^6$ is 2-methylsulfanylbenzyl, and the combination of $R^{2a}$, $R^{2b}$, $R^{2c}$ and $R^4$ for a compound corresponds in each case to one row of Table A Table 160

Compounds of the formula Ia.1 in which $R^6$ is 3-methylsulfanylbenzyl, and the combination of $R^{2a}$, $R^{2b}$, $R^{2c}$ and $R^4$ for a compound corresponds in each case to one row of Table A Table 161

Compounds of the formula Ia.1 in which $R^6$ is 4-methylsulfanylbenzyl, and the combination of $R^{2a}$, $R^{2b}$, $R^{2c}$ and $R^4$ for a compound corresponds in each case to one row of Table A Table 162

Compounds of the formula Ia.1 in which $R^6$ is 2-methylsulfonylbenzyl, and the combination of $R^{2a}$, $R^{2b}$, $R^{2c}$ and $R^4$ for a compound corresponds in each case to one row of Table A Table 163

Compounds of the formula Ia.1 in which $R^6$ is 3-methylsulfonylbenzyl, and the combination of $R^{2a}$, $R^{2b}$, $R^{2c}$ and $R^4$ for a compound corresponds in each case to one row of Table A Table 164

Compounds of the formula Ia.1 in which $R^6$ is 4-methylsulfonylbenzyl, and the combination of $R^{2a}$, $R^{2b}$, $R^{2c}$ and $R^4$ for a compound corresponds in each case to one row of Table A Table 165

Compounds of the formula Ia.1 in which $R^6$ is pyridin-2-yl-methyl, and the combination of $R^{2a}$, $R^{2b}$, $R^{2c}$ and $R^4$ for a compound corresponds in each case to one row of Table A Table 166

Compounds of the formula Ia.1 in which $R^6$ is pyridin-3-yl-methyl, and the combination of $R^{2a}$, $R^{2b}$, $R^{2c}$ and $R^4$ for a compound corresponds in each case to one row of Table A Table 167

Compounds of the formula Ia.1 in which $R^6$ is 6-chloropyridin-3-yl-methyl, and the combination of $R^{2a}$, $R^{2b}$, $R^{2c}$ and $R^4$ for a compound corresponds in each case to one row of Table A Table 168

Compounds of the formula Ia.1 in which $R^6$ is pyridin-4-yl-methyl, and the combination of $R^{2a}$, $R^{2b}$, $R^{2c}$ and $R^4$ for a compound corresponds in each case to one row of Table A Table 169

Compounds of the formula Ia.1 in which $R^6$ is 5-chloropyridin-2-yl-methyl, and the combination of $R^{2a}$, $R^{2b}$, $R^{2c}$ and $R^4$ for a compound corresponds in each case to one row of Table A Table 170

Compounds of the formula Ia.1 in which $R^6$ is 6-(trifluoromethyl)-pyridin-2-yl-methyl, and the combination of $R^{2a}$, $R^{2b}$, $R^{2c}$ and $R^4$ for a compound corresponds in each case to one row of Table A Table 171

Compounds of the formula Ia.1 in which $R^6$ is 6-(trifluoromethyl)-pyridin-3-yl-methyl, and the combination of $R^{2a}$, $R^{2b}$, $R^{2c}$ and $R^4$ for a compound corresponds in each case to one row of Table A Table 172
Compounds of the formula Ia.1 in which $R^6$ is pyrimidin-2-yl-methyl, and the combination of $R^{2a}$, $R^{2b}$, $R^{2c}$ and $R^4$ for a compound corresponds in each case to one row of Table A Table 173
Compounds of the formula Ia.1 in which $R^6$ is pyrimidin-4-yl-methyl, and the combination of $R^{2a}$, $R^{2b}$, $R^{2c}$ and $R^4$ for a compound corresponds in each case to one row of Table A Table 174
Compounds of the formula Ia.1 in which $R^6$ is pyrimidin-5-yl-methyl, and the combination of $R^{2a}$, $R^{2b}$, $R^{2c}$ and $R^4$ for a compound corresponds in each case to one row of Table A Table 175
Compounds of the formula Ia.1 in which $R^6$ is pyridazin-3-yl-methyl, and the combination of $R^{2a}$, $R^{2b}$, $R^{2c}$ and $R^4$ for a compound corresponds in each case to one row of Table A Table 176
Compounds of the formula Ia.1 in which $R^6$ is pyrazin-2-yl-methyl, and the combination of $R^{2a}$, $R^{2b}$, $R^{2c}$ and $R^4$ for a compound corresponds in each case to one row of Table A Table 177
Compounds of the formula Ia.1 in which $R^6$ is thien-2-yl-methyl, and the combination of $R^{2a}$, $R^{2b}$, $R^{2c}$ and $R^4$ for a compound corresponds in each case to one row of Table A Table 178
Compounds of the formula Ia.1 in which $R^6$ is thien-3-yl-methyl, and the combination of $R^{2a}$, $R^{2b}$, $R^{2c}$ and $R^4$ for a compound corresponds in each case to one row of Table A Table 179
Compounds of the formula Ia.1 in which $R^6$ is thiazol-2-yl-methyl, and the combination of $R^{2a}$, $R^{2b}$, $R^{2c}$ and $R^4$ for a compound corresponds in each case to one row of Table A Table 180
Compounds of the formula Ia.1 in which $R^6$ is thiazol-4-yl-methyl, and the combination of $R^{2a}$, $R^{2b}$, $R^{2c}$ and $R^4$ for a compound corresponds in each case to one row of Table A Table 181
Compounds of the formula Ia.1 in which $R^6$ is thiazol-5-yl-methyl, and the combination of $R^{2a}$, $R^{2b}$, $R^{2c}$ and $R^4$ for a compound corresponds in each case to one row of Table A Table 182
Compounds of the formula Ia.1 in which $R^6$ is 2-chloro-thiazol-5-yl-methyl, and the combination of $R^{2a}$, $R^{2b}$, $R^{2c}$ and $R^4$ for a compound corresponds in each case to one row of Table A Table 183
Compounds of the formula Ia.1 in which $R^6$ is isothiazol-3-yl-methyl, and the combination of $R^{2a}$, $R^{2b}$, $R^{2c}$ and $R^4$ for a compound corresponds in each case to one row of Table A Table 184
Compounds of the formula Ia.1 in which $R^6$ is isothiazol-4-yl-methyl, and the combination of $R^{2a}$, $R^{2b}$, $R^{2c}$ and $R^4$ for a compound corresponds in each case to one row of Table A Table 185
Compounds of the formula Ia.1 in which $R^6$ is isothiazol-5-yl-methyl, and the combination of $R^{2a}$, $R^{2b}$, $R^{2c}$ and $R^4$ for a compound corresponds in each case to one row of Table A Table 186
Compounds of the formula Ia.1 in which $R^6$ is oxazol-2-yl-methyl, and the combination of $R^{2a}$, $R^{2b}$, $R^{2c}$ and $R^4$ for a compound corresponds in each case to one row of Table A Table 187
Compounds of the formula Ia.1 in which $R^6$ is oxazol-4-yl-methyl, and the combination of $R^{2a}$, $R^{2b}$, $R^{2c}$ and $R^4$ for a compound corresponds in each case to one row of Table A Table 188
Compounds of the formula Ia.1 in which $R^6$ is oxazol-5-yl-methyl, and the combination of $R^{2a}$, $R^{2b}$, $R^{2c}$ and $R^4$ for a compound corresponds in each case to one row of Table A Table 189
Compounds of the formula Ia.1 in which $R^6$ is isoxazol-3-yl-methyl, and the combination of $R^{2a}$, $R^{2b}$, $R^{2c}$ and $R^4$ for a compound corresponds in each case to one row of Table A Table 190
Compounds of the formula Ia.1 in which $R^6$ is isoxazol-4-yl-methyl, and the combination of $R^{2a}$, $R^{2b}$, $R^{2c}$ and $R^4$ for a compound corresponds in each case to one row of Table A Table 191
Compounds of the formula Ia.1 in which $R^6$ is isoxazol-5-yl-methyl, and the combination of $R^{2a}$, $R^{2b}$, $R^{2c}$ and $R^4$ for a compound corresponds in each case to one row of Table A Table 192
Compounds of the formula Ia.1 in which $R^6$ is [1,2,3]-thiadiazol-4-yl-methyl, and the combination of $R^{2a}$, $R^{2b}$, $R^{2c}$ and $R^4$ for a compound corresponds in each case to one row of Table A Table 193
Compounds of the formula Ia.1 in which $R^6$ is [1,3,4]-thiadiazol-2-yl-methyl, and the combination of $R^{2a}$, $R^{2b}$, $R^{2c}$ and $R^4$ for a compound corresponds in each case to one row of Table A Table 194
Compounds of the formula Ia.1 in which $R^6$ is 1-methyl-imidazol-2-yl-methyl, and the combination of $R^{2a}$, $R^{2b}$, $R^{2c}$ and $R^4$ for a compound corresponds in each case to one row of Table A Table 195
Compounds of the formula Ia.1 in which $R^6$ is 1-methyl-imidazol-4-yl-methyl, and the combination of $R^{2a}$, $R^{2b}$, $R^{2c}$ and $R^4$ for a compound corresponds in each case to one row of Table A Table 196
Compounds of the formula Ia.1 in which $R^6$ is 1-methyl-imidazol-5-yl-methyl, and the combination of $R^{2a}$, $R^{2b}$, $R^{2c}$ and $R^4$ for a compound corresponds in each case to one row of Table A Table 197
Compounds of the formula Ia.1 in which $R^6$ is 1-methyl-pyrazol-3-yl-methyl, and the combination of $R^{2a}$, $R^{2b}$, $R^{2c}$ and $R^4$ for a compound corresponds in each case to one row of Table A Table 198
Compounds of the formula Ia.1 in which $R^6$ is 2-methyl-pyrazol-3-yl-methyl, and the combination of $R^{2a}$, $R^{2b}$, $R^{2c}$ and $R^4$ for a compound corresponds in each case to one row of Table A Table 199
Compounds of the formula Ia.1 in which $R^6$ is tetrahydrofuran-3-yl-methyl, and the combination of $R^{2a}$, $R^{2b}$, $R^{2c}$ and $R^4$ for a compound corresponds in each case to one row of Table A Table 200
Compounds of the formula Ia.1 in which $R^6$ is 1,3-dioxolan-2-yl-methyl, and the combination of $R^{2a}$, $R^{2b}$, $R^{2c}$ and $R^4$ for a compound corresponds in each case to one row of Table A Table 201
Compounds of the formula Ia.1 in which $R^6$ is 2-pyridyl-eth-1-yl, and the combination of $R^{2a}$, $R^{2b}$, $R^{2c}$ and $R^4$ for a compound corresponds in each case to one row of Table A Table 202
Compounds of the formula Ia.1 in which $R^6$ is (1R)-2-pyridyl-eth-1-yl, and the combination of $R^{2a}$, $R^{2b}$, $R^{2c}$ and $R^4$ for a compound corresponds in each case to one row of Table A Table 203
Compounds of the formula Ia.1 in which $R^6$ is (1S)-2-pyridyl-eth-1-yl, and the combination of $R^{2a}$, $R^{2b}$, $R^{2c}$ and $R^4$ for a compound corresponds in each case to one row of Table A Table 204
Compounds of the formula Ia.1 in which $R^6$ is —$CONH_2$, and the combination of $R^{2a}$, $R^{2b}$, $R^{2c}$ and $R^4$ for a compound corresponds in each case to one row of Table A Table 205
Compounds of the formula Ia.1 in which $R^6$ is —CONH—$CH_3$, and the combination of $R^{2a}$, $R^{2b}$, $R^{2c}$ and $R^4$ for a compound corresponds in each case to one row of Table A Table 206
Compounds of the formula Ia.1 in which $R^6$ is —CONH—$CH_2CH_3$, and the combination of $R^{2a}$, $R^{2b}$, $R^{2c}$ and $R^4$ for a compound corresponds in each case to one row of Table A Table 207
Compounds of the formula Ia.1 in which $R^6$ is —CONH—$CH_2CH_2CH_3$, and the combination of $R^{2a}$, $R^{2b}$, $R^{2c}$ and $R^4$ for a compound corresponds in each case to one row of Table A Table 208
Compounds of the formula Ia.1 in which $R^6$ is —CONH-cyclopropyl, and the combination of $R^{2a}$, $R^{2b}$, $R^{2c}$ and $R^4$ for a compound corresponds in each case to one row of Table A Table 209
Compounds of the formula Ia.1 in which $R^6$ is —CONH—$CH_2$-cyclopropyl, and the combination of $R^{2a}$, $R^{2b}$, $R^{2c}$ and $R^4$ for a compound corresponds in each case to one row of Table A Table 210
Compounds of the formula Ia.1 in which $R^6$ is —CONH-phenyl, and the combination of $R^{2a}$, $R^{2b}$, $R^{2c}$ and $R^4$ for a compound corresponds in each case to one row of Table A Table 211
Compounds of the formula Ia.1 in which $R^6$ is —CONH-benzyl, and the combination of $R^{2a}$, $R^{2b}$, $R^{2c}$ and $R^4$ for a compound corresponds in each case to one row of Table A Table 212
Compounds of the formula Ia.1 in which $R^6$ is —NHCO—NH—$CH_3$, and the combination of $R^{2a}$, $R^{2b}$, $R^{2c}$ and $R^4$ for a compound corresponds in each case to one row of Table A Table 213
Compounds of the formula Ia.1 in which $R^6$ is —NHCO—NH—$CH_2CH_3$, and the combination of $R^{2a}$, $R^{2b}$, $R^{2c}$ and $R^4$ for a compound corresponds in each case to one row of Table A Table 214
Compounds of the formula Ia.1 in which $R^6$ is —NHCO—NH—$CH_2CH_2CH_3$, and the combination of $R^{2a}$, $R^{2b}$, $R^{2c}$ and $R^4$ for a compound corresponds in each case to one row of Table A Table 215
Compounds of the formula Ia.1 in which $R^6$ is —NHCO—NH—$CH(CH_3)_2$, and the combination of $R^{2a}$, $R^{2b}$, $R^{2c}$ and $R^4$ for a compound corresponds in each case to one row of Table A Table 216
Compounds of the formula Ia.1 in which $R^6$ is —NHCO—NH—$CH_2CF_3$, and the combination of $R^{2a}$, $R^{2b}$, $R^{2c}$ and $R^4$ for a compound corresponds in each case to one row of Table A Table 217
Compounds of the formula Ia.1 in which $R^6$ is —NHCO—NH—$CH_2CHF_2$, and the combination of $R^{2a}$, $R^{2b}$, $R^{2c}$ and $R^4$ for a compound corresponds in each case to one row of Table A Table 218
Compounds of the formula Ia.1 in which $R^6$ is —NHCO—NH—$CH(CH_3)CF_3$, and the combination of $R^{2a}$, $R^{2b}$, $R^{2c}$ and $R^4$ for a compound corresponds in each case to one row of Table A Table 219
Compounds of the formula Ia.1 in which $R^6$ is —NHCO—NH—$CH(CF_3)_2$, and the combination of $R^{2a}$, $R^{2b}$, $R^{2c}$ and $R^4$ for a compound corresponds in each case to one row of Table A Table 220
Compounds of the formula Ia.1 in which $R^6$ is —NHCO—NH—$CH_2CN$, and the combination of $R^{2a}$, $R^{2b}$, $R^{2c}$ and $R^4$ for a compound corresponds in each case to one row of Table A Table 221
Compounds of the formula Ia.1 in which $R^6$ is —NHCO—NH—$CH_2$—CH=$CH_2$, and the combination of $R^{2a}$, $R^{2b}$, $R^{2c}$ and $R^4$ for a compound corresponds in each case to one row of Table A Table 222
Compounds of the formula Ia.1 in which $R^6$ is —NHCO—NH—$CH_2$—CH=CH, and the combination of $R^{2a}$, $R^{2b}$, $R^{2c}$ and $R^4$ for a compound corresponds in each case to one row of Table A Table 223
Compounds of the formula Ia.1 in which $R^6$ is —NHCO—NH-cyclopropyl, and the combination of $R^{2a}$, $R^{2b}$, $R^{2c}$ and $R^4$ for a compound corresponds in each case to one row of Table A Table 224
Compounds of the formula Ia.1 in which $R^6$ is —NHCO—NH-(1-cyanocyclopropyl), and the combination of $R^{2a}$, $R^{2b}$, $R^{2c}$ and $R^4$ for a compound corresponds in each case to one row of Table A Table 225
Compounds of the formula Ia.1 in which $R^6$ is —NHCO—NH-cyclobutyl, and the combination of $R^{2a}$, $R^{2b}$, $R^{2c}$ and $R^4$ for a compound corresponds in each case to one row of Table A Table 226
Compounds of the formula Ia.1 in which $R^6$ is —NHCO—NH-(1-cyanocyclobutyl), and the combination of $R^{2a}$, $R^{2b}$, $R^{2c}$ and $R^4$ for a compound corresponds in each case to one row of Table A Table 227
Compounds of the formula Ia.1 in which $R^6$ is —NHCO—NH—$CH_2$-cyclopropyl, and the combination of $R^{2a}$, $R^{2b}$, $R^{2c}$ and $R^4$ for a compound corresponds in each case to one row of Table A Table 228
Compounds of the formula Ia.1 in which $R^6$ is —NHCO—NH—$CH_2$-(1-cyanocyclopropyl), and the combination of $R^{2a}$, $R^{2b}$, $R^{2c}$ and $R^4$ for a compound corresponds in each case to one row of Table A Table 229
Compounds of the formula Ia.1 in which $R^6$ is —CH=NOCH$_3$, and the combination of $R^{2a}$, $R^{2b}$, $R^{2c}$ and $R^4$ for a compound corresponds in each case to one row of Table A Table 230
Compounds of the formula Ia.1 in which $R^6$ is —CH=NOCH$_2$CF$_3$, and the combination of $R^{2a}$, $R^{2b}$, $R^{2c}$ and $R^4$ for a compound corresponds in each case to one row of Table A Table 231
Compounds of the formula Ia.1 in which $R^6$ is 3-oxo-isoxazolidin-4-yl, and the combination of $R^{2a}$, $R^{2b}$, $R^{2c}$ and $R^4$ for a compound corresponds in each case to one row of Table A Table 232
Compounds of the formula Ia.1 in which $R^6$ is 2-methyl-3-oxo-isoxazolidin-4-yl, and the combination of $R^{2a}$, $R^{2b}$, $R^{2c}$ and $R^4$ for a compound corresponds in each case to one row of Table A Table 233
Compounds of the formula Ia.1 in which $R^6$ is 2-ethyl-3-oxo-isoxazolidin-4-yl, and the combination of $R^{2a}$, $R^{2b}$, $R^{2c}$ and $R^4$ for a compound corresponds in each case to one row of Table A Table 234
Compounds of the formula Ia.1 in which $R^6$ is 2-propyl-3-oxo-isoxazolidin-4-yl, and the combination of $R^{2a}$, $R^{2b}$, $R^{2c}$ and $R^4$ for a compound corresponds in each case to one row of Table A Table 235
Compounds of the formula Ia.1 in which $R^6$ is 2-butyl-3-oxo-isoxazolidin-4-yl, and the combination of $R^{2a}$, $R^{2b}$, $R^{2c}$ and $R^4$ for a compound corresponds in each case to one row of Table A Table 236
Compounds of the formula Ia.1 in which $R^6$ is 2-(but-2-yl)-3-oxo-isoxazolidin-4-yl, and the combination of $R^{2a}$, $R^{2b}$, $R^{2c}$ and $R^4$ for a compound corresponds in each case to one row of Table A Table 237
Compounds of the formula Ia.1 in which $R^6$ is 2-(3-bromopropyl)-3-oxo-isoxazolidin-4-yl, and the combination of $R^{2a}$, $R^{2b}$, $R^{2c}$ and $R^4$ for a compound corresponds in each case to one row of Table A Table 238
Compounds of the formula Ia.1 in which $R^6$ is 2-(2-fluoroethyl)-3-oxo-isoxazolidin-4-yl, and the combination of $R^{2a}$, $R^{2b}$, $R^{2c}$ and $R^4$ for a compound corresponds in each case to one row of Table A Table 239
Compounds of the formula Ia.1 in which $R^6$ is 2-(2,2-difluoroethyl)-3-oxo-isoxazolidin-4-yl, and the combination of $R^{2a}$, $R^{2b}$, $R^{2c}$ and $R^4$ for a compound corresponds in each case to one row of Table A Table 240
Compounds of the formula Ia.1 in which $R^6$ is 2-(2,2,2-trifluoroethyl)-3-oxo-isoxazolidin-4-yl, and the combination of $R^{2a}$, $R^{2b}$, $R^{2c}$ and $R^4$ for a compound corresponds in each case to one row of Table A Table 241
Compounds of the formula Ia.1 in which $R^6$ is 2-(3,3,3-trifluoropropyl)-3-oxo-isoxazolidin-4-yl, and the combination of $R^{2a}$, $R^{2b}$, $R^{2c}$ and $R^4$ for a compound corresponds in each case to one row of Table A Table 242
Compounds of the formula Ia.1 in which $R^6$ is 2-(2-methoxyethyl)-3-oxo-isoxazolidin-4-yl, and the combination of $R^{2a}$, $R^{2b}$, $R^{2c}$ and $R^4$ for a compound corresponds in each case to one row of Table A Table 243
Compounds of the formula Ia.1 in which $R^6$ is 2-(1-methoxy-prop-2-yl)-3-oxo-isoxazolidin-4-yl, and the combination of $R^{2a}$, $R^{2b}$, $R^{2c}$ and $R^4$ for a compound corresponds in each case to one row of Table A Table 244
Compounds of the formula Ia.1 in which $R^6$ is 2-cyclobutyl-3-oxo-isoxazolidin-4-yl, and the combination of $R^{2a}$, $R^{2b}$, $R^{2c}$ and $R^4$ for a compound corresponds in each case to one row of Table A Table 245
Compounds of the formula Ia.1 in which $R^6$ is 2-(2-methylcyclohex-1-yl)-3-oxo-isoxazolidin-4-yl, and the combination of $R^{2a}$, $R^{2b}$, $R^{2c}$ and $R^4$ for a compound corresponds in each case to one row of Table A Table 246
Compounds of the formula Ia.1 in which $R^6$ is 2-(phenylmethyl)-3-oxo-isoxazolidin-4-yl, and the combination of $R^{2a}$, $R^{2b}$, $R^{2c}$ and $R^4$ for a compound corresponds in each case to one row of Table A Table 247
Compounds of the formula Ia.1 in which $R^6$ is 2-(1-phenyl-eth-1-yl)-3-oxo-isoxaolidin-4-yl, and the combination of $R^{2a}$, $R^{2b}$, $R^{2c}$ and $R^4$ for a compound corresponds in each case to one row of Table A Table 248
Compounds of the formula Ia.1 in which $R^6$ is 2-(2-phenyl-eth-1-yl)-3-oxo-isoxazolidin-4-yl, and the combination of $R^{2a}$, $R^{2b}$, $R^{2c}$ and $R^4$ for a compound corresponds in each case to one row of Table A Table 249
Compounds of the formula Ia.1 in which $R^6$ is 2-[(3-chlorophenyl)-methyl]-3-oxo-isoxazolidin-4-yl, and the combination of $R^{2a}$, $R^{2b}$, $R^{2c}$ and $R^4$ for a compound corresponds in each case to one row of Table A Table 250
Compounds of the formula Ia.1 in which $R^6$ is 2-[(2-fluorophenyl)-methyl]-3-oxo-isoxazolidin-4-yl, and the combination of $R^{2a}$, $R^{2b}$, $R^{2c}$ and $R^4$ for a compound corresponds in each case to one row of Table A Table 251
Compounds of the formula Ia.1 in which $R^6$ is 2-[(4-methoxyphenyl)-methyl]-3-oxo-isoxazolidin-4-yl, and the combination of $R^{2a}$, $R^{2b}$, $R^{2c}$ and $R^4$ for a compound corresponds in each case to one row of Table A Table 252
Compounds of the formula Ia.1 in which $R^6$ is 2-[(2-trifluoromethylphenyl)-methyl]-3-oxo-isoxazolidin-4-yl, and the combination of $R^{2a}$, $R^{2b}$, $R^{2c}$ and $R^4$ for a compound corresponds in each case to one row of Table A Table 253
Compounds of the formula Ia.1 in which $R^6$ is 2-[(2-trifluoromethoxyphenyl)-methyl]-3-oxo-isoxazolidin-4-yl, and the combination of $R^{2a}$, $R^{2b}$, $R^{2c}$ and $R^4$ for a compound corresponds in each case to one row of Table A Table 254
Compounds of the formula Ia.1 in which $R^6$ is 2-(pyridin-2-yl-methyl)-3-oxo-isoxazolidin-4-yl, and the combination of $R^{2a}$, $R^{2b}$, $R^{2c}$ and $R^4$ for a compound corresponds in each case to one row of Table A Table 255
Compounds of the formula Ia.1 in which $R^6$ is 2-(pyridin-3-yl-methyl)-3-oxo-isoxazolidin-4-yl, and the combination of $R^{2a}$, $R^{2b}$, $R^{2c}$ and $R^4$ for a compound corresponds in each case to one row of Table A Table 256
Compounds of the formula Ia.1 in which $R^6$ is 2-[(2-chloropyridin-5-yl)-methyl]-3-oxo-isoxazolidin-4-yl, and the combination of $R^{2a}$, $R^{2b}$, $R^{2c}$ and $R^4$ for a compound corresponds in each case to one row of Table A Table 257
Compounds of the formula Ia.1 in which $R^6$ is 2-[(1-methyl-1H-imidazol-4-yl)-methyl]-3-oxo-isoxazolidin-4-yl, and the combination of $R^{2a}$, $R^{2b}$, $R^{2c}$ and $R^4$ for a compound corresponds in each case to one row of Table A Table 258
Compounds of the formula Ia.1 in which $R^6$ is 2-[(furan-2-yl)-methyl]-3-oxo-isoxazolidin-4-yl, and the combination of $R^{2a}$, $R^{2b}$, $R^{2c}$ and $R^4$ for a compound corresponds in each case to one row of Table A Table 259
Compounds of the formula Ia.1 in which $R^6$ is 2-[(2-thiophen-2'-yl)-eth-1-yl]-3-oxo-isoxazolidin-4-yl, and the combination of $R^{2a}$, $R^{2b}$, $R^{2c}$ and $R^4$ for a compound corresponds in each case to one row of Table A Table 260
Compounds of the formula Ia.1 in which $R^6$ is 2-[2-(indol-3'-yl)-eth-1-yl]-3-oxo-isoxazolidin-4-yl, and the combination of $R^{2a}$, $R^{2b}$, $R^{2c}$ and $R^4$ for a compound corresponds in each case to one row of Table A Table 261
Compounds of the formula Ia.1 in which $R^6$ is 2-[(1H-benzimidazol-2-yl)-methyl]-3-oxo-isoxazolidin-4-yl, and the combination of $R^{2a}$, $R^{2b}$, $R^{2c}$ and $R^4$ for a compound corresponds in each case to one row of Table A Table 262
Compounds of the formula Ia.1 in which $R^6$ is 2-[(oxetan-2-yl)-methyl]-3-oxo-isoxazolidin-4-yl, and the combination of $R^{2a}$, $R^{2b}$, $R^{2c}$ and $R^4$ for a compound corresponds in each case to one row of Table A Table 263
Compounds of the formula Ia.1 in which $R^6$ is 2-[(tetrahydrofuran-2-yl)-methyl]-3-oxo-isoxazolidin-4-yl, and the combination of $R^{2a}$, $R^{2b}$, $R^{2c}$ and $R^4$ for a compound corresponds in each case to one row of Table A Table 264
Compounds of the formula Ia.1 in which $R^6$ is 2-[(2-[1',3']dioxolan-2'-yl)-eth-1-yl]-3-oxo-isoxazolidin-4-yl, and the combination of $R^{2a}$, $R^{2b}$, $R^{2c}$ and $R^4$ for a compound corresponds in each case to one row of Table A Table 265
Compounds of the formula Ia.1 in which $R^6$ is 2-[(2-morpholin-4'-yl)-eth-1yl]-3-oxo-isoxazolidin-4-yl, and the combination of $R^{2a}$, $R^{2b}$, $R^{2c}$ and $R^4$ for a compound corresponds in each case to one row of Table A Table 266
Compounds of the formula Ia.1 in which $R^6$ is 2-[(2-benzo[1',3']dioxol-5'-yl)-eth-1-yl]-3-oxo-isoxazolidin-4-yl, and the combination of $R^{2a}$, $R^{2b}$, $R^{2c}$ and $R^4$ for a compound corresponds in each case to one row of Table A Table 267
Compounds of the formula Ia.1 in which $R^6$ is 2-[(2,3-dihydro-benzo[1,4]dioxin-6-yl)-methyl]-3-oxo-isoxazolidin-4-yl, and the combination of $R^{2a}$, $R^{2b}$, $R^{2c}$ and $R^4$ for a compound corresponds in each case to one row of Table A Table 268
Compounds of the formula Ia.1 in which $R^6$ is 2-(2-chlorophenyl)-3-oxo-isoxazolidin-4-yl, and the combination of $R^{2a}$, $R^{2b}$, $R^{2c}$ and $R^4$ for a compound corresponds in each case to one row of Table A Table 269
Compounds of the formula Ia.1 in which $R^6$ is 2-(3-fluorophenyl)-3-oxo-isoxazolidin-4-yl, and the combination of $R^{2a}$, $R^{2b}$, $R^{2c}$ and $R^4$ for a compound corresponds in each case to one row of Table A Table 270
Compounds of the formula Ia.1 in which $R^6$ is 2-(2-methylphenyl)-3-oxo-isoxazolidin-4-yl, and the combination of $R^{2a}$, $R^{2b}$, $R^{2c}$ and $R^4$ for a compound corresponds in each case to one row of Table A Table 271
Compounds of the formula Ia.1 in which $R^6$ is 2-(2-chloro-6-methylphenyl)-3-oxo-isoxazolidin-4-yl, and the combination of $R^{2a}$, $R^{2b}$, $R^{2c}$ and $R^4$ for a compound corresponds in each case to one row of Table A Table 272
Compounds of the formula Ia.1 in which $R^6$ is 2-(2-trifluoromethylphenyl)-3-oxo-isoxazolidin-4-yl, and the combination of $R^{2a}$, $R^{2b}$, $R^{2c}$ and $R^4$ for a compound corresponds in each case to one row of Table A Table 273
Compounds of the formula Ia.1 in which $R^6$ is 2-(2,4-dimethoxyphenyl)-3-oxo-isoxazolidin-4-yl, and the combination of $R^{2a}$, $R^{2b}$, $R^{2c}$ and $R^4$ for a compound corresponds in each case to one row of Table A Table 274
Compounds of the formula Ia.1 in which $R^6$ is 2-(3-methylpyrid-2-yl)-3-oxo-isoxazolidin-4-yl, and the combination of $R^{2a}$, $R^{2b}$, $R^{2c}$ and $R^4$ for a compound corresponds in each case to one row of Table A Table 275
Compounds of the formula Ia.1 in which $R^6$ is 2-(1,3-dimethyl-1H-pyrazol-5-yl)-3-oxo-isoxazolidin-4-yl, and the combination of $R^{2a}$, $R^{2b}$, $R^{2c}$ and $R^4$ for a compound corresponds in each case to one row of Table A Table 276
Compounds of the formula Ia.1 in which $R^6$ is 2-(4-methylthiazol-2-yl)-3-oxo-isoxazolidin-4-yl, and the combination of $R^{2a}$, $R^{2b}$, $R^{2c}$ and $R^4$ for a compound corresponds in each case to one row of Table A Table 277
Compounds of the formula Ia.1 in which $R^6$ is 2-(5-methylthiadiazol-2-yl)-3-oxo-isoxazolidin-4-yl, and the combination of $R^{2a}$, $R^{2b}$, $R^{2c}$ and $R^4$ for a compound corresponds in each case to one row of Table A Table 278
Compounds of the formula Ia.1 in which $R^6$ is 2-(quinolin-2-yl)-3-oxo-isoxazolidin-4-yl, and the combination of $R^{2a}$, $R^{2b}$, $R^{2c}$ and $R^4$ for a compound corresponds in each case to one row of Table A Table 279
Compounds of the formula Ia.1 in which $R^6$ is 2-(quinolin-5-yl)-3-oxo-isoxazolidin-4-yl, and the combination of $R^{2a}$, $R^{2b}$, $R^{2c}$ and $R^4$ for a compound corresponds in each case to one row of Table A Table 280
Compounds of the formula Ia.1 in which $R^6$ is 2-(benzothiazol-6-yl)-3-oxo-isoxazolidin-4-yl, and the combination of $R^{2a}$, $R^{2b}$, $R^{2c}$ and $R^4$ for a compound corresponds in each case to one row of Table A Table 281
Compounds of the formula Ia.1 in which $R^6$ is 2-(4-methylbenzothiazol-2-yl)-3-oxo-isoxazolidin-4-yl, and the combination of $R^{2a}$, $R^{2b}$, $R^{2c}$ and $R^4$ for a compound corresponds in each case to one row of Table A Table 282
Compounds of the formula Ia.1 in which $R^6$ is 2-(thietan-3-yl)-3-oxo-isoxazolidin-4-yl, and the combination of $R^{2a}$, $R^{2b}$, $R^{2c}$ and $R^4$ for a compound corresponds in each case to one row of Table A Table 283
Compounds of the formula Ia.1 in which $R^6$ is 2-(1-oxo-thietan-3-yl)-3-oxo-isoxazolidin-4-yl, and the combination of $R^{2a}$, $R^{2b}$, $R^{2c}$ and $R^4$ for a compound corresponds in each case to one row of Table A Table 284
Compounds of the formula Ia.1 in which $R^6$ is 2-(1,1-dioxo-thietan-3-yl)-3-oxo-isoxazolidin-4-yl, and the combination of $R^{2a}$, $R^{2b}$, $R^{2c}$ and $R^4$ for a compound corresponds in each case to one row of Table A Table 285
Compounds of the formula Ia.1 in which $R^6$ is 2-(3-methylthietan-3-yl)-3-oxo-isoxazolidin-4-yl, and the combination of $R^{2a}$, $R^{2b}$, $R^{2c}$ and $R^4$ for a compound corresponds in each case to one row of Table A Table 286
Compounds of the formula Ia.1 in which $R^6$ is 2-(oxetan-3-yl)-3-oxo-isoxazolidin-4-yl, and the combination of $R^{2a}$, $R^{2b}$, $R^{2c}$ and $R^4$ for a compound corresponds in each case to one row of Table A Table 287
Compounds of the formula Ia.1 in which $R^6$ is 2-(tetrahydropyran-4-yl)-3-oxo-isoxazolidin-4-yl, and the combination of $R^{2a}$, $R^{2b}$, $R^{2c}$ and $R^4$ for a compound corresponds in each case to one row of Table A Table 288
Compounds of the formula Ia.1 in which $R^6$ is —NH—$CH_3$, and the combination of $R^{2a}$, $R^{2b}$, $R^{2c}$ and $R^4$ for a compound corresponds in each case to one row of Table A Table 289
Compounds of the formula Ia.1 in which $R^6$ is —NH—$CH_2CH_3$, and the combination of $R^{2a}$, $R^{2b}$, $R^{2c}$ and $R^4$ for a compound corresponds in each case to one row of Table A Table 290
Compounds of the formula Ia.1 in which $R^6$ is —$CH_2CH_2SCH_2CH$=$CH_2$, and the combination of $R^{2a}$, $R^{2b}$, $R^{2c}$ and $R^4$ for a compound corresponds in each case to one row of Table A Table 291
Compounds of the formula Ia.1 in which $R^6$ is —$CH_2CH_2S(O)CH_2CH$=$CH_2$, and the combination of $R^{2a}$, $R^{2b}$, $R^{2c}$ and $R^4$ for a compound corresponds in each case to one row of Table A Table 292
Compounds of the formula Ia.1 in which $R^6$ is —$CH_2CH_2SCH_2C$—CH, and the combination of $R^{2a}$, $R^{2b}$, $R^{2c}$ and $R^4$ for a compound corresponds in each case to one row of Table A Table 293
Compounds of the formula Ia.1 in which $R^6$ is —$CH_2CH_2S(O)CH_2C$—CH, and the combination of $R^{2a}$, $R^{2b}$, $R^{2c}$ and $R^4$ for a compound corresponds in each case to one row of Table A Table 294
Compounds of the formula Ia.1 in which $R^6$ is —$CH_2CH_2SCH_2$-cyclopropyl, and the combination of $R^{2a}$, $R^{2b}$, $R^{2c}$ and $R^4$ for a compound corresponds in each case to one row of Table A Table 295
Compounds of the formula Ia.1 in which $R^6$ is —$CH_2CH_2S(O)CH_2$-cyclopropyl, and the combination of $R^{2a}$, $R^{2b}$, $R^{2c}$ and $R^4$ for a compound corresponds in each case to one row of Table A Table 296
Compounds of the formula Ia.1 in which $R^6$ is —CONH—$CH_2CF_3$, and the combination of $R^{2a}$, $R^{2b}$, $R^{2c}$ and $R^4$ for a compound corresponds in each case to one row of Table A Table 297
Compounds of the formula Ia.1 in which $R^6$ is —CONH—$CH_2CH_2CF_3$, and the combination of $R^{2a}$, $R^{2b}$, $R^{2c}$ and $R^4$ for a compound corresponds in each case to one row of Table A Table 298
Compounds of the formula Ia.1 in which $R^6$ is —$CH_2$-thietan-2-yl, and the combination of $R^{2a}$, $R^{2b}$, $R^{2c}$ and $R^4$ for a compound corresponds in each case to one row of Table A Table 299
Compounds of the formula Ia.1 in which $R^6$ is —$CH_2$-(1-oxo-thietan-2-yl), and the combination of $R^{2a}$, $R^{2b}$, $R^{2c}$ and $R^4$ for a compound corresponds in each case to one row of Table A Table 300
Compounds of the formula Ia.1 in which $R^6$ is —$CH_2$-(1,1-di-oxo-thietan-2-yl), and the combination of $R^{2a}$, $R^{2b}$, $R^{2c}$ and $R^4$ for a compound corresponds in each case to one row of Table A Tables 301 to 600
Compounds of the formula Ia.2 in which $R^6$ is as defined in tables 1 to 300, and the combination of $R^{2a}$, $R^{2b}$, $R^{2c}$ and $R^4$ for a compound corresponds in each case to one row of Table A Tables 601 to 900
Compounds of the formula Ia.3 in which $R^6$ is as defined in tables 1 to 300, and the combination of $R^{2a}$, $R^{2b}$, $R^{2c}$ and $R^4$ for a compound corresponds in each case to one row of Table A Tables 901 to 1200
Compounds of the formula Ia.4 in which $R^6$ is as defined in tables 1 to 300, and the combination of $R^{2a}$, $R^{2b}$, $R^{2c}$ and $R^4$ for a compound corresponds in each case to one row of Table A Tables 1201 to 1500
Compounds of the formula Ia.5 in which $R^6$ is as defined in tables 1 to 300, and the combination of $R^{2a}$, $R^{2b}$, $R^{2c}$ and $R^4$ for a compound corresponds in each case to one row of Table A Tables 1501 to 1800
Compounds of the formula Ia.6 in which $R^6$ is as defined in tables 1 to 300, and the combination of $R^{2a}$, $R^{2b}$, $R^{2c}$ and $R^4$ for a compound corresponds in each case to one row of Table A Tables 1801 to 2100
Compounds of the formula Ia.7 in which $R^6$ is as defined in tables 1 to 300, and the combination of $R^{2a}$, $R^{2b}$, $R^{2c}$ and $R^4$ for a compound corresponds in each case to one row of Table A Tables 2101 to 2400
Compounds of the formula Ia.8 in which $R^6$ is as defined in tables 1 to 300, and the combination of $R^{2a}$, $R^{2b}$, $R^{2c}$ and $R^4$ for a compound corresponds in each case to one row of Table A Tables 2401 to 2700

Compounds of the formula Ia.9 in which $R^6$ is as defined in tables 1 to 300, and the combination of $R^{2a}$, $R^{2b}$, $R^{2c}$ and $R^4$ for a compound corresponds in each case to one row of Table A Tables 2701 to 3000

Compounds of the formula Ia.10 in which $R^6$ is as defined in tables 1 to 300, and the combination of $R^{2a}$, $R^{2b}$, $R^{2c}$ and $R^4$ for a compound corresponds in each case to one row of Table A Tables 3001 to 3300

Compounds of the formula Ia.11 in which $R^6$ is as defined in tables 1 to 300, and the combination of $R^{2a}$, $R^{2b}$, $R^{2c}$ and $R^4$ for a compound corresponds in each case to one row of Table A Tables 3301 to 3600

Compounds of the formula Ia.12 in which $R^6$ is as defined in tables 1 to 300, and the combination of $R^{2a}$, $R^{2b}$, $R^{2c}$ and $R^4$ for a compound corresponds in each case to one row of Table A Table 3601

Compounds of the formula Ia.13 in which $R^{9a}$ and $R^{9b}$ are methyl, and the combination of $R^{2a}$, $R^{2b}$, $R^{2c}$ and $R^4$ for a compound corresponds in each case to one row of Table A Table 3602

Compounds of the formula Ia.13 in which $R^{9a}$ and $R^{9b}$ are ethyl, and the combination of $R^{2a}$, $R^{2b}$, $R^{2c}$ and $R^4$ for a compound corresponds in each case to one row of Table A Table 3603

Compounds of the formula Ia.13 in which $R^{9a}$ and $R^{9b}$ are n-propyl, and the combination of $R^{2a}$, $R^{2b}$, $R^{2c}$ and $R^4$ for a compound corresponds in each case to one row of Table A Table 3604

Compounds of the formula Ia.13 in which $R^{9a}$ and $R^{9b}$ are isopropyl, and the combination of $R^{2a}$, $R^{2b}$, $R^{2c}$ and $R^4$ for a compound corresponds in each case to one row of Table A Tables 3605 to 3608

Compounds of the formula Ia.14 in which $R^{9a}$ and $R^{9b}$ are as defined in tables 3601 to 3604, and the combination of $R^{2a}$, $R^{2b}$, $R^{2c}$ and $R^4$ for a compound corresponds in each case to one row of Table A Table 3609

Compounds of the formula Ia.15 in which $R^8$ is hydrogen, and the combination of $R^{2a}$, $R^{2b}$, $R^{2c}$ and $R^4$ for a compound corresponds in each case to one row of Table A Table 3610

Compounds of the formula Ia.15 in which $R^8$ is methyl, and the combination of $R^{2a}$, $R^{2b}$, $R^{2c}$ and $R^4$ for a compound corresponds in each case to one row of Table A Table 3611

Compounds of the formula Ia.15 in which $R^8$ is ethyl, and the combination of $R^{2a}$, $R^{2b}$, $R^{2c}$ and $R^4$ for a compound corresponds in each case to one row of Table A Table 3612

Compounds of the formula Ia.15 in which $R^8$ is propyl, and the combination of $R^{2a}$, $R^{2b}$, $R^{2c}$ and $R^4$ for a compound corresponds in each case to one row of Table A Table 3613

Compounds of the formula Ia.15 in which $R^8$ is isopropyl, and the combination of $R^{2a}$, $R^{2b}$, $R^{2c}$ and $R^4$ for a compound corresponds in each case to one row of Table A Table 3614

Compounds of the formula Ia.15 in which $R^8$ is n-butyl, and the combination of $R^{2a}$, $R^{2b}$, $R^{2c}$ and $R^4$ for a compound corresponds in each case to one row of Table A Table 3615

Compounds of the formula Ia.15 in which $R^8$ is sec-butyl, and the combination of $R^{2a}$, $R^{2b}$, $R^{2c}$ and $R^4$ for a compound corresponds in each case to one row of Table A Table 3616

Compounds of the formula Ia.15 in which $R^8$ is isobutyl, and the combination of $R^{2a}$, $R^{2b}$, $R^{2c}$ and $R^4$ for a compound corresponds in each case to one row of Table A Table 3617

Compounds of the formula Ia.15 in which $R^8$ is tert-butyl, and the combination of $R^{2a}$, $R^{2b}$, $R^{2c}$ and $R^4$ for a compound corresponds in each case to one row of Table A Table 3618

Compounds of the formula Ia.15 in which $R^8$ is $CH_2F$, and the combination of $R^{2a}$, $R^{2b}$, $R^{2c}$ and $R^4$ for a compound corresponds in each case to one row of Table A Table 3619

Compounds of the formula Ia.15 in which $R^8$ is $CHF_2$, and the combination of $R^{2a}$, $R^{2b}$, $R^{2c}$ and $R^4$ for a compound corresponds in each case to one row of Table A Table 3620

Compounds of the formula Ia.15 in which $R^8$ is $CF_3$, and the combination of $R^{2a}$, $R^{2b}$, $R^{2c}$ and $R^4$ for a compound corresponds in each case to one row of Table A Table 3621

Compounds of the formula Ia.15 in which $R^8$ is $CH_2CHF_2$, and the combination of $R^{2a}$, $R^{2b}$, $R^{2c}$ and $R^4$ for a compound corresponds in each case to one row of Table A Table 3622

Compounds of the formula Ia.15 in which $R^8$ is $CH_2CF_3$, and the combination of $R^{2a}$, $R^{2b}$, $R^{2c}$ and $R^4$ for a compound corresponds in each case to one row of Table A Table 3623

Compounds of the formula Ia.15 in which $R^8$ is $CF_2CF_3$, and the combination of $R^{2a}$, $R^{2b}$, $R^{2c}$ and $R^4$ for a compound corresponds in each case to one row of Table A Table 3624

Compounds of the formula Ia.15 in which $R^8$ is $CH_2CH_2CF_3$, and the combination of $R^{2a}$, $R^{2b}$, $R^{2c}$ and $R^4$ for a compound corresponds in each case to one row of Table A Table 3625

Compounds of the formula Ia.15 in which $R^8$ is $CH(CH_3)CF_3$, and the combination of $R^{2a}$, $R^{2b}$, $R^{2c}$ and $R^4$ for a compound corresponds in each case to one row of Table A Table 3626

Compounds of the formula Ia.15 in which $R^8$ is $CH(CF_3)_2$, and the combination of $R^{2a}$, $R^{2b}$, $R^{2c}$ and $R^4$ for a compound corresponds in each case to one row of Table A Table 3627

Compounds of the formula Ia.15 in which $R^8$ is $CF(CF_3)_2$, and the combination of $R^{2a}$, $R^{2b}$, $R^{2c}$ and $R^4$ for a compound corresponds in each case to one row of Table A Table 3628

Compounds of the formula Ia.15 in which $R^8$ is $CH_2CN$, and the combination of $R^{2a}$, $R^{2b}$, $R^{2c}$ and $R^4$ for a compound corresponds in each case to one row of Table A Table 3629

Compounds of the formula Ia.15 in which $R^8$ is —CH=$CH_2$, and the combination of $R^{2a}$, $R^{2b}$, $R^{2c}$ and $R^4$ for a compound corresponds in each case to one row of Table A Table 3630

Compounds of the formula Ia.15 in which $R^8$ is allyl, and the combination of $R^{2a}$, $R^{2b}$, $R^{2c}$ and $R^4$ for a compound corresponds in each case to one row of Table A Table 3631
Compounds of the formula Ia.15 in which $R^8$ is —C≡CH, and the combination of $R^{2a}$, $R^{2b}$, $R^{2c}$ and $R^4$ for a compound corresponds in each case to one row of Table A Table 3632
Compounds of the formula Ia.15 in which $R^8$ is propargyl, and the combination of $R^{2a}$, $R^{2b}$, $R^{2c}$ and $R^4$ for a compound corresponds in each case to one row of Table A Table 3633
Compounds of the formula Ia.15 in which $R^8$ is CN, and the combination of $R^{2a}$, $R^{2b}$, $R^{2c}$ and $R^4$ for a compound corresponds in each case to one row of Table A Table 3634
Compounds of the formula Ia.15 in which $R^8$ is —CH=CHF, and the combination of $R^{2a}$, $R^{2b}$, $R^{2c}$ and $R^4$ for a compound corresponds in each case to one row of Table A Table 3635
Compounds of the formula Ia.15 in which $R^8$ is —CH=CF$_2$, and the combination of $R^{2a}$, $R^{2b}$, $R^{2c}$ and $R^4$ for a compound corresponds in each case to one row of Table A Table 3636
Compounds of the formula Ia.15 in which $R^8$ is —CF=CF$_2$, and the combination of $R^{2a}$, $R^{2b}$, $R^{2c}$ and $R^4$ for a compound corresponds in each case to one row of Table A Table 3637
Compounds of the formula Ia.15 in which $R^8$ is cyclopropyl, and the combination of $R^{2a}$, $R^{2b}$, $R^{2c}$ and $R^4$ for a compound corresponds in each case to one row of Table A Table 3638
Compounds of the formula Ia.15 in which $R^8$ is 1-fluorocyclopropyl, and the combination of $R^{2a}$, $R^{2b}$, $R^{2c}$ and $R^4$ for a compound corresponds in each case to one row of Table A Table 3639
Compounds of the formula Ia.15 in which $R^8$ is 1-cyanocyclopropyl, and the combination of $R^{2a}$, $R^{2b}$, $R^{2c}$ and $R^4$ for a compound corresponds in each case to one row of Table A Table 3640
Compounds of the formula Ia.15 in which $R^8$ is cyclobutyl, and the combination of $R^{2a}$, $R^{2b}$, $R^{2c}$ and $R^4$ for a compound corresponds in each case to one row of Table A Table 3641
Compounds of the formula Ia.15 in which $R^8$ is 1-fluorocyclobutyl, and the combination of $R^{2a}$, $R^{2b}$, $R^{2c}$ and $R^4$ for a compound corresponds in each case to one row of Table A Table 3642
Compounds of the formula Ia.15 in which $R^8$ is 1-cyanocyclobutyl, and the combination of $R^{2a}$, $R^{2b}$, $R^{2c}$ and $R^4$ for a compound corresponds in each case to one row of Table A Table 3643
Compounds of the formula Ia.15 in which $R^8$ is cyclobut-1-enyl, and the combination of $R^{2a}$, $R^{2b}$, $R^{2c}$ and $R^4$ for a compound corresponds in each case to one row of Table A Table 3644
Compounds of the formula Ia.15 in which $R^8$ is —CH$_2$-cyclopropyl, and the combination of $R^{2a}$, $R^{2b}$, $R^{2c}$ and $R^4$ for a compound corresponds in each case to one row of Table A Table 3645
Compounds of the formula Ia.15 in which $R^8$ is —CH$_2$-(1-cyanocyclopropyl), and the combination of $R^{2a}$, $R^{2b}$, $R^{2c}$ and $R^4$ for a compound corresponds in each case to one row of Table A Table 3646
Compounds of the formula Ia.15 in which $R^8$ is —CH$_2$-cyclobutyl, and the combination of $R^{2a}$, $R^{2b}$, $R^{2c}$ and $R^4$ for a compound corresponds in each case to one row of Table A Table 3647
Compounds of the formula Ia.15 in which $R^8$ is —CH$_2$-(1-cyanocyclobutyl), and the combination of $R^{2a}$, $R^{2b}$, $R^{2c}$ and $R^4$ for a compound corresponds in each case to one row of Table A Table 3648
Compounds of the formula Ia.15 in which $R^8$ is oxetan-2-yl, and the combination of $R^{2a}$, $R^{2b}$, $R^{2c}$ and $R^4$ for a compound corresponds in each case to one row of Table A Table 3649
Compounds of the formula Ia.15 in which $R^8$ is oxetan-3-yl, and the combination of $R^{2a}$, $R^{2b}$, $R^{2c}$ and $R^4$ for a compound corresponds in each case to one row of Table A Table 3650
Compounds of the formula Ia.15 in which $R^8$ is tetrahydrofuran-2-yl, and the combination of $R^{2a}$, $R^{2b}$, $R^{2c}$ and $R^4$ for a compound corresponds in each case to one row of Table A Table 3651
Compounds of the formula Ia.15 in which $R^8$ is tetrahydrofuran-3-yl, and the combination of $R^{2a}$, $R^{2b}$, $R^{2c}$ and $R^4$ for a compound corresponds in each case to one row of Table A Table 3652
Compounds of the formula Ia.15 in which $R^8$ is thietan-3-yl, and the combination of $R^{2a}$, $R^{2b}$, $R^{2c}$ and $R^4$ for a compound corresponds in each case to one row of Table A Table 3653
Compounds of the formula Ia.15 in which $R^8$ is 1-oxo-thietan-3-yl, and the combination of $R^{2a}$, $R^{2b}$, $R^{2c}$ and $R^4$ for a compound corresponds in each case to one row of Table A Table 3654
Compounds of the formula Ia.15 in which $R^8$ is 1,1-dioxo-thietan-3-yl, and the combination of $R^{2a}$, $R^{2b}$, $R^{2c}$ and $R^4$ for a compound corresponds in each case to one row of Table A Table 3655
Compounds of the formula Ia.15 in which $R^8$ is phenyl, and the combination of $R^{2a}$, $R^{2b}$, $R^{2c}$ and $R^4$ for a compound corresponds in each case to one row of Table A Table 3656
Compounds of the formula Ia.15 in which $R^8$ is 2-fluorophenyl, and the combination of $R^{2a}$, $R^{2b}$, $R^{2c}$ and $R^4$ for a compound corresponds in each case to one row of Table A Table 3657
Compounds of the formula Ia.15 in which $R^8$ is 3-fluorophenyl, and the combination of $R^{2a}$, $R^{2b}$, $R^{2c}$ and $R^4$ for a compound corresponds in each case to one row of Table A Table 3658
Compounds of the formula Ia.15 in which $R^8$ is 4-fluorophenyl, and the combination of $R^{2a}$, $R^{2b}$, $R^{2c}$ and $R^4$ for a compound corresponds in each case to one row of Table A Table 3659
Compounds of the formula Ia.15 in which $R^8$ is 2,3-difluorophenyl, and the combination of $R^{2a}$, $R^{2b}$, $R^{2c}$ and $R^4$ for a compound corresponds in each case to one row of Table A Table 3660
Compounds of the formula Ia.15 in which $R^8$ is 2,4-difluorophenyl, and the combination of $R^{2a}$, $R^{2b}$, $R^{2c}$ and $R^4$ for a compound corresponds in each case to one row of Table A Table 3661
Compounds of the formula Ia.15 in which $R^8$ is 2,5-difluorophenyl, and the combination of $R^{2a}$, $R^{2b}$, $R^{2c}$ and $R^4$ for a compound corresponds in each case to one row of Table A Table 3662
Compounds of the formula Ia.15 in which $R^8$ is 2,6-difluorophenyl, and the combination of $R^{2a}$, $R^{2b}$, $R^{2c}$ and $R^4$ for a compound corresponds in each case to one row of Table A Table 3663
Compounds of the formula Ia.15 in which $R^8$ is 3,4-difluorophenyl, and the combination of $R^{2a}$, $R^{2b}$, $R^{2c}$ and $R^4$ for a compound corresponds in each case to one row of Table A Table 3664
Compounds of the formula Ia.15 in which $R^8$ is 3,5-difluorophenyl, and the combination of $R^{2a}$, $R^{2b}$, $R^{2c}$ and $R^4$ for a compound corresponds in each case to one row of Table A Table 3665
Compounds of the formula Ia.15 in which $R^8$ is 2-chlorophenyl, and the combination of $R^{2a}$, $R^{2b}$, $R^{2c}$ and $R^4$ for a compound corresponds in each case to one row of Table A Table 3666
Compounds of the formula Ia.15 in which $R^8$ is 3-chlorophenyl, and the combination of $R^{2a}$, $R^{2b}$, $R^{2c}$ and $R^4$ for a compound corresponds in each case to one row of Table A Table 3667
Compounds of the formula Ia.15 in which $R^8$ is 4-chlorophenyl, and the combination of $R^{2a}$, $R^{2b}$, $R^{2c}$ and $R^4$ for a compound corresponds in each case to one row of Table A Table 3668
Compounds of the formula Ia.15 in which $R^8$ is 2-methoxyphenyl, and the combination of $R^{2a}$, $R^{2b}$, $R^{2c}$ and $R^4$ for a compound corresponds in each case to one row of Table A Table 3669
Compounds of the formula Ia.15 in which $R^8$ is 3-methoxyphenyl, and the combination of $R^{2a}$, $R^{2b}$, $R^{2c}$ and $R^4$ for a compound corresponds in each case to one row of Table A Table 3670
Compounds of the formula Ia.15 in which $R^8$ is 4-methoxyphenyl, and the combination of $R^{2a}$, $R^{2b}$, $R^{2c}$ and $R^4$ for a compound corresponds in each case to one row of Table A Table 3671
Compounds of the formula Ia.15 in which $R^8$ is pyridin-2-yl, and the combination of $R^{2a}$, $R^{2b}$, $R^{2c}$ and $R^4$ for a compound corresponds in each case to one row of Table A Table 3672
Compounds of the formula Ia.15 in which $R^8$ is pyridin-3-yl, and the combination of $R^{2a}$, $R^{2b}$, $R^{2c}$ and $R^4$ for a compound corresponds in each case to one row of Table A Table 3673
Compounds of the formula Ia.15 in which $R^8$ is pyridin-4-yl, and the combination of $R^{2a}$, $R^{2b}$, $R^{2c}$ and $R^4$ for a compound corresponds in each case to one row of Table A Table 3674
Compounds of the formula Ia.15 in which $R^8$ is 4-chloropyridin-3-yl, and the combination of $R^{2a}$, $R^{2b}$, $R^{2c}$ and $R^4$ for a compound corresponds in each case to one row of Table A Table 3675
Compounds of the formula Ia.15 in which $R^8$ is pyrimidin-2-yl, and the combination of $R^{2a}$, $R^{2b}$, $R^{2c}$ and $R^4$ for a compound corresponds in each case to one row of Table A Table 3676
Compounds of the formula Ia.15 in which $R^8$ is methoxymethyl, and the combination of $R^{2a}$, $R^{2b}$, $R^{2c}$ and $R^4$ for a compound corresponds in each case to one row of Table A Table 3677
Compounds of the formula Ia.15 in which $R^8$ is ethoxymethyl, and the combination of $R^{2a}$, $R^{2b}$, $R^{2c}$ and $R^4$ for a compound corresponds in each case to one row of Table A Table 3678
Compounds of the formula Ia.15 in which $R^8$ is trifluoromethoxymethyl, and the combination of $R^{2a}$, $R^{2b}$, $R^{2c}$ and $R^4$ for a compound corresponds in each case to one row of Table A Table 3679
Compounds of the formula Ia.15 in which $R^8$ is methylthiomethyl, and the combination of $R^{2a}$, $R^{2b}$, $R^{2c}$ and $R^4$ for a compound corresponds in each case to one row of Table A Table 3680
Compounds of the formula Ia.15 in which $R^8$ is ethylthiomethyl, and the combination of $R^{2a}$, $R^{2b}$, $R^{2c}$ and $R^4$ for a compound corresponds in each case to one row of Table A Table 3681
Compounds of the formula Ia.15 in which $R^8$ is trifluoromethylthiomethyl, and the combination of $R^{2a}$, $R^{2b}$, $R^{2c}$ and $R^4$ for a compound corresponds in each case to one row of Table A Table 3682
Compounds of the formula Ia.15 in which $R^8$ is methylsulfinylmethyl, and the combination of $R^{2a}$, $R^{2b}$, $R^{2c}$ and $R^4$ for a compound corresponds in each case to one row of Table A Table 3683
Compounds of the formula Ia.15 in which $R^8$ is ethylsulfinylmethyl, and the combination of $R^{2a}$, $R^{2b}$, $R^{2c}$ and $R^4$ for a compound corresponds in each case to one row of Table A Table 3684
Compounds of the formula Ia.15 in which $R^8$ is trifluoromethylsulfinylmethyl, and the combination of $R^{2a}$, $R^{2b}$, $R^{2c}$ and $R^4$ for a compound corresponds in each case to one row of Table A Table 3685
Compounds of the formula Ia.15 in which $R^8$ is methylsulfonylmethyl, and the combination of $R^{2a}$, $R^{2b}$, $R^{2c}$ and $R^4$ for a compound corresponds in each case to one row of Table A Table 3686
Compounds of the formula Ia.15 in which $R^8$ is ethylsulfonylmethyl, and the combination of $R^{2a}$, $R^{2b}$, $R^{2c}$ and $R^4$ for a compound corresponds in each case to one row of Table A Table 3687
Compounds of the formula Ia.15 in which $R^8$ is trifluoromethylsulfonylmethyl, and the combination of $R^{2a}$, $R^{2b}$, $R^{2c}$ and $R^4$ for a compound corresponds in each case to one row of Table A Table 3688
Compounds of the formula Ia.15 in which $R^8$ is —CH($CH_3$)—$SO_2$—$CH_3$, and the combination of $R^{2a}$, $R^{2b}$, $R^{2c}$ and $R^4$ for a compound corresponds in each case to one row of Table A Table 3689
Compounds of the formula Ia.15 in which $R^8$ is —C(CH$_3$)$_2$—SO$_2$—CH$_3$, and the combination of $R^{2a}$, $R^{2b}$, $R^{2c}$ and $R^4$ for a compound corresponds in each case to one row of Table A Table 3690
Compounds of the formula Ia.15 in which $R^8$ is —CH$_2$—N(CH$_3$)$_2$, and the combination of $R^{2a}$, $R^{2b}$, $R^{2c}$ and $R^4$ for a compound corresponds in each case to one row of Table A Table 3691
Compounds of the formula Ia.15 in which $R^8$ is —CH$_2$—CH$_2$—N(CH$_3$)$_2$, and the combination of $R^{2a}$, $R^{2b}$, $R^{2c}$ and $R^4$ for a compound corresponds in each case to one row of Table A Table 3692
Compounds of the formula Ia.15 in which $R^8$ is —N(H)CH$_3$, and the combination of $R^{2a}$, $R^{2b}$, $R^{2c}$ and $R^4$ for a compound corresponds in each case to one row of Table A Table 3693
Compounds of the formula Ia.15 in which $R^8$ is —N(H)CH$_2$CH$_3$, and the combination of $R^{2a}$, $R^{2b}$, $R^{2c}$ and $R^4$ for a compound corresponds in each case to one row of Table A Table 3694
Compounds of the formula Ia.15 in which $R^8$ is —N(H)CH$_2$CHF$_2$, and the combination of $R^{2a}$, $R^{2b}$, $R^{2c}$ and $R^4$ for a compound corresponds in each case to one row of Table A Table 3695
Compounds of the formula Ia.15 in which $R^8$ is —N(H)CH$_2$CF$_3$, and the combination of $R^{2a}$, $R^{2b}$, $R^{2c}$ and $R^4$ for a compound corresponds in each case to one row of Table A Table 3696
Compounds of the formula Ia.15 in which $R^8$ is —N(H)CH$_2$CH=CH$_2$, and the combination of $R^{2a}$, $R^{2b}$, $R^{2c}$ and $R^4$ for a compound corresponds in each case to one row of Table A Table 3697
Compounds of the formula Ia.15 in which $R^8$ is —N(H)CH$_2$C—CH, and the combination of $R^{2a}$, $R^{2b}$, $R^{2c}$ and $R^4$ for a compound corresponds in each case to one row of Table A Table 3698
Compounds of the formula Ia.15 in which $R^8$ is —N(H)CH$_2$CN, and the combination of $R^{2a}$, $R^{2b}$, $R^{2c}$ and $R^4$ for a compound corresponds in each case to one row of Table A Table 3699
Compounds of the formula Ia.15 in which $R^8$ is —N(H)-cyclopropyl, and the combination of $R^{2a}$, $R^{2b}$, $R^{2c}$ and $R^4$ for a compound corresponds in each case to one row of Table A Table 3700
Compounds of the formula Ia.15 in which $R^8$ is —N(H)-(1-cyanocyclopropyl), and the combination of $R^{2a}$, $R^{2b}$, $R^{2c}$ and $R^4$ for a compound corresponds in each case to one row of Table A Table 3701
Compounds of the formula Ia.15 in which $R^8$ is —N(H)—CH$_2$-cyclopropyl, and the combination of $R^{2a}$, $R^{2b}$, $R^{2c}$ and $R^4$ for a compound corresponds in each case to one row of Table A Table 3702
Compounds of the formula Ia.15 in which $R^8$ is —N(H)—CH$_2$-(1-cyanocyclopropyl), and the combination of $R^{2a}$, $R^{2b}$, $R^{2c}$ and $R^4$ for a compound corresponds in each case to one row of Table A Table 3703
Compounds of the formula Ia.15 in which $R^8$ is —C(O)—N(H)CH$_3$, and the combination of $R^{2a}$, $R^{2b}$, $R^{2c}$ and $R^4$ for a compound corresponds in each case to one row of Table A Table 3704
Compounds of the formula Ia.15 in which $R^8$ is —C(O)—N(H)CH$_2$CH$_3$, and the combination of $R^{2a}$, $R^{2b}$, $R^{2c}$ and $R^4$ for a compound corresponds in each case to one row of Table A Table 3705
Compounds of the formula Ia.15 in which $R^8$ is —C(O)—N(H)CH$_2$CHF$_2$, and the combination of $R^{2a}$, $R^{2b}$, $R^{2c}$ and $R^4$ for a compound corresponds in each case to one row of Table A Table 3706
Compounds of the formula Ia.15 in which $R^8$ is —C(O)—N(H)CH$_2$CF$_3$, and the combination of $R^{2a}$, $R^{2b}$, $R^{2c}$ and $R^4$ for a compound corresponds in each case to one row of Table A Table 3707
Compounds of the formula Ia.15 in which $R^8$ is —C(O)—N(H)CH$_2$CH=CH$_2$, and the combination of $R^{2a}$, $R^{2b}$, $R^{2c}$ and $R^4$ for a compound corresponds in each case to one row of Table A Table 3708
Compounds of the formula Ia.15 in which $R^8$ is —C(O)—N(H)CH$_2$C—CH, and the combination of $R^{2a}$, $R^{2b}$, $R^{2c}$ and $R^4$ for a compound corresponds in each case to one row of Table A Table 3709
Compounds of the formula Ia.15 in which $R^8$ is —C(O)—N(H)CH$_2$CN, and the combination of $R^{2a}$, $R^{2b}$, $R^{2c}$ and $R^4$ for a compound corresponds in each case to one row of Table A Table 3710
Compounds of the formula Ia.15 in which $R^8$ is —C(O)—N(H)-cyclopropyl, and the combination of $R^{2a}$, $R^{2b}$, $R^{2c}$ and $R^4$ for a compound corresponds in each case to one row of Table A Table 3711
Compounds of the formula Ia.15 in which $R^8$ is —C(O)—N(H)-(1-cyanocyclopropyl), and the combination of $R^{2a}$, $R^{2b}$, $R^{2c}$ and $R^4$ for a compound corresponds in each case to one row of Table A Table 3712
Compounds of the formula Ia.15 in which $R^8$ is —C(O)—N(H)—CH$_2$-cyclopropyl, and the combination of $R^{2a}$, $R^{2b}$, $R^{2c}$ and $R^4$ for a compound corresponds in each case to one row of Table A Table 3713
Compounds of the formula Ia.15 in which $R^8$ is —C(O)—N(H)—CH$_2$-(1-cyanocyclopropyl), and the combination of $R^{2a}$, $R^{2b}$, $R^{2c}$ and $R^4$ for a compound corresponds in each case to one row of Table A Table 3714
Compounds of the formula Ia.15 in which $R^8$ is —CH$_2$—C(O)—N(H)CH$_3$, and the combination of $R^{2a}$, $R^{2b}$, $R^{2c}$ and $R^4$ for a compound corresponds in each case to one row of Table A Table 3715
Compounds of the formula Ia.15 in which $R^8$ is —CH$_2$—C(O)—N(H)CH$_2$CH$_3$, and the combination of $R^{2a}$, $R^{2b}$, $R^{2c}$ and $R^4$ for a compound corresponds in each case to one row of Table A Table 3716
Compounds of the formula Ia.15 in which $R^8$ is —CH$_2$—C(O)—N(H)CH$_2$CHF$_2$, and the combination of $R^{2a}$, $R^{2b}$, $R^{2c}$ and $R^4$ for a compound corresponds in each case to one row of Table A Table 3717
Compounds of the formula Ia.15 in which $R^8$ is —$CH_2$—C(O)—N(H)$CH_2CF_3$, and the combination of $R^{2a}$, $R^{2b}$, $R^{2c}$ and $R^4$ for a compound corresponds in each case to one row of Table A Table 3718
Compounds of the formula Ia.15 in which $R^8$ is —$CH_2$—C(O)—N(H)$CH_2CH=CH_2$, and the combination of $R^{2a}$, $R^{2b}$, $R^{2c}$ and $R^4$ for a compound corresponds in each case to one row of Table A Table 3719
Compounds of the formula Ia.15 in which $R^8$ is —$CH_2$—C(O)—N(H)$CH_2C≡CH$, and the combination of $R^{2a}$, $R^{2b}$, $R^{2c}$ and $R^4$ for a compound corresponds in each case to one row of Table A Table 3720
Compounds of the formula Ia.15 in which $R^8$ is —$CH_2$—C(O)—N(H)$CH_2CN$, and the combination of $R^{2a}$, $R^{2b}$, $R^{2c}$ and $R^4$ for a compound corresponds in each case to one row of Table A Table 3721
Compounds of the formula Ia.15 in which $R^8$ is —$CH_2$—C(O)—N(H)-cyclopropyl, and the combination of $R^{2a}$, $R^{2b}$, $R^{2c}$ and $R^4$ for a compound corresponds in each case to one row of Table A Table 3722
Compounds of the formula Ia.15 in which $R^8$ is —$CH_2$—C(O)—N(H)-(1-cyanocyclopropyl), and the combination of $R^{2a}$, $R^{2b}$, $R^{2c}$ and $R^4$ for a compound corresponds in each case to one row of Table A Table 3723
Compounds of the formula Ia.15 in which $R^8$ is —$CH_2$—C(O)—N(H)—$CH_2$-cyclopropyl, and the combination of $R^{2a}$, $R^{2b}$, $R^{2c}$ and $R^4$ for a compound corresponds in each case to one row of Table A Table 3724
Compounds of the formula Ia.15 in which $R^8$ is —$CH_2$—C(O)—N(H)—$CH_2$-(1-cyanocyclopropyl), and the combination of $R^{2a}$, $R^{2b}$, $R^{2c}$ and $R^4$ for a compound corresponds in each case to one row of Table A Table 3725
Compounds of the formula Ia.15 in which $R^8$ is —NH—C(O)—N(H)$CH_3$, and the combination of $R^{2a}$, $R^{2b}$, $R^{2c}$ and $R^4$ for a compound corresponds in each case to one row of Table A Table 3726
Compounds of the formula Ia.15 in which $R^8$ is —NH—C(O)—N(H)$CH_2CH_3$, and the combination of $R^{2a}$, $R^{2b}$, $R^{2c}$ and $R^4$ for a compound corresponds in each case to one row of Table A Table 3727
Compounds of the formula Ia.15 in which $R^8$ is —NH—C(O)—N(H)$CH_2CHF_2$, and the combination of $R^{2a}$, $R^{2b}$, $R^{2c}$ and $R^4$ for a compound corresponds in each case to one row of Table A Table 3728
Compounds of the formula Ia.15 in which $R^8$ is —NH—C(O)—N(H)$CH_2CF_3$, and the combination of $R^{2a}$, $R^{2b}$, $R^{2c}$ and $R^4$ for a compound corresponds in each case to one row of Table A Table 3729
Compounds of the formula Ia.15 in which $R^8$ is —NH—C(O)—N(H)$CH_2CH=CH_2$, and the combination of $R^{2a}$, $R^{2b}$, $R^{2c}$ and $R^4$ for a compound corresponds in each case to one row of Table A Table 3730
Compounds of the formula Ia.15 in which $R^8$ is —NH—C(O)—N(H)$CH_2C≡CH$, and the combination of $R^{2a}$, $R^{2b}$, $R^{2c}$ and $R^4$ for a compound corresponds in each case to one row of Table A Table 3731
Compounds of the formula Ia.15 in which $R^8$ is —NH—C(O)—N(H)$CH_2CN$, and the combination of $R^{2a}$, $R^{2b}$, $R^{2c}$ and $R^4$ for a compound corresponds in each case to one row of Table A Table 3732
Compounds of the formula Ia.15 in which $R^8$ is —NH—C(O)—N(H)-cyclopropyl, and the combination of $R^{2a}$, $R^{2b}$, $R^{2c}$ and $R^4$ for a compound corresponds in each case to one row of Table A Table 3733
Compounds of the formula Ia.15 in which $R^8$ is —NH—C(O)—N(H)-(1-cyanocyclopropyl), and the combination of $R^{2a}$, $R^{2b}$, $R^{2c}$ and $R^4$ for a compound corresponds in each case to one row of Table A Table 3734
Compounds of the formula Ia.15 in which $R^8$ is —NH—C(O)—N(H)—$CH_2$-cyclopropyl, and the combination of $R^{2a}$, $R^{2b}$, $R^{2c}$ and $R^4$ for a compound corresponds in each case to one row of Table A Table 3735
Compounds of the formula Ia.15 in which $R^8$ is —NH—C(O)—N(H)—$CH_2$-(1-cyanocyclopropyl), and the combination of $R^{2a}$, $R^{2b}$, $R^{2c}$ and $R^4$ for a compound corresponds in each case to one row of Table A Table 3736
Compounds of the formula Ia.15 in which $R^8$ is —CH=N—$OCH_3$, and the combination of $R^{2a}$, $R^{2b}$, $R^{2c}$ and $R^4$ for a compound corresponds in each case to one row of Table A Table 3737
Compounds of the formula Ia.15 in which $R^8$ is —CH=N—$OCH_2CH_3$, and the combination of $R^{2a}$, $R^{2b}$, $R^{2c}$ and $R^4$ for a compound corresponds in each case to one row of Table A Table 3738
Compounds of the formula Ia.15 in which $R^8$ is —CH=N—$OCH_2CHF_2$, and the combination of $R^{2a}$, $R^{2b}$, $R^{2c}$ and $R^4$ for a compound corresponds in each case to one row of Table A Table 3739
Compounds of the formula Ia.15 in which $R^8$ is —CH=N—$OCH_2CF_3$, and the combination of $R^{2a}$, $R^{2b}$, $R^{2c}$ and $R^4$ for a compound corresponds in each case to one row of Table A Table 3740
Compounds of the formula Ia.15 in which $R^8$ is —CH=N—$OCH_2CH=CH_2$, and the combination of $R^{2a}$, $R^{2b}$, $R^{2c}$ and $R^4$ for a compound corresponds in each case to one row of Table A Table 3741
Compounds of the formula Ia.15 in which $R^8$ is —CH=N—$OCH_2C≡CH$, and the combination of $R^{2a}$, $R^{2b}$, $R^{2c}$ and $R^4$ for a compound corresponds in each case to one row of Table A Table 3742
Compounds of the formula Ia.15 in which $R^8$ is —CH=N—$OCH_2CN$, and the combination of $R^{2a}$, $R^{2b}$, $R^{2c}$ and $R^4$ for a compound corresponds in each case to one row of Table A Table 3743

Compounds of the formula Ia.15 in which $R^8$ is —CH=N—O-cyclopropyl, and the combination of $R^{2a}$, $R^{2b}$, $R^{2c}$ and $R^4$ for a compound corresponds in each case to one row of Table A Table 3744

Compounds of the formula Ia.15 in which $R^8$ is —CH=N—O-(1-cyanocyclopropyl), and the combination of $R^{2a}$, $R^{2b}$, $R^{2c}$ and $R^4$ for a compound corresponds in each case to one row of Table A Table 3745

Compounds of the formula Ia.15 in which $R^8$ is —CH=N—O-(2,2-difluorocyclopropyl), and the combination of $R^{2a}$, $R^{2b}$, $R^{2c}$ and $R^4$ for a compound corresponds in each case to one row of Table A Table 3746

Compounds of the formula Ia.15 in which $R^8$ is —CH=N—O—$CH_2$-cyclopropyl, and the combination of $R^{2a}$, $R^{2b}$, $R^{2c}$ and $R^4$ for a compound corresponds in each case to one row of Table A Table 3747

Compounds of the formula Ia.15 in which $R^8$ is —CH=N—O—$CH_2$-(1-cyanocyclopropyl), and the combination of $R^{2a}$, $R^{2b}$, $R^{2c}$ and $R^4$ for a compound corresponds in each case to one row of Table A Table 3748

Compounds of the formula Ia.15 in which $R^8$ is —CH=N—O—$CH_2$-(2,2-difluorocyclopropyl), and the combination of $R^{2a}$, $R^{2b}$, $R^{2c}$ and $R^4$ for a compound corresponds in each case to one row of Table A Tables 3749 to 3888

Compounds of the formula Ia.16 in which $R^8$ is as defined in tables 3609 to 3748, and the combination of $R^{2a}$, $R^{2b}$, $R^{2c}$ and $R^4$ for a compound corresponds in each case to one row of Table A Tables 3889 to 4028

Compounds of the formula Ia.17 in which $R^8$ is as defined in tables 3609 to 3748, and the combination of $R^{2a}$, $R^{2b}$, $R^{2c}$ and $R^4$ for a compound corresponds in each case to one row of Table A Tables 4029 to 4168

Compounds of the formula Ia.18 in which $R^8$ is as defined in tables 3609 to 3748, and the combination of $R^{2a}$, $R^{2b}$, $R^{2c}$ and $R^4$ for a compound corresponds in each case to one row of Table A Tables 4169 to 4308

Compounds of the formula Ia.19 in which $R^8$ is as defined in tables 3609 to 3748, and the combination of $R^{2a}$, $R^{2b}$, $R^{2c}$ and $R^4$ for a compound corresponds in each case to one row of Table A Tables 4309 to 4448

Compounds of the formula Ia.20 in which $R^8$ is as defined in tables 3609 to 3748, and the combination of $R^{2a}$, $R^{2b}$, $R^{2c}$ and $R^4$ for a compound corresponds in each case to one row of Table A Tables 4449 to 4588

Compounds of the formula Ia.21 in which $R^8$ is as defined in tables 3609 to 3748, and the combination of $R^{2a}$, $R^{2b}$, $R^{2c}$ and $R^4$ for a compound corresponds in each case to one row of Table A Tables 4589 to 4728

Compounds of the formula Ia.22 in which $R^8$ is as defined in tables 3609 to 3748, and the combination of $R^{2a}$, $R^{2b}$, $R^{2c}$ and $R^4$ for a compound corresponds in each case to one row of Table A Tables 4729 to 4868

Compounds of the formula Ia.23 in which $R^8$ is as defined in tables 3609 to 3748, and the combination of $R^{2a}$, $R^{2b}$, $R^{2c}$ and $R^4$ for a compound corresponds in each case to one row of Table A Tables 4869 to 5008

Compounds of the formula Ia.24 in which $R^8$ is as defined in tables 3609 to 3748, and the combination of $R^{2a}$, $R^{2b}$, $R^{2c}$ and $R^4$ for a compound corresponds in each case to one row of Table A Tables 5009 to 5148

Compounds of the formula Ia.25 in which $R^8$ is as defined in tables 3609 to 3748, and the combination of $R^{2a}$, $R^{2b}$, $R^{2c}$ and $R^4$ for a compound corresponds in each case to one row of Table A Tables 5149 to 5288

Compounds of the formula Ia.26 in which $R^8$ is as defined in tables 3609 to 3748, and the combination of $R^{2a}$, $R^{2b}$, $R^{2c}$ and $R^4$ for a compound corresponds in each case to one row of Table A Table 5289

Compounds of the formula Ia.27 in which $A^3$ is 1H-pyrrol-1-yl, and the combination of $R^{2a}$, $R^{2b}$, $R^{2c}$ and $R^4$ for a compound corresponds in each case to one row of Table A Table 5290

Compounds of the formula Ia.27 in which $A^3$ is 1H-3-chloro-pyrrol-1-yl, and the combination of $R^{2a}$, $R^{2b}$, $R^{2c}$ and $R^4$ for a compound corresponds in each case to one row of Table A Table 5291

Compounds of the formula Ia.27 in which $A^3$ is 1H-3-cyano-pyrrol-1-yl, and the combination of $R^{2a}$, $R^{2b}$, $R^{2c}$ and $R^4$ for a compound corresponds in each case to one row of Table A Table 5292

Compounds of the formula Ia.27 in which $A^3$ is 1H-pyrazol-1-yl, and the combination of $R^{2a}$, $R^{2b}$, $R^{2c}$ and $R^4$ for a compound corresponds in each case to one row of Table A Table 5293

Compounds of the formula Ia.27 in which $A^3$ is 1H-4-cloro-pyrazol-1-yl, and the combination of $R^{2a}$, $R^{2b}$, $R^{2c}$ and $R^4$ for a compound corresponds in each case to one row of Table A Table 5294

Compounds of the formula Ia.27 in which $A^3$ is 1H-4-cyano-pyrazol-1-yl, and the combination of $R^{2a}$, $R^{2b}$, $R^{2c}$ and $R^4$ for a compound corresponds in each case to one row of Table A Table 5295

Compounds of the formula Ia.27 in which $A^3$ is 1H-imidazol-1-yl, and the combination of $R^{2a}$, $R^{2b}$, $R^{2c}$ and $R^4$ for a compound corresponds in each case to one row of Table A Table 5296

Compounds of the formula Ia.27 in which $A^3$ is 1H-4-chloro-imidazol-1-yl, and the combination of $R^{2a}$, $R^{2b}$, $R^{2c}$ and $R^4$ for a compound corresponds in each case to one row of Table A Table 5297

Compounds of the formula Ia.27 in which $A^3$ is 1H-4-cyano-imidazol-1-yl, and the combination of $R^{2a}$, $R^{2b}$, $R^{2c}$ and $R^4$ for a compound corresponds in each case to one row of Table A Table 5298

Compounds of the formula Ia.27 in which $A^3$ is 1H-[1,2,4]-triazol-1-yl, and the combination of $R^{2a}$, $R^{2b}$, $R^{2c}$ and $R^4$ for a compound corresponds in each case to one row of Table A Table 5299
Compounds of the formula Ia.27 in which $A^3$ is 1H-[1,2,4]-3-chloro-triazol-1-yl, and the combination of $R^{2a}$, $R^{2b}$, $R^{2c}$ and $R^4$ for a compound corresponds in each case to one row of Table A Table 5300
Compounds of the formula Ia.27 in which $A^3$ is 1H-[1,2,4]-3-cyano-triazol-1-yl, and the combination of $R^{2a}$, $R^{2b}$, $R^{2c}$ and $R^4$ for a compound corresponds in each case to one row of Table A Table 5301
Compounds of the formula Ia.27 in which $A^3$ is 1H-1-methyl-pyrrol-2-yl, and the combination of $R^{2a}$, $R^{2b}$, $R^{2c}$ and $R^4$ for a compound corresponds in each case to one row of Table A Table 5302
Compounds of the formula Ia.27 in which $A^3$ is 1H-1-methyl-pyrrol-3-yl, and the combination of $R^{2a}$, $R^{2b}$, $R^{2c}$ and $R^4$ for a compound corresponds in each case to one row of Table A Table 5303
Compounds of the formula Ia.27 in which $A^3$ is 1H-1-methyl-pyrazol-4-yl, and the combination of $R^{2a}$, $R^{2b}$, $R^{2c}$ and $R^4$ for a compound corresponds in each case to one row of Table A Table 5304
Compounds of the formula Ia.27 in which $A^3$ is 1H-1-methyl-pyrazol-5-yl, and the combination of $R^{2a}$, $R^{2b}$, $R^{2c}$ and $R^4$ for a compound corresponds in each case to one row of Table A Table 5305
Compounds of the formula Ia.27 in which $A^3$ is 1H-1,3-dimethyl-pyrazol-5-yl, and the combination of $R^{2a}$, $R^{2b}$, $R^{2c}$ and $R^4$ for a compound corresponds in each case to one row of Table A Table 5306
Compounds of the formula Ia.27 in which $A^3$ is 1H-1-methyl-3-trifluoromethyl-pyrazol-5-yl, and the combination of $R^{2a}$, $R^{2b}$, $R^{2c}$ and $R^4$ for a compound corresponds in each case to one row of Table A Table 5307
Compounds of the formula Ia.27 in which $A^3$ is 1H-1-[1,2,3]-triazol-5-yl, and the combination of $R^{2a}$, $R^{2b}$, $R^{2c}$ and $R^4$ for a compound corresponds in each case to one row of Table A Table 5308
Compounds of the formula Ia.27 in which $A^3$ is pyridin-2-yl, and the combination of $R^{2a}$, $R^{2b}$, $R^{2c}$ and $R^4$ for a compound corresponds in each case to one row of Table A Table 5309
Compounds of the formula Ia.27 in which $A^3$ is pyridin-3-yl, and the combination of $R^{2a}$, $R^{2b}$, $R^{2c}$ and $R^4$ for a compound corresponds in each case to one row of Table A Table 5310
Compounds of the formula Ia.27 in which $A^3$ is pyridin-4-yl, and the combination of $R^{2a}$, $R^{2b}$, $R^{2c}$ and $R^4$ for a compound corresponds in each case to one row of Table A Table 5311
Compounds of the formula Ia.27 in which $A^3$ is pyrimidin-2-yl, and the combination of $R^{2a}$, $R^{2b}$, $R^{2c}$ and $R^4$ for a compound corresponds in each case to one row of Table A Table 5312
Compounds of the formula Ia.27 in which $A^3$ is pyrimidin-4-yl, and the combination of $R^{2a}$, $R^{2b}$, $R^{2c}$ and $R^4$ for a compound corresponds in each case to one row of Table A Table 5313
Compounds of the formula Ia.27 in which $A^3$ is pyrimidin-5-yl, and the combination of $R^{2a}$, $R^{2b}$, $R^{2c}$ and $R^4$ for a compound corresponds in each case to one row of Table A Table 5314
Compounds of the formula Ia.27 in which $A^3$ is pyrazin-2-yl, and the combination of $R^{2a}$, $R^{2b}$, $R^{2c}$ and $R^4$ for a compound corresponds in each case to one row of Table A Tables 5315 to 5614
Compounds of the formula Ia.28 in which $R^6$ is as defined in tables 1 to 300, and the combination of $R^{2a}$, $R^{2b}$, $R^{2c}$ and $R^4$ for a compound corresponds in each case to one Tables 5615 to 5914
Compounds of the formula Ia.29 in which $R^6$ is as defined in tables 1 to 300, and the combination of $R^{2a}$, $R^{2b}$, $R^{2c}$ and $R^4$ for a compound corresponds in each case to one Tables 5915 to 6214
Compounds of the formula Ia.30 in which $R^6$ is as defined in tables 1 to 300, and the combination of $R^{2a}$, $R^{2b}$, $R^{2c}$ and $R^4$ for a compound corresponds in each case to one Tables 6215 to 6514
Compounds of the formula Ia.31 in which $R^6$ is as defined in tables 1 to 300, and the combination of $R^{2a}$, $R^{2b}$, $R^{2c}$ and $R^4$ for a compound corresponds in each case to one Tables 6515 to 6814
Compounds of the formula Ia.32 in which $R^6$ is as defined in tables 1 to 300, and the combination of $R^{2a}$, $R^{2b}$, $R^{2c}$ and $R^4$ for a compound corresponds in each case to one Tables 6815 to 7114
Compounds of the formula Ia.33 in which $R^6$ is as defined in tables 1 to 300, and the combination of $R^{2a}$, $R^{2b}$, $R^{2c}$ and $R^4$ for a compound corresponds in each case to one Tables 7115 to 7414
Compounds of the formula Ia.34 in which $R^6$ is as defined in tables 1 to 300, and the combination of $R^{2a}$, $R^{2b}$, $R^{2c}$ and $R^4$ for a compound corresponds in each case to one Tables 7415 to 7714
Compounds of the formula Ia.35 in which $R^6$ is as defined in tables 1 to 300, and the combination of $R^{2a}$, $R^{2b}$, $R^{2c}$ and $R^4$ for a compound corresponds in each case to one Tables 7715 to 8014
Compounds of the formula Ia.36 in which $R^6$ is as defined in tables 1 to 300, and the combination of $R^{2a}$, $R^{2b}$, $R^{2c}$ and $R^4$ for a compound corresponds in each case to one Tables 8015 to 8314
Compounds of the formula Ia.37 in which $R^6$ is as defined in tables 1 to 300, and the combination of $R^{2a}$, $R^{2b}$, $R^{2c}$ and $R^4$ for a compound corresponds in each case to one Tables 8315 to 8614
Compounds of the formula Ia.38 in which $R^6$ is as defined in tables 1 to 300, and the combination of $R^{2a}$, $R^{2b}$, $R^{2c}$ and $R^4$ for a compound corresponds in each case to one Tables 8615 to 8914
Compounds of the formula Ia.39 in which $R^6$ is as defined in tables 1 to 300, and the combination of $R^{2a}$, $R^{2b}$, $R^{2c}$ and $R^4$ for a compound corresponds in each case to one Table 8915 to 8918
Compounds of the formula Ia.40 in which $R^{9a}$ and $R^{9b}$ are as defined in tables 3601 to 3604, and the combination of $R^{2a}$, $R^{2b}$, $R^{2c}$ and $R^4$ for a compound corresponds in each case to one row of Table A Table 8919 to 8922
Compounds of the formula Ia.41 in which $R^{9a}$ and $R^{9b}$ are as defined in tables 3601 to 3604, and the combination of $R^{2a}$, $R^{2b}$, $R^{2c}$ and $R^4$ for a compound corresponds in each case to one row of Table A Tables 8923 to 9062
Compounds of the formula Ia.42 in which $R^8$ is as defined in tables 3609 to 3748, and the combination of $R^{2a}$, $R^{2b}$, $R^{2c}$ and $R^4$ for a compound corresponds in each case to one row of Table A Tables 9063 to 9202
Compounds of the formula Ia.43 in which $R^8$ is as defined in tables 3609 to 3748, and the combination of $R^{2a}$, $R^{2b}$, $R^{2c}$ and $R^4$ for a compound corresponds in each case to one row of Table A Tables 9203 to 9342
Compounds of the formula Ia.44 in which $R^8$ is as defined in tables 3609 to 3748, and the combination of $R^{2a}$, $R^{2b}$, $R^{2c}$ and $R^4$ for a compound corresponds in each case to one row of Table A Tables 9343 to 9482
Compounds of the formula Ia.45 in which $R^8$ is as defined in tables 3609 to 3748, and the combination of $R^{2a}$, $R^{2b}$, $R^{2c}$ and $R^4$ for a compound corresponds in each case to one row of Table A Tables 9483 to 9622
Compounds of the formula Ia.46 in which $R^8$ is as defined in tables 3609 to 3748, and the combination of $R^{2a}$, $R^{2b}$, $R^{2c}$ and $R^4$ for a compound corresponds in each case to one row of Table A Tables 9623 to 9762
Compounds of the formula Ia.47 in which $R^8$ is as defined in tables 3609 to 3748, and the combination of $R^{2a}$, $R^{2b}$, $R^{2c}$ and $R^4$ for a compound corresponds in each case to one row of Table A Tables 9763 to 9902
Compounds of the formula Ia.48 in which $R^8$ is as defined in tables 3609 to 3748, and the combination of $R^{2a}$, $R^{2b}$, $R^{2c}$ and $R^4$ for a compound corresponds in each case to one row of Table A Tables 9903 to 10042
Compounds of the formula Ia.49 in which $R^8$ is as defined in tables 3609 to 3748, and the combination of $R^{2a}$, $R^{2b}$, $R^{2c}$ and $R^4$ for a compound corresponds in each case to one row of Table A Tables 10043 to 10182
Compounds of the formula Ia.50 in which $R^8$ is as defined in tables 3609 to 3748, and the combination of $R^{2a}$, $R^{2b}$, $R^{2c}$ and $R^4$ for a compound corresponds in each case to one row of Table A Tables 10183 to 10322
Compounds of the formula Ia.51 in which $R^8$ is as defined in tables 3609 to 3748, and the combination of $R^{2a}$, $R^{2b}$, $R^{2c}$ and $R^4$ for a compound corresponds in each case to one row of Table A Tables 10323 to 10462
Compounds of the formula Ia.52 in which $R^8$ is as defined in tables 3609 to 3748, and the combination of $R^{2a}$, $R^{2b}$, $R^{2c}$ and $R^4$ for a compound corresponds in each case to one row of Table A Tables 10463 to 10602
Compounds of the formula Ia.53 in which $R^8$ is as defined in tables 3609 to 3748, and the combination of $R^{2a}$, $R^{2b}$, $R^{2c}$ and $R^4$ for a compound corresponds in each case to one row of Table A Tables 10603 to 10628
Compounds of the formula Ia.54 in which $A^3$ is as defined in tables 5289 to 5314, and the combination of $R^{2a}$, $R^{2b}$, $R^{2c}$ and $R^4$ for a compound corresponds in each case to one row of Table A Tables 10629 to 10928
Compounds of the formula Ia.55 in which $R^6$ is as defined in tables 1 to 300, and the combination of $R^{2a}$, $R^{2b}$, $R^{2c}$ and $R^4$ for a compound corresponds in each case to one row of Table A Tables 10929 to 11228
Compounds of the formula Ia.56 in which $R^6$ is as defined in tables 1 to 300, and the combination of $R^{2a}$, $R^{2b}$, $R^{2c}$ and $R^4$ for a compound corresponds in each case to one row of Table A Tables 11229 to 11528
Compounds of the formula Ia.57 in which $R^6$ is as defined in tables 1 to 300, and the combination of $R^{2a}$, $R^{2b}$, $R^{2c}$ and $R^4$ for a compound corresponds in each case to one row of Table A Tables 11529 to 11828
Compounds of the formula Ia.58 in which $R^6$ is as defined in tables 1 to 300, and the combination of $R^{2a}$, $R^{2b}$, $R^{2c}$ and $R^4$ for a compound corresponds in each case to one row of Table A Tables 11829 to 12128
Compounds of the formula Ia.59 in which $R^6$ is as defined in tables 1 to 300, and the combination of $R^{2a}$, $R^{2b}$, $R^{2c}$ and $R^4$ for a compound corresponds in each case to one row of Table A Tables 12129 to 12428
Compounds of the formula Ia.60 in which $R^6$ is as defined in tables 1 to 300, and the combination of $R^{2a}$, $R^{2b}$, $R^{2c}$ and $R^4$ for a compound corresponds in each case to one row of Table A Tables 12429 to 12728
Compounds of the formula Ia.61 in which $R^6$ is as defined in tables 1 to 300, and the combination of $R^{2a}$, $R^{2b}$, $R^{2c}$ and $R^4$ for a compound corresponds in each case to one row of Table A Tables 12729 to 13028
Compounds of the formula Ia.62 in which $R^6$ is as defined in tables 1 to 300, and the combination of $R^{2a}$, $R^{2b}$, $R^{2c}$ and $R^4$ for a compound corresponds in each case to one row of Table A Tables 13029 to 13328
Compounds of the formula Ia.63 in which $R^6$ is as defined in tables 1 to 300, and the combination of $R^{2a}$, $R^{2b}$, $R^{2c}$ and $R^4$ for a compound corresponds in each case to one row of Table A Tables 13329 to 13628
Compounds of the formula Ia.64 in which $R^6$ is as defined in tables 1 to 300, and the combination of $R^{2a}$, $R^{2b}$, $R^{2c}$ and $R^4$ for a compound corresponds in each case to one row of Table A Tables 13629 to 13928
Compounds of the formula Ia.65 in which $R^6$ is as defined in tables 1 to 300, and the combination of $R^{2a}$, $R^{2b}$, $R^{2c}$ and $R^4$ for a compound corresponds in each case to one row of Table A Tables 13929 to 14228
Compounds of the formula Ia.66 in which $R^6$ is as defined in tables 1 to 300, and the combination of $R^{2a}$, $R^{2b}$, $R^{2c}$ and $R^4$ for a compound corresponds in each case to one row of Table A Table 14229 to 14232
Compounds of the formula Ia.67 in which $R^{9a}$ and $R^{9b}$ are as defined in tables 3601 to 3604, and the combination of $R^{2a}$, $R^{2b}$, $R^{2c}$ and $R^4$ for a compound corresponds in each case to one row of Table A Table 14233 to 14236

Compounds of the formula Ia.68 in which $R^{9a}$ and $R^{9b}$ are as defined in tables 3601 to 3604, and the combination of $R^{2a}$, $R^{2b}$, $R^{2c}$ and $R^4$ for a compound corresponds in each case to one row of Table A Tables 14237 to 14376

Compounds of the formula Ia.69 in which $R^8$ is as defined in tables 3609 to 3748, and the combination of $R^{2a}$, $R^{2b}$, $R^{2c}$ and $R^4$ for a compound corresponds in each case to one row of Table A Tables 14377 to 14516

Compounds of the formula Ia.70 in which $R^8$ is as defined in tables 3609 to 3748, and the combination of $R^{2a}$, $R^{2b}$, $R^{2c}$ and $R^4$ for a compound corresponds in each case to one row of Table A Tables 14517 to 14656

Compounds of the formula Ia.71 in which $R^8$ is as defined in tables 3609 to 3748, and the combination of $R^{2a}$, $R^{2b}$, $R^{2c}$ and $R^4$ for a compound corresponds in each case to one row of Table A Tables 14657 to 14796

Compounds of the formula Ia.72 in which $R^8$ is as defined in tables 3609 to 3748, and the combination of $R^{2a}$, $R^{2b}$, $R^{2c}$ and $R^4$ for a compound corresponds in each case to one row of Table A Tables 14797 to 14936

Compounds of the formula Ia.73 in which $R^8$ is as defined in tables 3609 to 3748, and the combination of $R^{2a}$, $R^{2b}$, $R^{2c}$ and $R^4$ for a compound corresponds in each case to one row of Table A Tables 14937 to 15076

Compounds of the formula Ia.74 in which $R^8$ is as defined in tables 3609 to 3748, and the combination of $R^{2a}$, $R^{2b}$, $R^{2c}$ and $R^4$ for a compound corresponds in each case to one row of Table A Tables 15077 to 15216

Compounds of the formula Ia.75 in which $R^8$ is as defined in tables 3609 to 3748, and the combination of $R^{2a}$, $R^{2b}$, $R^{2c}$ and $R^4$ for a compound corresponds in each case to one row of Table A Tables 15217 to 15356

Compounds of the formula Ia.76 in which $R^8$ is as defined in tables 3609 to 3748, and the combination of $R^{2a}$, $R^{2b}$, $R^{2c}$ and $R^4$ for a compound corresponds in each case to one row of Table A Tables 15357 to 15496

Compounds of the formula Ia.77 in which $R^8$ is as defined in tables 3609 to 3748, and the combination of $R^{2a}$, $R^{2b}$, $R^{2c}$ and $R^4$ for a compound corresponds in each case to one row of Table A Tables 15497 to 15636

Compounds of the formula Ia.78 in which $R^8$ is as defined in tables 3609 to 3748, and the combination of $R^{2a}$, $R^{2b}$, $R^{2c}$ and $R^4$ for a compound corresponds in each case to one row of Table A Tables 15637 to 15776

Compounds of the formula Ia.79 in which $R^8$ is as defined in tables 3609 to 3748, and the combination of $R^{2a}$, $R^{2b}$, $R^{2c}$ and $R^4$ for a compound corresponds in each case to one row of Table A Tables 15777 to 15916

Compounds of the formula Ia.80 in which $R^8$ is as defined in tables 3609 to 3748, and the combination of $R^{2a}$, $R^{2b}$, $R^{2c}$ and $R^4$ for a compound corresponds in each case to one row of Table A Tables 15917 to 15942

Compounds of the formula Ia.81 in which $A^3$ is as defined in tables 5289 to 5314, and the combination of $R^{2a}$, $R^{2b}$, $R^{2c}$ and $R^4$ for a compound corresponds in each case to one row of Table A

TABLE A

| No. | $R^{2a}$ | $R^{2b}$ | $R^{2c}$ | $R^4$ |
|---|---|---|---|---|
| A-1 | F | H | F | H |
| A-2 | F | F | F | H |
| A-3 | F | Cl | F | H |
| A-4 | F | Br | F | H |
| A-5 | F | H | Cl | H |
| A-6 | F | H | Br | H |
| A-7 | Cl | H | Cl | H |
| A-8 | Cl | F | H | H |
| A-9 | Cl | Cl | Cl | H |
| A-10 | Cl | F | Cl | H |
| A-11 | Cl | Br | Cl | H |
| A-12 | Cl | H | Br | H |
| A-13 | Br | H | Br | H |
| A-14 | Br | F | Br | H |
| A-15 | Br | Cl | Br | H |
| A-16 | $CF_3$ | H | F | H |
| A-17 | $CF_3$ | H | Cl | H |
| A-18 | $CF_3$ | H | Br | H |
| A-19 | $CF_3$ | H | $CF_3$ | H |
| A-20 | $CF_3$ | F | F | H |
| A-21 | $CF_3$ | Cl | Cl | H |
| A-22 | $CF_3$ | Br | Br | H |
| A-23 | $OCF_3$ | H | F | H |
| A-24 | $OCF_3$ | H | Cl | H |
| A-25 | $OCF_3$ | H | Br | H |
| A-26 | $OCF_3$ | H | $CF_3$ | H |
| A-27 | $OCF_3$ | H | H | H |
| A-28 | $CF_3$ | H | H | H |
| A-29 | Br | H | H | H |
| A-30 | Cl | H | H | H |
| A-31 | F | H | H | H |
| A-32 | F | H | F | $CH_3$ |
| A-33 | F | F | F | $CH_3$ |
| A-34 | F | Cl | F | $CH_3$ |
| A-35 | F | Br | F | $CH_3$ |
| A-36 | F | H | Cl | $CH_3$ |
| A-37 | F | H | Br | $CH_3$ |
| A-38 | Cl | H | Cl | $CH_3$ |
| A-39 | Cl | F | H | $CH_3$ |
| A-40 | Cl | Cl | Cl | $CH_3$ |
| A-41 | Cl | F | Cl | $CH_3$ |
| A-42 | Cl | Br | Cl | $CH_3$ |
| A-43 | Cl | H | Br | $CH_3$ |
| A-44 | Br | H | Br | $CH_3$ |
| A-45 | Br | F | Br | $CH_3$ |
| A-46 | Br | Cl | Br | $CH_3$ |
| A-47 | $CF_3$ | H | F | $CH_3$ |
| A-48 | $CF_3$ | H | Cl | $CH_3$ |
| A-49 | $CF_3$ | H | Br | $CH_3$ |
| A-50 | $CF_3$ | H | $CF_3$ | $CH_3$ |
| A-51 | $CF_3$ | F | F | $CH_3$ |
| A-52 | $CF_3$ | Cl | Cl | $CH_3$ |
| A-53 | $CF_3$ | Br | Br | $CH_3$ |
| A-54 | $OCF_3$ | H | F | $CH_3$ |
| A-55 | $OCF_3$ | H | Cl | $CH_3$ |
| A-56 | $OCF_3$ | H | Br | $CH_3$ |
| A-57 | $OCF_3$ | H | $CF_3$ | $CH_3$ |
| A-58 | $OCF_3$ | H | H | $CH_3$ |
| A-59 | $CF_3$ | H | H | $CH_3$ |
| A-60 | Br | H | H | $CH_3$ |
| A-61 | Cl | H | H | $CH_3$ |
| A-62 | F | H | H | $CH_3$ |
| A-63 | F | H | F | $CHF_2$ |
| A-64 | F | F | F | $CHF_2$ |
| A-65 | F | Cl | F | $CHF_2$ |
| A-66 | F | Br | F | $CHF_2$ |
| A-67 | F | H | Cl | $CHF_2$ |
| A-68 | F | H | Br | $CHF_2$ |
| A-69 | Cl | H | Cl | $CHF_2$ |
| A-70 | Cl | F | H | $CHF_2$ |
| A-71 | Cl | Cl | Cl | $CHF_2$ |
| A-72 | Cl | F | Cl | $CHF_2$ |

TABLE A-continued

| No. | $R^{2a}$ | $R^{2b}$ | $R^{2c}$ | $R^4$ |
|---|---|---|---|---|
| A-73 | Cl | Br | Cl | $CHF_2$ |
| A-74 | Cl | H | Br | $CHF_2$ |
| A-75 | Br | H | Br | $CHF_2$ |
| A-76 | Br | F | Br | $CHF_2$ |
| A-77 | Br | Cl | Br | $CHF_2$ |
| A-78 | $CF_3$ | H | F | $CHF_2$ |
| A-79 | $CF_3$ | H | Cl | $CHF_2$ |
| A-80 | $CF_3$ | H | Br | $CHF_2$ |
| A-81 | $CF_3$ | H | $CF_3$ | $CHF_2$ |
| A-82 | $CF_3$ | F | F | $CHF_2$ |
| A-83 | $CF_3$ | Cl | Cl | $CHF_2$ |
| A-84 | $CF_3$ | Br | Br | $CHF_2$ |
| A-85 | $OCF_3$ | H | F | $CHF_2$ |
| A-86 | $OCF_3$ | H | Cl | $CHF_2$ |
| A-87 | $OCF_3$ | H | Br | $CHF_2$ |
| A-88 | $OCF_3$ | H | $CF_3$ | $CHF_2$ |
| A-89 | $OCF_3$ | H | H | $CHF_2$ |
| A-90 | $CF_3$ | H | H | $CHF_2$ |
| A-91 | Br | H | H | $CHF_2$ |
| A-92 | Cl | H | H | $CHF_2$ |
| A-93 | F | H | H | $CHF_2$ |
| A-94 | F | H | F | $CF_3$ |
| A-95 | F | F | F | $CF_3$ |
| A-96 | F | Cl | F | $CF_3$ |
| A-97 | F | Br | F | $CF_3$ |
| A-98 | F | H | Cl | $CF_3$ |
| A-99 | F | H | Br | $CF_3$ |
| A-100 | Cl | H | Cl | $CF_3$ |
| A-101 | Cl | F | H | $CF_3$ |
| A-102 | Cl | Cl | Cl | $CF_3$ |
| A-103 | Cl | F | Cl | $CF_3$ |
| A-104 | Cl | Br | Cl | $CF_3$ |
| A-105 | Cl | H | Br | $CF_3$ |
| A-106 | Br | H | Br | $CF_3$ |
| A-107 | Br | F | Br | $CF_3$ |
| A-108 | Br | Cl | Br | $CF_3$ |
| A-109 | $CF_3$ | H | F | $CF_3$ |
| A-110 | $CF_3$ | H | Cl | $CF_3$ |
| A-111 | $CF_3$ | H | Br | $CF_3$ |
| A-112 | $CF_3$ | H | $CF_3$ | $CF_3$ |
| A-113 | $CF_3$ | F | F | $CF_3$ |
| A-114 | $CF_3$ | Cl | Cl | $CF_3$ |
| A-115 | $CF_3$ | Br | Br | $CF_3$ |
| A-116 | $OCF_3$ | H | F | $CF_3$ |
| A-117 | $OCF_3$ | H | Cl | $CF_3$ |
| A-118 | $OCF_3$ | H | Br | $CF_3$ |
| A-119 | $OCF_3$ | H | $CF_3$ | $CF_3$ |
| A-120 | $OCF_3$ | H | H | $CF_3$ |
| A-121 | $CF_3$ | H | H | $CF_3$ |
| A-122 | Br | H | H | $CF_3$ |
| A-123 | Cl | H | H | $CF_3$ |
| A-124 | F | H | H | $CF_3$ |
| A-125 | F | H | F | F |
| A-126 | F | F | F | F |
| A-127 | F | Cl | F | F |
| A-128 | F | Br | F | F |
| A-129 | F | H | Cl | F |
| A-130 | F | H | Br | F |
| A-131 | Cl | H | Cl | F |
| A-132 | Cl | F | H | F |
| A-133 | Cl | Cl | Cl | F |
| A-134 | Cl | F | Cl | F |
| A-135 | Cl | Br | Cl | F |
| A-136 | Cl | H | Br | F |
| A-137 | Br | H | Br | F |
| A-138 | Br | F | Br | F |
| A-139 | Br | Cl | Br | F |
| A-140 | $CF_3$ | H | F | F |
| A-141 | $CF_3$ | H | Cl | F |
| A-142 | $CF_3$ | H | Br | F |
| A-143 | $CF_3$ | H | $CF_3$ | F |
| A-144 | $CF_3$ | F | F | F |
| A-145 | $CF_3$ | Cl | Cl | F |
| A-146 | $CF_3$ | Br | Br | F |
| A-147 | $OCF_3$ | H | F | F |
| A-148 | $OCF_3$ | H | Cl | F |
| A-149 | $OCF_3$ | H | Br | F |
| A-150 | $OCF_3$ | H | $CF_3$ | F |
| A-151 | $OCF_3$ | H | H | F |
| A-152 | $CF_3$ | H | H | F |
| A-153 | Br | H | H | F |
| A-154 | Cl | H | H | F |
| A-155 | F | H | H | F |
| A-156 | F | H | F | Cl |
| A-157 | F | F | F | Cl |
| A-158 | F | Cl | F | Cl |
| A-159 | F | Br | F | Cl |
| A-160 | F | H | Cl | Cl |
| A-161 | F | H | Br | Cl |
| A-162 | Cl | H | Cl | Cl |
| A-163 | Cl | F | H | Cl |
| A-164 | Cl | Cl | Cl | Cl |
| A-165 | Cl | F | Cl | Cl |
| A-166 | Cl | Br | Cl | Cl |
| A-167 | Cl | H | Br | Cl |
| A-168 | Br | H | Br | Cl |
| A-169 | Br | F | Br | Cl |
| A-170 | Br | Cl | Br | Cl |
| A-171 | $CF_3$ | H | F | Cl |
| A-172 | $CF_3$ | H | Cl | Cl |
| A-173 | $CF_3$ | H | Br | Cl |
| A-174 | $CF_3$ | H | $CF_3$ | Cl |
| A-175 | $CF_3$ | F | F | Cl |
| A-176 | $CF_3$ | Cl | Cl | Cl |
| A-177 | $CF_3$ | Br | Br | Cl |
| A-178 | $OCF_3$ | H | F | Cl |
| A-179 | $OCF_3$ | H | Cl | Cl |
| A-180 | $OCF_3$ | H | Br | Cl |
| A-181 | $OCF_3$ | H | $CF_3$ | Cl |
| A-182 | $OCF_3$ | H | H | Cl |
| A-183 | $CF_3$ | H | H | Cl |
| A-184 | Br | H | H | Cl |
| A-185 | Cl | H | H | Cl |
| A-186 | F | H | H | Cl |
| A-187 | F | H | F | Br |
| A-188 | F | F | F | Br |
| A-189 | F | Cl | F | Br |
| A-190 | F | Br | F | Br |
| A-191 | F | H | Cl | Br |
| A-192 | F | H | Br | Br |
| A-193 | Cl | H | Cl | Br |
| A-194 | Cl | F | H | Br |
| A-195 | Cl | Cl | Cl | Br |
| A-196 | Cl | F | Cl | Br |
| A-197 | Cl | Br | Cl | Br |
| A-198 | Cl | H | Br | Br |
| A-199 | Br | H | Br | Br |
| A-200 | Br | F | Br | Br |
| A-201 | Br | Cl | Br | Br |
| A-202 | $CF_3$ | H | F | Br |
| A-203 | $CF_3$ | H | Cl | Br |
| A-204 | $CF_3$ | H | Br | Br |
| A-205 | $CF_3$ | H | $CF_3$ | Br |
| A-206 | $CF_3$ | F | F | Br |
| A-207 | $CF_3$ | Cl | Cl | Br |
| A-208 | $CF_3$ | Br | Br | Br |
| A-209 | $OCF_3$ | H | F | Br |
| A-210 | $OCF_3$ | H | Cl | Br |
| A-211 | $OCF_3$ | H | Br | Br |
| A-212 | $OCF_3$ | H | $CF_3$ | Br |
| A-213 | $OCF_3$ | H | H | Br |
| A-214 | $CF_3$ | H | H | Br |
| A-215 | Br | H | H | Br |
| A-216 | Cl | H | H | Br |
| A-217 | F | H | H | Br |
| A-218 | F | H | F | CN |
| A-219 | F | F | F | CN |
| A-220 | F | Cl | F | CN |
| A-221 | F | Br | F | CN |
| A-222 | F | H | Cl | CN |
| A-223 | F | H | Br | CN |
| A-224 | Cl | H | Cl | CN |
| A-225 | Cl | F | H | CN |
| A-226 | Cl | Cl | Cl | CN |
| A-227 | Cl | F | Cl | CN |
| A-228 | Cl | Br | Cl | CN |

TABLE A-continued

| No. | R²ᵃ | R²ᵇ | R²ᶜ | R⁴ |
|---|---|---|---|---|
| A-229 | Cl | H | Br | CN |
| A-230 | Br | H | Br | CN |
| A-231 | Br | F | Br | CN |
| A-232 | Br | Cl | Br | CN |
| A-233 | CF₃ | H | F | CN |
| A-234 | CF₃ | H | Cl | CN |
| A-235 | CF₃ | H | Br | CN |
| A-236 | CF₃ | H | CF₃ | CN |
| A-237 | CF₃ | F | F | CN |
| A-238 | CF₃ | Cl | Cl | CN |
| A-239 | CF₃ | Br | Br | CN |
| A-240 | OCF₃ | H | F | CN |
| A-241 | OCF₃ | H | Cl | CN |
| A-242 | OCF₃ | H | Br | CN |
| A-243 | OCF₃ | H | CF₃ | CN |
| A-244 | OCF₃ | H | H | CN |
| A-245 | CF₃ | H | H | CN |
| A-246 | Br | H | H | CN |
| A-247 | Cl | H | H | CN |
| A-248 | F | H | H | CN |
| A-249 | F | H | F | OCH₃ |
| A-250 | F | F | F | OCH₃ |
| A-251 | F | Cl | F | OCH₃ |
| A-252 | F | Br | F | OCH₃ |
| A-253 | F | H | Cl | OCH₃ |
| A-254 | F | H | Br | OCH₃ |
| A-255 | Cl | H | Cl | OCH₃ |
| A-256 | Cl | F | H | OCH₃ |
| A-257 | Cl | Cl | Cl | OCH₃ |
| A-258 | Cl | F | Cl | OCH₃ |
| A-259 | Cl | Br | Cl | OCH₃ |
| A-260 | Cl | H | Br | OCH₃ |
| A-261 | Br | H | Br | OCH₃ |
| A-262 | Br | F | Br | OCH₃ |
| A-263 | Br | Cl | Br | OCH₃ |
| A-264 | CF₃ | H | F | OCH₃ |
| A-265 | CF₃ | H | Cl | OCH₃ |
| A-266 | CF₃ | H | Br | OCH₃ |
| A-267 | CF₃ | H | CF₃ | OCH₃ |
| A-268 | CF₃ | F | F | OCH₃ |
| A-269 | CF₃ | Cl | Cl | OCH₃ |
| A-270 | CF₃ | Br | Br | OCH₃ |
| A-271 | OCF₃ | H | F | OCH₃ |
| A-272 | OCF₃ | H | Cl | OCH₃ |
| A-273 | OCF₃ | H | Br | OCH₃ |
| A-274 | OCF₃ | H | CF₃ | OCH₃ |
| A-275 | OCF₃ | H | H | OCH₃ |
| A-276 | CF₃ | H | H | OCH₃ |
| A-277 | Br | H | H | OCH₃ |
| A-278 | Cl | H | H | OCH₃ |
| A-279 | F | H | H | OCH₃ |
| A-280 | F | H | F | OCHF₂ |
| A-281 | F | F | F | OCHF₂ |
| A-282 | F | Cl | F | OCHF₂ |
| A-283 | F | Br | F | OCHF₂ |
| A-284 | F | H | Cl | OCHF₂ |
| A-285 | F | H | Br | OCHF₂ |
| A-286 | Cl | H | Cl | OCHF₂ |
| A-287 | Cl | F | H | OCHF₂ |
| A-288 | Cl | Cl | Cl | OCHF₂ |
| A-289 | Cl | F | Cl | OCHF₂ |
| A-290 | Cl | Br | Cl | OCHF₂ |
| A-291 | Cl | H | Br | OCHF₂ |
| A-292 | Br | H | Br | OCHF₂ |
| A-293 | Br | F | Br | OCHF₂ |
| A-294 | Br | Cl | Br | OCHF₂ |
| A-295 | CF₃ | H | F | OCHF₂ |
| A-296 | CF₃ | H | Cl | OCHF₂ |
| A-297 | CF₃ | H | Br | OCHF₂ |
| A-298 | CF₃ | H | CF₃ | OCHF₂ |
| A-299 | CF₃ | F | F | OCHF₂ |
| A-300 | CF₃ | Cl | Cl | OCHF₂ |
| A-301 | CF₃ | Br | Br | OCHF₂ |
| A-302 | OCF₃ | H | F | OCHF₂ |
| A-303 | OCF₃ | H | Cl | OCHF₂ |
| A-304 | OCF₃ | H | Br | OCHF₂ |
| A-305 | OCF₃ | H | CF₃ | OCHF₂ |
| A-306 | OCF₃ | H | H | OCHF₂ |
| A-307 | CF₃ | H | H | OCHF₂ |
| A-308 | Br | H | H | OCHF₂ |
| A-309 | Cl | H | H | OCHF₂ |
| A-310 | F | H | H | OCHF₂ |
| A-311 | F | H | F | OCF₃ |
| A-312 | F | F | F | OCF₃ |
| A-313 | F | Cl | F | OCF₃ |
| A-314 | F | Br | F | OCF₃ |
| A-315 | F | H | Cl | OCF₃ |
| A-316 | F | H | Br | OCF₃ |
| A-317 | Cl | H | Cl | OCF₃ |
| A-318 | Cl | F | H | OCF₃ |
| A-319 | Cl | Cl | Cl | OCF₃ |
| A-320 | Cl | F | Cl | OCF₃ |
| A-321 | Cl | Br | Cl | OCF₃ |
| A-322 | Cl | H | Br | OCF₃ |
| A-323 | Br | H | Br | OCF₃ |
| A-324 | Br | F | Br | OCF₃ |
| A-325 | Br | Cl | Br | OCF₃ |
| A-326 | CF₃ | H | F | OCF₃ |
| A-327 | CF₃ | H | Cl | OCF₃ |
| A-328 | CF₃ | H | Br | OCF₃ |
| A-329 | CF₃ | H | CF₃ | OCF₃ |
| A-330 | CF₃ | F | F | OCF₃ |
| A-331 | CF₃ | Cl | Cl | OCF₃ |
| A-332 | CF₃ | Br | Br | OCF₃ |
| A-333 | OCF₃ | H | F | OCF₃ |
| A-334 | OCF₃ | H | Cl | OCF₃ |
| A-335 | OCF₃ | H | Br | OCF₃ |
| A-336 | OCF₃ | H | CF₃ | OCF₃ |
| A-337 | OCF₃ | H | H | OCF₃ |
| A-338 | CF₃ | H | H | OCF₃ |
| A-339 | Br | H | H | OCF₃ |
| A-340 | Cl | H | H | OCF₃ |
| A-341 | F | H | H | OCF₃ |
| A-342 | F | H | F | SCH₃ |
| A-343 | F | F | F | SCH₃ |
| A-344 | F | Cl | F | SCH₃ |
| A-345 | F | Br | F | SCH₃ |
| A-346 | F | H | Cl | SCH₃ |
| A-347 | F | H | Br | SCH₃ |
| A-348 | Cl | H | Cl | SCH₃ |
| A-349 | Cl | F | H | SCH₃ |
| A-350 | Cl | Cl | Cl | SCH₃ |
| A-351 | Cl | F | Cl | SCH₃ |
| A-352 | Cl | Br | Cl | SCH₃ |
| A-353 | Cl | H | Br | SCH₃ |
| A-354 | Br | H | Br | SCH₃ |
| A-355 | Br | F | Br | SCH₃ |
| A-356 | Br | Cl | Br | SCH₃ |
| A-357 | CF₃ | H | F | SCH₃ |
| A-358 | CF₃ | H | Cl | SCH₃ |
| A-359 | CF₃ | H | Br | SCH₃ |
| A-360 | CF₃ | H | CF₃ | SCH₃ |
| A-361 | CF₃ | F | F | SCH₃ |
| A-362 | CF₃ | Cl | Cl | SCH₃ |
| A-363 | CF₃ | Br | Br | SCH₃ |
| A-364 | OCF₃ | H | F | SCH₃ |
| A-365 | OCF₃ | H | Cl | SCH₃ |
| A-366 | OCF₃ | H | Br | SCH₃ |
| A-367 | OCF₃ | H | CF₃ | SCH₃ |
| A-368 | OCF₃ | H | H | SCH₃ |
| A-369 | CF₃ | H | H | SCH₃ |
| A-370 | Br | H | H | SCH₃ |
| A-371 | Cl | H | H | SCH₃ |
| A-372 | F | H | H | SCH₃ |
| A-373 | F | H | F | SCF₃ |
| A-374 | F | F | F | SCF₃ |
| A-375 | F | Cl | F | SCF₃ |
| A-376 | F | Br | F | SCF₃ |
| A-377 | F | H | Cl | SCF₃ |
| A-378 | F | H | Br | SCF₃ |
| A-379 | Cl | H | Cl | SCF₃ |
| A-380 | Cl | F | H | SCF₃ |
| A-381 | Cl | Cl | Cl | SCF₃ |
| A-382 | Cl | F | Cl | SCF₃ |
| A-383 | Cl | Br | Cl | SCF₃ |
| A-384 | Cl | H | Br | SCF₃ |

TABLE A-continued

| No. | $R^{2a}$ | $R^{2b}$ | $R^{2c}$ | $R^4$ |
|---|---|---|---|---|
| A-385 | Br | H | Br | $SCF_3$ |
| A-386 | Br | F | Br | $SCF_3$ |
| A-387 | Br | Cl | Br | $SCF_3$ |
| A-388 | $CF_3$ | H | F | $SCF_3$ |
| A-389 | $CF_3$ | H | Cl | $SCF_3$ |
| A-390 | $CF_3$ | H | Br | $SCF_3$ |
| A-391 | $CF_3$ | H | $CF_3$ | $SCF_3$ |
| A-392 | $CF_3$ | F | F | $SCF_3$ |
| A-393 | $CF_3$ | Cl | Cl | $SCF_3$ |
| A-394 | $CF_3$ | Br | Br | $SCF_3$ |
| A-395 | $OCF_3$ | H | F | $SCF_3$ |
| A-396 | $OCF_3$ | H | Cl | $SCF_3$ |
| A-397 | $OCF_3$ | H | Br | $SCF_3$ |
| A-398 | $OCF_3$ | H | $CF_3$ | $SCF_3$ |
| A-399 | $OCF_3$ | H | H | $SCF_3$ |
| A-400 | $CF_3$ | H | H | $SCF_3$ |
| A-401 | Br | H | H | $SCF_3$ |
| A-402 | Cl | H | H | $SCF_3$ |
| A-403 | F | H | H | $SCF_3$ |

Among the above compounds preference is given to compounds of formulae Ia.1, Ia.15, Ia.16, Ia.28 and Ia.55, and in particular to compounds Ia.1.

The compounds of the formula I can be prepared by the methods as described in the below schemes or and in the synthesis descriptions of the working examples, or by standard methods of organic chemistry. The substituents, variables and indices are as defined above for formula (I), if not otherwise specified.

Compounds of formula I.1 and I.2 can be prepared by dehydrating a compound of formula 1 as shown in scheme 1 below. A' is A or a precursor of A. Typical precursors of A are a halogen atom, CN, carboxy, —$CO_2$—$R^{z1}$, such as tert-butoxycarbonyl (carboxy and $C(O)OR^{z1}$ are of course only "precursors" if in the desired compound I W is S and/or $R^{z1}$ is not the desired radical $R^9$ and/or if Y is to be —$NR^5R^6$), an acetale group, a protected aldehyde group or —$OSO_2$—$R^{z1}$, where $R^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy. Compounds I.1' and I.2' correspond to compounds I.1 and I.2 when A' is A. $R^{31}$, $R^{32}$, $R^{33}$, $R^{34}$, $R^{35}$ and $R^{36}$ have one of the meanings given for $R^{3a}$, $R^{3b}$ and $R^{3c}$, with the proviso that at least one of $R^{32}$ and $R^{34}$ is hydrogen. In compounds I.1' $R^{31}$ and $R^{32}$ correspond to $R^{3a}$ and $R^{3b}$ and $R^{33}$ corresponds to $R^{3c}$, whereas in compounds I.2' $R^{31}$ corresponds to $R^{3c}$ and $R^{33}$ and $R^{34}$ correspond to $R^{3a}$ and $R^{3b}$. In compounds 1, I.1' and I.2' $R^{35}$ and $R^{36}$ correspond to $R^{3a}$ and $R^{3b}$. Dehydration either occurs spontaneously or with the help of dehydrating agents, such as molecular sieves, acid-washed molecular sieves, magnesium sulfate, sodium sulfate, silica gel, $SOCl_2$, $POCl_3$, Burgess reagent, trifluoroacetic anhydride, p-toluene sulfonic acid, anhydrous HCl or sulfuric acid. The water formed may alternatively be removed, e.g. by azeotropic distillation, e.g. with benzene/toluene as entrainer, e.g. using a Dean Stark trap. If necessary (i.e. if A' is a precursor of A), A' is then converted into a group A.

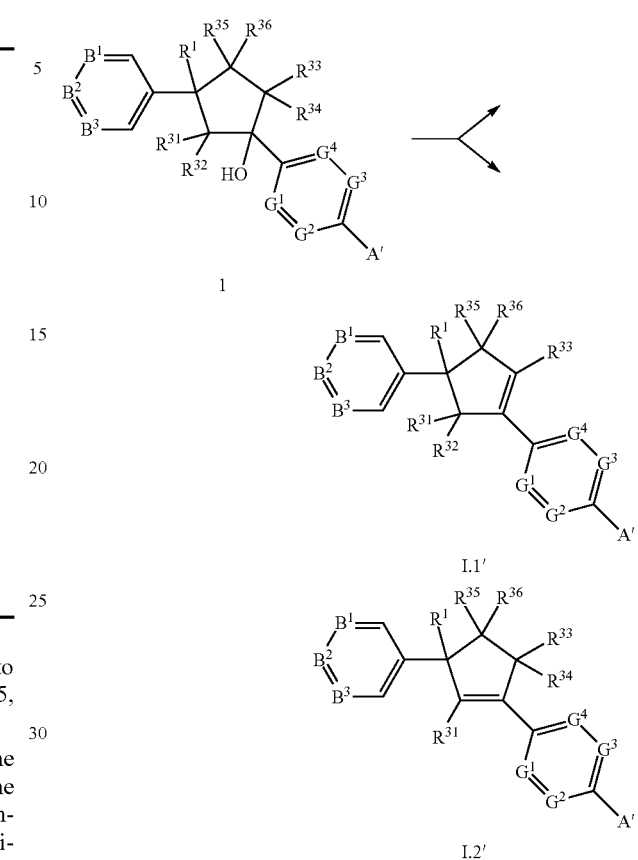

Scheme 1

Compounds 1 wherein $R^{31}$, $R^{32}$, $R^{33}$, $R^{34}$, $R^{35}$ and $R^{36}$ are hydrogen (in the following compounds 1') can be prepared as shown in scheme 2 below by reacting the cyclopentanone compound 2 with the Grignard reagent 3. Instead of the MgBr compound 3 the corresponding MgCl or MgI compound can be used.

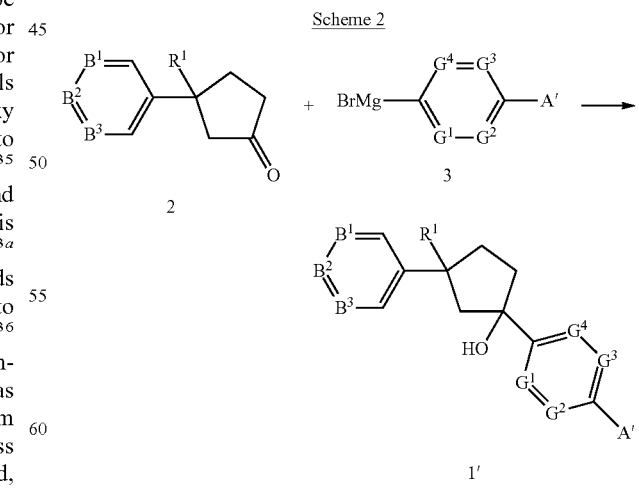

Scheme 2

Alternatively, compounds I.1' and I.2' wherein $R^{31}$, $R^{32}$, $R^{33}$, $R^{34}$, $R^{35}$ and $R^{36}$ are hydrogen (in the following compounds I.1'" and I.2'") can be prepared as shown in scheme 3 below by reacting the vinyl trifalte 4 (in case of I.1''') or the vinyl triflate 5 (in case of I.2''') with the aryl boron reagent 6 (wherein each $R^B$ stands independently for hydrogen or $C_1$-$C_4$-alkyl or the two $R^B$ form together a $C_2$-$C_6$-alkylene bridge, e.g. —C(CH$_3$)$_2$—C(CH$_3$)$_2$—) under Suzuki reaction conditions via Pd-catalyzed cross coupling, such as described, for example, in WO 2007/075459. A typical catalyst is tetrakis(triphenylphosphine)palladium(0). Solvents such as tetrahydrofuran, acetonitrile, diethyl ether and dioxane are suitable. The vinyl triflates 4 and 5 can be obtained from ketone 2 using standard conditions, e.g. lithiumdiisopropylamide ("LDA") or lithium 2,2,6,6-tetramethylpiperidide (LTMP) as base and N-Phenyl-bis(trifluoromethanesulfonimide) ("PhNTf$_2$", CAS 37595-74-7) as triflating agent.

Scheme 4

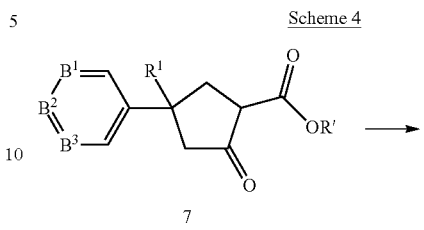

Scheme 3

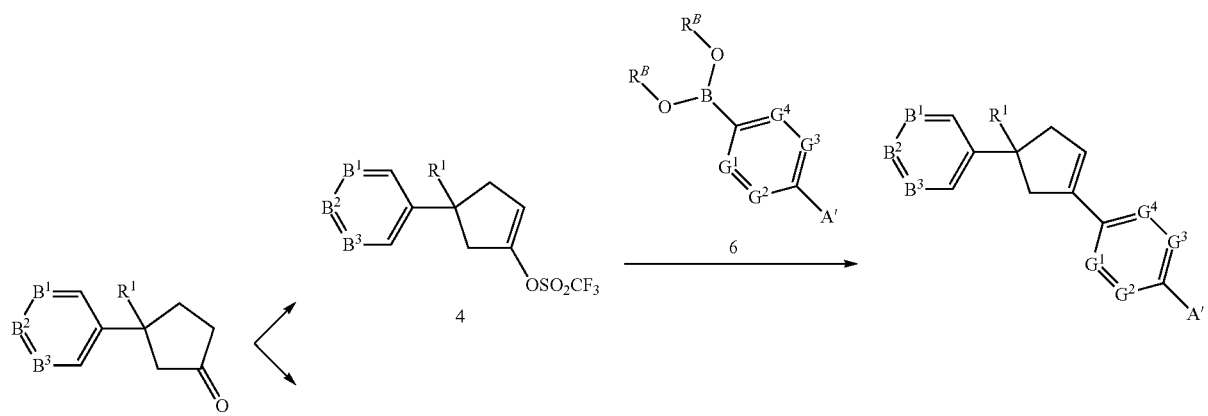

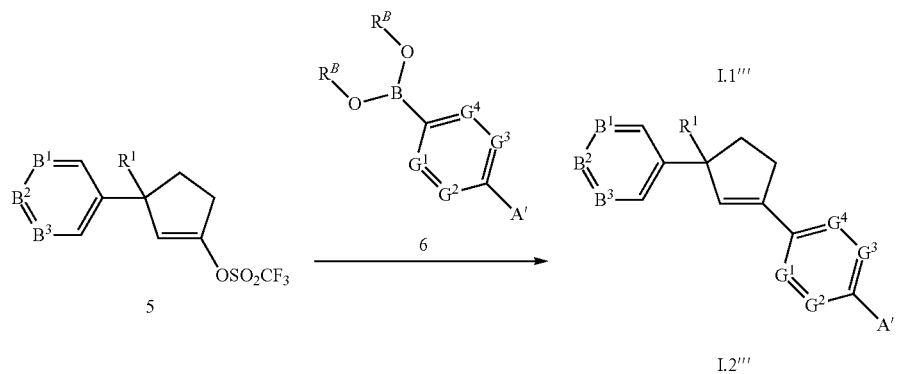

The cyclopentanone 2 can be prepared by decarboxylation of the carboxylic acid 8, e.g. under heat, as shown in scheme 4 below. This acid can in turn be prepared by hydrolysis of the ester 7, where R' is a $C_1$-$C_4$-alkyl group. Hydrolysis can be carried out under acidic or, preferably, basic conditions. Suitable bases are for example inorganic bases such as alkali metal hydroxides, e.g. lithium, sodium or potassium hydroxide, or carbonates, such as sodium or potassium carbonate. Alternatively, hydrolysis and decarboxylation can be carried out in a single step reaction using sulfuric acid and water.

-continued

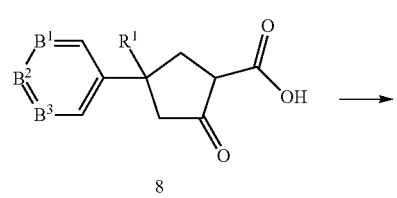

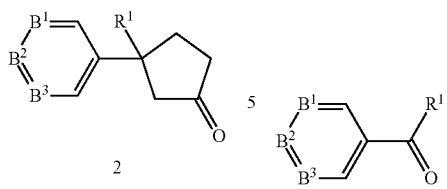

2

The ester 7 can be prepared as shown in scheme 5 by a Claisen (to be more precise: Dieckmann) condensation of the diester 9. R and R' are $C_1$-$C_4$-alkyl groups. The condensation reaction is carried out in the presence of a strong base, such as sodium methanolate, sodium ethanolate, potassium tert-butylate, sodium amide, sodium hydride or LDA.

Scheme 5

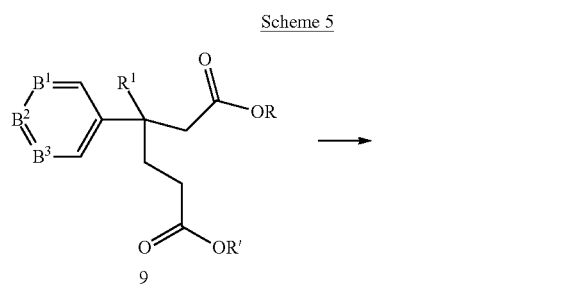

The diester 9 can in turn be prepared in an addition of 11 to the acrylate 10, as shown in scheme 6 below. X is MgZ, ZnZ or Li, where Z is Cl, Br or I. The addition reaction is generally carried out under condition suitable for Grignard reactions, especially under anhydrous conditions.

Scheme 6

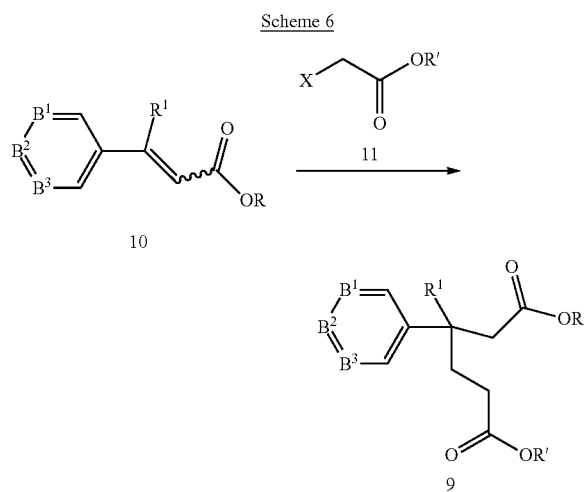

The acrylate 10 can be prepared from the ketone 12 in a Wittig reaction with 13, as shown in scheme 7 below (Ph=phenyl).

Scheme 7

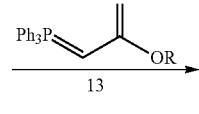

12

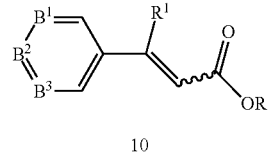

10

An alternative route from ketone 12 to ketone 2 is shown in scheme 8 below. First, ketone 12 is converted to the alkene 14 in a Wittig reaction (Ph=phenyl). The alkene 14 is then converted into exocyclic alkene 16 by a trimethylenemethane cycloaddition ("TMM cycloaddition") using reagent 15 and Pd(OAc)$_2$ (OAc=acetate; TMS=trimethylsilyl) as catalyst. Suitable conditions for the TMM cycloaddition are described, for example, in Organic Reactions 2004, 61, 1-217. The exocyclic alkene 16 is then converted into ketone 2 using standard ozonolysis conditions.

Scheme 8

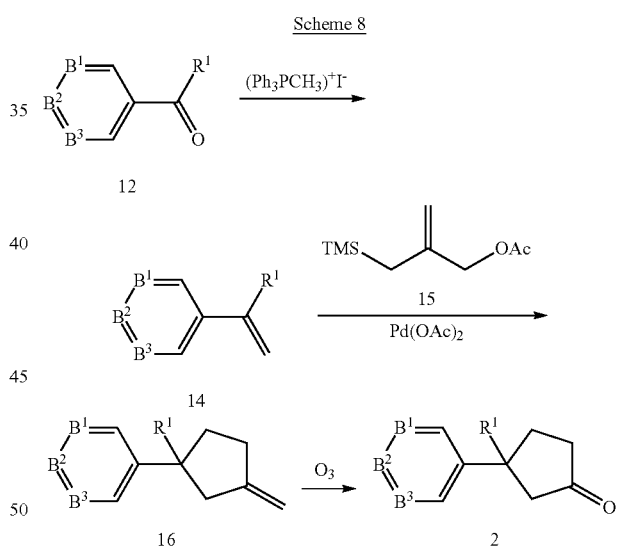

Compounds 1 wherein at least one of $R^{31}$, $R^{32}$, $R^{33}$, $R^{34}$, $R^{35}$ and $R^{36}$ is different from hydrogen (but wherein at least one of $R^{32}$ and $R^{34}$ is hydrogen) can be prepared analogously by using the correspondingly substituted starting compounds.

Compounds I.3' can be prepared from compounds I.2" as shown in scheme 9 below. Compounds I.2" are compounds I.2' where $R^{33}$ and $R^{36}$ are hydrogen. The allylic carbon atom of the cyclopentene ring in I.2" is subjected to a Riley oxidation using selenium dioxide to give the cyclopentenol 17. Suitably the reaction is carried out in dichloromethane or in a polar solvent, such as a lower alkanol, e.g. methanol, ethanol or isopropanol, a cyclic ether, such as tetrahydrofuran or dioxane, or a carboxylic acid, such as acetic acid.

The reaction can be either carried out by using stoichiometric amounts of $SeO_2$, or by using catalytic amounts of the selenium compound in presence of a co-oxidant such as hydrogen peroxide or a hydroperoxide, such as tert-butyl hydroperoxide. Alternatively, compound I.2″ is converted into cyclopentenol 17 in a two-step process via the corresponding allylbromide 17a. Thereto, the allylic carbon of cyclopentene I.2″ is brominated using e.g. $Br_2$ in a solvent such as $CHCl_3$ to obtain compound 17a. The allylbromide 17a is then hydrolyzed to the corresponding allylalcohol 17 using e.g. $AgClO_4$ in a solvent such as a mixture of water and acetone. Cyclopentenol 17 is then dehydrated to obtain cyclopentadiene I.3′. Dehydration either occurs spontaneously or with the help of dehydrating agents, such as molecular sieves, acid-washed molecular sieves, magnesium sulfate, sodium sulfate, silica gel, $SOCl_2$, $POCl_3$, Burgess reagent, trifluoroacetic anhydride, p-toluene sulfonic acid, anhydrous HCl or sulfuric acid. The water formed may alternatively be removed, e.g. by azeotropic distillation, e.g. with benzene/toluene as entrainer, e.g. using a Dean Stark trap.

fate, silica gel, $SOCl_2$, $POCl_3$, Burgess reagent, trifluoroacetic anhydride, p-toluene sulfonic acid, anhydrous HCl or sulfuric acid. The water formed may alternatively be removed, e.g. by azeotropic distillation, e.g. with benzene/toluene as entrainer, e.g. using a Dean Stark trap. Alternatively, the alcohol group of cyclopentanol 17b is converted into a leaving group, which is then eliminated to form cyclopentene I.1″. Suitable conditions are reaction of the alcohol 17b with methanesulfonyl chloride ("MsCl"), preferably in the presence of a base such as an amine base (e.g. $Et_3N$) and in a solvent. Preferably, chlorinated solvents such as $CH_2Cl_2$ or ethereal solvents such as THF are used. The obtained mesylate is then eliminated using e.g. a base such as 1,8-diazabicyclo[5.4.0]undec-7-ene ("DBU").

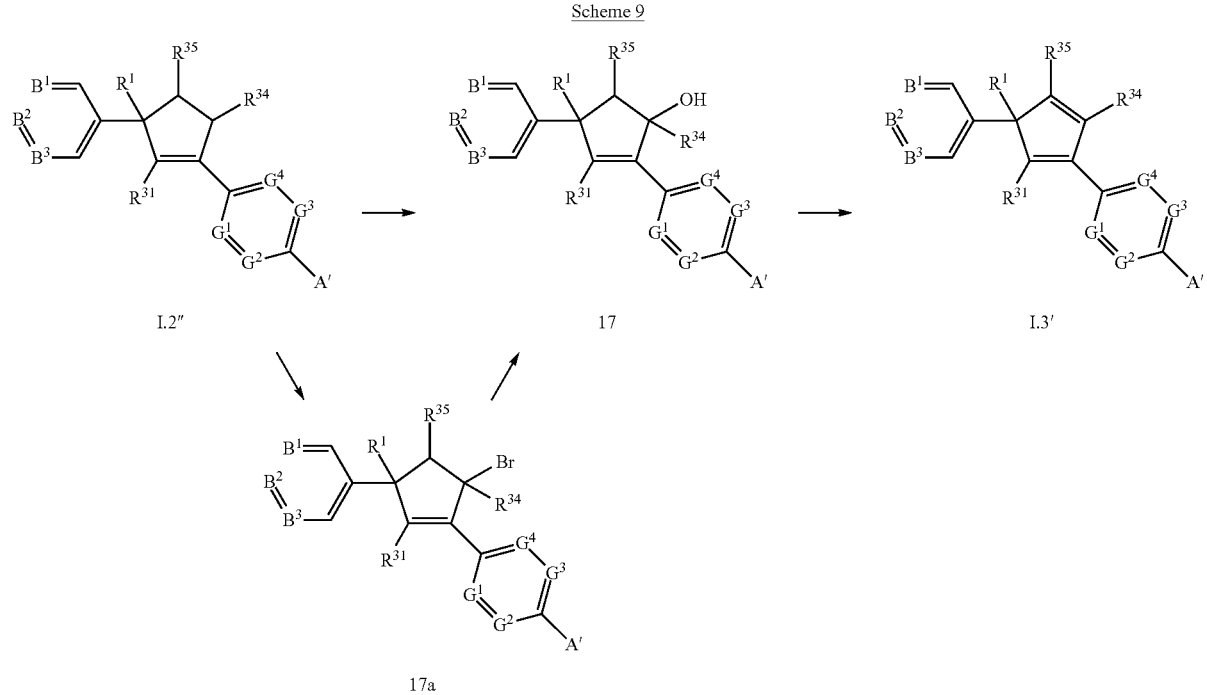

Compounds I.1″ can be prepared from allylalcohols 17 as shown in scheme 10 below. Compounds I.1″ are compounds I.1′ where $R^{33}$ and $R^{36}$ are hydrogen. Cyclpentenol 17 is hydrogenated to give cycopentanol 17b. Suitably, the reaction is carried out under hydrogen gas in a solvent, such as a lower alkanol, e.g. methanol, or ethanol, or in ethyl acetate, or a carboxylic acid, such as acetic acid. Additionally, a suitable hydrogenation catalyst such as palladium on charcoal (Pd/C) or rhodium on charcoal (Rh/C) is to be used. Cyclopentanol 17b is then dehydrated to give cyclopentene I.1″. Dehydration either occurs spontaneously or with the help of dehydrating agents, such as molecular sieves, acid-washed molecular sieves, magnesium sulfate, sodium sul-

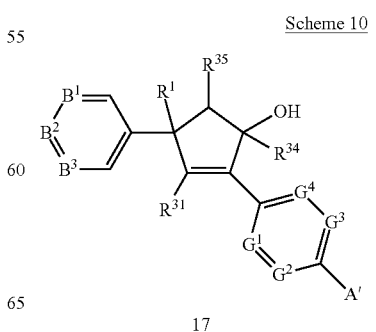

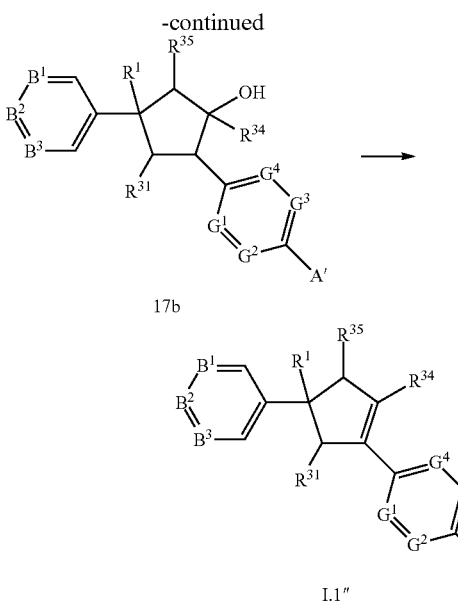

Compounds I.1', I.2' and I.3', in which A' is a precursor of A can be converted as shown below into the different groups A¹ to A³. The conversion reactions are shown below for compounds I.1', but they apply all the same for all compounds I, i.e. also for compounds I.2' and I.3'.

Compounds I.1 wherein A is a group A¹, wherein W is O can be prepared by reacting a compound I.1' wherein A' is Cl, Br, I or triflate with carbon monoxide in the presence of a palladium catalyst and an alcohol ROH, wherein R is $C_1$-$C_4$-alkyl or $R^9$, to a compound of formula 18. Suitable palladium catalysts are for example those described in PCT/EP 2011/060388.

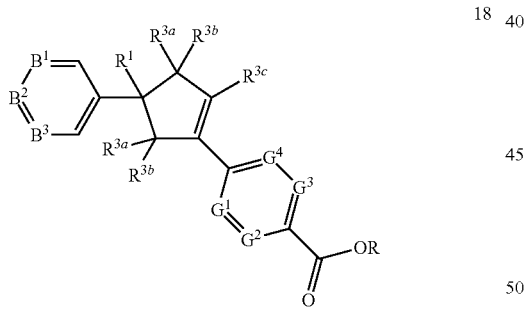

This ester is then hydrolyzed to the respective carboxylic acid, which is the reacted under standard amidation conditions with an amine $NHR^5R^6$. Hydrolyzation can be carried out under standard conditions, e.g. under acidic conditions using for example hydrochloric acid, sulfuric acid or trifluoroacetic acid, or under basic conditions using for example an alkali metal hydroxide, such as LiOH, NaOH or KOH. Amidation is preferably carried out by activation of the carboxylic acids with oxalylchloride [$(COCl)_2$] or thionylchloride ($SOCl_2$) to the respective acid chlorides, followed by reaction with an amine $NHR^5R^6$. Alternatively, amidation is carried out in the presence of a coupling reagent. Suitable coupling reagent (activators) are well known and are for instance selected from carbodiimides, such as DCC (dicyclohexylcarbodiimide) and DIC (diisopropylcarbodiimide), benzotriazol derivatives, such as HATU (O-(7-azabenzotriazol-1-yl)-N,N,N',N'-tetramethyluronium hexafluorophosphate), HBTU ((O-benzotriazol-1-yl)-N,N,N',N'-tetramethyluronium hexafluorophosphate) and HCTU (1H-benzotriazolium-1-[bis(dimethylamino)methylene]-5-chloro tetrafluoroborate) and phosphonium-derived activators, such as BOP ((benzotriazol-1-yloxy)-tris(dimethyl-amino)phosphonium hexafluorophosphate), Py-BOP ((benzotriazol-1-yloxy)-tripyrrolidinphosphonium hexafluorophosphate) and Py-BrOP (bromotripyrrolidin-phosphonium hexafluorophosphate). Generally, the activator is used in excess. The benzotriazol and phosphonium coupling reagents are generally used in a basic medium.

Compounds I.1 wherein A is a group A¹, wherein W is S, can be prepared by reacting the corresponding oxo-compound (W is O) with Lawesson's reagent (CAS 19172-47-5), see for example Jesberger et al., Synthesis, 2003, 1929-1958 and references therein. Solvents such as HMPA or THF at an elevated temperature such as 60° C. to 100° C. can be used. Preferred reaction conditions are THF at 65° C.

Compounds I.1 wherein A is a group A², wherein $R^{7a}$ and $R^{7b}$ are hydrogen, can be prepared by reducing a compound 18 or 19 for example with LAH (lithium aluminium hydride) or DIBAL-H (diisobutyl aluminium hydride) to a compound 20.

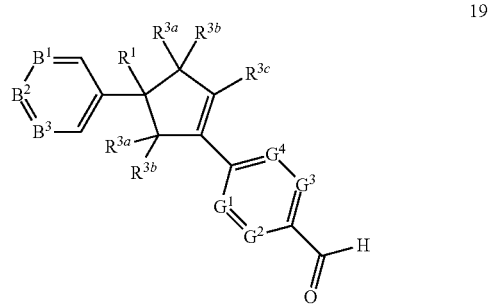

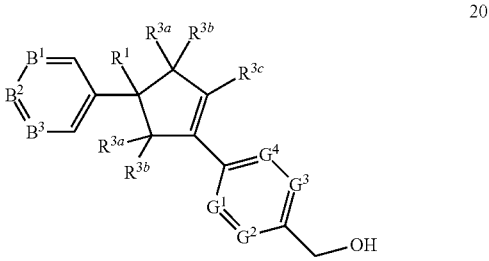

This is then reacted in an $S_N$ reaction with an amine $NHR^5R^6$. For this purpose, the OH group can first be converted into a better leaving group, e.g. into a sulfonate (for example mesylate, tosylate or a triflate group). If $R^6$ is a group —$C(O)R^8$, it is alternatively possible to react compound 20 with an amine $NH_2R^5$ and react then the resulting benzylic amine with an acid $R^8$—COOH or a derivative thereof, such as its acid chloride $R^8$—COCl, in an amidation reaction.

Compounds I.1 wherein A is a group A², wherein $R^{7a}$ is optionally substituted alkyl or optionally substituted cycloalkyl and $R^{7b}$ is hydrogen, can be prepared by subjecting a ketone 22 (see below scheme 10), where $R^{7a}$ is optionally substituted $C_1$-$C_6$-alkyl or optionally substituted $C_3$-$C_8$-cycloalkyl, to a reductive amination to furnish compounds 21. Typical conditions for the reductive amination are: Reacting ketone 16 with an amine $H_2NR^5$ to yield the corresponding imine which is reduced to amine 21 with a reducing agent reagent such as NaBH$_3$CN. The reaction from ketone 22 to amine 21 may also be carried out as a one pot procedure.

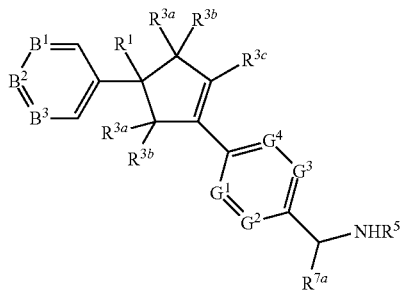

21

The ketone 22 is prepared from the carbonyl compound 19 which is reacted with a Grignard reagent R$^{7a}$—MgHal, where Hal is Cl, Br or I, or an organolithium compound R$^{7a}$—Li to obtain an alcohol of formula 23, which is then oxidized to a carbonyl compound of the formula 22, as shown in scheme 10.

Scheme 10

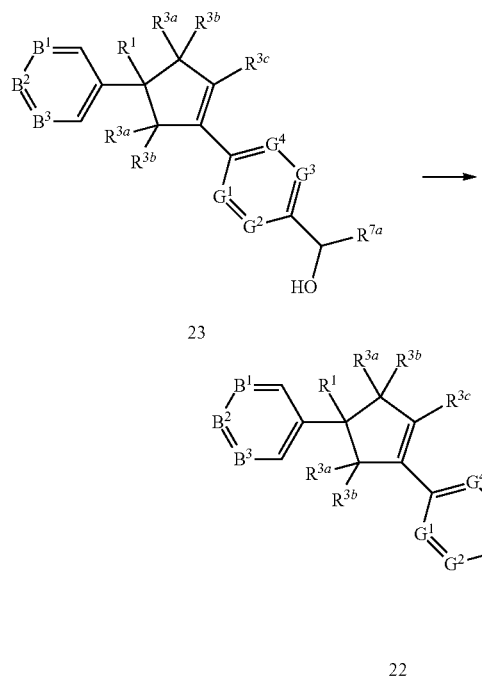

For obtaining compounds in which R$^{7a}$ and R$^{7b}$ are optionally substituted alkyl, optionally substituted cycloalkyl, optionally substituted alkenyl or optionally substituted alkynyl, carbonyl compounds such as 22, where R$^{7a}$ is optionally substituted C$_1$-C$_6$-alkyl, optionally substituted C$_3$-C$_8$-cycloalkyl, optionally substituted C$_2$-C$_6$-alkenyl or optionally substituted C$_2$-C$_6$-alkynyl, is reacted with a Grignard reagent R$^{7b}$—MgHal, where Hal is Cl, Br or I, or an organolithium compound R$^{7b}$—Li, where R$^{7b}$ is optionally substituted C$_1$-C$_6$-alkyl, optionally substituted C$_3$-C$_8$-cycloalkyl, optionally substituted C$_2$-C$_6$-alkenyl or optionally substituted C$_2$-C$_6$-alkynyl, to obtain an alcohol of formula 24.

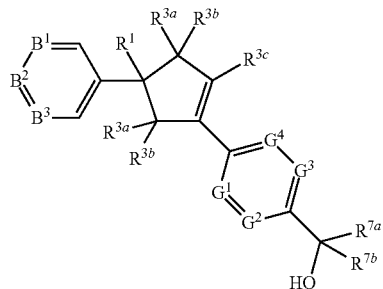

24

Alcohol 24 can then be converted into amine 25 via the corresponding azide, as described, for example, in Organic Letters, 2001, 3(20), 3145-3148.

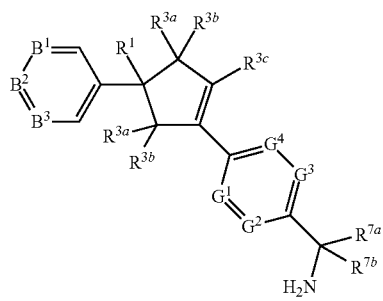

25

If desired, this can be converted into compounds I.1 wherein R$^5$ and R$^6$ are different from hydrogen, for example by standard alkylation or acylation reactions.

Compounds I.1 wherein A is a group A$^2$, wherein R$^{7a}$ is optionally substituted alkyl, alkenyl, alkynyl, cycloalkyl or CN and R$^{7b}$ is hydrogen, can be prepared by converting an aldehyde 19 into an imine 26 by reaction with an amine derivative NH$_2$R$^6$, wherein R$^6$ is tert-butyl sulfinyl, or, for preparing a compound with R$^{7a}$=CN, tosylate.

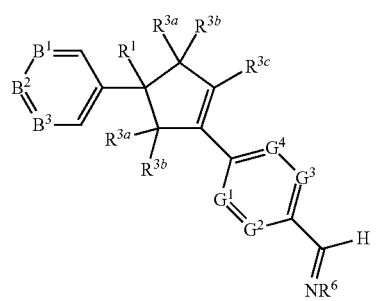

26

This imine is then reacted with a compound H—R$^{7a}$ in an addition reaction under conditions as described for example in J. Am. Chem. Soc. 2009, 3850-3851 and the references cited therein, or, for introducing CN as a group R$^{7a}$, Chemistry—A European Journal 2009, 15, 11642-11659.

Compounds I.1 wherein A is a group A$^2$, wherein both R$^{7a}$ and R$^{7b}$ are optionally substituted alkyl, alkenyl, alkynyl, cycloalkyl or CN, can be prepared analogously by converting a ketone 22, wherein $R^{7a}$ is optionally substituted alkyl, alkenyl, alkynyl, cycloalkyl or CN, into an imine by reaction with an amine derivative $NH_2R^6$, wherein $R^6$ is tert-butyl sulfinyl, for preparing an imine compound 27.

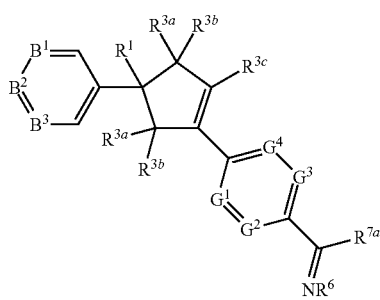

27

This imine is then reacted with a compound H—$R^{7b}$ in an addition reaction under conditions as described for example in J. Org. Chem 2002, 67, 7819-7832 and the references cited therein, or, for introducing CN as a group $R^{7a}$, Chemistry—A European Journal 2009, 15, 11642-11659. If desired, $R^6$ can then be removed to yield an amino group $NH_2$.

Compounds 19 can be prepared by reaction of a compound I.1', in which A' is Cl, Br, I or —$OSO_2$—$R^{z1}$, where $R^{z1}$ is as defined above, with carbon monoxide and a hydride source, such as triethylsilane, in the presence of a transition metal complex catalyst, preferably a palladium catalyst, to the aldehyde 19. This reaction converts the starting group A' into a carbonyl group —C(=O)H.

Compounds I.1 wherein A is $A^3$ can be prepared by standard ring coupling reactions. For example, compounds, wherein $A^3$ is an N-bound heterocyclic ring can be prepared by reacting a compound I.1' wherein A' is Cl, Br or I with the respective ring $A^3$-H (H being on the nitrogen ring atom to be coupled) under Ullmann coupling conditions, such as described, for example, in WO 2007/075459. Typically, copper(I) iodide or copper(I) oxide and a ligand such as 1,2-cyclohexyldiamine is used, see for example Kanemasa et al., European Journal of Organic Chemistry, 2004, 695-709. If A' is F, the reaction is typically run in a polar aprotic solvent such as N,N-dimethylformamide, N,N-dimethylacetamide or N-methylpyrrolidone, and in the presence of an inorganic base such as sodium, potassium or cesium carbonate.

Compounds, wherein $A^3$ is a C-bound heterocyclic ring can be prepared by reacting a compound I.1' wherein A' is Br or I with the boronic acid of the respective ring $A^3$-B(OH)$_2$ or the boronate ester of the respective ring $A^3$-B(OR)$_2$ under Suzuki reaction conditions via Pd-catalyzed cross coupling, such as described, for example, in WO 2007/075459. A typical catalyst is tetrakis(triphenylphosphine)palladium(0). Solvents such as tetrahydrofuran, acetonitrile, diethyl ether and dioxane are suitable. The boronic acids $A^3$-B(OH)$_2$ are either commercially available or can be prepared by known methods. Other methods for introduction of the heterocyclic groups $A^3$ are the Heck, Stille, Kumada and Buchwald-Hartwig coupling procedures; see for example Tetrahedron, 2004, 60, 8991-9016.

As a rule, the compounds of formula I including their stereoisomers, salts, and N-oxides, and their precursors in the synthesis process, can be prepared by the methods described above. If individual compounds can not be prepared via the above-described routes, they can be prepared by derivatization of other compounds I or the respective precursor or by customary modifications of the synthesis routes described. For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or on silica gel. Some of the intermediates and end products may be obtained in the form of colorless or pale brown viscous oils which are freed or purified from volatile components under reduced pressure and at moderately elevated temperature. If the intermediates and end products are obtained as solids, they may be purified by recrystallization or trituration.

Due to their excellent activity, the compounds of the present invention may be used for controlling invertebrate pests.

Accordingly, the present invention also provides a method for controlling invertebrate pests which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of the present invention or a composition as defined above. The invention also relates to the use of a compound of the invention, of a stereoisomer and/or of an agriculturally or veterinarily acceptable salt thereof for combating invertebrate pests Preferably, the method of the invention serves for protecting plant propagation material (such as seed) and the plant which grows therefrom from invertebrate pest attack or infestation and comprises treating the plant propagation material (such as seed) with a pesticidally effective amount of a compound of the present invention as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

Alternatively preferably, the method of the invention serves for protecting plants from attack or infestation by invertebrate pests, which method comprises treating the plants with a pesticidally effective amount of at least one compound of the invention, a stereoisomer thereof and/or at least one agriculturally acceptable salt thereof.

In the sense of the present invention, "invertebrate pests" are preferably selected from arthropods and nematodes, more preferably from harmful insects, arachnids and nematodes, and even more preferably from insects, acarids and nematodes. In the sense of the present invention, "invertebrate pests" are most preferably insects.

The invention further provides an agricultural composition for combating invertebrate pests, which comprises such an amount of at least one compound according to the invention and at least one inert liquid and/or solid agronomically acceptable carrier that has a pesticidal action and, if desired, at least one surfactant.

Such a composition may comprise a single active compound of the present invention or a mixture of several active compounds of the present invention. The composition according to the present invention may comprise an individual isomer or mixtures of isomers or a salt as well as individual tautomers or mixtures of tautomers.

The compounds of the present invention, including their salts, stereoisomers and tautomers, are in particular suitable for efficiently controlling arthropodal pests such as arachnids, myriapedes and insects as well as nematodes. They are especially suitable for efficiently combating or controlling the following pests:

insects from the order of the lepidopterans (Lepidoptera), for example *Acronicta major, Adoxophyes orana, Aedia leucomelas, Agrotis* spp. such as *Agrotis fucosa, Agrotis segetum, Agrotis ipsilon; Alabama argillacea, Anticarsia gemmatalis, Anticarsia* spp., *Argyresthia conjugella, Autographa gamma, Barathra brassicae, Bucculatrix thurberiella, Bupalus piniarius, Cacoecia murinana, Cacoecia podana, Capua reticulana, Carpocapsa pomonella, Cheimatobia brumata, Chilo* spp. such as *Chilo suppressalis; Choristoneura fumiferana, Choristoneura occidentalis, Cirphis unipuncta, Clysia ambiguella, Cnaphalocerus* spp., *Cydia pomonella, Dendrolimus pini, Diaphania nitidalis, Diatraea grandiosella, Earias insulana, Elasmopalpus lignosellus, Ephestia cautella, Ephestia kuehniella, Eupoecilia ambiguella, Euproctis chrysorrhoea, Euxoa* spp., *Evetria bouliana, Feltia* spp. such as *Feltia subterranean; Galleria mellonella, Grapholitha funebrana, Grapholitha molesta, Helicoverpa* spp. such as *Helicoverpa armigera, Helicoverpa zea; Heliothis* spp. such as *Heliothis armigera, Heliothis virescens, Heliothis zea; Hellula undalis, Hibernia defoliaria, Hofmannophila pseudospretella, Homona magnanima, Hyphantria cunea, Hyponomeuta padella, Hyponomeuta malinellus, Keiferia lycopersicella, Lambdina fiscellaria, Laphygma* spp. such as *Laphygma exigua; Leucoptera coffeella, Leucoptera scitella, Lithocolletis blancardella, Lithophane antennata, Lobesia botrana, Loxagrotis albicosta, Loxostege sticticalis, Lymantria* spp. such as *Lymantria dispar, Lymantria monacha; Lyonetia clerkella, Malacosoma neustria, Mamestra* spp. such as *Mamestra brassicae; Mocis repanda, Mythimna separata, Orgyia pseudotsugata, Oria* spp., *Ostrinia* spp. such as *Ostrinia nubilalis; Oulema oryzae, Panolis flammea, Pectinophora* spp. such as *Pectinophora gossypiella; Peridroma saucia, Phalera bucephala, Phthorimaea* spp. such as *Phthorimaea operculella; Phyllocnistis citrella, Pieris* spp. such as *Pieris brassicae, Pieris rapae; Plathypena scabra, Plutella maculipennis, Plutella xylostella, Prodenia* spp., *Pseudaletia* spp., *Pseudoplusia includens, Pyrausta nubilalis, Rhyacionia frustrana, Scrobipalpula absoluta, Sitotroga cerealella, Sparganothis pilleriana, Spodoptera* spp. such as *Spodoptera frugiperda, Spodoptera littoralis, Spodoptera litura; Thaumatopoea pityocampa, Thermesia gemmatalis, Tinea pellionella, Tineola bisselliella, Tortrix viridana, Trichoplusia* spp. such as *Trichoplusia ni; Tuta absoluta*, and *Zeiraphera canadensis*, beetles (Coleoptera), for example *Acanthoscehdes obtectus, Adoretus* spp., *Agelastica alni, Agrilus sinuatus, Agriotes* spp. such as *Agriotes fuscicollis, Agriotes lineatus, Agriotes obscurus; Amphimallus solstitialis, Anisandrus dispar, Anobium punctatum, Anomala rufocuprea, Anoplophora* spp. such as *Anoplophora glabripennis; Anthonomus* spp. such as *Anthonomus grandis, Anthonomus pomorum; Anthrenus* spp., *Aphthona euphoridae, Apogonia* spp., *Athous haemorrhoidalis, Atomaria* spp. such as *Atomaria lineariris; Attagenus* spp., *Aulacophora femoralis, Blastophagus piniperda, Blitophaga undata, Bruchidius obtectus, Bruchus* spp. such as *Bruchus lentis, Bruchus pisorum, Bruchus rufimanus; Byctiscus betulae, Callosobruchus chinensis, Cassida nebulosa, Cerotoma trifurcata, Cetonia aurata, Ceuthorhynchus* spp. such as *Ceuthorrhynchus assimilis, Ceuthorrhynchus napi; Chaetocnema tibialis, Cleonus mendicus, Conoderus* spp. such as *Conoderus vespertinus; Cosmopolites* spp., *Costelytra zealandica, Crioceris asparagi, Cryptorhynchus lapathi, Ctenicera* ssp. such as *Ctenicera destructor; Curculio* spp., *Dectes texanus, Dermestes* spp., *Diabrotica* spp. such as *Diabrotica 12-punctata Diabrotica speciosa, Diabrotica longicornis, Diabrotica semipunctata, Diabrotica virgifera; Epilachna* spp. such as *Epilachna varivestis, Epilachna vigintioctomaculata; Epitrix* spp. such as *Epitrix hirtipennis; Eutinobothrus brasiliensis, Faustinus cubae, Gibbium psylloides, Heteronychus arator, Hylamorpha elegans, Hylobius abietis, Hylotrupes bajulus, Hypera brunneipennis, Hypera postica, Hypothenemus* spp., *Ips typographus, Lachnosterna consanguinea, Lema bilineata, Lema melanopus, Leptinotarsa* spp. such as *Leptinotarsa decemlineata; Limonius californicus, Lissorhoptrus oryzophilus, Lissorhoptrus oryzophilus, Lixus* spp., *Lyctus* spp. such as *Lyctus bruneus; Melanotus communis, Meligethes* spp. such as *Meligethes aeneus; Melolontha hippocastani, Melolontha melolontha, Migdolus* spp., *Monochamus* spp. such as *Monochamus alternatus; Naupactus xanthographus, Niptus hololeucus, Oryctes rhinoceros, Oryzaephilus surinamensis, Otiorrhynchus sulcatus, Otiorrhynchus ovatus, Otiorrhynchus sulcatus, Oulema oryzae, Oxycetonia jucunda, Phaedon cochleariae, Phyllobius pyri, Phyllopertha horticola, Phyllophaga* spp., *Phyllotreta* spp. such as *Phyllotreta chrysocephala, Phyllotreta nemorum, Phyllotreta striolata; Phyllophaga* spp., *Phyllopertha horticola, Popillia japonica, Premnotrypes* spp., *Psylliodes chrysocephala, Ptinus* spp., *Rhizobius ventralis, Rhizopertha dominica, Sitona lineatus, Sitophilus* spp. such as *Sitophilus granaria, Sitophilus zeamais; Sphenophorus* spp. such as *Sphenophorus levis; Sternechus* spp. such as *Sternechus subsignatus; Symphyletes* spp., *Tenebrio molitor, Tribolium* spp. such as *Tribolium castaneum; Trogoderma* spp., *Tychius* spp., *Xylotrechus* spp., and *Zabrus* spp. such as *Zabrus tenebrioides*, flies, mosquitoes (Diptera), e.g. *Aedes* spp. such as *Aedes aegypti, Aedes albopictus, Aedes vexans; Anastrepha ludens, Anopheles* spp. such as *Anopheles albimanus, Anopheles crucians, Anopheles freeborni, Anopheles gambiae, Anopheles leucosphyrus, Anopheles maculipennis, Anopheles minimus, Anopheles quadrimaculatus, Anopheles sinensis; Bibio hortulanus, Calliphora erythrocephala, Calliphora vicina, Cerafitis capitata, Ceratitis capitata, Chrysomyia* spp. such as *Chrysomya bezziana, Chrysomya homnivorax, Chrysomya macellaria; Chrysops atlanticus, Chrysops discalis, Chrysops silacea, Cochliomyia* spp. such as *Cochliomyia hominivorax; Contarinia* spp. such as *Contarinia sorghicola; Cordylobia anthropophaga, Culex* spp. such as *Culex nigripalpus, Culex pipiens, Culex quinquefasciatus, Culex tarsalis, Culex tritaeniorhynchus; Culicoides furens, Culiseta inornata, Culiseta melanura, Cuterebra* spp., *Dacus cucurbitae, Dacus oleae, Dasineura brassicae, Delia* spp. such as *Delia antique, Delia coarctata, Delia platura, Delia radicum; Dermatobia hominis, Drosophila* spp., *Fannia* spp. such as *Fannia canicularis; Gasterophilus* spp. such as *Gasterophilus intestinalis; Geomyza Tripunctata, Glossina fuscipes, Glossina morsitans, Glos-*

*sina palpalis, Glossina tachinoides, Haematobia irritans, Haplodiplosis equestris, Hippelates* spp., *Hylemyia* spp. such as *Hylemyia platura; Hypoderma* spp. such as *Hypoderma lineata; Hyppobosca* spp., *Leptoconops torrens, Liriomyza* spp. such as *Liriomyza sativae, Liriomyza trifolii; Lucilia* spp. such as *Lucilia caprina, Lucilia cuprina, Lucilia sericata; Lycoria pectoralis, Mansonia titillanus, Mayetiola* spp. such as *Mayetiola destructor; Musca* spp. such as *Musca autumnalis, Musca domestica; Muscina stabulans, Oestrus* spp. such as *Oestrus ovis; Opomyza florum, Oscinella* spp. such as *Oscinella frit; Pegomya hysocyami, Phlebotomus argentipes, Phorbia* spp. such as *Phorbia antiqua, Phorbia brassicae, Phorbia coarctata; Prosimulium mixtum, Psila rosae, Psorophora columbiae, Psorophora discolor, Rhagoletis cerasi, Rhagoletis pomonella, Sarcophaga* spp. such as *Sarcophaga haemorrhoidalis; Simulium vittatum, Stomoxys* spp. such as *Stomoxys calcitrans; Tabanus* spp. such as *Tabanus atratus, Tabanus bovinus, Tabanus lineola, Tabanus similis; Tannia* spp., *Tipula oleracea, Tipula paludosa*, and *Wohlfahrtia* spp., thrips (Thysanoptera), e.g. *Baliothrips biformis, Dichromothrips corbetti, Dichromothrips* ssp., *Enneothrips flavens, Frankliniella* spp. such as *Frankliniella fusca, Frankliniella occidentalis, Frankliniella tritici; Heliothrips* spp., *Hercinothrips femoralis, Kakothrips* spp., *Rhipiphorothrips cruentatus, Scirtothrips* spp. such as *Scirtothrips citri; Taeniothrips cardamoni, Thrips* spp. such as *Thrips oryzae, Thrips palmi, Thrips tabaci;* termites (Isoptera), e.g. *Calotermes flavicollis, Coptotermes formosanus, Heterotermes aureus, Heterotermes longiceps, Heterotermes tenuis, Leucotermes flavipes, Odontotermes* spp., *Reticulitermes* spp. such as *Reticulitermes speratus, Reticulitermes flavipes, Reticulitermes grassei, Reticulitermes lucifugus, Reticulitermes santonensis, Reticulitermes virginicus; Termes natalensis,* cockroaches (*Blattaria-Blattodea*), e.g. *Acheta domesticus, Blatta orientalis, Blattella asahinae, Blattella germanica, Gryllotalpa* spp., *Leucophaea maderae, Locusta* spp., *Melanoplus* spp., *Periplaneta americana, Periplaneta australasiae, Periplaneta brunnea, Periplaneta fuligginosa, Periplaneta japonica,* bugs, aphids, leafhoppers, whiteflies, scale insects, cicadas (Hemiptera), e.g. *Acrosternum* spp. such as *Acrosternum hilare; Acyrthosipon* spp. such as *Acyrthosiphon onobrychis, Acyrthosiphon pisum; Adelges laricis, Aeneolamia* spp., *Agonoscena* spp., *Aleurodes* spp., *Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *Aphis fabae, Aphis forbesi, Aphis gossypii, Aphis grossulariae, Aphis pomi, Aphis sambuci, Aphis schneideri, Aphis spiraecola; Arboridia apicalis, Arilus critatus, Aspidiella* spp., *Aspidiotus* spp., *Atanus* spp., *Aulacorthum solani, Bemisia* spp. such as *Bemisia argentifolii, Bemisia tabaci; Blissus* spp. such as *Blissus leucopterus; Brachycaudus cardui, Brachycaudus helichrysi, Brachycaudus persicae, Brachycaudus prunicola, Brachycolus* spp., *Brevicoryne brassicae, Calligypona marginata, Calocoris* spp., *Campylomma livida, Capitophorus horni, Carneocephala fulgida, Cavelerius* spp., *Ceraplastes* spp., *Ceratovacuna lanigera, Cercopidae, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *Cimex hemipterus, Cimex lectularius; Coccomytilus halli, Coccus* spp., *Creontiades dilutus, Cryptomyzus ribis, Cryptomyzus ribis, Cyrtopeltis notatus, Dalbulus* spp., *Dasynus piperis, Dialeurodes* spp., *Diaphorina* spp., *Diaspis* spp., *Dichelops furcatus, Diconocoris hewetti, Doralis* spp., *Dreyfusia nordmannianae, Dreyfusia piceae, Drosicha* spp., *Dysaphis* spp. such as *Dysaphis plantaginea, Dysaphis pyri, Dysaphis radicola; Dysaulacorthum pseudosolani, Dysdercus* spp. such as *Dysdercus cingulatus, Dysdercus intermedius; Dysmicoccus* spp., *Empoasca* spp. such as *Empoasca fabae, Empoasca solana; Eriosoma* spp., *Erythroneura* spp., *Eurygaster* spp. such as *Eurygaster integriceps; Euscelis bilobatus, Euschistus* spp. such as *Euschistuos heros, Euschistus impictiventris, Euschistus servus; Geococcus coffeae, Halyomorpha* spp. such as *Halyomorpha halys; Heliopeltis* spp., *Homalodisca coagulata, Horcias nobilellus, Hyalopterus pruni, Hyperomyzus lactucae, Icerya* spp., *Idiocerus* spp., *Idioscopus* spp., *Laodelphax striatellus, Lecanium* spp., *Lepidosaphes* spp., *Leptocorisa* spp., *Leptoglossus phyllopus, Lipaphis erysimi, Lygus* spp. such as *Lygus hesperus, Lygus lineolaris, Lygus pratensis; Macropes excavatus, Macrosiphum* spp. such as *Macrosiphum rosae, Macrosiphum avenae, Macrosiphum euphorbiae; Mahanarva fimbriolata, Megacopta cribraria, Megoura viciae, Melanaphis pyrarius, Melanaphis sacchari, Metcafiella* spp., *Metopolophium dirhodum, Miridae* spp., *Monellia costalis, Monelliopsis pecanis, Myzus* spp. such as *Myzus ascalonicus, Myzus cerasi, Myzus persicae, Myzus varians; Nasonovia ribis-nigri, Nephotettix* spp. such as *Nephotettix malayanus, Nephotettix nigropictus, Nephotettix parvus, Nephotettix virescens; Nezara* spp. such as *Nezara viridula; Nilaparvata lugens, Oebalus* spp., *Oncometopia* spp., *Orthezia praelonga, Parabemisia myricae, Paratrioza* spp., *Parlatoria* spp., *Pemphigus* spp. such as *Pemphigus bursarius; Pentomidae, Peregrinus maidis, Perkinsiella saccharicida, Phenacoccus* spp., *Phloeomyzus passerinii, Phorodon humuli, Phylloxera* spp., *Piesma quadrata, Piezodorus* spp. such as *Piezodorus guildinii, Pinnaspis aspidistrae, Planococcus* spp., *Protopulvinaria pyriformis, Psallus seriatus, Pseudacysta persea, Pseudaulacaspis pentagona, Pseudococcus* spp. such as *Pseudococcus comstocki; Psylla* spp. such as *Psylla mali, Psylla piri; Pteromalus* spp., *Pyrilla* spp., *Quadraspidiotus* spp., *Quesada gigas, Rastrococcus* spp., *Reduvius senilis, Rhodnius* spp., *Rhopalomyzus ascalonicus, Rhopalosiphum* spp. such as *Rhopalosiphum pseudobrassicas, Rhopalosiphum insertum, Rhopalosiphum maidis, Rhopalosiphum padi; Sagatodes* spp., *Sahlbergella singularis, Saissetia* spp., *Sappaphis mala, Sappaphis mali, Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Stephanitis nashi, Stictocephala festina, Tenalaphara malayensis, Thyanta* spp. such as *Thyanta perditor; Tibraca* spp., *Tinocallis caryaefoliae, Tomaspis* spp., *Toxoptera* spp. such as *Toxoptera aurantii; Trialeurodes* spp. such as *Trialeurodes vaporariorum; Triatoma* spp., *Trioza* spp., *Typhlocyba* spp., *Unaspis* spp. such as *Unaspis yanonensis;* and *Viteus vitifolii,* ants, bees, wasps, sawflies (Hymenoptera), e.g. *Athalia rosae, Atta capiguara, Atta cephalotes, Atta cephalotes, Atta laevigata, Atta robusta, Atta sexdens, Atta texana, Bombus* spp., *Camponotus floridanus, Crematogaster* spp., *Dasymutilla occidentalis, Diprion* spp., *Dolichovespula maculata, Hoplocampa* spp. such as *Hoplocampa minuta, Hoplocampa testudinea; Lasius* spp. such as *Lasius niger, Linepithema humile, Monomorium pharaonis, Paravespula germanica, Paravespula pennsylvanica, Paravespula vulgaris, Pheidole megacephala, Pogonomyrmex barbatus, Pogonomyrmex californicus, Polistes rubiginosa, Solenop-* sis geminata, Solenopsis invicta, Solenopsis richteri, Solenopsis xyloni, Vespa spp. such as Vespa crabro, and Vespula squamosa, crickets, grasshoppers, locusts (Orthoptera), e.g. Acheta domestica, Calliptamus italicus, Chortoicetes terminifera, Dociostaurus maroccanus, Gryllotalpa africana, Gryllotalpa gryllotalpa, Hieroglyphus daganensis, Kraussaria angulifera, Locusta migratoria, Locustana pardalina, Melanoplus bivittatus, Melanoplus femurrubrum, Melanoplus mexicanus, Melanoplus sanguinipes, Melanoplus spretus, Nomadacris septemfasciata, Oedaleus senegalensis, Schistocerca americana, Schistocerca gregaria, Tachycines asynamorus, and Zonozerus variegatus, arachnids (Arachnida), such as acari, e.g. of the families Argasidae, Ixodidae and Sarcoptidae, such as *Amblyomma* spp. (e.g. *Amblyomma americanum, Amblyomma variegatum, Amblyomma maculatum*), *Argas* spp. (e.g. *Argas persicus*), *Boophilus* spp. (e.g. *Boophilus annulatus, Boophilus decoloratus, Boophilus microplus*), *Dermacentor silvarum, Dermacentor andersoni, Dermacentor variabilis, Hyalomma* spp. (e.g. *Hyalomma truncatum*), *Ixodes* spp. (e.g. *Ixodes ricinus, Ixodes rubicundus, Ixodes scapularis, Ixodes holocyclus, Ixodes pacificus*), *Ornithodorus* spp. (e.g. *Ornithodorus moubata, Ornithodorus hermsi, Ornithodorus turicata*), *Ornithonyssus bacoti, Otobius megnini, Dermanyssus gallinae, Psoroptes* spp. (e.g. *Psoroptes ovis*), *Rhipicephalus* spp. (e.g. *Rhipicephalus sanguineus, Rhipicephalus appendiculatus, Rhipicephalus evertsi*), *Rhizoglyphus* spp., *Sarcoptes* spp. (e.g. *Sarcoptes scabiei*), and Eriophyidae spp. such as *Acaria sheldoni, Aculops* spp. (e.g. *Aculops pelekassi*) *Aculus* spp. (e.g. *Aculus schlechtendali*), *Epitrimerus pyri, Phyllocoptruta oleivora* and *Eriophyes* spp. (e.g. *Eriophyes sheldoni*); Tarsonemidae spp. such as *Hemitarsonemus* spp., *Phytonemus pallidus* and *Polyphagotarsonemus latus, Stenotarsonemus* spp.; Tenuipalpidae spp. such as *Brevipalpus* spp. (e.g. *Brevipalpus phoenicis*); Tetranychidae spp. such as *Eotetranychus* spp., *Eutetranychus* spp., *Oligonychus* spp., *Tetranychus cinnabarinus, Tetranychus kanzawai, Tetranychus pacificus, Tetranychus telarius* and *Tetranychus urticae; Bryobia praetiosa, Panonychus* spp. (e.g. *Panonychus ulmi, Panonychus citri*), *Metatetranychus* spp. and *Oligonychus* spp. (e.g. *Oligonychus pratensis*), *Vasates lycopersici; Araneida,* e.g. *Latrodectus mactans,* and *Loxosceles reclusa.* And *Acarus siro, Chorioptes* spp., *Scorpio maurus* fleas (Siphonaptera), e.g. *Ceratophyllus* spp., *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Geophilus* spp., *Scutigera* spp. such as *Scutigera coleoptrata;* millipedes (Diplopoda), e.g. *Blaniulus guttulatus, Narceus* spp.,

Earwigs (Dermaptera), e.g. *forficula auricularia,* lice (Phthiraptera), e.g. *Damalinia* spp., *Pediculus* spp. such as *Pediculus humanus capitis, Pediculus humanus corporis; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., springtails (Collembola), e.g. *Onychiurus* ssp. such as *Onychiurus armatus,*

They are also suitable for controlling nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species such as *Aphelenchoides besseyi*; Sting nematodes, *Belonolaimus longicaudatus* and other *Belonolaimus* species; Pine nematodes, *Bursaphelenchus lignicolus* Mamiya et Kiyohara, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus brachyurus, Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species such as *Tylenchulus semipenetrans*; Dagger nematodes, *Xiphinema* species; and other plant parasitic nematode species.

Examples of further pest species which may be controlled by compounds of formula (I) include: from the class of the Bivalva, for example, *Dreissena* spp.; from the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichiura, Wuchereria bancrofti;* from the order of the Isopoda, for example, *Armadillidium vulgare, Oniscus asellus, Porcellio scaber;* from the order of the Symphyla, for example, *Scutigerella immaculata;*

Further examples of pest species which may be controlled by compounds of formula (I) include: *Anisoplia austriaca, Apamea* spp., *Austroasca viridigrisea, Baliothrips biformis, Caenorhabditis elegans, Cephus* spp., *Ceutorhynchus napi, Chaetocnema aridula, Chilo auricilius, Chilo indicus, Chilo polychrysus, Chortiocetes terminifera, Cnaphalocroci medinalis, Cnaphalocrosis* spp., *Colias eurytheme, Collops* spp.,

*Cornitermes cumulans, Creontiades* spp., *Cyclocephala* spp., *Dalbulus maidis, Deraceras reticulatum, Diatrea saccharalis, Dichelops furcatus, Dicladispa armigera, Diloboderus* spp. such as *Diloboderus abderus; Edessa* spp., *Epinotia* spp., *Formicidae, Geocoris* spp., *Globitermes sulfureus, Gryllotalpidae, Halotydeus destructor, Hipnodes bicolor, Hydrellia philippina, Julus* spp., *Laodelphax* spp., *Leptocorsia acuta, Leptocorsia oratorius, Liogenys fuscus, Lucillia* spp., *Lyogenys fuscus, Mahanarva* spp., *Maladera matrida, Marasmia* spp., *Mastotermes* spp., Mealybugs, *Megascelis* ssp, *Metamasius hemipterus, Microtheca* spp., *Mocis latipes, Murgantia* spp., *Mythemina separata, Neocapritermes opacus, Neocapritermes parvus, Neomegalotomus* spp., *Neotermes* spp., *Nymphula depunctalis, Oebalus pugnax, Orseolia* spp. such as *Orseolia oryzae; Oxycaraenus hyalinipennis, Plusia* spp., *Pomacea canaliculata, Procornitermes* ssp, *Procornitermes triacifer, Psylloides* spp., *Rachiplusia* spp., *Rhodopholus* spp., *Scaptocoris castanea, Scaptocoris* spp., *Scirpophaga* spp. such as *Scirpophaga incertulas, Scirpophaga innotata; Scotinophara* spp. such as *Scotinophara coarctata; Sesamia* spp. such as *Sesamia inferens, Sogaella frucifera, Solenapsis geminata, Spissistilus* spp., Stalk borer, *Stenchaetothrips biformis, Steneotarsonemus spinki, Sylepta derogata, Telehin licus, Trichostrongylus* spp.

The compounds of the present invention, including their salts, stereoisomers and tautomers, are particularly useful for controlling insects, preferably sucking or piercing and chewing and biting insects such as insects from the genera Lepidoptera, Coleoptera and Hemiptera, in particular Lepidoptera, Coleoptera and true bugs.

The compounds of the present invention, including their salts, stereoisomers and tautomers, are moreover useful for controlling insects of the orders Thysanoptera, Diptera (especially flies, mosquitos), Hymenoptera (especially ants) and Isoptera (especially termites.

The compounds of the present invention, including their salts, stereoisomers and tautomers, are particularly useful for controlling insects of the orders Lepidoptera and Coleoptera.

The invention also relates to agrochemical compositions comprising an auxiliary and at least one compound I according to the invention.

An agrochemical composition comprises a pesticidally effective amount of a compound I. The term "effective amount" denotes an amount of the composition or of the compounds I, which is sufficient for controlling harmful fungi on cultivated plants or in the protection of materials and which does not result in a substantial damage to the treated plants. Such an amount can vary in a broad range and is dependent on various factors, such as the species to be controlled, the treated cultivated plant or material, the climatic conditions and the specific compound I used.

The compounds I, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.
ii) Dispersible Concentrates (DC)

5-25 wt % of a compound I according to the invention and 1-10 wt % dispersant (e.g. polyvinylpyrrolidone) are dissolved in organic solvent (e.g. cyclohexanone) ad 100 wt %. Dilution with water gives a dispersion.
iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.
iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.
v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0, 1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.
vi) Water-Dispersible Granules and Water-Soluble Granules (WG, SG)

50-80 wt % of a compound I according to the invention are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.
vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.
viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.
iv) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.
iv) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsules. The monomers amount to 1-10 wt %. The wt % relate to the total CS composition.
ix) Dustable Powders (DP, DS)

1-10 wt % of a compound I according to the invention are ground finely and mixed intimately with solid carrier (e.g. finely divided kaolin) ad 100 wt %.

x) Granules (GR, FG)

0.5-30 wt % of a compound I according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a compound I according to the invention are dissolved in organic solvent (e.g. aromatic hydrocarbon) ad 100 wt %.

The compositions types i) to xi) may optionally comprise further auxiliaries, such as 0, 1-1 wt % bactericides, 5-15 wt % anti-freezing agents, 0, 1-1 wt % anti-foaming agents, and 0, 1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha.

In treatment of plant propagation materials such as seeds, e.g. by dusting, coating or drenching seed, amounts of active substance of from 0.1 to 1000 g, preferably from 1 to 1000 g, more preferably from 1 to 100 g and most preferably from 5 to 100 g, per 100 kilogram of plant propagation material (preferably seeds) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate. In a further embodiment, either individual components of the composition according to the invention or partially premixed components, e.g. components comprising compounds I and/or active substances from the groups M) or F) (see below), may be mixed by the user in a spray tank and further auxiliaries and additives may be added, if appropriate.

In a further embodiment, either individual components of the composition according to the invention or partially premixed components, e. g. components comprising compounds I and/or active substances from the groups M.1 to M.UN.X or F.I to F.XIII, can be applied jointly (e.g. after tank mix) or consecutively.

The following list M of pesticides, grouped according the Mode of Action Classification of the Insecticide Resistance Action Committee (IRAC), together with which the compounds according to the invention can be used and with which potential synergistic effects might be produced, is intended to illustrate the possible combinations, but not to impose any limitation:

M.1 Acetylcholine esterase (AChE) inhibitors from the class of

M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as:

M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of

M.3A pyrethroids, for example acrinathrin, allethrin, d-cis-trans allethrin, d-trans allethrin, bifenthrin, bioallethrin, bio-allethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, meperfluthrin, metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of

M.4A neonicotinoids, for example acteamiprid, chlothianidin, dinotefuran, imidacloprid, nitenpyram, thiacloprid and thiamethoxam; or the compounds M.4A.1: 1-[(6-chloro-3-pyridinyl)methyl]-2,3,5,6,7,8-hexahydro-9-nitro-(5S,8R)-5,8-Epoxy-1H-imidazo[1,2-a]azepine; or M.4A.2: 1-[(6-chloro-3-pyridyl)methyl]-2-nitro-1-[(E)-pentylideneamino]guanidine; or M4.A.3: 1-[(6-chloro-3-pyridyl)methyl]-7-methyl-8-nitro-5-propoxy-3,5,6,7-tetrahydro-2H-imidazo[1,2-a]pyridine; or M.4B nicotine.

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as

M.7A juvenile hormone analogues as hydroprene, kinoprene and methoprene; or others as M.7B fenoxycarb or M.7C pyriproxyfen;

M.8 miscellaneous non-specific (multi-site) inhibitors, for example

M.8A alkyl halides as methyl bromide and other alkyl halides, or

M.8B chloropicrin, or M.8C sulfuryl fluoride, or M.8D borax, or M.8E tartar emetic;

M.9 Selective homopteran feeding blockers, for example

M.9B pymetrozine, or M.9C flonicamid;

M.10 Mite growth inhibitors, for example

M.10A clofentezine, hexythiazox and diflovidazin, or M.10B etoxazole;

M.11 Microbial disruptors of insect midgut membranes, for example *bacillus thuringiensis* or *bacillus sphaericus* and the insecticdal proteins they produce such as *bacillus thuringiensis* subsp. *israelensis, bacillus sphaericus, bacillus thuringiensis* subsp. *aizawai, bacillus thuringiensis* subsp. *kurstaki* and *bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example

M.12A diafenthiuron, or

M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example

M.20A hydramethylnon, or M.20B acequinocyl, or M.20C fluacrypyrim;

M.21 Mitochondrial complex I electron transport inhibitors, for example

M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example

M.22A indoxacarb, or M.22B metaflumizone, or M.22C 1-[(E)-[2-(4-cyanophenyl)-1-[3-(trifluoromethyl)phenyl]ethylidene]amino]-3-[4-(difluoromethoxy)phenyl]urea;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example

M.24A phosphine such as aluminium phosphide, calcium phosphide, phosphine or zinc phosphide, or M.24B cyanide.

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chlorpyridin-2-yl)-1H-pyrazole-5-carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino)benzoyl]-1,2-dimethylhydrazinecarboxylate; or a compound selected from M.28.5a) to M.28.5l):

M.28.5a)N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide;

M.28.5b)N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide;

M.28.5c)N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide;

M.28.5d)N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide;

M.28.5e)N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide;

M.28.5f) N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide;
M.28.5g) N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide;
M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;
M.28.5i) N-[2-(5-amino-1,3,4-thiadiazol-2-yl)-4-chloro-6-methyl-phenyl]-5-bromo-2-(3-chloro-2-pyridyl)pyrazole-3-carboxamide;
M.28.5j) 5-chloro-2-(3-chloro-2-pyridyl)-N-[2,4-dichloro-6-[(1-cyano-1-methyl-ethyl)carbamoyl]phenyl]pyrazole-3-carboxamide;
M.28.5k) 5-bromo-N-[2,4-dichloro-6-(methylcarbamoyl)phenyl]-2-(3,5-dichloro-2-pyridyl)pyrazole-3-carboxamide;
M.28.5l) N-[2-(tert-butylcarbamoyl)-4-chloro-6-methyl-phenyl]-2-(3-chloro-2-pyridyl)-5-(fluoromethoxy)pyrazole-3-carboxamide; or a compound selected from
M.28.6 N2-(1-cyano-1-methyl-ethyl)-N1-(2,4-dimethylphenyl)-3-iodo-phthalamide; or
M.28.7 3-chloro-N2-(1-cyano-1-methyl-ethyl)-N1-(2,4-dimethylphenyl)phthalamide;

M.UN.X insecticidal active compounds of unknown or uncertain mode of action, as for example afidopyropen, azadirachtin, amidoflumet, benzoximate, bifenazate, bromopropylate, chinomethionat, cryolite, dicofol, flufenerim, flometoquin, fluensulfone, flupyradifurone, piperonyl butoxide, pyridalyl, pyrifluquinazon, sulfoxaflor, pyflubumide or the compounds
M.UN.X.1: 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide, or the compound
M.UN.X.2: 4-[5-[3-chloro-5-(trifluoromethyl)phenyl]-5-(trifluoromethyl)-4H-isoxazol-3-yl]-N-[2-oxo-2-(2,2,2-trifluoroethylamino)ethyl]naphthalene-1-carboxamide, or the compound
M.UN.X.3: 11-(4-chloro-2,6-dimethylphenyl)-12-hydroxy-1,4-dioxa-9-azadispiro[4.2.4.2]-tetradec-11-en-10-one, or the compound
M.UN.X.4: 3-(4'-fluoro-2,4-dimethylbiphenyl-3-yl)-4-hydroxy-8-oxa-1-azaspiro[4.5]dec-3-en-2-one, or the compound
M.UN.X.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *bacillus firmus* (Votivo, I-1582); or
M.UN.X.6; a compound selected from the group of
M.UN.X.6a) (E/Z)—N-[1-[(6-chloro-3-pyridyl)methyl]-2-pyridylidene]-2,2,2-trifluoro-acetamide;
M.UN.X.6b) (E/Z)—N-[1-[(6-chloro-5-fluoro-3-pyridyl)methyl]-2-pyridylidene]-2,2,2-trifluoro-acetamide;
M.UN.X.6c) (E/Z)-2,2,2-trifluoro-N-[1-[(6-fluoro-3-pyridyl)methyl]-2-pyridylidene]acetamide;
M.UN.X.6d) (E/Z)—N-[1-[(6-bromo-3-pyridyl)methyl]-2-pyridylidene]-2,2,2-trifluoro-acetamide;
M.UN.X.6e) (E/Z)—N-[1-[1-(6-chloro-3-pyridyl)ethyl]-2-pyridylidene]-2,2,2-trifluoro-acetamide;
M.UN.X.6f) (E/Z)—N-[1-[(6-chloro-3-pyridyl)methyl]-2-pyridylidene]-2,2-difluoro-acetamide;
M.UN.X.6g) (E/Z)-2-chloro-N-[1-[(6-chloro-3-pyridyl)methyl]-2-pyridylidene]-2,2-difluoro-acetamide;
M.UN.X.6h) (E/Z)—N-[1-[(2-chloropyrimidin-5-yl)methyl]-2-pyridylidene]-2,2,2-trifluoro-acetamide and
M.UN.X.6i) (E/Z)—N-[1-[(6-chloro-3-pyridyl)methyl]-2-pyridylidene]-2,2,3,3,3-pentafluoro-propanamide.); or of the compounds
M.UN.X.7: 3-[3-chloro-5-(trifluoromethyl)phenyl]-4-oxo-1-(pyrimidin-5-ylmethyl)pyrido[1,2-a]pyrimidin-1-ium-2-olate; or
M.UN.X.8: 1-[(2-chlorothiazol-5-yl)methyl]-3-(3,5-dichlorophenyl)-9-methyl-4-oxo-pyrido[1,2-a]pyrimidin-1-ium-2-olate; or
M.UN.X.9: 8-chloro-N-[2-chloro-5-methoxyphenyl)sulfonyl]-6-trifluoromethyl)-imidazo[1,2-a]pyridine-2-carboxamide; or
M.UN.X.10: 4-[5-(3,5-dichlorophenyl)-5-(trifluoromethyl)-4H-isoxazol-3-yl]-2-methyl-N-(1-oxothietan-3-yl)benzamide; or
M.UN.X.11: 5-[3-[2,6-dichloro-4-(3,3-dichloroallyloxy)phenoxy]propoxy]-1H-pyrazole.

The commercially available compounds of the group M listed above may be found in The Pesticide Manual, 15th Edition, C. D. S. Tomlin, British Crop Protection Council (2011) among other publications.

The quinoline derivative flometoquin is shown in WO2006/013896. The aminofuranone compounds flupyradifurone is known from WO 2007/115644. The sulfoximine compound sulfoxaflor is known from WO2007/149134. The pyrethroid momfluorothrin is known from U.S. Pat. No. 6,908,945. The pyrazole acaricide pyflubumide is known from WO2007/020986. The isoxazoline compounds have been described likewise M.UN.X.1 in WO2005/085216, M.UN.X2. in WO2009/002809 and in WO2011/149749 and the isoxazoline M.UN.X.10 in WO2013/050317. The pyripyropene derivative afidopyropen has been described in WO 2006/129714. The spiroketal-substituted cyclic ketoenol derivative M.UN.X.3 is known from WO2006/089633 and the biphenyl-substituted spirocyclic ketoenol derivative M.UN.X.4 from WO2008/067911. Finally triazoylphenylsulfide like M.UN.X.5 have been described in WO2006/043635 and biological control agents on basis of *bacillus firmus* in WO2009/124707. The neonicotinids 4A.1 is known from WO20120/069266 and WO2011/06946, the M.4.A.2 from WO2013/003977, the M4.A.3. from WO2010/069266.

The Metaflumizone analogue M.22C is described in CN 10171577. The phthalamides M.28.1 and M.28.2 are both known from WO 2007/101540. The anthranilamide M.28.3 has been described in WO2005/077934. The hydrazide compound M.28.4 has been described in WO 2007/043677. The anthranilamides M.28.5a) to M.28.5h) can be prepared as described in WO 2007/006670, WO2013/024009 and WO2013/024010, the anthranilamide M.28.5i) is described in WO2011/085575, the M.28.5j) in WO2008/134969, the M.28.5k) in US2011/046186 and the M.28.5l) in WO2012/034403. The diamide compounds M.28.6 and M.28.7 can be found in CN102613183.

The compounds M.UN.X.6a) to M.UN.X.6i) listed in M.UN.X.6 have been described in WO2012/029672. The mesoionic antagonist compound M.UN.X.7 was described in WO2012/092115, the mesoionic antagonist compound M.UN.X.8 was described in WO 2013/192035, the nematicide M.UN.X.9 in WO2013/055584 and the pyridalyl-type analogue M.UN.X.11 in WO2010/060379.

Preferred additional pesticidally active ingredients are those selected from the IRAC group 1, the Acetylcholinesterase (AChE) inhibitors, herein from the group 1A (Carbamtes) Thiodicarb, Methomyl and Carbaryl, and from the group 1B(Organophosphates), especially Acephate, Chlorpyriphos and Dimethoate, from the group 2B, the fiproles, here especially ethiprole and fipronil, from the group 3, the pyrethroids, here especially lambda-cyhalothrin, alpha-cypermethrin or deltametrin, and from the group 4A, the neonicotinoids, here especially acetamiprid, clothianidin, dinotefuran, imidacloprid, nitenpyram, thiacloprid or thiomethoxam.

Especially combinations of compounds of the invention with fiproles, neonictinoids or pyrethroids may possibly exhibit synergistic control of stinkbugs (according to the Colby formula), in particular *Euschistus*, e.g. *Euschistus heros*.

The following list F of active substances, in conjunction with which the compounds according to the invention can be used, is intended to illustrate the possible combinations but does not limit them:

F.I) Respiration Inhibitors
- F.I 1) Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, mandestrobine, metominostrobin, orysastrobin, picoxystrobin, pyraclostrobin, pyrametostrobin, pyraoxystrobin, trifloxystrobin and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;
- F.I 2) inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate;
- F.I 3) inhibitors of complex II (e. g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethylindan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide, N-[2-(2,4-difluorophenyl)phenyl]-3-(trifluoromethyl)pyrazine-2-carboxamide;
- F.I 4) other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

F.II) Sterol Biosynthesis Inhibitors (SBI Fungicides)
- F.II 1) C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2 S;3R)-3-(2-chlorophenyl)-2-(2,4-difluorophenyl)-oxiranylmethyl]-5-thio-cyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;
- F.II 2) Delta14-reductase inhibitors: aldimorph, dodemorph, dodemorph-acetate, fenpropimorph, tridemorph, fenpropidin, piperalin, spiroxamine;
- F.II 3) Inhibitors of 3-keto reductase: fenhexamid;

F.III) Nucleic Acid Synthesis Inhibitors
- F.III 1) phenylamides or acyl amino acid fungicides: benalaxyl, benalaxyl-M, kiralaxyl, metalaxyl, metalaxyl-M (mefenoxam), ofurace, oxadixyl;
- F.III 2) others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

F.IV) Inhibitors of Cell Division and Cytoskeleton
- F.IV 1) tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine;
- F.IV 2) other cell division inhibitors: diethofencarb, ethaboxam, pencycuron, fluopicolide, zoxamide, metrafenone, pyriofenone;

F.V) Inhibitors of Amino Acid and Protein Synthesis
- F.V 1) methionine synthesis inhibitors (anilino-pyrimidines): cyprodinil, mepanipyrim, pyrimethanil;

F.V 2) protein synthesis inhibitors: blasticidin-S, kasugamycin, kasugamycin hydrochloride-hydrate, mildiomycin, streptomycin, oxytetracyclin, polyoxine, validamycin A;

F.VI) Signal Transduction Inhibitors
  F.VI 1) MAP/histidine kinase inhibitors: fluoroimid, iprodione, procymidone, vinclozolin, fenpiclonil, fludioxonil;
  F.VI 2) G protein inhibitors: quinoxyfen;

F.VII) Lipid and Membrane Synthesis Inhibitors
  F.VII 1) Phospholipid biosynthesis inhibitors: edifenphos, iprobenfos, pyrazophos, isoprothiolane;
  F.VII 2) lipid peroxidation: dicloran, quintozene, tecnazene, tolclofos-methyl, biphenyl, chloroneb, etridiazole;
  F.VII 3) phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl)carbamic acid-(4-fluorophenyl) ester;
  F.VII 4) compounds affecting cell membrane permeability and fatty acids: propamocarb, propamocarb-hydrochlorid;
  F.VII 5) fatty acid amide hydrolase inhibitors: oxathiapiprolin;

F.VIII) Inhibitors with Multi Site Action
  F.VIII 1) inorganic active substances: Bordeaux mixture, copper acetate, copper hydroxide, copper oxychloride, basic copper sulfate, sulfur;
  F.VIII 2) thio- and dithiocarbamates: ferbam, mancozeb, maneb, metam, metiram, propineb, thiram, zineb, ziram;
  F.VIII 3) organochlorine compounds (e.g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;
  F.VIII 4) guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

F.IX) Cell Wall Synthesis Inhibitors
  F.IX 1) inhibitors of glucan synthesis: validamycin, polyoxin B;
  F.IX 2) melanin synthesis inhibitors: pyroquilon, tricyclazole, carpropamid, dicyclomet, fenoxanil;

F.X) Plant Defense Inducers
  F.X 1) acibenzolar-S-methyl, probenazole, isotianil, tiadinil, prohexadione-calcium;
  F.X 2) phosphonates: fosetyl, fosetyl-aluminum, phosphorous acid and its salts, 4-cyclopropyl-N-(2,4-dimethoxyphenyl)thiadiazole-5-carboxamide;

F.XI) Unknown Mode of Action
  bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propyl-chromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethyl-silanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

F.XII) Biopesticides
  F.XII 1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum; T. stromaticum, T. virens* (also named *Gliocladium virens*), *T. viride, Typhula phacorrhiza, Ulocladium oudemansii, Verticillium dahlia*, zucchini yellow mosaic virus (avirulent strain);
  F.XII 2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;

The fungicidal active compounds mentioned above of groups F.I to F.XI, their preparation and their action against harmful fungi are generally known (cf., for example, http://www.hclrss.demon.co.uk/index.html).

The fungicides of chemical nature described by common names, their preparation and their activity against pests are known (cf.: http://www.alanwood.net/pesticides/); these pesticides are often commercially available.

The fungicides described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 11/77514; WO13/047749, WO 10/069882, WO 13/047441, WO 03/16303, WO 09/90181, WO 13/007767, WO 13/010862, WO 13/024009 and WO 13/024010).

The biopesticides from group F.XII) of fungicides, their preparation and their pesticidal activity e.g. against harmful fungi or insects are known (e-Pesticide Manual V 5.2 (ISBN 978 1 901396 85 0) (2008-2011); http://www.epa.gov/opp00001/biopesticides/, see product lists therein; http://www.omri.org/omri-lists, see lists therein; Bio-Pesticides Database BPDB http://sitem.herts.ac.uk/aeru/bpdb/, see A to Z link therein).

The biopesticides from group F.XII. may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group F.XII may also have fungicidal, bactericidal, viricidal, plant defense activator, insecticidal, acaricidal, molluscidal, pheromone and/or nematicidal activity.

Many of these biopesticides are registered and/or are commercially available: aluminium silicate (Screen™ Duo from Certis LLC, USA), *Agrobacterium* radiobacter K1026 (e.g. NoGall® from Becker Underwood Pty Ltd., Australia), *A. radiobacter* K84 (Nature 280, 697-699, 1979; e.g. Gall-Troll® from AG Biochem, Inc., C, USA), *Ampelomyces quisqualis* M-10 (e.g. AQ 10® from Intrachem Bio GmbH & Co. KG, Germany), Ascophyllum nodosum (Norwegian kelp, Brown kelp) extract or filtrate (e.g. ORKA GOLD from Becker Underwood, South Africa; or Goemar® from Laboratoires Goemar, France), *Aspergillus flavus* NRRL 21882 isolated from a peanut in Georgia in 1991 by the USDA, National Peanut Research Laboratory (e.g. in Afla-Guard® from Syngenta, CH), mixtures of *Aureobasidium pullulans* DSM14940 and DSM 14941 (e.g. blastospores in Blossom-Protect® from bio-ferm GmbH, Germany), Azospirillum brasilense XOH (e.g. AZOS from Xtreme Gardening, USA or RTI Reforestation Technologies International; USA), *Bacillus amyloliquefaciens* FZB42 (e.g. in RhizoVital® 42 from AbiTEP GmbH, Berlin, Germany), *B. amyloliquefaciens* IN937a (J. Microbiol. Biotechnol. 17(2), 280-286, 2007; e.g. in BioYield® from Gustafson LLC, TX, USA), *B. amyloliquefaciens* IT-45 (CNCM I-3800) (e.g. Rhizocell C from ITHEC, France), *B. amyloliquefaciens* subsp. *plantarum* MBI600 (NRRL B-50595, deposited at United States Department of Agriculture) (e.g. Integral®, Subtilex® NG from Becker Underwood, USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *B. pumilus* GB34 (ATCC 700814; e.g. in YieldShield® from Gustafson LLC, TX, USA), and *Bacillus pumilus* KFP9F (NRRL B-50754) (e.g. in BAC-UP or FUSION-P from Becker Underwood South Africa), *B. pumilus* QST 2808 (NRRL B-30087) (e.g. Sonata® and Ballad® Plus from AgraQuest Inc., USA), *B. subtilis* GB03 (e.g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B-21661 in Rhapsody®, Serenade® MAX and Serenade® ASO from AgraQuest Inc., USA), *B. subtilis* var. *amylolique-faciens* FZB24 (e.g. Taegro® from Novozyme Biologicals, Inc., USA), *B. subtilis* var. *amyloliquefaciens* D747 (e.g. Double Nickel 55 from Certis LLC, USA), *B. thuringiensis* ssp. *aizawai* ABTS-1857 (e.g. in XenTari® from BioFa AG, Müunsingen, Germany), B. t. ssp. *aizawai* SAN 401 I, ABG-6305 and ABG-6346, *Bacillus* t. ssp. *israelensis* AM65-52 (e.g. in VectoBac® from Valent Biosciences, IL, USA), *Bacillus thuringiensis* ssp. *kurstaki* SB4 (NRRL B-50753; e.g. Beta Pro® from Becker Underwood, South Africa), B. t. ssp. *kurstaki* ABTS-351 identical to HD-1 (ATCC SD-1275; e.g. in Dipel® DF from Valent BioSciences, IL, USA), B. t. ssp. *kurstaki* EG 2348 (e.g. in Lepinox® or Rapax® from CBC (Europe) S.r.I., Italy), B. t. ssp. *tenebrionis* DSM 2803 (EP 0 585 215 B1; identical to NRRL B-15939; Mycogen Corp.), B. t. ssp. *tenebrionis* NB-125 (DSM 5526; EP 0 585 215 B1; also referred to as SAN 418 I or ABG-6479; former production strain of Novo-Nordisk), B. t. ssp. *tenebrionis* NB-176 (or NB-176-1) a gamma-irridated, induced high-yielding mutant of strain NB-125 (DSM 5480; EP 585 215 B1; Novodor® from Valent BioSciences, Switzerland), *Beauveria bassiana* ATCC 74040 (e.g. in Naturalis® from CBC (Europe) S.r.I., Italy), *B. bassiana* DSM 12256 (US 200020031495; e.g. BioExpert® SC from Live Systems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e.g. BroadBand® from Becker Underwood, South Africa), *B. brongniartii* (e.g. in Melocont® from Agrifutur, Agrianello, Italy, for control of cockchafer; J. Appl. Microbiol. 100(5), 1063-72, 2006), *Bradyrhizobium* sp. (e.g. Vault® from Becker Underwood, USA), *B. japonicum* (e.g. VAULT® from Becker Underwood, USA), *Candida oleophila* I-182 (NRRL Y-18846; e.g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e.g. Biocure® (in mixture with lysozyme) and BioCoat® from Micro Flo Company, USA (BASF SE) and Arysta), Chitosan (e.g. Armour-Zen® from BotriZen Ltd., NZ), *Clonostachys rosea* f. *catenulata*, also named *Gliocladium catenulatum* (e.g. isolate J 1446: Prestop® from Verdera Oy, Finland), *Chromobacterium subtsugae* PRAA4-1 isolated from soil under an eastern hemlock (*Tsuga canadensis*) in the Catoctin Mountain region of central Maryland (e.g. in GRANDEVO from Marrone Bio Innovations, USA), *Coniothyrium minitans* CON/M/91-08 (e.g. Contans® WG from Prophyta, Germany), *Cryphonectria parasitica* (e.g. *Endothia parasitica* from CNICM, France), *Cryptococcus albidus* (e.g. YIELD PLUS® from Anchor Bio-Technologies, South Africa), *Cryptophlebia leucotreta* granulovirus (CrleGV) (e.g. in CRYPTEX from Adermatt Biocontrol, Switzerland), *Cydia pomonella* granulovirus (CpGV) V03 (DSM GV-0006; e.g. in MADEX Max from Andermatt Biocontrol, Switzerland), CpGV V22 (DSM GV-0014; e.g. in MADEX Twin from Adermatt Biocontrol, Switzerland), *Delftia acidovorans* RAY209 (ATCC PTA-4249; WO 2003/57861; e.g. in BIOBOOST from Brett Young, Winnipeg, Canada), *Dilophosphora alopecuri* (Twist Fungus from Becker Underwood, Australia), Ecklonia maxima (kelp) extract (e.g. KELPAK SL from Kelp Products Ltd, South Africa), formononetin (e.g. in MYCONATE from Plant Health Care plc, U.K.), *Fusarium oxysporum* (e.g. BIO-FOX® from S.I.A.P.A., Italy, FUSACLEAN® from Natural Plant Protection, France), *Glomus intraradices* (e.g. MYC 4000 from ITHEC, France), *Glomus intraradices* RTI-801 (e.g. MYKOS from Xtreme Gardening, USA or RTI Reforestation Technologies International; USA), grapefruit seeds and pulp extract (e.g. BC-1000 from Chemie S.A., Chile), harpin (alpha-beta) protein (e.g. MESSENGER or HARP-N-Tek from Plant Health Care plc, U.K.; Science 257, 1-132, 1992), *Heterorhabditis bacteriophaga* (e.g. Nemasys® G from Becker Underwood Ltd., UK), Isaria fumosorosea Apopka-97 (ATCC 20874) (PFR-97™ from Certis LLC, USA), cis-jasmone (U.S. Pat. No. 8,221,736), laminarin (e.g. in VACCIPLANT from Laboratoires Goemar, St. Malo, France or Stähler SA, Switzerland), *Lecanicillium longisporum* KV42 and KV71 (e.g. VERTALEC® from Koppert BV, Netherlands), *L. muscarium* KV01 (formerly *Verticillium lecanii*) (e.g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in *Niger*; also NRRL 50758) (e.g. GREEN MUSCLE® from Becker Underwood, South Africa), M. a. var. *acridum* FI-985 (e.g. GREEN GUARD® SC from Becker Underwood Pty Ltd, Australia), *M. anisopliae* FI-1045 (e.g. BIOCANE® from Becker Underwood Pty Ltd, Australia), *M. anisopliae* F52 (DSM 3884, ATCC 90448; e.g. MET52® Novozymes Biologicals BioAg Group, Canada), *M. anisopliae* ICIPE 69 (e.g. METATHRIPOL from ICIPE, Nairobe, Kenya), *Metschnikowia fructicola* (NRRL Y-30752; e.g. SHEMER® from Agrogreen, Israel, now distributed by Bayer CropSciences, Germany; U.S. Pat. No. 6,994,849), *Microdochium dimerum* (e.g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e.g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e.g. NO FLY™ from Natural Industries, Inc., USA), *P. lilacinus* 251 (e.g. in BioAct®/MeloCon® from Prophyta, Germany; Crop Protection 27, 352-361, 2008; originally isolated from infected nematode eggs in the Philippines), *P. lilacinus* DSM 15169 (e.g. NEMATA® SC from Live Systems Technology S.A., Colombia), *P. lilacinus* BCP2 (NRRL 50756; e.g. PL GOLD from Becker Underwood BioAg SA Ltd, South Africa), mixture of *Paenibacillus alvei* NAS6G6 (NRRL B-50755), *Pantoea vagans* (formerly *agglomerans*) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* spp. ATCC PTA-9643 (WO 2010/085795), *Pasteuria* spp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e.g. Jump Start® from Novozymes Biologicals BioAg Group, Canada, originally isolated from soil in southern Alberta; Fertilizer Res. 39, 97-103, 1994), *Phlebiopsis gigantea* (e.g. Rot-Stop® from Verdera Oy, Finland), *Pichia anomala* WRL-076 (NRRL Y-30842; U.S. Pat. No. 8,206,972), potassium bicarbonate (e.g. Amicarb® fromm Stähler SA, Switzerland), potassium silicate (e.g. Sil-MATRIX™ from Certis LLC, USA), *Pseudozyma flocculosa* PF-A22 UL (e.g. Sporodex® from Plant Products Co. Ltd., Canada), *Pseudomonas* sp. DSM 13134 (WO 2001/40441, e.g. in PRORADIX from Sourcon Padena GmbH & Co. KG, Hechinger Str. 262, 72072 Tubingen, Germany), *P. chloraphis* MA 342 (e.g. in CERALL or CEDEMON from BioAgri AB, Uppsala, Sweden), *P. fluorescens* CL 145A (e.g. in ZEQUANOX from Marrone BioInnovations, Davis, Calif., USA; J. Invertebr. Pathol. 113(1):104-14, 2013), *Pythium oligandrum* DV 74 (ATCC 38472; e.g. POLYVERSUM® from Remeslo SSRO, Biopreparaty, Czech Rep. and GOWAN, USA; US 2013/0035230), *Reynoutria sachlinensis* extract (e.g. REGALIA® SC from Marrone BioInnovations, Davis, Calif., USA), *Rhizobium leguminosarum* bv. *phaseolii* (e.g. RHIZO-STICK from Becker Underwood, USA), R. I. *trifolii* RP113-7 (e.g. DORMAL from Becker Underwood, USA; Appl. Environ. Microbiol. 44(5), 1096-1101), R. I. bv. *viciae* P1NP3Cst (also referred to as 1435; New Phytol 179(1), 224-235, 2008; e.g. in NODULATOR PL Peat Granule from Becker Underwood, USA; or in NODULATOR XL PL bfrom Becker Underwood, Canada), R. I. bv. *viciae* SU303 (e.g. NODULAID Group E from Becker Underwood, Australia), R. I. bv. *viciae* WSM1455 (e.g. NODULAID Group F from Becker Underwood, Australia), *R. tropici* SEMIA 4080 (identical to PRF 81; Soil Biology & Biochemistry 39, 867-876, 2007), *Sinorhizobium meliloti* MSDJ0848 (INRA, France) also referred to as strain 2011 or RCR2011 (Mol Gen Genomics (2004) 272: 1-17; e.g. DORMAL ALFALFA from Becker Underwood, USA; NITRAGIN® Gold from Novozymes Biologicals BioAg Group, Canada), *Sphaerodes mycoparasitica* IDAC 301008-01 (WO 2011/022809), *Steinernema carpocapsae* (e.g. MILLENIUM® from Becker Underwood Ltd., UK), *S. feltiae* (NEMASHIELD® from BioWorks, Inc., USA; NEMASYS® from Becker Underwood Ltd., UK), *S. kraussei* L137 (NEMASYS® L from Becker Underwood Ltd., UK), *Streptomyces griseoviridis* K61 (e.g. MYCOSTOP® from Verdera Oy, Espoo, Finland; Crop Protection 25, 468-475, 2006), *S. lydicus* WYEC 108 (e.g. Actinovate® from Natural Industries, Inc., USA, U.S. Pat. No. 5,403,584), *S. violaceusniger* YCED-9 (e.g. DT-9® from Natural Industries, Inc., USA, U.S. Pat. No. 5,968,503), *Talaromyces flavus* V117b (e.g. PROTUS® from Prophyta, Germany), *Trichoderma* asperellum SKT-1 (e.g. ECO-HOPE® from Kumiai Chemical Industry Co., Ltd., Japan), *T. asperellum* ICC 012 (e.g. in TENET WP, REMDIER WP, BIOTEN WP from Isagro N.C., USA, BIO-TAM from AgraQuest, USA), *T. atroviride* LC52 (e.g. SENTINEL® from Agrimm Technologies Ltd, NZ), *T. atroviride* CNCM 1-1237 (e.g. in Esquive WG from Agrauxine S.A., France, e.g. against pruning wound diseases on vine and plant root pathogens), *T. fertile* JM41R (NRRL 50759; e.g. RICHPLUS™ from Becker Underwood Bio Ag SA Ltd, South Africa), *T. gamsii* ICC 080 (e.g. in TENET WP, REMDIER WP, BIOTEN WP from Isagro N.C., USA, BIO-TAM from AgraQuest, USA), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and TRICHODERMA 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (also named *Gliocladium virens*) (e.g. SOILGARD® from Certis LLC, USA), *T. viride* (e.g. TRIECO® from Ecosense Labs. (India) Pvt. Ltd., Indien, BIO-CURE® F from T. Stanes & Co. Ltd., Indien), *T. viride* TV1 (e.g. *T. viride* TV1 from Agribiotec srl, Italy) and *Ulocladium oudemansii* HRU3 (e.g. in BOTRY-ZEN® from Botry-Zen Ltd, NZ).

Strains can be sourced from genetic resource and deposition centers: American Type Culture Collection, 10801 University Blvd., Manassas, Va. 20110-2209, USA (strains with ATCC prefic); CABI Europe—International Mycological Institute, Bakeham Lane, Egham, Surrey, TW20 9TYN-RRL, UK (strains with prefices CABI and IMI); Centraalbureau voor Schimmelcultures, Fungal Biodiversity Centre, Uppsalaan 8, PO Box 85167, 3508 AD Utrecht, Netherlands (strains with prefic CBS); Division of Plant Industry, CSIRO, Canberra, Australia (strains with prefix CC); Collection Nationale de Cultures de Microorganismes, Institut Pasteur, 25 rue du Docteur Roux, F-75724 PARIS Cedex 15 (strains with prefix CNCM); Leibniz-Institut DSMZ-Deutsche Sammlung von Mikroorganismen und Zellkulturen GmbH, Inhoffenstrale 7 B, 38124 Braunschweig, Germany (strains with prefix DSM); International Depositary Authority of Canada Collection, Canada (strains with prefix IDAC); International Collection of Microorganisms from Plants, Landcare Research, Private Bag 92170, Auckland Mail Centre, Auckland 1142, New Zealand (strans with prefix ICMP); IITA, PMB 5320, Ibadan, Nigeria (straisn with prefix IITA); The National Collections of Industrial and Marine Bacteria Ltd., Torry Research Station, P.O. Box 31, 135 Abbey Road, Aberdeen, AB9 8DG, Scotland (strains with prefix NCIMB); ARS Culture Collection of the National Center for Agricultural Utilization Research, Agricultural Research Service, U.S. Department of Agriculture, 1815 North University Street, Peoria, Ill. 61604, USA (strains with prefix NRRL); Department of Scientific and Industrial Research Culture Collection, Applied Biochemistry Division, Palmerston North, New Zealand (strains with prefix NZP); FEPAGRO-Fundação Estadual de Pesquisa Agropecuária, Rua Gonçalves Dias, 570, Bairro Menino Deus, Porto Alegre/RS, Brazil (strains with prefix SEMIA); SARDI, Adelaide, South Australia (strains with prefix SRDI); U.S. Department of Agriculture, Agricultural Research Service, Soybean and Alfalfa Research Laboratory, BARC-West, 10300 Baltimore Boulevard, Building 011, Room 19-9, Beltsville, Md. 20705, USA (strains with prefix USDA: Beltsville *Rhizobium* Culture Collection Catalog March 1987 USDA-ARS ARS-30: http://pdf.usaid.gov/pdf_docs/PNAAW891.pdf); and Murdoch University, Perth, Western Australia (strains with prefix WSM). Further strains may be found at the Global catalogue of Microorganisms: http://gcm.wfcc.info/ and http://www.landcareresearch-.co.nz/resources/collections/icmp and further references to strain collections and their prefixes at http://refs.wdcm.org/collections.htm. *Bacillus amyloliquefaciens* subsp. *plantarum* MBI600 (NRRL B-50595) is deposited under accession number NRRL B-50595 with the strain designation *Bacillus subtilis* 1430 (and identical to NCIMB 1237). Recently, MBI 600 has been re-classified as *Bacillus amyloliquefaciens* subsp. *plantarum* based on polyphasic testing which combines classical microbiological methods relying on a mixture of traditional tools (such as culture-based methods) and molecular tools (such as genotyping and fatty acids analysis). Thus, *Bacillus subtilis* MBI600 (or MBI 600 or MBI-600) is identical to *Bacillus amyloliquefaciens* subsp. *plantarum* MBI600, formerly *Bacillus subtilis* MBI600. *Bacillus amyloliquefaciens* MBI600 is known as plant growth-promoting rice seed treatment from Int. J. Microbiol. Res. 3(2) (2011), 120-130 and further described e.g. in US 2012/0149571 A1. This strain MBI600 is e.g. commercially available as liquid formulation product INTEGRAL® (Becker-Underwood Inc., USA).

*Bacillus subtilis* strain FB17 was originally isolated from red beet roots in North America (System Appl. Microbiol 27 (2004) 372-379). This *B. subtilis* strain promotes plant health (US 2010/0260735 A1; WO 2011/109395 A2). *B. subtilis* FB17 has also been deposited at ATCC under number PTA-11857 on Apr. 26, 2011. *Bacillus subtilis* strain FB17 may be referred elsewhere to as UD1022 or UD10-22.

*Bacillus amyloliquefaciens* AP-136 (NRRL B-50614), *B. amyloliquefaciens* AP-188 (NRRL B-50615), *B. amyloliquefaciens* AP-218 (NRRL B-50618), *B. amyloliquefaciens* AP-219 (NRRL B-50619), *B. amyloliquefaciens* AP-295 (NRRL B-50620), *B. japonicum* SEMIA 5079 (e.g. Gelfix 5 or Adhere 60 from Nitral Urbana Laoboratories, Brazil, a BASF Company), *B. japonicum* SEMIA 5080 (e.g. GELFIX 5 or ADHERE 60 from Nitral Urbana Laoboratories, Brazil, a BASF Company), *B. mojavensis* AP-209 (NRRL B-50616), *B. solisalsi* AP-217 (NRRL B-50617), *B. pumilus* strain INR-7 (otherwise referred to as BU-F22 (NRRL B-50153) and BU-F33 (NRRL B-50185)), *B. simplex* ABU 288 (NRRL B-50340) and *B. amyloliquefaciens* subsp. *plantarum* MBI600 (NRRL B-50595) have been mentioned i.a. in US patent appl. 20120149571, U.S. Pat. No. 8,445,255, WO 2012/079073. *Bradyrhizobium japonicum* USDA 3 is known from U.S. Pat. No. 7,262,151. Jasmonic acid or salts (jasmonates) or derivatives include without limitation potassium jasmonate, sodium jasmonate, lithium jasmonate, ammonium jasmonate, dimethyl-ammonium jasmonate, isopropylammonium jasmonate, diolammonium jasmonate, diethtriethanolammonium jasmonate, jasmonic acid methyl ester, jasmonic acid amide, jasmonic acid methylamide, jasmonic acid-L-amino acid (amide-linked) conjugates (e.g., conjugates with L-isoleucine, L-valine, L-leucine, or L-phenylalanine), 12-oxo-phytodienoic acid, coronatine, coronafacoyl-L-serine, coronafacoyl-L-threonine, methyl esters of 1-oxo-indanoyl-isoleucine, methyl esters of 1-oxo-indanoyl-leucine, coronalon (2-[(6-ethyl-1-oxo-indane-4-carbonyl)-amino]-3-methyl-pentanoic acid methyl ester), linoleic acid or derivatives thereof and cis-jasmone, or combinations of any of the above.

Humates are humic and fulvic acids extracted from a form of lignite coal and clay, known as leonardite. Humic acids are organic acids that occur in humus and other organically derived materials such as peat and certain soft coal. They have been shown to increase fertilizer efficiency in phosphate and micro-nutrient uptake by plants as well as aiding in the development of plant root systems.

The compounds of the invention may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same The invertebrate pest (also referred to as "animal pest"), i.e. the insects, arachnids and nematodes, the plant, soil or water in which the plant is growing or may grow can be contacted with the compounds of the present invention or composition(s) comprising them by any application method known in the art. As such, "contacting" includes both direct contact (applying the compounds/compositions directly on the invertebrate pest or plant—typically to the foliage, stem or roots of the plant) and indirect contact (applying the compounds/compositions to the locus of the invertebrate pest or plant).

The compounds of the present invention or the pesticidal compositions comprising them may be used to protect growing plants and crops from attack or infestation by animal pests, especially insects, acaridae or arachnids by contacting the plant/crop with a pesticidally effective amount of compounds of the present invention. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

Moreover, invertebrate pests may be controlled by contacting the target pest, its food supply, habitat, breeding ground or its locus with a pesticidally effective amount of compounds of the present invention. As such, the application may be carried out before or after the infection of the locus, growing crops, or harvested crops by the pest.

The compounds of the present invention can also be applied preventively to places at which occurrence of the pests is expected.

The compounds of the present invention may be also used to protect growing plants from attack or infestation by pests by contacting the plant with a pesticidally effective amount of compounds of the present invention. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 5 g to 500 g per hectare, more desirably from 5 g to 200 g per hectare.

The compounds of the present invention are effective through both contact (via soil, glass, wall, bed net, carpet, plant parts or animal parts), and ingestion (bait, or plant part).

The compounds of the present invention may also be applied against non-crop insect pests, such as ants, termites, wasps, flies, mosquitos, crickets, or cockroaches. For use against said non-crop pests, compounds of the present invention are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics. The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active ingredient.

Formulations of compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene. The impregnation of curtains and bednets is done in general by dipping the textile material into emulsions or dispersions of the insecticide or spraying them onto the nets.

The compounds of the present invention and their compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of the present invention are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

The compounds of the present invention are also suitable for the treatment of plant propagation material, especially seeds, in order to protect them from insect pest, in particular from soil-living insect pests and the resulting plant's roots and shoots against soil pests and foliar insects.

The compounds of the present invention are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the present invention, including a salt thereof. Particularly preferred is a method, wherein the plant's roots and shoots are protected, more preferably a method, wherein the plants shoots are protected form piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A 242 236, EP-A 242 246) (WO 92/00377) (EP-A 257 993, U.S. Pat. No. 5,013,659) or in transgenic crop plants, for example cotton, with the capability of producing Bacillus thuringiensis toxins (Bt toxins) which make the plants resistant to certain pests (EP-A 142 924, EP-A 193 259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:
A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter.

In a preferred embodiment a FS formulation is used for seed treatment. Typically, a FS formulation may comprise 1-800 g/l of active ingredient, 1-200 g/I Surfactant, 0 to 200 g/I antifreezing agent, 0 to 400 g/l of binder, 0 to 200 g/l of a pigment and up to 1 liter of a solvent, preferably water.

Especially preferred FS formulations of compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, polysaccharides like celluloses, tylose and starch, polyolefin homo- and copolymers like olefin/maleic anhydride copolymers, polyurethanes, polyesters, polystyrene homo and copolymers.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a gelling agent is carrageen (Satiagel®)

In the treatment of seed, the application rates of the compounds of the present invention are generally from 0.01 g to 10 kg per 100 kg of seed, preferably from 0.05 g to 5 kg per 100 kg of seed, more preferably from 0.1 g to 1000 g per 100 kg of seed and in particular from 0.1 g to 200 g per 100 kg of seed.

The invention therefore also relates to seed comprising a compound of the present invention, including an agriculturally useful salt of it, as defined herein. The amount of the compound of the present invention, including an agriculturally useful salt thereof will in general vary from 0.01 g to 10 kg per 100 kg of seed, preferably from 0.05 g to 5 kg per 100 kg of seed, in particular from 0.1 g to 1000 g per 100 kg of seed. For specific crops such as lettuce the rate can be higher.

Methods which can be employed for treating the seed are, in principle, all suitable seed treatment and especially seed dressing techniques known in the art, such as seed coating (e.g. seed pelleting), seed dusting and seed imbibition (e.g. seed soaking). Here, "seed treatment" refers to all methods that bring seeds and the compounds of the present invention into contact with each other, and "seed dressing" to methods of seed treatment which provide the seeds with an amount of the compounds of the present invention, i.e. which generate a seed comprising a compound of the present invention. In principle, the treatment can be applied to the seed at any time from the harvest of the seed to the sowing of the seed. The seed can be treated immediately before, or during, the planting of the seed, for example using the "planter's box" method. However, the treatment may also be carried out several weeks or months, for example up to 12 months, before planting the seed, for example in the form of a seed dressing treatment, without a substantially reduced efficacy being observed.

Expediently, the treatment is applied to unsown seed. As used herein, the term "unsown seed" is meant to include seed at any period from the harvest of the seed to the sowing of the seed in the ground for the purpose of germination and growth of the plant.

Specifically, a procedure is followed in the treatment in which the seed is mixed, in a suitable device, for example a mixing device for solid or solid/liquid mixing partners, with the desired amount of seed treatment formulations, either as such or after previous dilution with water, until the composition is distributed uniformly on the seed. If appropriate, this is followed by a drying step.

The compounds of the present invention, including their stereoisomers, veterinarily acceptable salts or N-oxides, are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions comprising a parasiticidally effective amount of compounds of the present invention, including their stereoisomers, veterinarily acceptable salts or N-oxides, and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of the present invention, including its stereoisomers, veterinarily acceptable salts or N-oxides, or a composition comprising it.

The invention also provides the use of a compound of the present invention, including its stereoisomers, veterinarily acceptable salts or N-oxides, for treating or protecting an animal from infestation or infection by invertebrate pests.

The invention also provides a process for the preparation of a composition for treating, controlling, preventing or protecting animals against infestation or infection by parasites which comprises a parasiticidally effective amount of a compound of the present invention, including its stereoisomers, veterinarily acceptable salts or N-oxides, or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula (I) and their stereoisomers, veterinarily acceptable salts, tautomers and N-oxides, are suitable for combating endo- and ectoparasites in and on animals.

The compounds of the present invention, especially compounds of formula (I) and their stereoisomers, veterinarily acceptable salts, tautomers and N-oxides, and compositions comprising them are preferably used for controlling and preventing infestations of and infections in animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of the present invention, including their stereoisomers, veterinarily acceptable salts or N-oxides, and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention, including their stereoisomers, veterinarily acceptable salts or N-oxides, and compositions comprising them are suitable for systemic and/or non-systemic control of ecto- and/or endoparasites. They are active against all or some stages of development.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*, cockroaches (*Blattaria-Blattodea*), e.g. *Blattella germanica, Blattella asahinae, Periplaneta americana, Periplaneta japonica, Periplaneta brunnea, Periplaneta fuligginosa, Periplaneta australasiae*, and *Blatta orientalis*, flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*, lice (Phthiraptera), e.g. *Pediculus humanus* capitis, *Pediculus humanus* corporis, *Pthirus pubis, Haematopinus eurysternus, Haematopinus suis, Linognathus vituli, Bovicola bovis, Menopon gallinae, Menacanthus stramineus* and *Solenopotes capillatus*.

ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae*, Actinedida (Prostigmata) und Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp., Bugs (Heteropterida): *Cimex lectularius, Cimex hemipterus, Reduvius senilis, Triatoma* spp., *Rhodnius* ssp., *Panstrongylus* ssp. and *Arilus critatus*, Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus.*, *Ostertagia* spp., *Cooperia* spp., *Nematodirus* spp., *Dictyocaulus* spp., *Cyathostoma* spp., *Oesophagostomum* spp., *Stephanurus dentatus*, *Ollulanus* spp., *Chabertia* spp., *Stephanurus dentatus*, *Syngamus trachea*, *Ancylostoma* spp., *Uncinaria* spp., *Globocephalus* spp., *Necator* spp., *Metastrongylus* spp., *Muellerius capillaris*, *Protostrongylus* spp., *Angiostrongylus* spp., *Parelaphostrongylus* spp. *Aleurostrongylus abstrusus*, and *Dioctophyma renale*, Intestinal roundworms (Ascaridida), e.g. *Ascaris lumbricoides*, *Ascaris suum*, *Ascaridia galli*, *Parascaris equorum*, *Enterobius vermicularis* (Threadworm), *Toxocara canis*, *Toxascaris leonine*, *Skrjabinema* spp., and *Oxyuris equi*, *Camallanida*, e.g. *Dracunculus medinensis* (guinea worm) *Spirurida*, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp., Thorny headed worms (Acanthocephala), e.g. *Acanthocephalus* spp.,

*Macracanthorhynchus hirudinaceus* and *Oncicola* spp.,

Planarians (Plathelminthes):

Flukes (Trematoda), e.g. *Faciola* spp., *Fascioloides magna*, *Paragonimus* spp., *Dicrocoelium* spp., *Fasciolopsis buski*, *Clonorchis sinensis*, *Schistosoma* spp., *Trichobilharzia* spp., *Alaria alata*, *Paragonimus* spp., and *Nanocyetes* spp., *Cercomeromorpha*, in particular *Cestoda* (Tapeworms), e.g. *Diphyllobothrium* spp., *Tenia* spp., *Echinococcus* spp., *Dipylidium caninum*, *Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The present invention relates to the therapeutic and the non-therapeutic use of compounds of the present invention and compositions comprising them for controlling and/or combating parasites in and/or on animals. The compounds of the present invention and compositions comprising them may be used to protect the animals from attack or infestation by parasites by contacting them with a parasiticidally effective amount of compounds of the present invention and compositions containing them. The compounds of the present invention and compositions comprising them can be effective through both contact (via soil, glass, wall, bed net, carpet, blankets or animal parts) and ingestion (e.g. baits). As such, "contacting" includes both direct contact (applying the pesticidal mixtures/compositions containing the compounds of the present invention directly on the parasite, which may include an indirect contact at its locus-P, and optionally also administrating the pesticidal mixtures/composition directly on the animal to be protected) and indirect contact (applying the compounds/compositions to the locus of the parasite). The contact of the parasite through application to its locus is an example of a non-therapeutic use of compounds of the present invention. "Locus-P" as used above means the habitat, food supply, breeding ground, area, material or environment in which a parasite is growing or may grow outside of the animal.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions of the present invention. A parasiticidally effective amount of the compositions will also vary according to the prevailing conditions such as desired parasiticidal effect and duration, target species, mode of application, and the like.

The compounds of the present invention can also be applied preventively to places at which occurrence of the pests or parasites are expected.

Administration can be carried out both prophylactically and therapeutically.

Administration of the active compounds is carried out directly or in the form of suitable preparations, orally, topically/dermally or parenterally.

The compounds of the invention are better bio-degradable than those of the prior art and in addition retain a high level of pest control. This makes them superior in terms of environmental safety. In light of the structural similarities of the compounds of formula I, this significant difference in bio-degradability in favour of the compounds of the invention is unexpected and cannot be derived from what is known from the prior art.

EXAMPLES

The present invention is now illustrated in further details by the following examples, without imposing any limitation thereto.

II. Preparation Examples

Compounds can be characterized e.g. by coupled High Performance Liquid Chromatography/mass spectrometry (HPLC/MS), by $^1$H-NMR and/or by their melting points.
Analytical HPLC column:

Method A: Analytical UPLC column: Phenomenex Kinetex 1.7 µm XB-C18 100A; 50×2.1 mm from Phenomenex, Germany. Elution: acetonitrile/water+0.1% trifluoroacetic acid (TFA) in a ratio from 5:95 to 100:0 in 1.5 min; 100% B 0.24 min; Flow: 0.8 mL/min to 1 mL/min in 1.5 min at 60° C. MS-method: quadrupole electrospray ionization, 80 V (positive mode).

$^1$H-NMR: The signals are characterized by chemical shift (ppm, δ [delta]) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singlett.

Abbreviations used are: h for hour(s), min for minute(s), r.t./room temperature for 20-25° C., THF for tetrahydrofuran, MTBE for methyl-tert-butylether, OAc for acetate, O i-Pr for isopropoxy, Et$_2$O for diethylether, MeOH for methanol.

C.1 Compound Examples 1

Compound examples 1-1 to 1-13 correspond to compounds of formula C.1

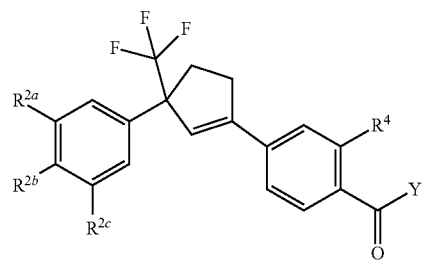

wherein $R^{2a}$, $R^{2b}$, $R^{2c}$, $R^4$ and Y of each synthesized compound is defined in one row of table C.1 below.

The compounds were synthesized in analogy to Synthesis Example S.1 and S.2

TABLE C.1

| Ex. | $R^{2a}, R^{2b}, R^{2c}$ | $R^4$ | —Y | HPLC-MS: Method, $R_t$ (min) & $[M + H]^+$ or $^1$H-NMR |
|---|---|---|---|---|
| 1-1 | Cl, H, Cl | Cl | —NHCH$_2$—C(=O)NHCH$_2$CF$_3$ | 1H NMR (400 MHz, methanol-d$_4$): δ 7.76 (s, 1H), 7.66-7.63 (m, 2H), 7.55 (s, 2H), 7.48 (s, 1H), 6.85 (s, 1H), 4.12 (s, 2H), 4.1-3.9 (m, 2H), 3.1-2.8 (m, 3H), 2.55-2.4 (m, 1H) |
| 1-2 | Cl, H, Cl | Cl | —NHCH$_2$-(2-pyridyl) | 1H NMR (400 MHz, CDCl$_3$): δ 8.57 (s, 1H), 7.8-7.2 (m, 9H), 6.44 (s, 1H), 4.82 (s, 2H), 3.0-2.9 (m, 1H), 2.9-2.8 (m, 2H), 2.5-2.4 (m, 1H) |
| 1-3 | Cl, H, Cl | Cl | —NHCH$_2$-(2-pyrimidyl) | 1H NMR (400 MHz, CDCl$_3$): δ 8.76 (s, 2H), 7.9-7.3 (m, 7H), 6.45 (s, 1H), 4.96 (s, 2H), 3.1-2.9 (m, 1H), 2.9-2.8 (m, 2H), 2.5-2.4 (m, 1H) |
| 1-4 | Cl, H, Cl | Cl | —NHCH$_2$CH=CH$_2$ | 1H NMR (400 MHz, CDCl$_3$): δ 7.77 (d, 1H), 7.55 (s, 1H), 7.48 (d, 1H), 7.35-7.33 (m, 3H), 6.44 (s, 1H), 6.4-6.3 (m, 1H), 6.1-5.9 (m, 1H), 5.35-5.21 (m, 2H), 4.15-4.12 (m, 2H), 3.05-2.9 (m, 1H), 2.9-2.75 (m, 2H), 2.5-2.4 (m, 1H) |
| 1-5 | Cl, H, Cl | Cl | —NHCH$_2$CF$_3$ | 1H NMR (400 MHz, CDCl$_3$): δ 7.73 (d, 1H), 7.55 (s, 1H), 7.48 (d, 1H), 7.35-7.33 (m, 3H), 6.85-6.75 (m, 1H), 6.46 (s, 1H), 4.17-4.10 (m, 2H), 3.05-2.9 (m, 1H), 2.9-2.8 (m, 2H), 2.5-2.4 (m, 1H) |
| 1-6 | Cl, H, Cl | Cl | —NHCH$_2$CCH | 1H NMR (400 MHz, CDCl$_3$): δ 7.79 (d, 1H), 7.55 (s, 1H), 7.49 (d, 1H), 7.35-7.33 (m, 3H), 6.55 (s, 1H), 6.45 (s, 1H), 4.30 (s, 2H), 3.05-2.9 (m, 1H), 2.9-2.7 (m, 2H), 2.5-2.4 (m, 1H), 2.32 (s, 1H) |
| 1-7 | Cl, H, Cl | Cl | —NHNH-(2-pyrimidyl) | 1H NMR (400 MHz, DMSO-d$_6$): δ 10.34 (s, 1H), 9.28 (s, 1H), 8.53-8.44 (m, 2H), 7.97 (s, 1H), 7.80-7.67 (m, 5H), 7.25 (s, 1H), 6.89-6.86 (m, 1H), 3.04-2.84 (m, 4H) |
| 1-8 | Cl, H, Cl | Cl | —NHCH$_2$-cyclopropyl | 1H NMR (400 MHz, CDCl$_3$): δ 7.74 (d, 1H), 7.54 (s, 1H), 7.47 (d, 1H), 7.35-7.33 (m, 3H), 6.43 (s, 1H), 6.40 (s, 1H), 3.37-3.34 (m, 2H), 3.05-2.9 (m, 1H), 2.9-2.8 (m, 2H), 2.5-2.4 (m, 1H), 1.11-1.07 (m, 1H), 0.59-0.57 (m, 2H), 0.31-0.29 (m, 2H) |
| 1-9 | Cl, H, Cl | Cl | —NH$_2$ | 1H NMR (400 MHz, CDCl$_3$): δ 7.88 (d, 1H), 7.56 (s, 1H), 7.50 (d, 1H), 7.35-7.33 (m, 3H), 6.46 (s, 2H), 6.09 (s, 1H), 3.05-2.95 (m, 1H), 2.90-2.7 (m, 2H), 2.5-2.4 (m, 1H) |
| 1-10 | Cl, H, Cl | Cl | —NH-cyclopropyl | 1H NMR (400 MHz, CDCl$_3$): δ 7.74 (d, 1H), 7.52 (s, 1H), 7.46 (d, 1H), 7.35-7.33 (m, 3H), 6.43 (s, 1H), 6.41 (s, 1H), 3.0-2.8 (m, 4H), 2.5-2.4 (m, 1H), 0.9-0.8 (m, 2H), 0.7-0.6 (m, 2H) |
| 1-11 | Cl, H, Cl | Cl | —NH-(1,1-dioxo-thietan-3-yl) | 1H NMR (400 MHz, CDCl$_3$): δ 7.7-7.3 (m, 6H), 6.5 (s, 1H), 4.9-4.8 (m, 1H), 4.7-4.5 (m, 2H), 4.2-4.1 (m, 2H), 3.0-2.9 (m, 1H), 2.9-2.7 (m, 2H), 2.5-2.3 (m, 1H). |
| 1-12 | Cl, H, Cl | Cl | —OH | 1H NMR (400 MHz, methanol-d$_4$): δ 7.86 (d, 1H), 7.72 (d, 1H), 7.62 (dd, 1H), 7.51 (s, 2H), 7.43 (d, 1H), 6.84 (s, 1H), 3.02-2.77 (m, 3H), 2.5-2.4 (m, 1H). |
| 1-13 | Cl, H, Cl | Cl | —OCH$_3$ | 1H NMR (400 MHz, CDCl$_3$): δ 7.88 (d, 1H), 7.59 (s, 1H), 7.34 (d, 1H), 7.35-7.33 (m, 3H), 6.47 (s, 1H), 3.96 (s, 3H), 3.05-2.9 (m, 1H), 2.9-2.8 (m, 2H), 2.5-2.4 (m, 1H) |

Synthesis Example S.1

2-Chloro-4-[3-(3,5-dichlorophenyl)-3-(trifluoromethyl)cyclopenten-1-yl]benzoic acid Compound Example 1-12; Compound of Formula C.1, Wherein $R^{2a}$ and $R^{2c}$ are Cl, $R^{2b}$ is H, $R^4$ is Cl, and —Y is —OH

Step 1: 1,3-Dichloro-5-[3-methylene-1-(trifluoromethyl)cyclopentyl]benzene

To a solution of 1,3-dichloro-5-[1-(trifluoromethyl)vinyl]benzene (16 g, CAS 864725-22-4) in THF (150 mL) was added $Pd(OAc)_2$ (0.9 g), 2-(trimethylsilylmethyl)allyl acetate (16 g, CAS 72047-94-0) and $P(O\ i-Pr)_3$ under $N_2$ at r.t. The mixture was refluxed overnight, then poured into water and extracted with $Et_2O$. The organic layer was washed with brine, dried over $Na_2SO_4$ and concentrated. The residue was purified by flash chromatography on silica gel to afford the product (16 g, 82%).

$^1$H NMR (400 MHz, $CDCl_3$): δ 7.34 (s, 1H), 7.30 (s, 2H), 5.01 (s, 1H), 4.92 (s, 1H), 3.11 (d, 1H), 2.86 (d, 1H), 2.65-2.47 (m, 2H), 2.4-2.3 (m, 1H), 2.28-2.18 (m, 1H).

Step 2: 3-(3,5-Dichlorophenyl)-3-(trifluoromethyl)cyclopentanone

Into a solution of the product of step 1 (16 g) in $CH_2Cl_2$/MeOH (4:1, 1.25 L) at −78° C. was bubbled $O_3$ for 30 min. Then, the blue solution was purged with $O_2$ until the colour faded. $Ph_3P$ (43 g) was added and the mixture stirred at r.t. overnight. The mixture was concentrated and the residue was purified by flash chromatography on silica gel to afford the product (15 g, 90%).

$^1$H NMR (400 MHz, $CDCl_3$): δ 7.37 (s, 1H), 7.23 (s, 2H), 3.03 (d, 1H), 2.92-2.83 (m, 1H), 2.70 (d, 1H), 2.59-2.49 (m, 1H), 2.47-2.30 (m, 2H).

Step 3: [3-(3,5-Dichlorophenyl)-3-(trifluoromethyl)cyclopenten-1-yl]trifluoromethanesulfonate To a solution of the product of step 2 (10 g) in THF (300 mL) was added a solution of lithium diisopropylamide ("LDA", 2 M, 34 mL) and the reaction was stirred at −78° C. for 1 h. Then, a solution of N-phenyl-bis(trifluoromethanesulfonimide) ("PhNTf$_2$", 18 g, CAS 37595-74-7) in THF (200 mL) was added at −78° C. and the reaction stirred at −78° C. for 1 h and for 2 h at r.t. Then, the mixture was quenched with saturated aqueous $NH_4Cl$ solution and extracted with ethyl acetate. The organic layer was washed with brine, dried over $Na_2SO_4$ and concentrated. The residue was purified by flash chromatography on silica gel to afford the product (16 g, 56%).

$^1$H NMR (400 MHz, $CDCl_3$): δ 7.38 (s, 1H), 7.24 (s, 2H), 5.99 (s, 1H), 2.92-2.66 (m, 3H), 2.42-2.30 (m, 1H).

Step 4: Methyl 2-chloro-4-[3-(3,5-dichlorophenyl)-3-(trifluoromethyl)cyclopenten-1-yl]-benzoate (Compound Example 1-13)

A mixture of the product of step 3 (16 g), methyl 2-chloro-4-(4,4,5,5-tetramethyl-1,3,2-dioxaborolan-2-yl)benzoate (12 g, CAS 334018-52-9) and $K_3PO_4$ (16 g) in THF (200 mL) was stirred at r.t. for 10 min. Then, [1,1'-bis(diphenylphosphino)ferrocene]dichloro-palladium(II) (complex with dichloromethane, "Pd(dppf)Cl$_2$·CH$_2$Cl$_2$", 1.5 g, CAS 95464-05-4) was added and the mixture was refluxed overnight under $N_2$. The reaction was quenched with saturated aqueous $NH_4Cl$ solution and extracted with ethyl acetate. The organic layer was washed with brine, dried over $Na_2SO_4$ and concentrated. The residue was purified by flash chromatography on silica gel to afford the product (13 g, 76%).

$^1$H NMR (400 MHz, $CDCl_3$): δ 7.89 (d, 1H), 7.60 (s, 1H), 7.47 (d, 1H), 7.35-7.33 (m, 3H), 6.49 (s, 1H), 3.97 (s, 3H), 3.03-2.77 (m, 3H), 2.48-2.36 (m, 1H).

Step 5: 2-Chloro-4-[3-(3,5-dichlorophenyl)-3-(trifluoromethyl)cyclopenten-1-yl]benzoic acid To a solution of the product of step 4 (11 g) in THF/$H_2O$ (3:1, 160 mL) was added LiOH (2 g) at 0° C., and the mixture was stirred at r.t. overnight. Then, the mixture was diluted with water and washed with MTBE. The aqueous layer was then acidified with aqueous HCl solution (1 M) to pH 4 and extracted with ethyl acetate. The organic layer was washed with brine, dried over $Na_2SO_4$ and concentrated to afford the product (9 g, 85%).

$^1$H NMR (400 MHz, methanol-$d_4$): δ 7.86 (d, 1H), 7.72 (d, 1H), 7.62 (dd, 1H), 7.51 (s, 2H), 7.43 (d, 1H), 6.84 (s, 1H), 3.02-2.77 (m, 3H), 2.5-2.4 (m, 1H).

Synthesis Example S.2

Compound Example 1-11; Compound of Formula C.1, Wherein $R^{2a}$ and $R^{2c}$ are Cl, $R^{2b}$ is H, $R^4$ is Cl, and —Y is —NH-(1,1-dioxo-thietan-3-yl)

2-Chloro-4-[3-(3,5-dichlorophenyl)-3-(trifluoromethyl)cyclopenten-1-yl]-N-(1,1-dioxothietan-3-yl)benzamide To a mixture of 2-chloro-4-[3-(3,5-dichlorophenyl)-3-(trifluoromethyl)cyclopenten-1-yl]benzoic acid (compound example 1-12, 1 g), 1,1-dioxothietan-3-amine hydrochloride (0.44 g, CAS 1422344-24-8) and bromotripyrrolidinophosphonium hexafluorophosphate ("PyBroP", 1.3 g) in $CH_2Cl_2$ (50 mL) at r.t. was added N,N-diisopropylethylamine (0.96 g). The reaction was stirred at r.t. overnight. Then, the reaction was concentrated, the residue re-dissolved in ethyl acetate and washed twice with water. The organic layer was dried ($Na_2SO_4$), filtered, and concentrated. The residue was purified by flash chromatography on silica to afford the product (0.38 g, 30%).

$^1$H NMR (400 MHz, $CDCl_3$): δ 7.7-7.3 (m, 6H), 6.5 (s, 1H), 4.9-4.8 (m, 1H), 4.7-4.5 (m, 2H), 4.2-4.1 (m, 2H), 3.0-2.9 (m, 1H), 2.9-2.7 (m, 2H), 2.5-2.3 (m, 1H).

C.2 Compound Examples 2

Compound examples 2-1 to 2-13 correspond to compounds of formula C.2

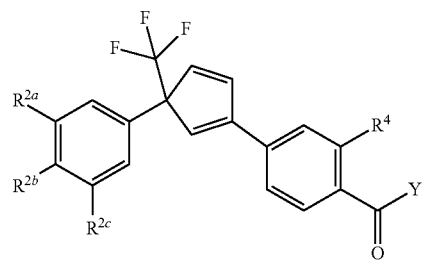

C.2 wherein $R^{2a}$, $R^{2b}$, $R^{2c}$, $R^4$ and Y of each synthesized compound is defined in one row of table C.2 below.

The compounds were synthesized in analogy to Synthesis Example S.3.

TABLE C.2

| Ex. | $R^{2a}, R^{2b}, R^{2c}$ | $R^4$ | —Y | HPLC-MS: Method, $R_t$ (min) & $[M + H]^+$ or $^1$H-NMR | |
|---|---|---|---|---|---|
| 2-1 | Cl, H, Cl | Cl | —NHCH$_2$CF$_3$ | 1.426 | 515.7 |
| 2-2 | Cl, H, Cl | Cl | —NHCH$_2$C≡CH | 1.372 | 469.8 |
| 2-3 | Cl, H, Cl | Cl | —NHCH$_2$-cyclopropyl | 1.438 | 487.7 |
| 2-4 | Cl, H, Cl | Cl | —NHCH$_2$—C(=O)NHCH$_2$CF$_3$ | 1.350 | 572.8 |
| 2-5 | Cl, H, Cl | Cl | —NHCH$_2$-(2-pyridyl) | 1.164 | 524.7 |
| 2-6 | Cl, H, Cl | Cl | —NHNH-(2-pyrimidyl) | 1.341 | 525.7 |
| 2-7 | Cl, H, Cl | Cl | —NHCH$_2$CH=CH$_2$ | 1.405 | 473.8 |
| 2-8 | Cl, H, Cl | Cl | —NHNH-(2-pyrimidyl) | 1.294 | 526.8 |
| 2-9 | Cl, H, Cl | Cl | —NH$_2$ | 1.299 | 433.7 |
| 2-10 | Cl, H, Cl | Cl | —NH-cyclopropyl | 1.386 | 471.9 |
| 2-11 | Cl, H, Cl | Cl | —OCH$_3$ | 1.536 | 448.7 |
| 2-12 | Cl, H, Cl | Cl | —NH-(1,1-dioxo-thietan-3-yl) | $^1$H NMR (400 MHz, CDCl$_3$): δ 7.8-7.7 (m, 1H), 7.6 (m, 1H), 7.6-7.5 (m, 1H), 7.45-7.35 (m, 3H), 7.25 (d, 1H), 7.0-6.95 (m, 1H), 6.9 (m, 1H), 6.9-6.8 (m, 1H), 5.0-4.85 (m, 1H), 4.7-4.55 (m, 2H), 4.2-4.15 (m, 2H). | |
| 2-13 | Cl, H, Cl | Cl | —OH | $^1$H NMR (400 MHz, CDCl$_3$): δ 8.09 (d, 1H), 7.72 (s, 1H), 7.57 (d, 1H), 7.42-7.39 (m, 3H), 7.03 (d, 1H), 6.97 (s, 1H), 6.86 (d, 1H). | |

Synthesis Example S.3

2-Chloro-4-[3-(3,5-dichlorophenyl)-3-(trifluoromethyl)cyclopenta-1,4-dien-1-yl]-N-(1,1-dioxothietan-3-yl)benzamide Compound Example 2-12; Compound of Formula C.2, Wherein $R^{2a}$ and $R^{2c}$ are Cl, $R^{2b}$ is H, $R^4$ is Cl, and —Y is —NH-(1,1-dioxothietan-3-yl)

Step 1: 2-chloro-4-[3-(3,5-dichlorophenyl)-3-(trifluoromethyl)cyclopenten-1-yl]benzoic acid (Compound Example 2-13)

To a solution of methyl 2-chloro-4-[3-(3,5-dichlorophenyl)-3-(trifluoromethyl)-cyclopenten-1-yl]benzoate (i.e. "compound example 1-13") (16 g) in CHCl$_3$ (200 mL) was added Br$_2$ (11.4 g) dropwise at 0° C., and the mixture was stirred at r.t. overnight. Then, the reaction was quenched by dropwise addition of a mixed aqueous solution of Na$_2$SO$_3$ and NaHCO$_3$. The aqueous layer was extracted with CH$_2$Cl$_2$ (3×), and the combined organic layers were dried over Na$_2$SO$_4$, filtered and concentrated. The residue was purified by flash chromatography on silica gel to afford "methyl 4-[5-bromo-3-(3,5-dichlorophenyl)-3-(trifluoromethyl)cyclopenten-1-yl]-2-chloro-benzoate" (15 g, 80%).

A solution of "methyl 4-[5-bromo-3-(3,5-dichlorophenyl)-3-(trifluoromethyl)cyclopenten-1-yl]-2-chloro-benzoate" (12 g) in THF (200 mL) was treated with sodium methanolate (2.46 g), and the reaction stirred at r.t. overnight. Then, water was added and the aqueous layer was extracted with ethyl acetate (3×). The combined organic layers were washed with brine, dried over Na$_2$SO$_4$, filtered and concentrated. The residue was purified by flash chromatography on silica gel to afford the product (8 g, 82%).

$^1$H NMR (400 MHz, CDCl$_3$): δ 8.09 (d, 1H), 7.72 (s, 1H), 7.57 (d, 1H), 7.42-7.39 (m, 3H), 7.03 (d, 1H), 6.97 (s, 1H), 6.86 (d, 1H).

Step 2: 2-Chloro-4-[3-(3,5-dichlorophenyl)-3-(trifluoromethyl)cyclopenta-1,4-dien-1-yl]-N-(1,1-dioxothietan-3-yl)benzamide To a mixture of the product of step 1 (0.5 g), 1,1-dioxothietan-3-amine hydrochloride (0.22 g, CAS 1422344-24-8) and bromotripyrrolidinophosphonium hexafluorophosphate ("PyBroP", 0.65 g) in CH$_2$Cl$_2$ (40 mL) at r.t. was added N,N-diisopropylethylamine (0.48 g). The reaction was stirred at r.t. overnight. Then, the reaction was quenched with water. The organic layer was separated, dried (Na$_2$SO$_4$), filtered, and concentrated. The residue was purified by flash chromatography on silica to afford the product (0.28 g, 41%).

$^1$H NMR (400 MHz, CDCl$_3$): δ 7.8-7.7 (m, 1H), 7.6 (m, 1H), 7.6-7.5 (m, 1H), 7.45-7.35 (m, 3H), 7.25 (d, 1H), 7.0-6.95 (m, 1H), 6.9 (m, 1H), 6.9-6.8 (m, 1H), 5.0-4.85 (m, 1H), 4.7-4.55 (m, 2H), 4.2-4.15 (m, 2H).

C.3 Compound Examples 3

Compound examples 3-1 to 3-11 correspond to compounds of formula C.3

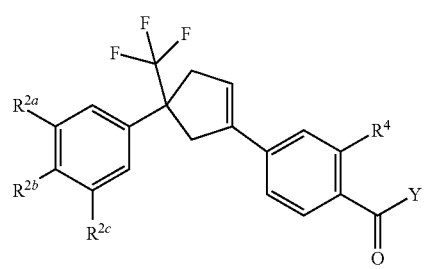

C.3 wherein $R^{2a}$, $R^{2b}$, $R^{2c}$, $R^4$ and Y of each synthesized compound is defined in one row of table C.3 below.

The compounds were synthesized in analogy to Synthesis Example S.4

TABLE C.3

| Ex. | $R^{2a}, R^{2b}, R^{2c}$ | $R^4$ | —Y | HPLC-MS: Method, $R_t$ (min) & $[M + H]^+$ or $^1$H-NMR (400 MHz, CDCl$_3$) | |
|---|---|---|---|---|---|
| 3-1 | Cl, H, Cl | Cl | —NHCH$_2$-(2-pyridyl) | A | 1.220 | 527.0 |
| 3-2 | Cl, H, Cl | Cl | —OCH$_3$ | δ 7.85 (m, 1H), 7.51 (s, 1H), 7.42-7.30 (m, 4H), 6.39-6.22 (m, 1H), 3.95 (s, 3H), 3.59-3.49 (m, 1H), 3.45-3.36 (m, 1H), 3.33-3.24 (m, 1H), 3.17-3.12 (m, 1H) | |
| 3-3 | Cl, H, Cl | Cl | —NHCH$_2$CH=CH$_2$ | A | 1.436 | 474.0 |
| 3-4 | Cl, H, Cl | Cl | —NH$_2$ | A | 1.331 | 435.9 |
| 3-5 | Cl, H, Cl | Cl | —NHCH$_2$C≡CH | A | 1.401 | 473.9 |
| 3-6 | Cl, H, Cl | Cl | —NHCH$_2$CF$_3$ | A | 1.452 | 515.9 |
| 3-7 | Cl, H, Cl | Cl | —NHCH$_2$-(2-pyrimidyl) | A | 1.370 | 527.9 |
| 3-8 | Cl, H, Cl | Cl | —NHCH$_2$—C(=O)NHCH$_2$CF$_3$ | A | 1.380 | 574.9 |
| 3-9 | Cl, H, Cl | Cl | —NH-(1,1-dioxo-thietan-3-yl) | A | 1.344 | 537.9 |
| 3-10 | Cl, H, Cl | Cl | —NHCH$_2$-cyclopropyl | A | 1.466 | 489.9 |
| 3-11 | Cl, H, Cl | Cl | —OH | δ 8.03 (m, 1H), 7.54 (m, 1H), 7.43-7.33 (m, 4H), 6.35 (m, 1H), 3.55 (m, 1H), 3.42 (m, 1H), 3.29 (m, 1H), 3.16 (m, 1H). | |

Synthesis Example S.4

2-Chloro-4-[4-(3,5-dichlorophenyl)-4-(trifluoromethyl)cyclopenten-1-yl]-N-(1,1-dioxothietan-3-yl)benzamide Compound Example 3-9; Compound of Formula C.3, Wherein $R^{2a}$ and $R^{2c}$ are Cl, $R^{2b}$ is H, $R^4$ is Cl, and —Y is —NH-(1,1-dioxo-thietan-3-yl)

Step 1: Methyl 4-[5-bromo-3-(3,5-dichlorophenyl)-3-(trifluoromethyl)cyclopenten-1-yl]-2-chloro-benzoate To a solution of methyl 2-chloro-4-[3-(3,5-dichlorophenyl)-3-(trifluoromethyl)-cyclopenten-1-yl]benzoate (compound example 1-13, 16 g) in CHCl$_3$ (200 mL) at 0° C., Br$_2$ (11.4 g) was added dropwise. The mixture was stirred at r.t. overnight. Then, the reaction was quenched at 0° C. by dropwise addition of an aqueous solution of Na$_2$SO$_3$/NaHCO$_3$. The aqueous layer was extracted with CH$_2$Cl$_2$ (3×100 mL). The combined organic layers were dried (Na$_2$SO$_4$), filtered, and concentrated. The residue was purified by flash chromatography on silica to afford the product (15 g, 79%).

$^1$H NMR (400 MHz, CDCl$_3$): δ 7.97-7.87 (m, 1H), 7.76-7.66 (m, 1H), 7.59-7.48 (m, 1H), 7.42-7.33 (m, 3H), 6.79-6.60 (m, 1H), 5.42 (m, 1H), 3.97 (s, 3H), 3.5-3.4 (m, 1H), 3.12-2.89 (m, 1H).

Step 2: Methyl 2-chloro-4-[3-(3,5-dichlorophenyl)-5-hydroxy-3-(trifluoromethyl)-cyclopenten-1-yl]benzoate To a solution of the product of step 1 (4 g) in acetone (60 mL) was added a solution of AgClO$_4$ (3.17 g) in water (60 mL) and acetone (60 mL). The mixture was stirred at 20° C. for 16 h. Then, the reaction was filtered and the aqueous layer was extracted with CH$_2$Cl$_2$ (3×200 mL). The combined organic layers were dried (Na$_2$SO$_4$), and concentrated. The residue was purified by flash chromatography on silica to afford the product (2.8 g, 79%).

$^1$H NMR (400 MHz, CDCl$_3$): δ 7.92-7.85 (m, 1H), 7.78 (m, 1H), 7.64-7.57 (m, 1H), 7.39-7.28 (m, 3H), 6.64-6.50 (m, 1H), 5.44-5.37 (m, 0.2H), 5.28-5.19 (m, 0.8H), 3.95 (s, 3H), 3.30-3.18 (m, 0.2H), 2.93-2.80 (m, 0.8H), 2.74-2.65 (m, 0.8H), 2.38-2.29 (m, 0.2H).

Step 3: Methyl 2-chloro-4-[4-(3,5-dichlorophenyl)-2-hydroxy-4-(trifluoromethyl)-cyclopentyl]benzoate To a solution of the product of step 2 (6 g) in MeOH (300 mL) was added rhodium on carbon ("Rh/C", 5%, 600 mg). The reaction was stirred under an atmosphere of H$_2$ (30 psi) at 20° C. for 16 h. The reaction was filtered and concentrated to give the crude product (4 g) which was used in the next step without any further purification.

Step 4: Methyl 2-chloro-4-[4-(3,5-dichlorophenyl)-4-(trifluoromethyl)cyclopenten-1-yl]benzoate (Compound Example 3-2)

A solution of the crude product of step 3 (1.3 g) in Et$_3$N (0.4 g) in CH$_2$Cl$_2$ was treated with methanesulfonyl chloride ("MsCl", 0.38 g) dropwise at 0° C. The mixture was stirred at 20° C. for 1 h. Water was added an the aqueous layer was extracted with CH$_2$Cl$_2$ (3×200 mL). The combined organic layers were dried (Na$_2$SO$_4$), filtered, and concentrated to give the crude "mesylat" (1 g) which was used in the next step without any further purification.

To a solution of the crude "mesylate" (1 g) in CH$_2$Cl$_2$ (20 mL) was added 1,8-diazabicyclo[5.4.0]undec-7-ene ("DBU", 0.84 g) dropwise at 0° C. The mixture was stirred at 20° C. for 16 h. Then, the reaction was diluted with water, and the aqueous layer extracted with CH$_2$Cl$_2$ (3×200 mL). The combined organic layers were dried (Na$_2$SO$_4$), filtered, and concentrated. The residue was purified by flash chromatography on silica to afford the product (0.5 g, 36%).

$^1$H NMR (400 MHz, CDCl$_3$): δ 7.85 (m, 1H), 7.51 (s, 1H), 7.42-7.30 (m, 4H), 6.39-6.22 (m, 1H), 3.95 (s, 3H), 3.59-3.49 (m, 1H), 3.45-3.36 (m, 1H), 3.33-3.24 (m, 1H), 3.17-3.12 (m, 1H).

Step 5: 2-Chloro-4-[4-(3,5-dichlorophenyl)-4-(trifluoromethyl)cyclopenten-1-yl]benzoic acid (Compound Example 3-11)

To a solution of the compound of step 4 (5.5 g) in a mixture of THF (150 mL) and MeOH (50 mL) was added a solution of NaOH (0.67 g) in water (50 mL). The mixture was stirred at 25° C. for 16 h. Then, the mixture was concentrated, diluted with water and adjusted to pH 3 using a 1 M aqueous HCl solution. The aqueous layer was extracted with methyl-tert-butylether ("MTBE", 3×50 mL). The organic layers were combined, dried (Na$_2$SO$_4$), filtered, and concentrated to afford a residue which was purified by preparative HPLC to give the product (1.7 g, 70%).

$^1$H NMR (400 MHz, CDCl$_3$): δ 8.03 (m, 1H), 7.54 (m, 1H), 7.43-7.33 (m, 4H), 6.35 (m, 1H), 3.55 (m, 1H), 3.42 (m, 1H), 3.29 (m, 1H), 3.16 (m, 1H).

Step 6: 2-Chloro-4-[4-(3,5-dichlorophenyl)-4-(trifluoromethyl)cyclopenten-1-yl]-N-(1,1-dioxothietan-3-yl)benzamide To a mixture of the product of step 5 (0.2 g), 1,1-dioxothietan-3-amine hydrochloride (0.09 g, CAS 1422344-24-8) and bromotripyrrolidinophosphonium hexafluorophosphate ("PyBroP", 0.26 g) in CH$_2$Cl$_2$ (25 mL) at r.t. was added N,N-diisopropylethylamine (0.19 g). The reaction was stirred at r.t. overnight. Then, the reaction was concentrated, the residue re-dissolved in ethyl acetate and washed with water. The organic layer was dried (Na$_2$SO$_4$), filtered, and concentrated. The residue was purified by flash chromatography on silica to afford the product (0.19 g, 74%).

HPLC-MS (method A): 1.344 min, M=537.9.

II. Evaluation of Pesticidal Activity

The activity of the compounds of formula I of the present invention can be demonstrated and evaluated by the following biological test.

B.1 Green Peach Aphid (*Myzus persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-1, 1-2, 1-3, 1-4, 1-5, 1-6, 1-7, 1-8, 1-9, 1-10, 1-11, 2-1, 2-2, 2-3, 2-4, 2-5, 2-6, 2-7, 2-8, 2-9, 2-10, 2-12, 3-1, 3-3, 3-5, 3-6, 3-7, 3-8, 3-9, 3-10 at 2500 ppm, respectively, showed a mortality of at least 75% in comparison with untreated controls.

B.2 Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications.

After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-2, 1-3, 1-4, 1-5, 1-6, 1-7, 1-8, 1-9, 1-10, 1-11, 2-1, 2-2, 2-3, 2-4, 2-5, 2-6, 2-7, 2-8, 2-9, 2-10, 2-12, 3-1, 3-3, 3-4, 3-5, 3-6, 3-7, 3-8, 3-9, 3-10 at 2500 ppm, respectively, showed a mortality of at least 75% in comparison with untreated controls.

B.3 Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 2-1, 2-2, 2-3, 2-4, 2-5, 2-6, 2-7, 2-8, 2-9, 2-10, 2-12, 3-1, 3-3, 3-4, 3-5, 3-6, 3-7, 3-8, 3-9, 3-10 at 2500 ppm, respectively, showed a mortality of at least 75% in comparison with untreated controls.

B.4 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 1-12, 1-13, 2-1, 2-2, 2-3, 2-4, 2-5, 2-6, 2-7, 2-8, 2-9, 2-10, 2-12, 2-13, 3-1, 3-3, 3-4, 3-5, 3-6, 3-7, 3-8, 3-9, 3-10, 3-11 at 2500 ppm, respectively, showed a mortality of at least 75% in comparison with untreated controls.

B.5 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 µl, using a custom built micro atomizer, at two replications.

After application, microtiter plates were incubated at about 28±1° C. and about 80±5% relative humidity for 5 days. Egg and larval mortality was then visually assessed.

In this test, the compounds 1-1, 1-2, 1-3, 1-4, 1-5, 1-6, 1-7, 1-8, 1-9, 1-10, 1-11, 2-1, 2-2, 2-3, 2-4, 2-6, 2-7, 2-9, 2-12, 3-1, 3-3, 3-4, 3-5, 3-6, 3-7, 3-8, 3-9, 3-10 at 2500 ppm showed a mortality of at least 75% in comparison with untreated controls.

B.6 Diamond Back Moth (*Plutella Xylostella*)

The active compound was dissolved at the desired concentration in a mixture of 1:1 (vol:vol) distilled water:aceteone. Surfactant (Kinetic HV) was added at a rate of 0.01% (vol/vol). The test solution was prepared at the day of use.

Leaves of cabbage were dipped in test solution and air-dried. Treated leaves were placed in petri dishes lined with moist filter paper and inoculated with ten 3$^{rd}$ instar larvae. Mortality was recorded 72 hours after treatment. Feeding damages were also recorded using a scale of 0-100%.

In this test, the compounds 1-1, 1-2, 1-3, 1-4, 1-5, 1-6, 1-7, 1-8, 1-9, 1-10, 1-11, 1-13, 2-1, 2-2, 2-3, 2-4, 2-5, 2-6, 2-7, 2-8, 2-9, 2-10, 2-12, 3-1, 3-3, 3-4, 3-5, 3-6, 3-7, 3-8, 3-9, 3-10 at 500 ppm, respectively, showed a mortality of at least 75% in comparison with untreated controls.

B.7 Orchid Thrips (Dichromothrips Corbetti)

Dichromothrips corbetti adults used for bioassay were obtained from a colony maintained continuously under laboratory conditions. For testing purposes, the test compound was diluted in a 1:1 mixture of acetone:water (vol:vol), plus Kinetic HV at a rate of 0.01% v/v.

Thrips potency of each compound was evaluated by using a floral-immersion technique. All petals of individual, intact orchid flowers were dipped into treatment solution and allowed to dry in Petri dishes. Treated petals were placed into individual re-sealable plastic along with about 20 adult thrips. All test arenas were held under continuous light and a temperature of about 28° C. for duration of the assay. After 3 days, the numbers of live thrips were counted on each petal. The percent mortality was recorded 72 hours after treatment.

In this test, the compounds 1-1, 1-2, 1-3, 1-4, 1-5, 1-6, 1-7, 1-8, 1-10, 1-11, 2-1, 2-2, 2-3, 2-4, 2-5, 2-6, 2-7, 2-8, 2-9, 2-10, 2-12, 3-1, 3-3, 3-5, 3-6, 3-7, 3-8, 3-9, 3-10 at 500 ppm, respectively, showed a mortality of at least 75% in comparison with untreated controls.

B.8 Rice Green Leafhopper (Nephotettix virescens)

Rice seedlings were cleaned and washed 24 hours before spraying. The active compounds were formulated in 1:1 acetone:water (vol:vol), and 0.01% vol/vol surfactant (Kinetic HV) was added. Potted rice seedlings were sprayed with 5-6 ml test solution, air dried, covered with Mylar cages and inoculated with 10 adults. Treated rice plants were kept at about 28-29° C. and relative humidity of about 50-60%. Percent mortality was recorded after 72 hours.

In this test, the compounds 1-1, 1-2, 1-3, 1-5, 1-7, 1-8, 1-10, 1-11, 2-4, 2-5, 2-6, 2-8, 2-10, 2-12, 3-3, 3-5, 3-6, 3-7, 3-9 at 500 ppm, respectively, showed a mortality of at least 75% in comparison with untreated controls.

B.9 Red Spider Mite (Tetranychus kanzawai)

The active compound was dissolved at the desired concentration in a mixture of 1:1 (vol:vol) distilled water: acetone. Surfactant (Kinetic HV) was added at a rate of 0.01% (vol/vol). The test solution was prepared at the day of use.

Potted cowpea beans of 4-5 days of age were cleaned with tap water and sprayed with 1-2 ml of the test solution using air driven hand atomizer. The treated plants were allowed to air dry and afterwards inoculated with 30 or more mites by clipping a cassava leaf section from rearing population. Treated plants were placed inside a holding room at about 25-27° C. and about 50-60% relative humidity. Percent mortality was assessed 72 hours after treatment.

In this test, the compound 1-4, 1-8, 1-11, 2-4, 2-5, 2-12, 3-6, 3-9 at 500 ppm showed a mortality of at least 75% in comparison with untreated controls.

We claim:
1. A cyclopentene or cyclopentadiene compound of the formula (I)

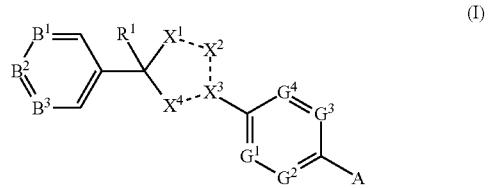

wherein
the ring

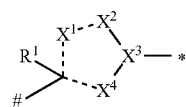

is selected from following rings II-1 to II-3:

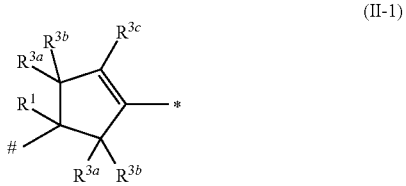

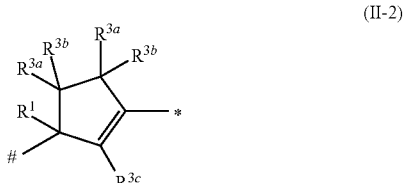

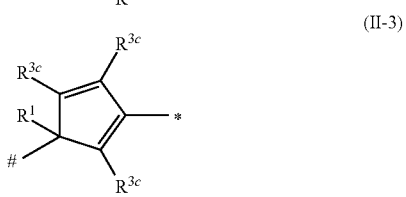

is the attachment point to the ring with the ring members $B^1$, $B^2$ and $B^3$; and
is the attachment point to the ring with the ring members $G^1$, $G^2$, $G^3$ and $G^4$;
A is a group $A^1$, $A^2$ or $A^3$;
wherein
$A^1$ is a group of following formula:

wherein
# denotes the attachment point to the remainder of the molecule;

W is O;
Y is selected from the group consisting of —N(R$^5$)R$^6$ and —OR$^9$;
wherein
R$^5$ is hydrogen or C1-C$_{10}$-alkyl;
R$^6$ is selected from the group consisting of hydrogen, C1-C$_{10}$-alkyl, C$_3$-C$_8$-cycloalkyl, C$_2$-C$_{10}$-alkenyl, C$_2$-C$_{10}$-alkynyl, wherein the four last-mentioned aliphatic and cycloaliphatic radicals may be partially or fully halogenated; C$_1$-C$_{10}$-alkyl substituted by one substituent R$^8$; —NR$^{10a}$R$^{10b}$, —CH=NOR$^{9a}$, and a 4-, 5- or 6-membered saturated heteromonocyclic ring containing 1 or 2 heteroatoms or heteroatom groups independently selected from N, O, S, SO and SO$_2$, as ring members;
wherein
each R$^8$ is independently selected from the group consisting of C$_3$-C$_8$-cycloalkyl, C$_3$-C$_8$-halocycloalkyl, —S(O)$_n$R$^{9a}$, —C(=O)N(R$^{10a}$)R$^{10b}$, and a 5- or 6-membered heteroaromatic ring comprising 1, 2 or 3 heteroatoms or heteroatom groups selected from N, O and S, as ring members, where the heterocyclic ring is optionally substituted with one or more substituents R$^{16}$,
R$^{9a}$ is C$_1$-C$_6$-alkyl;
R$^{10a}$, R$^{10b}$ are selected independently from one another from the group consisting of hydrogen, C$_1$-C$_6$-alkyl, C$_1$-C$_6$-haloalkyl and a 5- or 6-membered heteroaromatic ring comprising 1, 2, 3 or 4 heteroatoms or heteroatom groups selected from N, O and S, as ring members, where the heteroaromatic ring is optionally substituted with one or more substituents R$^{16}$;
each R$^{16}$ is independently C$_1$-C$_6$-alkyl; and
each n is independently 0, 1 or 2;
and
R$^9$ is selected from the group consisting of hydrogen and C$_1$-C$_6$-alkyl;
A$^2$ is a group of following formula:

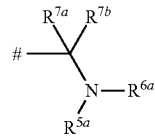

(A$^2$)

wherein
# denotes the attachment point to the remainder of the molecule;
R$^{7a}$ and R$^{7b}$ are hydrogen;
R$^{5a}$ is hydrogen; and
R$^{6a}$ is —C(=O)R$^{8a}$,
wherein
R$^8$a is selected from the group consisting of C$_1$-C$_6$-alkyl, C$_1$-C$_6$-haloalkyl, C$_1$-C$_6$-alkyl substituted by a radical R$^{13}$, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, and a 4-membered saturated heterocyclic ring comprising 1 heteroatom or heteroatom group selected from S, SO and SO$_2$ as ring member;

wherein
R$^{13}$ is selected from the group consisting of C$_1$-C$_6$-alkylsulfonyl, C$_3$-C$_8$-cycloalkyl; and a 5- or 6-membered saturated heterocyclic ring containing 1 or 2 O atoms as ring members;
A$^3$ is a 5 or 6 membered aromatic heteromonocyclic ring containing 1, 2, 3 or 4 heteroatoms or heteroatom groups selected from the group consisting of N, O and S, as ring members;
each of B$^1$, B$^2$ and B$^3$ is independently CR$^2$;
each of G$^2$, G$^3$ and G$^4$ is independently CR$^4$;
R$^1$ is C$_1$-C$_4$-haloalkyl;
each R$^2$ is independently selected from the group consisting of hydrogen, halogen, and C$_1$-C$_6$-haloalkyl;
R$^{3a}$, R$^{3b}$, R$^{3c}$ are hydrogen;
each R$^4$ is independently selected from the group consisting of hydrogen, halogen, cyano, and C$_1$-C$_6$-alkyl which may be partially or fully halogenated;
or a stereoisomer, or an agriculturally or veterinarily acceptable salt thereof.

2. The compound of claim 1, wherein the compound of formula (I) is a compound of formula I.1

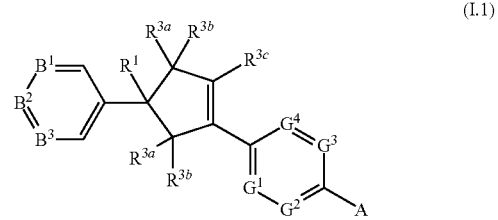

(I.1)

wherein B$^1$, B$^2$, B$^3$, G$^2$, G$^3$, G$^4$, A, R$^1$, R$^{3a}$, R$^{3b}$ and R$^{3c}$ are as defined in claim 1.

3. The compound of claim 1, wherein the compound of formula (I) is a compound of formula I.2

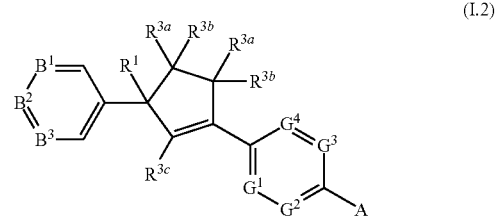

(I.2)

wherein B$^1$, B$^2$, B$^3$, G$^1$, G$^2$, G$^3$, G$^4$, A, R$^1$, R$^{3a}$, R$^{3b}$ and R$^{3c}$ are as defined in claim 1.

4. The compound of claim 1, wherein the compound of formula (I) is a compound of formula I.3

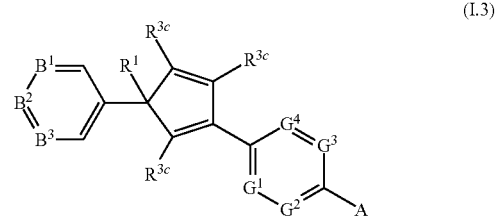

(I.3)

wherein B$^1$, B$^2$, B$^3$, G$^1$, G$^2$, G$^3$, G$^4$, A, R$^1$ and R$^{3c}$ are as defined in claim 1.

5. The compound of claim 1, where A is $A^1$.
6. The compound of claim 1, where in $A^1$ Y is —$OR^9$.
7. The compound of claim 1, where in $A^1$ Y is —$N(R^5)R^6$, wherein
   $R^5$ selected from the group consisting of hydrogen and $C_1$-$C_6$-alkyl; and
   $R^6$ is selected from the group consisting of hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 or 2 F atoms;
   $N(R^{10a})R^{10b}$,
     wherein
     $R^{10a}$ is selected from the group consisting of hydrogen and $C_1$-$C_6$-alkyl; and
     $R^{10b}$ is a heterocyclic ring selected from rings of formulae E-1 to E42;

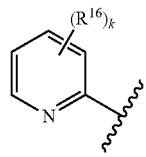
E-1

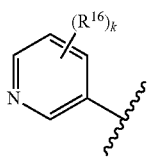
E-2

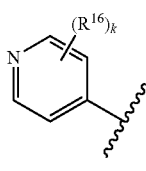
E-3

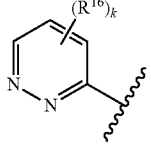
E-4

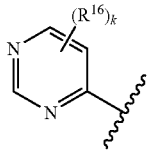
E-5

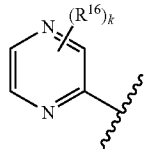
E-6

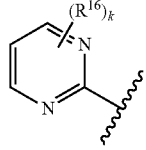
E-7

-continued

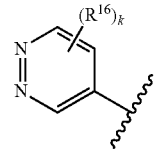
E-8

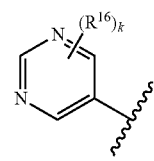
E-9

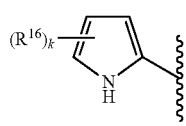
E-10

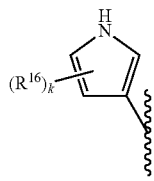
E-11

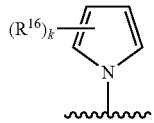
E-12

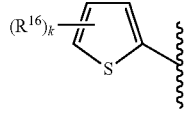
E-13

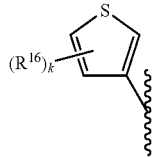
E-14

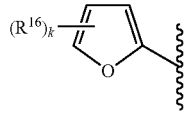
E-15

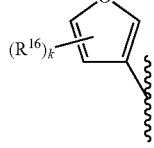
E-16

E-17

-continued
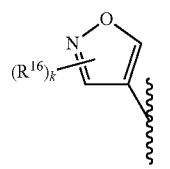 E-18
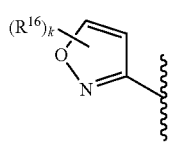 E-19
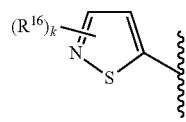 E-20
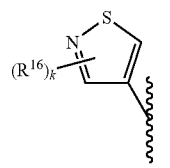 E-21
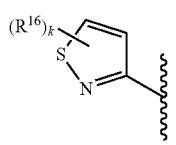 E-22
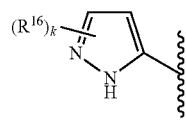 E-23
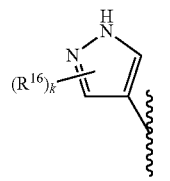 E-24
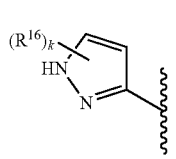 E-25
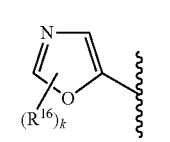 E-26
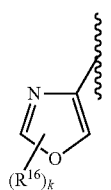 E-27
-continued
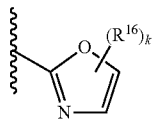 E-28
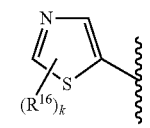 E-29
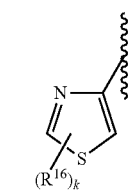 E-30
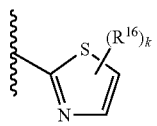 E-31
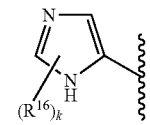 E-32
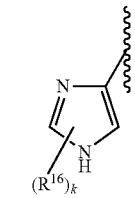 E-33
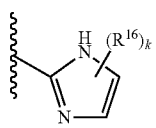 E-34
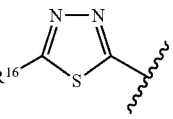 E-35
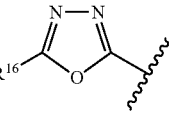 E-36
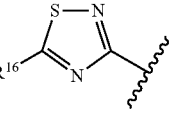 E-37
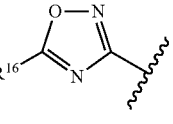 E-38

-continued

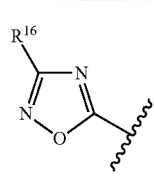
E-39

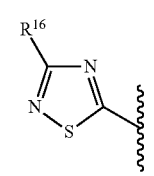
E-40

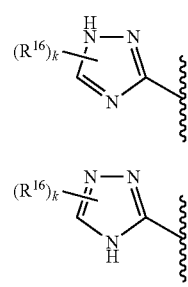
E-41

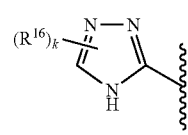
E-42 wherein
the zigzag line denotes the attachment point to the remainder of the molecule;
k is 0, 1, 2 or 3,
and
each $R^{16}$ is independently $C_1$-$C_4$-alkyl;
—CH=NOR$^{9a}$,
wherein
$R^{9a}$ is $C_1$-$C_6$-alkyl;
and a 4-, 5- or 6-membered saturated heteromonocyclic ring containing 1, 2 or 3 heteroatoms or heteroatom groups independently selected from the group consisting of N, O, S, NO, SO and SO$_2$, as ring members;
wherein
each $R^8$ is independently selected from the group consisting of $C_3$-$C_8$-cycloalkyl, $C_3$-$C_8$-halocycloalkyl, $C_1$-$C_6$-alkylthio, $C_1$-$C_6$-haloalkylthio, $C_1$-$C_6$-alkylsulfonyl, $C_1$-$C_6$-haloalkylsulfonyl, —C(=O)N($R^{10a}$)$R^{10b}$, and a 5 or 6-membered aromatic heteromonocyclic ring containing 1 or 2 heteroatoms or heteroatom groups independently selected from the group consisting of N, O and S, as ring members, where the heteromonocyclic ring may be substituted with one or more substituents $R^{16}$;
wherein
$R^{10a}$ is selected from the group consisting of hydrogen and $C_1$-$C_6$-alkyl;
$R^{10b}$ is selected from the group consisting of $C_1$-$C_6$-alkyl, and $C_1$-$C_6$-haloalkyl; and
each $R^{16}$ as a substituent on the heteromonocyclic ring is independently $C_1$-$C_4$-alkyl.

8. The compound of claim 7, where
$R^5$ is hydrogen or $C_1$-$C_3$-alkyl;
$R^6$ is selected from the group consisting of hydrogen, $C_1$-$C_6$-alkyl, $C_1$-$C_6$-haloalkyl, $C_1$-$C_4$-alkyl which carries one radical $R^8$, wherein $R^8$ is as defined below; $C_2$-$C_6$-alkenyl, $C_2$-$C_6$-haloalkenyl, $C_2$-$C_6$-alkynyl, $C_3$-$C_6$-cycloalkyl which may be substituted by 1 or 2 F atoms;

N($R^{10a}$)$R^{10b}$, wherein $R^{10a}$ is selected from the group consisting of hydrogen and $C_1$-$C_6$-alkyl and $R^{10a}$ is a heteroaromatic ring selected from rings of formulae E-1 to E-42;

—CH=NOR$^{9a}$, wherein $R^{9a}$ is $C_1$-$C_6$-alkyl; and a heteromonocyclic ring selected from rings of formulae F-43 to F-54

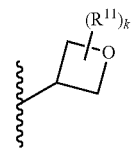
F-43

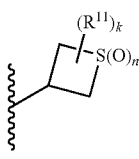
F-44

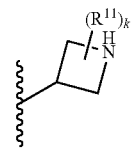
F-45

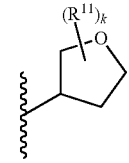
F-46

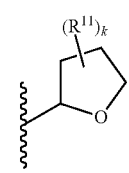
F-47

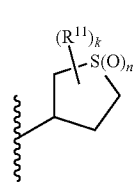
F-48

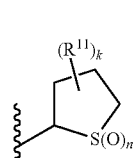
F-49

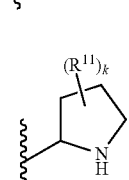
F-50

-continued

F-51
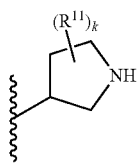

F-52
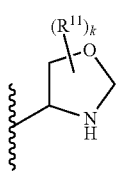

F-53
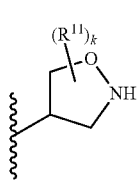

F-54
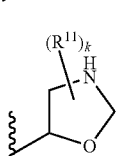

wherein
the zigzag line denotes the attachment point to the remainder of the molecule;
k is 0,
n is 0, 1 or 2, and
$R^8$ is selected from the group consisting of $C_3$-$C_8$-cycloalkyl, $C_3$-$C_8$-halocycloalkyl, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{10a}$)$R^{10b}$, and a heterocyclic ring selected from rings of formulae E-1 to E-42;
wherein
$R^{10a}$ is selected from the group consisting of hydrogen and $C_1$-$C_6$-alkyl;
$R^{10b}$ is selected from the group consisting of hydrogen, $C_1$-$C_6$-alkyl, and $C_1$-$C_6$-haloalkyl; and
each $R^{16}$ as a substituent on heterocyclic rings of formulae E-1 to E-42 is independently $C_1$-$C_4$-alkyl.

9. The compound of claim 8, where
$R^5$ is hydrogen.

10. The compound of claim 1, where A is $A^2$.

11. The compound of claim 1, where A is $A^3$ and $A^3$ is selected from rings of formulae D-1 to D-66

D-1
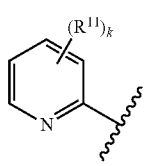

D-2
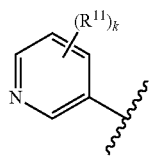

D-3
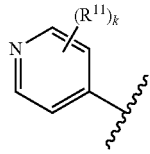

D-4
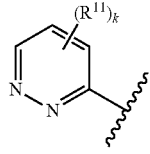

D-5
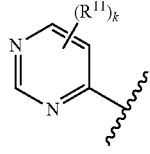

D-6
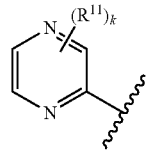

D-7
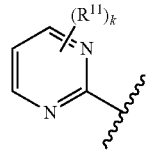

D-8
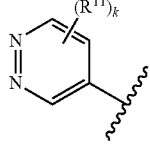

D-9
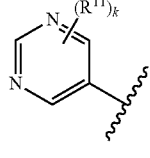

D-10
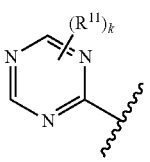

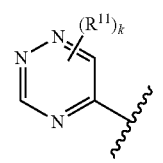 D-11
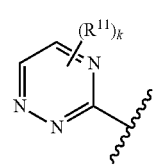 D-12
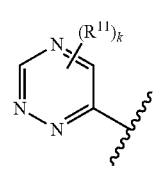 D-13
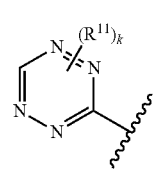 D-14
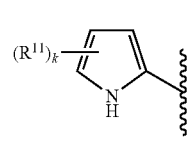 D-15
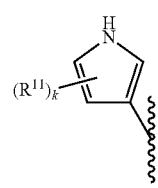 D-16
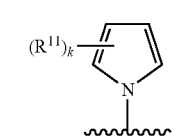 D-17
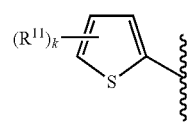 D-18
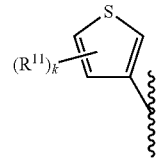 D-19
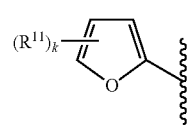 D-20
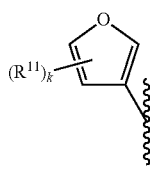 D-21
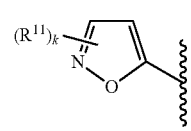 D-22
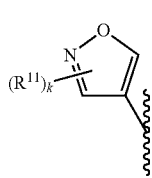 D-23
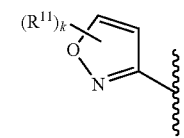 D-24
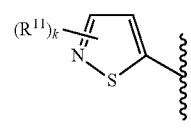 D-25
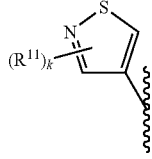 D-26
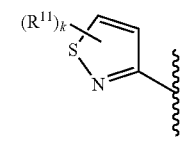 D-27
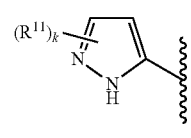 D-28
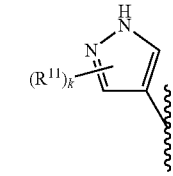 D-29
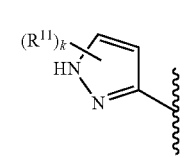 D-30

-continued
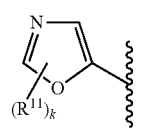 D-31
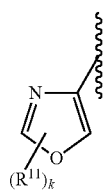 D-32
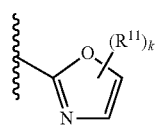 D-33
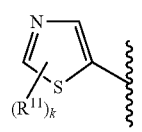 D-34
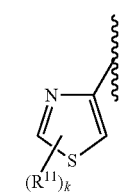 D-35
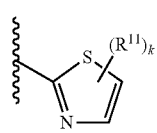 D-36
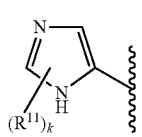 D-37
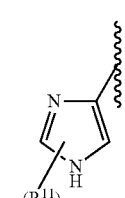 D-38
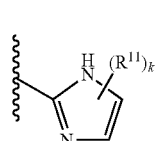 D-39
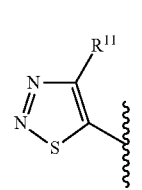 D-40
-continued
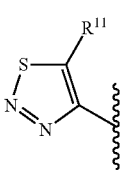 D-41
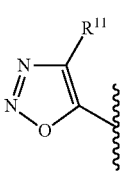 D-42
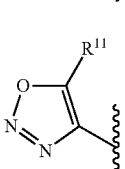 D-43
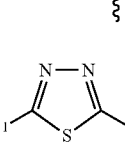 D-44
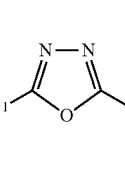 D-45
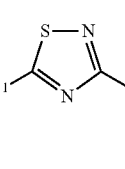 D-46
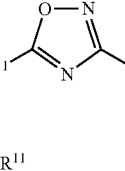 D-47
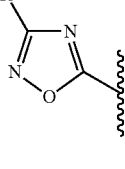 D-48
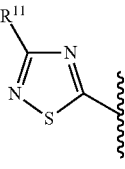 D-49
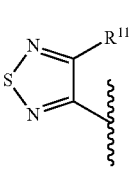 D-50

-continued

D-51 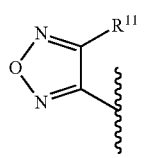

D-52 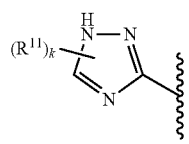

D-53 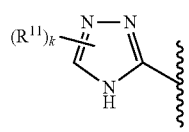

D-54 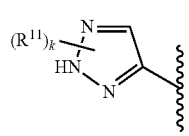

D-55 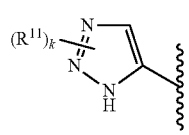

D-56 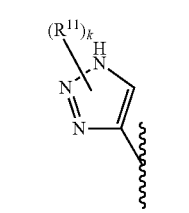

D-57 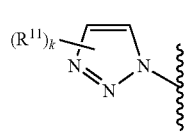

D-58 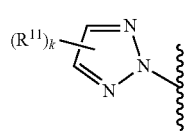

D-59 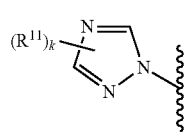

D-60 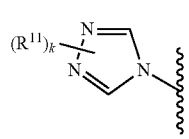

D-61 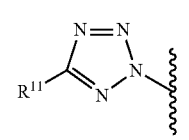

D-62 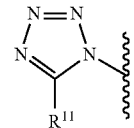

D-63 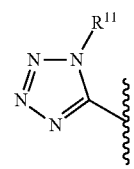

D-64 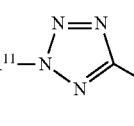

D-65 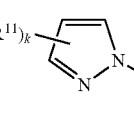

D-66 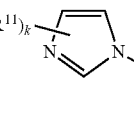

wherein
the zigzag line denotes the attachment point to the remainder of the molecule; and
k is 0.

12. The compound of claim 11, where $A^3$ is selected from rings of formulae D-59, D-65 and D-66.

13. The compound of claim 12, where $A^3$ is the ring of formula D-59.

14. The compound of claim 1, where $R^2$ is selected from the group consisting of hydrogen, halogen, and $C_1$-$C_6$-haloalkyl; provided that at least one of $R^2$ groups at the positions meta to the ring containing X groups is not hydrogen.

15. The compound of claim 14, where $R^2$ is selected from the group consisting of hydrogen, halogen, and $C_1$-$C_2$-haloalkyl.

16. The compound of claim 15, where $R^2$ is selected from the group consisting of hydrogen, F, Cl, Br and $CF_3$.

17. The compound of claim 1, where $R^4$ is selected from the group consisting of hydrogen, halogen, cyano, $C_1$-$C_4$-alkyl, and $C_1$-$C_4$-haloalkyl provided that $R^4$ at the two positions ortho to, and one of the two positions meta to, the ring containing X groups are hydrogen.

18. The compound of claim 17, where $R^4$ is selected from the group consisting of hydrogen, F, Cl, Br, $CH_3$ and $CF_3$.

19. The compound of claim 1, where $R^1$ is $CF_3$.

20. An agricultural or veterinary composition comprising at least one compound of the formula I, as defined in claim 1, a stereoisomer thereof and/or at least one agriculturally or veterinarily acceptable salt thereof, and at least one inert liquid and/or solid agriculturally or veterinarily acceptable carrier.

21. A method for combating invertebrate pests comprising treating the pests, their food supply, their habitat, breeding grounds, or cultivated plants, plant propagation material, soil, area, material or environment to be protected from pest attack or infestation with a compound as defined in claim 1, of a stereoisomer and/or of an agriculturally or veterinarily acceptable salt thereof.

22. A method for treating or protecting an animal from infestation or infection by invertebrate pests comprising treating the animal with a compound as defined in claim 1, of a stereoisomer and/or of a veterinarily acceptable salt thereof.

23. A method for protecting plant propagation material and/or plants which grow therefrom from attack or infestation by invertebrate pests, which method comprises treating plant propagation material with a pesticidally effective amount of at least one compound of the formula I as defined in claim 1, a stereoisomer thereof and/or at least one agriculturally acceptable salt thereof.

\* \* \* \* \*